(12) United States Patent
Wang et al.

(10) Patent No.: US 6,706,262 B1
(45) Date of Patent: Mar. 16, 2004

(54) COMPOUNDS AND METHODS FOR THERAPY AND DIAGNOSIS OF LUNG CANCER

(75) Inventors: Tongtong Wang, Medina, WA (US); Nancy A. Hosken, Seattle, WA (US); Michael D. Kalos, Seattle, WA (US); Gary R. Fanger, Mill Creek, WA (US)

(73) Assignee: Corixa Corporation, Seattle, WA (US)

( * ) Notice: Subject to any disclaimer, the term of this patent is extended or adjusted under 35 U.S.C. 154(b) by 0 days.

(21) Appl. No.: 09/476,496

(22) Filed: Dec. 30, 1999

Related U.S. Application Data

(63) Continuation-in-part of application No. 09/466,396, filed on Dec. 17, 1999, which is a continuation-in-part of application No. 09/285,479, filed on Apr. 2, 1999, which is a continuation-in-part of application No. PCT/US99/05798, filed on Mar. 17, 1999, which is a continuation-in-part of application No. 09/221,107, filed on Dec. 22, 1998, which is a continuation-in-part of application No. 09/123,912, filed on Jul. 27, 1998, now Pat. No. 6,312,695, which is a continuation-in-part of application No. 09/040,802, filed on Mar. 18, 1998, now abandoned.

(51) Int. Cl.$^7$ ......................... A01N 63/00; C07H 21/04; C12N 15/00; C12N 5/00; C12N 15/63

(52) U.S. Cl. ................... 424/93.2; 536/23.5; 435/320.1; 435/325; 435/455

(58) Field of Search ....................... 536/23.5; 435/320.1, 435/325, 455; 424/93.2; 514/44

(56) References Cited

U.S. PATENT DOCUMENTS

| | | | |
|---|---|---|---|
| 5,589,579 A | 12/1996 | Torczynski et al. | 536/23.1 |
| 5,705,159 A | 1/1998 | Irie et al. | 424/185.1 |
| 5,783,422 A | 7/1998 | Suminami et al. | 435/69.3 |

FOREIGN PATENT DOCUMENTS

| | | |
|---|---|---|
| EP | 0695760 A1 | 2/1996 |
| WO | WO 91/18926 | 12/1991 |
| WO | WO 94/06929 | 3/1994 |
| WO | WO 95/21862 | 8/1995 |
| WO | WO96/02552 | 2/1996 |
| WO | WO 96/28473 | 9/1996 |
| WO | WO96/30389 | 10/1996 |
| WO | WO 97/07244 | 2/1997 |
| WO | WO 98/35985 | 8/1998 |
| WO | WO 98/46788 | 10/1998 |
| WO | WO 99/11793 | 3/1999 |
| WO | WO 99/38973 | 8/1999 |
| WO | WO 99/47674 | 9/1999 |
| WO | WO 99/54738 | 10/1999 |
| WO | WO 00/61612 | 10/2000 |
| WO | WO 01/55367 | 8/2001 |
| WO | WO 01/64834 | 9/2001 |
| WO | WO 01/64835 | 9/2001 |

OTHER PUBLICATIONS

Adams et al., 1998, EST Accession No. AQ 040645, p. 3.*
Ruginger et al., Characteristic of the amino acids as components of a peptide hormorne sequence, 1976, pp. 1–7.*
Kaye et al., A singel amino acid substitution results in a retinoblastoma protein defective in phosphorylation and oncoprotein binding, Sep. 1990, Proc. Natl. Acad. Sci., vol. 87, pp. 6922–6926.*
Deonarain, Ligand–targeted receptor–mediated vectors for gene delivery, 1998, Exp. Opin. Ther. Patents, vol. 8, No. 1, pp. 53–69.*
Crystal, Transfer of Genes to Humans: Early Lesson and Obstacles to Success, 1995, Science, vol. 270, pp. 404–410.*
Verma et al., Gene therapy–promises, problems and prospects, Sep. 18, 1997, Nature, vol. 389, pp. 239–242.*
Eck et al., Gene–Based Therapy, 1996, Goodman & Gilman's, Ninth Edition, pp. 77–101.*
Ohgi et al., Expression of RNase Rh from Rhizopus niveus in Yeast and Characterization of the Secreted Proteins, 1991, J. Biochem, vol. 109, pp. 776–785.*
Wintero et al., Accession F15080, Sep. 9, 1996.*
Brass et al., "Translation initiation factor eIF–4gamma is encoded by an amplified gene and induces an immune response in squamous cell lung carcinoma," *Human Molecular Genetics*, 6(1): 33–39, 1997.
Database EMBLest17 Accession No. AA340797:EST46165 Fetal kidney II Homo sapiens cDNA 3' end, Apr. 18, 1997.
Database EMBLest17 Accession No. W22264:Human retina cDNATsp–509I–cleaved sublibrary Homo sapiens cDNA not directional, May 9, 1996.
Finch et al., "Identification of a cloned sequence activated during multi–stage carcinogenesis in mouse skin," *Carcinogenesis,* 12(8):1519–1522, Aug. 1991.
Gerhold and Caskey, "It's the genes? EST access to human genome content," *BioEssays* 18(12):973–981, 1996.
Russell and Barton, "Structural features can be unconserved in proteins with similar folds," *J.Mol. Biol.* 244:332–350, 1994.
Wells and Peitsch, "The chemokine information source: identification and characterization of novel chemokines using the WorldWideWeb and expressed sequence tag databases," *Journal of Leukocyte Biology* 61:545–550, May 1997.

(List continued on next page.)

*Primary Examiner*—Shin-Lin Chen
(74) *Attorney, Agent, or Firm*—Seed IP Law Group PLLC

(57) ABSTRACT

Compounds and methods for the treatment and diagnosis of lung cancer are provided. The inventive compounds include polypeptides containing at least a portion of a lung tumor protein. Vaccines and pharmaceutical compositions for immunotherapy of lung cancer comprising such polypeptides, or DNA molecules encoding such polypeptides, are also provided, together with DNA molecules for preparing the inventive polypeptides.

6 Claims, No Drawings

OTHER PUBLICATIONS

Baldi et al., "Differential expression of Rb2/p130 and p107 in normal human tissues and in primary lung cancer," *Clinical Cancer Research* 3(10):1691–1697, Oct. 1997.

Database EMBL Nucleotide and Protein Sequence, Accession No. AI468638, Mar. 17, 1999.

Davidson et al., "Lung tumours immunoreactive for parathyroid hormone related peptide: analysis of serum calcium levels and tumour type," *Journal of Pathology* 178:398–401, Jan. 1996.

Hara et al., "Characterization of cell phenotype by a novel cDNA library subtraction system: expression of CD8α in a mast cell–derived interleukin–4–dependent cell line," *Blood* 84(1):189–199, Jul. 1, 1994.

Henderson et al., "Identification of lung tumor antigens for cancer immunotherapy: immunological and molecular approaches," *Immunological Investigation* 29(2):87–91, May 2000.

Hogan et al., "The peptide recognized by HLA–A68.2–restricted, squamous cell carcinoma of the lung–specific cytotoxic T lymphocytes is derived from a mutated elongation factor 2 gene," *Cancer Research* 58(22):5144–5150, Nov. 15, 1998.

Lelievre et al., "Structural properties of chimeric peptides containing a T–cell epitope linked to a fusion peptide and their importance for in vivo induction of cytotoxic T–cell responses," *European Journal of Biochemistry* 249(3):895–904, 1997.

Marshall and Hodgson, "DNA chips: an array of possibilities," *Nature Biotechnology* 16:27 Jan. 31, 1998.

Pastor et al., "Diagnostic value of SCC, CEA and CYFRA 21.1 in lung cancer: a Bayesian analysis," *Eur. Respir J.* 10(3):603–609, Mar. 1997.

Ramsay, G., "DNA chips: state–of–the–art," *Nature Biotechnology* 16:40–44, Jan 1998.

Rammensee et al., "MHC ligands and peptide motifs: first listing," *Immunogenetics* 41:178–228, 1995.

Ruppert et al., "Prominent role of secondary anchor residues in peptide binding to HLA–A2.1 molecules," *Cell* 74:929–937, Sep. 10, 1993.

Theobald et al., "Targeting p53 as a general tumor antigen," *Proc. Natl. Acad. Sci. USA* 92:11993–11997, Dec. 1995.

Visseren et al., "Identification of HLA–A *0201–restricted CTL epitopes encoded by the tumor–specific MAGE–2 gene product," *International Journal of Cancer* 73(1):125–130, 1997.

Wang et al., "Identification of genes differentially over–expressed in lung squamous cell carcinoma using combination cDNA subtraction and microarray analysis," *Oncogene* 19(12):1519–1528, Mar. 16, 2000.

GenBank Accession No. AF043977, Jun. 23, 1999.

GenBank Accession No. U85946, Jul. 30, 1999.

Geneseq Accession No. AAZ24653, Dec. 7, 1999.

Gruber et al., "Molecular cloning and transmembrane structure of hCLCA2 from human lung, trachea, and mammary gland," *Am. J. Physiol.* 276(Cell Physiol 45):C1261–C1270, 1999.

Guo et al., "Identification and characterization of homologues of the Exocyst componenet Sec10p," *FEBS Letters* 404(2–3):135–139, 1997.

Chen, Shen–Lin et al., "Isolation and characterization of a novel gene expressed in multiple cancers," *Oncogene* 12:741–751, 1996.

Güre, A.O. et al., "Human Lung Cancer Antigens Recognized by Autologous Antibodies: Definition of a Novel cDNA Derived from the Tumor Suppressor," *Cancer Research* 58:1034–1041, Mar. 1, 1998.

GenBank Database, Accession No. AC009247, Dec. 8, 1999.

GenBank Database, Accession No. BAB28172, Dec. 5, 2002.

GenBank Database, Accession No. NP_065728, Dec. 10, 2001.

Genseq Database (Derwent), Accession No. AAB69189, May 2, 2001.

Genseq Database (Derwent), Accession No. AAI84852, Nov. 6, 2001.

Genseq Database (Derwent), Accession No. AAO04921, Nov. 6, 2001.

* cited by examiner

SEQUENCE LISTING

<160> NUMBER OF SEQ ID NOS: 254

<210> SEQ ID NO 1
<211> LENGTH: 315
<212> TYPE: DNA
<213> ORGANISM: Homo sapien
<220> FEATURE:
<221> NAME/KEY: misc_feature
<222> LOCATION: (1)...(315)
<223> OTHER INFORMATION: n = A,T,C or G

<400> SEQUENCE: 1
gcagagacag actggtggtt gaacctggag gtgccaaaaa agccagctgc gggcccagga    60

```
cagctgccgt gagactcccg atgtcacagg cagtctgtgt ggttacagcg cccctcagtg    120
ttcatctcca gcagagacaa cggaggaggc tcccaccagg acggttctca ttatttatat    180
gttaatatgt ttgtaaactc atgtacagtt ttttttgggg gggaagcaat gggaaggta     240 naaattacaa atagaatcat ttgctgtaat ccttaaatgg caaacggtca ggccacgtga    300
aaaaaaaaaa aaaaa                                                      315

<210> SEQ ID NO 2
<211> LENGTH: 380
<212> TYPE: DNA
<213> ORGANISM: Homo sapien

<400> SEQUENCE: 2
atttaggctt aagattttgt ttacccttgt tactaaggag caaattagta ttaaagtata     60
atatatataa acaaatacaa aaagttttga gtggttcagc ttttttattt ttttttaatgg   120 cataactttt aacaacactg ctctgtaatg ggttgaactg tggtactcag actgagataa    180
ctgaaatgag tggatgtata gtgttattgc ataattatcc cactatgaag caaagggact    240
ggataaattc ccagtctaga ttattagcct ttgttaacca tcaagcacct agaagaagaa    300
ttattggaaa ttttgtcctc tgtaactggc actttggggt gtgacttatc ttttgccttt    360
gtaaaaaaaa aaaaaaaaaa                                                380

<210> SEQ ID NO 3
<211> LENGTH: 346
<212> TYPE: DNA
<213> ORGANISM: Homo sapien
<220> FEATURE:
<221> NAME/KEY: misc_feature
<222> LOCATION: (1)...(346)
<223> OTHER INFORMATION: n = A,T,C or G

<400> SEQUENCE: 3
ttgtaagtat acaattttag aaaggattaa atgttattga tcattttact gaatactgca     60
catcctcacc atacaccatc cactttccaa taacatttaa tcctttctaa aattgtaagt   120
atacaattgt actttctttg gattttcata acaaatatac catagactgt taattttatt   180
gaagtttcct taatggaatg agtcattttt gtcttgtgct tttgaggtta ccttttgcttt   240 gacttccaac aatttgatca tatagtgttg agctgtggaa atctttaagt ttattctata   300
gcaataattt ctattnnnag anncngggnn naaaannann annaaa                    346

<210> SEQ ID NO 4
<211> LENGTH: 372
<212> TYPE: DNA
<213> ORGANISM: Homo sapien
<220> FEATURE:
<221> NAME/KEY: misc_feature
<222> LOCATION: (1)...(372)
<223> OTHER INFORMATION: n = A,T,C or G

<400> SEQUENCE: 4
actagtctca ttactccaga attatgctct tgtacctgtg tggctgggtt tcttagtcgt     60
tggtttggtt tggttttttg aactggtatg tagggtggtt cacagttcta atgtaagcac    120
tctcttctcc aagttgtgct ttgtggggac aatcattctt tgaacattag agaggaaggc    180
agttcaagct gttgaaaaga ctattgctta ttttgttttt taaagaccta cttgacgtca    240
tgtggacagt gcacgtgcct tacgctacat cttgttttct aggaagaagg ggatgcgggg    300
aaggantggg tgctttgtga tggataaaac gnctaaataa cacacccttta cattttgaaa   360
```
aaaacaaaac aa								372

<210> SEQ ID NO 5
<211> LENGTH: 698
<212> TYPE: DNA
<213> ORGANISM: Homo sapien
<220> FEATURE:
<221> NAME/KEY: misc_feature
<222> LOCATION: (1)...(698)
<223> OTHER INFORMATION: n = A,T,C or G

<400> SEQUENCE: 5
actagtanga tagaaacact gtgtcccgag agtaaggaga gaagctacta ttgattagag			60 cctaacccag gttaactgca agaagaggcg ggatactttc agctttccat gtaactgtat			120 gcataaagcc aatgtagtcc agtttctaag atcatgttcc aagctaactg aatcccactt			180 caatacacac tcatgaactc ctgatggaac aataacaggc ccaagcctgt ggtatgatgt			240 gcacacttgc tagactcaga aaaatacta ctctcataaa tgggtgggag tattttgggt			300 gacaacctac tttgcttggc tgagtgaagg aatgatattc atatnttcat ttattccatg			360 gacatttagt tagtgctttt tatataccag gcatgatgct gagtgacact cttgtgtata			420 tntccaaatn ttngtncngt cgctgcacat atctgaaatc ctatattaag antttcccaa			480 natgangtcc ctggtttttc cacgccactt gatcngtcaa ngatctcacc tctgtntgtc			540 ctaaaaccnt ctnctnnang gttagacngg acctctcttc tcccttcccg aanaataag			600 tgtgngaaga nanccncncn cccccctncn tncnnctng ccngctnnnc cncntgtngg			660 gggngccgcc ccgcgggg gacccccccn ttttcccc					698

<210> SEQ ID NO 6
<211> LENGTH: 740
<212> TYPE: DNA
<213> ORGANISM: Homo sapien
<220> FEATURE:
<221> NAME/KEY: misc_feature
<222> LOCATION: (1)...(740)
<223> OTHER INFORMATION: n = A,T,C or G

<400> SEQUENCE: 6
actagtcaaa aatgctaaaa taatttggga gaaaatattt tttaagtagt gttatagttt			60 catgtttatc ttttattatg tnttgtgaag ttgtgtcttt tcactaatta cctatactat			120 gccaatattt ccttatatct atccataaca tttatactac atttgtaaga gaatatgcac			180 gtgaaactta acactttata aggtaaaaat gaggtttcca agatttaata atctgatcaa			240 gttcttgtta tttccaaata gaatggactt ggtctgttaa ggggctaagg gagaagaaga			300 agataaggtt aaaagttgtt aatgaccaaa cattctaaaa gaaatgcaaa aaaaattta			360 ttttcaagcc ttcgaactat ttaaggaaag caaaatcatt tcctanatgc atatcatttg			420 tgaganttc tcantaatat cctgaatcat tcatttcagc tnaggcttca tgttgactcg			480 atatgtcatc tagggaaagt ctatttcatg gtccaaacct gttgccatag ttggtnaggc			540 tttccttaa ntgtgaanta ttnacangaa attttctctt tnanagttct tnatagggtt			600 agggtgtgg gaaaagcttc taacaatctg tagtgttncg tgttatctgt ncagaaccan			660 aatnacggat cgnangaagg actgggtcta tttacangaa cgaatnatct ngttnnntgt			720 gtnnncaact ccngggagcc							740

<210> SEQ ID NO 7

<211> LENGTH: 670
<212> TYPE: DNA
<213> ORGANISM: Homo sapien
<220> FEATURE:
<221> NAME/KEY: misc_feature
<222> LOCATION: (1)...(670)
<223> OTHER INFORMATION: n = A,T,C or G

<400> SEQUENCE: 7

| | | | | | |
|---|---|---|---|---|---|
| gctggggagc | tcggcatggc | ggtccccgct | gcagccatgg | ggccctcggc | gttgggccag | 60 |
| agcggccccg | gctcgatggc | cccgtggtgc | tcagtgagca | gcggcccgtc | gcgctacgtg | 120 |
| cttgggatgc | aggagctgtt | ccggggccac | agcaagaccg | cgagttcctg | gcgcacagcg | 180 |
| ccaaggtgca | ctcggtggcc | tggagttgcg | acgggcgtcg | cctacctcgg | ggtcttcgac | 240 |
| aagacgccac | gtcttcttgc | tgganaanga | ccgttggtca | agaaaacaa | ttatcgggga | 300 |
| catgggata | gtgtggacca | ctttgttggc | atccaagtaa | tcctgaccta | tttgttacgg | 360 |
| cgtctggaga | taaaaccatt | cgcatctggg | atgtgaggac | tacaaaatgc | attgccactg | 420 |
| tgaacactaa | aggggagaac | attaatatct | gctggantcc | tgatgggcan | accattgctg | 480 |
| tagcnacaag | gatgatgtgg | tgactttatt | gatgccaaga | accccgttc | caaagcaaaa | 540 |
| aaacanttcc | aanttcgaag | tcaccnaaat | ctcctggaac | aatgaacatn | aatatnttct | 600 |
| tcctgacaat | ggncctlggg | tgtntcacat | cctcagctnc | cccaaaactg | aanccttgtnc | 660 |
| natccacccc | | | | | 670 |

<210> SEQ ID NO 8
<211> LENGTH: 689
<212> TYPE: DNA
<213> ORGANISM: Homo sapien
<220> FEATURE:
<221> NAME/KEY: misc_feature
<222> LOCATION: (1)...(689)
<223> OTHER INFORMATION: n = A,T,C or G

<400> SEQUENCE: 8

| | | | | | |
|---|---|---|---|---|---|
| actagtatct | aggaatgaac | agtaaaagag | gagcagttgg | ctacttgatt | acaacagagt | 60 |
| aaatgaagta | ctggatttgg | gaaaacctgg | ttttattaga | acatatggaa | tgaaagccta | 120 |
| cacctagcat | tgcctactta | gccccctgaa | ttaacagagc | ccaattgaga | caaacccctg | 180 |
| gcaacaggaa | attcaaggga | gaaaagtaa | gcaacttggg | ctaggatgag | ctgactccct | 240 |
| tagagcaaag | ganagacagc | ccccattacc | aaataccatt | tttgcctggg | gcttgtgcag | 300 |
| ctggcagtgt | tcctgcccca | gcatggcacc | ttatngtttt | gatagcaact | tcgttgaatt | 360 |
| ttcaccaact | tattacttga | aattataata | tagcctgtcc | gtttgctgtn | tccaggctgt | 420 |
| gatatatntt | cctagtggtt | tgactttnaa | aataaatnag | gtttantttt | ctcccccnn | 480 |
| cnntnctncc | nntcnctcnn | cnntccccc | cnctcngtcc | tccnnnnttn | gggggggccn | 540 |
| ccccncggn | ggacccccct | ttggtccctt | agtggaggtt | natggcccct | ggnnttatcc | 600 |
| nggccntann | tttccccgtn | nnaaatgntt | ccccctccca | ntcccnccac | ctcaanccgg | 660 |
| aagcctaagt | ttntaccctg | ggggtcccc | | | 689 |

<210> SEQ ID NO 9
<211> LENGTH: 674
<212> TYPE: DNA
<213> ORGANISM: Homo sapien
<220> FEATURE:
<221> NAME/KEY: misc_feature
<222> LOCATION: (1)...(674)
<223> OTHER INFORMATION: n = A,T,C or G

<400> SEQUENCE: 9

```
gtccactctc ctttgagtgt actgtcttac tgtgcactct gttttttcaac tttctagata      60 taaaaaatgc ttgttctata gtggagtaag agctcacaca cccaaggcag caagataact     120
gaaaaaagcg aggcttttttt gccaccttgg taaaggccag ttcactgcta tagaactgct     180
ataagcctga agggaagtag ctatgagact ttccattttt cttagttctc ccaataggct     240
ccttcatgga aaaaggcttc ctgtaataat tttcacctaa tgaattagca gtgtgattat     300
ttctgaaata agagacaaat tgggccgcag agtcttcctg tgatttaaaa taaacaaccc     360
aaagttttgt ttggtcttca ccaaaggaca tactctaggg ggtatgttgt tgaagacatt     420
caaaaacatt agctgttctg tctttcaatt tcaagttatt ttggagactg cctccatgtg     480
agttaattac tttgctctgg aactagcatt attgtcatta tcatcacatt ctgtcatcat     540
catctgaata atattgtgga tttcccctc tgcttgcatc ttctttttgac tcctctggga     600 anaaatgtca aaaaaaagg tcgatctact cngcaaggnc catctaatca ctgcgctgga     660
aggacccnct gccc                                                       674
```

<210> SEQ ID NO 10
<211> LENGTH: 346
<212> TYPE: DNA
<213> ORGANISM: Homo sapien
<220> FEATURE:
<221> NAME/KEY: misc_feature
<222> LOCATION: (1)...(346)
<223> OTHER INFORMATION: n = A,T,C or G

<400> SEQUENCE: 10

```
actagtctgc tgatagaaag cactatacat cctattgttt ctttctttcc aaaatcagcc      60
ttctgtctgt aacaaaaatg tactttatag agatggagga aaaggtctaa tactacatag     120
ccttaagtgt ttctgtcatt gttcaagtgt attttctgta acagaaacat atttggaatg     180 ttttttctttt cccttataa attgtaattc ctgaaatact gctgcttttaa aaagtccccac     240 tgtcagatta tattatctaa caattgaata ttgtaaatat acttgtctta cctctcaata     300
aaagggtact tttctattan nnagnngnnn gnnnnataaa anaaaa                    346
```

<210> SEQ ID NO 11
<211> LENGTH: 602
<212> TYPE: DNA
<213> ORGANISM: Homo sapien

<400> SEQUENCE: 11

```
actagtaaaa agcagcattg ccaaataatc cctaattttc cactaaaaat ataatgaaat      60
gatgttaagc ttttttgaaaa gtttaggtta aacctactgt tgttagatta atgtatttgt     120 tgcttcccctt tatctggaat gtggcattag ctttttttatt ttaaccctct ttaattctta     180
ttcaattcca tgacttaagg ttggagagct aaacactggg attttttggat aacagactga     240 cagttttgca taattataat cggcattgta catagaaagg atatggctac cttttgttaa     300
atctgcactt tctaaatatc aaaaaggga atgaagtta taatcaatt tttgtataat     360 ctgtttgaaaa catgagtttt atttgcttaa tattagggct ttgccccttt tctgtaagtc     420
tcttgggatc ctgtgtagaa ctgttctcat taaacaccaa acagttaagt ccattctctg     480
gtactagcta caaattcggt ttcatattct acttaacaat ttaaataaac tgaaatattt     540
ctagatggtc tacttctgtt catataaaaa caaaacttga tttccaaaaa aaaaaaaaaa     600
```

<210> SEQ ID NO 12
<211> LENGTH: 685
<212> TYPE: DNA
<213> ORGANISM: Homo sapien
<220> FEATURE:
<221> NAME/KEY: misc_feature
<222> LOCATION: (1)...(685)
<223> OTHER INFORMATION: n = A,T,C or G

<400> SEQUENCE: 12

| | | | | |
|---|---|---|---|---|
| actagtcctg | tgaaagtaca | actgaaggca | gaaagtgtta | ggattttgca | tctaatgttc | 60 |
| attatcatgg | tatttgatgga | cctaagaaaa | taaaaattag | actaagcccc | caaataagct | 120 |
| gcatgcattt | gtaacatgat | tagtagattt | gaatatatag | atgtagtatn | ttgggtatct | 180 |
| aggtgttta | tcattatgta | aaggaattaa | agtaaaggac | tttgtagttg | tttttattaa | 240 |
| atatgcatat | agtagagtgc | aaaaatatag | caaaaatana | aactaaaggt | agaaaagcat | 300 |
| tttagatatg | ccttaatnta | nnaactgtgc | caggtggccc | tcggaataga | tgccaggcag | 360 |
| agaccagtgc | ctgggtggtg | cctccccttg | tctgccccc | tgaagaactt | ccctcacgtg | 420 |
| angtagtgcc | ctcgtaggtg | tcacgtggan | tantgggang | aggccgnncn | gtnanaagaa | 480 |
| ancanngtga | nagtttcncc | gtngangcng | aactgtccct | gngccnnnac | gctcccanaa | 540 |
| cntntccaat | ngacaatcga | gtttccnnnc | tccngnaacc | tngccgnnnn | cnngcccnnc | 600 |
| cantntgnta | accccgcgcc | cggatcgctc | tcnnntcgtt | ctcncncnaa | ngggntttcn | 660 |
| cnnccgccgt | cncnncccg | cnncc | | | | 685 |

<210> SEQ ID NO 13
<211> LENGTH: 694
<212> TYPE: DNA
<213> ORGANISM: Homo sapien
<220> FEATURE:
<221> NAME/KEY: misc_feature
<222> LOCATION: (1)...(694)
<223> OTHER INFORMATION: n = A,T,C or G

<400> SEQUENCE: 13

| | | | | | | |
|---|---|---|---|---|---|---|
| cactagtcac | tcattagcgt | tttcaatagg | gctcttaagt | ccagtagatt | acgggtagtc | 60 |
| agttgacgaa | gatctggttt | acaagaacta | attaaatgtt | tcattgcatt | tttgtaagaa | 120 |
| cagaataatt | ttataaaatg | tttgtagttt | ataattgccg | aaaataattt | aaagacactt | 180 |
| tttctctgtg | tgtgcaaatg | tgtgtttgtg | atccattttt | ttttttttt | taggacacct | 240 |
| gtttactagc | tagctttaca | atatgccaaa | aaaggatttc | tccctgaccc | catccgtggt | 300 |
| tcaccctctt | ttccccccat | gcttttttgcc | ctagtttata | acaaaggaat | gatgatgatt | 360 |
| taaaagtag | ttctgtatct | tcagtatctt | ggtcttccag | aaccctctgg | ttgggaaggg | 420 |
| gatcattttt | tactggtcat | ttcccttttgg | agtgtactac | tttaacagat | ggaaagaact | 480 |
| cattggccat | ggaaacagcc | gangtgttgg | gagccagcag | tgcatggcac | cgtccggcat | 540 |
| ctggcntgat | tggtctggct | gccgtcattg | tcagcacagt | gccatgggac | atggggaana | 600 |
| ctgactgcac | ngccaatggt | tttcatgaag | aatacngcat | ncncngtgat | cacgtnancc | 660 |
| angacgctat | gggggncana | gggccanttg | cttc | | | 694 |

<210> SEQ ID NO 14
<211> LENGTH: 679
<212> TYPE: DNA
<213> ORGANISM: Homo sapien
<220> FEATURE:
<221> NAME/KEY: misc_feature
<222> LOCATION: (1)...(679)
<223> OTHER INFORMATION: n = A,T,C or G

<400> SEQUENCE: 14

| | | | | | |
|---|---|---|---|---|---|
| cagccgcctg | catctgtatc | cagcgccang | tcccgccagt | cccagctgcg | cgcgccccc 60 |
| agtcccgnac | ccgttcggcc | cangctnagt | tagncctcac | catnccggtc | aaaggangca 120 |
| ccaagtgcat | caaatacctg | cngtncggat | ntaaattcat | cttctggctt | gccgggattg 180 |
| ctgtccntgc | cattggacta | nggctccgat | ncgactctca | gaccanganc | atcttcganc 240 |
| naganactaa | tnatnattnt | tccagcttct | acacaggagt | ctatattctg | atcggatccg 300 |
| gcnccctcnt | gatgctggtg | ggcttcctga | gctgctgcgg | ggctgtgcaa | gagtcccant 360 |
| gcatgctggg | actgttcttc | ggcttcntct | tggtgatatn | cgccattgaa | atacctgcgg 420 |
| ccatctgggg | atattccact | ncgatnatgt | gattaaggaa | ntccacggag | ttttacaagg 480 |
| acacgtacaa | cnacctgaaa | accnnggatg | anccccaccg | ggaancnctg | aangccatcc 540 |
| actatgcgtt | gaactgcaat | ggtttggctg | gggnccttga | acaatttaat | cncatacatc 600 |
| tggccccann | aaaggacntn | ctcganncct | tcnccgtgna | attcngttct | gatnccatca 660 |
| cagaagtctc | gaacaatcc | | | | 679 |

<210> SEQ ID NO 15
<211> LENGTH: 695
<212> TYPE: DNA
<213> ORGANISM: Homo sapien
<220> FEATURE:
<221> NAME/KEY: misc_feature
<222> LOCATION: (1)...(695)
<223> OTHER INFORMATION: n = A,T,C or G

<400> SEQUENCE: 15

| | | | | | |
|---|---|---|---|---|---|
| actagtggat | aaaggccagg | gatgctgctc | aacctcctac | catgtacagg | gacgtctccc 60 |
| cattacaact | acccaatccg | aagtgtcaac | tgtgtcagga | ctaanaaacc | ctggttttga 120 |
| ttaaaaaagg | gcctgaaaaa | agggagcca | caaatctgtc | tgcttcctca | cnttantcnt 180 |
| tggcaaatna | gcattctgtc | tcnttggctg | cngcctcanc | ncaaaaaanc | ngaactcnat 240 |
| cnggcccagg | aatacatctc | ncaatnaacn | aaattganca | aggcnntggg | aaatgccnga 300 |
| tgggattatc | ntccgcttgt | tganccttcta | agtttcnttc | ccttcattcn | accctgccag 360 |
| ccnagttctg | ttagaaaaat | gccngaattc | naacnccggt | tttcntactc | ngaatttaga 420 |
| tctncanaaa | cttcctggcc | acnattcnaa | ttnanggnca | cgnacanatn | ccttccatna 480 |
| ancncacccc | acntttgana | gccangacaa | tgactgcntn | aantgaaggc | ntgaaggaan 540 |
| aactttgaaa | ggaaaaaaaa | ctttgtttcc | ggcccttcc | aacncttctg | tgttnancac 600 |
| tgccttctng | naaccctgga | agcccngnga | cagtgttaca | tgttgttcta | nnaaacngac 660 |
| ncttnaatnt | cnatcttccc | nanaacgatt | ncncc | | 695 |

<210> SEQ ID NO 16
<211> LENGTH: 669
<212> TYPE: DNA
<213> ORGANISM: Homo sapien
<220> FEATURE:
<221> NAME/KEY: misc_feature
<222> LOCATION: (1)...(669)
<223> OTHER INFORMATION: n = A,T,C or G

<400> SEQUENCE: 16

```
cgccgaagca gcagcgcagg ttgtccccgt ttcccctccc ccttcccttc tccggttgcc        60
ttcccgggcc ccttacactc cacagtcccg gtcccgccat gtcccagaaa caagaagaag       120
agaaccctgc ggaggagacc ggcgaggaga agcaggacac gcaggagaaa gaaggtattc       180
tgcctgagag agctgaagag gcaaagctaa aggccaaata cccaagccta ggacaaaagc       240
ctggaggctc cgacttcctc atgaagagac tccagaaagg gcaaaagtac tttgactcng       300
gagactacaa catggccaaa gccaacatga agaataagca gctgccaagt gcangaccag       360
acaagaacct ggtgactggt gatcacatcc ccaccccaca ggatctgccc agagaaagtc       420
ctcgctcgtc accagcaagc ttgcgggtgg ccaagttgaa tgatgctgcc ggggctctgc       480
canatctgag acgcttccct ccctgcccca cccgggtcct gtgctggctc ctgcccttcc       540
tgcttttgca gccanggggtc aggaagtggc ncngtngtg gctggaaagc aaaacccttt       600
cctgttggtg tcccacccat ggagcccctg gggcgagccc angaacttga nccttttgt       660 tntcttncc                                                              669
```

<210> SEQ ID NO 17
<211> LENGTH: 697
<212> TYPE: DNA
<213> ORGANISM: Homo sapien
<220> FEATURE:
<221> NAME/KEY: misc_feature
<222> LOCATION: (1)...(697)
<223> OTHER INFORMATION: n = A,T,C or G

<400> SEQUENCE: 17

```
gcaagatatg gacaactaag tgagaaggta atnctctact gctctagntn ctccnggcnn        60
gacgcgctga ggagannnac gctggcccan ctgccggcca cacacgggga tcntggtnat       120
gcctgcccan gggancccca ncnctcggan cccatntcac accgnnccn tncgcccacn       180 ncctggctcn cncngcccng nccagctcnc gnccccctcc gccnnnctcn ttnncntctc       240 cncncctcc ncnacnacct cctacccncg gctccctccc cagccccccc ccgcaanccct       300 ccacnacncc ntcnncncga ancnccctc gcnctcngcc cngccccct gcccccgcc         360 cncnacnncg cgntccccg cgcncgcngc ctcncccct cccacnacag ncncacccgc         420
agncacgcnc tccgcccnct gacgcccnn cccgccgcgc tcaccttcat ggnccnacng       480
ccccgctcnc nccnctgcnc gccgncnngg cgcccgccc cnnccgngtn ccncncgnng       540
cccncngcgn angcngtgcg cnncangnccg gngccgnncn ncaccctccg nccnccgccc       600
cgcccgctgg gggctcccgc cncgcggntc antccccncc cntncgccca ctntccgntc       660
cnncnctcnc gctcngcgcn cgcccnccnc ccccccc                               697
```

<210> SEQ ID NO 18
<211> LENGTH: 670
<212> TYPE: DNA
<213> ORGANISM: Homo sapien
<220> FEATURE:
<221> NAME/KEY: misc_feature
<222> LOCATION: (1)...(670)
<223> OTHER INFORMATION: n = A,T,C or G

<400> SEQUENCE: 18

```
ctcgtgtgaa gggtgcagta cctaagccgg agcggggtag aggcgggccg gcaccccctt        60
ctgacctcca gtgccgccgg cctcaagatc agacatggcc cagaacttga acgacttggc       120
gggacggctg cccgccgggc cccggggcat gggcacggcc ctgaagctgt tgctgggggc       180
cggcgccgtg gcctacggtg tgcgcgaatc tgtgttcacc gtggaaggcg ggcncagagc       240
```

-continued

```
catcttcttc aatcggatcg gtggagtgca caggacacta tcctgggccg anggccttca      300
cttcaggatc cttggttcca gtaccccanc atctatgaca ttcgggccag acctcgaaaa      360
aatctcctcc ctacaggctc caaagaccta cagatggtga atatctccct gcgagtgttg      420
tctcgaccaa tgctcangaa cttcctaaca tgttccancg cctaagggct ggactacnaa      480
gaacgantgt tgccgtccat tgtcacgaag tgctcaagaa tttnggtggc caagttcaat      540
gnccctcacn nctgatcncc cagcggggcca agttanccct ggttgatccc cggggactg      600 acnnaaaagg gccaaggact tcccctcatc ctggataatg tggccntcac aaagctcaac      660 tttanccacc                                                              670
```

<210> SEQ ID NO 19
<211> LENGTH: 606
<212> TYPE: DNA
<213> ORGANISM: Homo sapien
<220> FEATURE:
<221> NAME/KEY: misc_feature
<222> LOCATION: (1)...(606)
<223> OTHER INFORMATION: n = A,T,C or G

<400> SEQUENCE: 19

```
actagtgcca acctcagctc ccaggccagt tctctgaatg tcgaggagtt ccaggatctc       60
tggcctcagt tgtccttggt tattgatggg ggacaaattg gggatggcca gagccccgag      120
tgtcgccttg gctcaactgt ggttgatttg tctgtgcccg gaaagtttgg catcattcgt      180
ccaggctgtg ccctggaaag tactacagcc atcctccaac agaagtacgg actgctcccc      240
tcacatgcgt cctacctgtg aaactctggg aagcaggaag gcccaagacc tggtgctgga      300
tactatgtgt ctgtccactg acgactgtca aggcctcatt tgcagaggcc accggagcta      360
gggcactagc ctgactttta aggcagtgtg tctttctgag cactgtagac caagcccttg      420
gagctgctgg tttagccttg cacctgggga aaggatgtat ttatttgtat tttcatatat      480
cagccaaaag ctgaatggaa aagttnagaa cattcctagg tggccttatt ctaataagtt      540
tcttctgtct gttttgtttt tcaattgaaa agttattaaa taacagattt agaatctagt      600
gagacc                                                                  606
```

<210> SEQ ID NO 20
<211> LENGTH: 449
<212> TYPE: DNA
<213> ORGANISM: Homo sapien

<400> SEQUENCE: 20

```
actagtaaac aacagcagca gaaacatcag tatcagcagc gtcgccagca ggagaatatg       60
cagcgccaga gccgaggaga accccgctc cctgaggagg acctgtccaa actcttcaaa      120
ccaccacagc cgcctgccag gatggactcg ctgctcattg caggccagat aaacacttac      180
tgccagaaca tcaaggagtt cactgcccaa aacttaggca agctcttcat ggcccaggct      240
cttcaagaat acaacaacta gaaaaggaa gtttccagaa aagaagttaa catgaactct      300
tgaagtcaca ccagggcaac tcttggaaga aatatatttg catattgaaa agcacagagg      360 atttcttttag tgtcattgcc gattttggct ataacagtgt ctttctagcc ataataaaat      420
aaaacaaaat cttgactgct tgctcaaaa                                         449
```

<210> SEQ ID NO 21
<211> LENGTH: 409
<212> TYPE: DNA

<213> ORGANISM: Homo sapien

<400> SEQUENCE: 21

| tatcaatcaa | ctggtgaata | attaaacaat | gtgtggtgtg | atcatacaaa | gggtaccact | 60 |
| caatgataaa | aggaacaagc | tgcctatatg | tggaacaaca | tggatgcatt | tcagaaactt | 120 |
| tatgttgagt | gaaagaacaa | acacggagaa | catactatgt | ggttctcttt | atgtaacatt | 180 |
| acagaaataa | aaacagaggc | aaccacccttt | gaggcagtat | ggagtgagat | agactggaaa | 240 |
| aaggaaggaa | ggaaactcta | cgctgatgga | aatgtctgtg | tcttcattgg | gtggtagtta | 300 |
| tgtggggata | tacatttgtc | aaaatttatt | gaactatata | ctaaagaact | ctgcatttta | 360 |
| ttgggatgta | aataatacct | caattaaaaa | gacaaaaaaa | aaaaaaaaa | | 409 |

<210> SEQ ID NO 22
<211> LENGTH: 649
<212> TYPE: DNA
<213> ORGANISM: Homo sapien
<220> FEATURE:
<221> NAME/KEY: misc_feature
<222> LOCATION: (1)...(649)
<223> OTHER INFORMATION: n = A,T,C or G

<400> SEQUENCE: 22

| acaattttca | ttatcttaag | cacattgtac | atttctacag | aacctgtgat | tattctcgca | 60 |
| tgataaggat | ggtacttgca | tatggtgaat | tactactgtt | gacagtttcc | gcagaaatcc | 120 |
| tatttcagtg | gaccaacatt | gtggcatggc | agcaaatgcc | aacattttgt | ggaatagcag | 180 |
| caaatctaca | agagaccctg | gttggttttt | cgttttgttt | tctttgtttt | ttccccttc | 240 |
| tcctgaatca | gcagggatgg | aangagggta | gggaagttat | gaattactcc | ttccagtagt | 300 |
| agctctgaag | tgtcacattt | aatatcagtt | tttttttaaac | atgattctag | ttnaatgtag | 360 |
| aagagagaag | aaagaggaag | tgttcacttt | tttaatacac | tgatttagaa | atttgatgtc | 420 |
| ttatatcagt | agttctgagg | tattgatagc | ttgctttatt | tctgccttta | cgttgacagt | 480 |
| gttgaagcag | ggtgaataac | taggggcata | tatatttttt | tttttttgtaa | gctgtttcat | 540 |
| gatgttttct | ttggaatttc | cggataagtt | caggaaaaca | tctgcatgtt | gttatctagt | 600 |
| ctgaagttcn | tatccatctc | attacaacaa | aaacncccag | aacggnttg | | 649 |

<210> SEQ ID NO 23
<211> LENGTH: 669
<212> TYPE: DNA
<213> ORGANISM: Homo sapien
<220> FEATURE:
<221> NAME/KEY: misc_feature
<222> LOCATION: (1)...(669)
<223> OTHER INFORMATION: n = A,T,C or G

<400> SEQUENCE: 23

| actagtgccg | tactggctga | atccctgca | ggaccaggaa | gagaaccagt | tcagactttg | 60 |
| tactctcagt | caccagctct | ggaattagat | aaattccttg | aagatgtcag | gaatgggatc | 120 |
| tatcctctga | cagcctttgg | gctgcctcgg | ccccagcagc | cacagcagga | ggaggtgaca | 180 |
| tcacctgtcg | tgcccccctc | tgtcaagact | ccgacacctg | aaccagctga | ggtggagact | 240 |
| cgcaaggtgg | tgctgatgca | gtgcaacatt | gagtcggtgg | aggagggagt | caaacaccac | 300 |
| ctgacacttc | tgctgaagtt | ggaggacaaa | ctgaaccggc | acctgagctg | tgacctgatg | 360 |
| ccaaatgaga | atatccccga | gttggcggct | gagctggtgc | agctgggctt | cattagtgag | 420 |
| gctgaccaga | gccggttgac | ttctctgcta | gaagagactt | gaacaagttc | aattttgcca | 480 |

```
ggaacagtac cctcaactca gccgctgtca ccgtctcctc ttagagctca ctcgggccag    540
gccctgatct gcgctgtggc tgtcctggac gtgctgcacc ctctgtcctt cccccagtc    600 agtattacct gtgaagccct tccctccttt attattcagg anggctgggg gggctccttg    660 nttctaacc                                                          669
```

<210> SEQ ID NO 24
<211> LENGTH: 442
<212> TYPE: DNA
<213> ORGANISM: Homo sapien

<400> SEQUENCE: 24

```
actagtacca tcttgacaga ggatacatgc tcccaaaacg tttgttacca cacttaaaaa     60
tcactgccat cattaagcat cagtttcaaa attatagcca ttcatgattt acttttcca    120 gatgactatc attattctag tcctttgaat ttgtaagggg aaaaaaaaca aaaacaaaaa    180
cttacgatgc acttttctcc agcacatcag atttcaaatt gaaattaaa gacatgctat    240 ggtaatgcac ttgctagtac tacacacttt ggtacaacaa aaaacagagg caagaaacaa    300
cggaaagaga aaagccttcc tttgttggcc cttaaactga gtcaagatct gaaatgtaga    360
gatgatctct gacgatacct gtatgttctt attgtgtaaa taaaattgct ggtatgaaat    420
gacctaaaaa aaaaaaaga aa                                             442
```

<210> SEQ ID NO 25
<211> LENGTH: 656
<212> TYPE: DNA
<213> ORGANISM: Homo sapien
<220> FEATURE:
<221> NAME/KEY: misc_feature
<222> LOCATION: (1)...(656)
<223> OTHER INFORMATION: n = A,T,C or G

<400> SEQUENCE: 25

```
tgcaagtacc acacactgtt tgaattttgc acaaaaagtg actgtaggat caggtgatag     60
ccccggaatg tacagtgtct tggtgcacca agatgccttc taaaggctga catccttgg    120 accctaatgg ggcagagagt atagccctag cccagtggtg acatgaccac tcccttggg    180 aggcctgagg tagaggggag tggtatgtgt tttctcagtg gaagcagcac atgagtgggt    240
gacaggatgt tagataaagg ctctagttag ggtgtcattg tcatttgaga gactgacaca    300
ctcctagcag ctggtaaagg ggtgctggan gccatggagg anctctagaa acattagcat    360
gggctgatct gattacttcc tggcatcccg ctcacttta tgggaagtct tattagangg    420
atgggacagt tttccatatc cttgctgtgg agctctggaa cactctctaa atttccctct    480
attaaaaatc actgccctaa ctacacttcc tccttgaagg aatagaaatg gaactttctc    540
tgacatantt cttggcatgg ggagccagcc acaaatgana atctgaacgt gtccaggttt    600
ctcctganac tcatctacat agaattggtt aaaccctccc ttggaataag gaaaaa       656
```

<210> SEQ ID NO 26
<211> LENGTH: 434
<212> TYPE: DNA
<213> ORGANISM: Homo sapien
<220> FEATURE:
<221> NAME/KEY: misc_feature
<222> LOCATION: (1)...(434)
<223> OTHER INFORMATION: n = A,T,C or G

<400> SEQUENCE: 26

```
actagttcag actgccacgc caaccccaga aaatacccca catgccagaa aagtgaagtc      60
ctaggtgttt ccatctatgt ttcaatctgt ccatctacca ggcctcgcga taaaaacaaa     120
acaaaaaaac gctgccaggt tttagaagca gttctggtct caaaaccatc aggatcctgc     180
caccagggtt cttttgaaat agtaccacat gtaaaaggga atttggcttt cacttcatct     240
aataactgaa ttgtcaggct ttgattgata attgtagaaa taagtagcct tctgttgtgg     300
gaataagtta taatcagtat tcatctcttt gttttttgtc actcttttct ctctaattgt     360
gtcatttgta ctgtttgaaa aatatttctt ctatnaaatt aaactaacct gccttaaaaa     420
aaaaaaaaaa aaaa                                                      434

<210> SEQ ID NO 27
<211> LENGTH: 654
<212> TYPE: DNA
<213> ORGANISM: Homo sapien
<220> FEATURE:
<221> NAME/KEY: misc_feature
<222> LOCATION: (1)...(654)
<223> OTHER INFORMATION: n = A,T,C or G

<400> SEQUENCE: 27
actagtccaa cacagtcaga aacattgttt tgaatcctct gtaaaccaag gcattaatct      60
taataaacca ggatccattt aggtaccact tgatataaaa aggatatcca taatgaatat     120
tttatactgc atcctttaca ttagccacta aatacgttat tgcttgatga agaccttttca    180 cagaatccta tggattgcag catttcactt ggctacttca tacccatgcc ttaaagaggg     240
gcagtttctc aaaagcagaa acatgccgcc agttctcaag ttttcctcct aactccattt     300
gaatgtaagg gcagctggcc cccaatgtgg ggaggtccga acatttctg aattcccatt     360 ttcttgttcg cggctaaatg acagtttctg tcattactta gattccgatc tttcccaaag     420
gtgttgattt acaagaggc cagctaatag cagaaatcat gaccctgaaa gagagatgaa     480
attcaagctg tgagccaggc agganctcag tatggcaaag gtcttgagaa tcngccattt     540
ggtacaaaaa aaattttaaa gcntttatgt tataccatgg aaccatagaa anggcaaggg     600
aattgttaag aanaatttta agtgtccaga cccanaanga aaaaaaaaa aaaa           654

<210> SEQ ID NO 28
<211> LENGTH: 670
<212> TYPE: DNA
<213> ORGANISM: Homo sapien
<220> FEATURE:
<221> NAME/KEY: misc_feature
<222> LOCATION: (1)...(670)
<223> OTHER INFORMATION: n = A,T,C or G

<400> SEQUENCE: 28
cgtgtgcaca tactgggagg atttccacag ctgcacggtc acagcccta cggattgcca      60 ggaaggggcg aaagatatgt gggataaact gagaaaagaa nccaaaaacc tcaacatcca     120
aggcagctta ttcgaactct gcggcagcgg caacgggcg cgggtgtccc tgctcccggc     180
gttcccggtg ctcctggtgt ctctctcggc agctttagcg acctgnctttt ccttctgagc    240 gtggggccag ctcccccgc ggcgccacc cacnctcact ccatgctccc ggaaatcgag      300
aggaagatca ttagttcttt ggggacgttn gtgattctct gtgatgctga aaaacactca    360
tatagggaat gtgggaaatc ctganctctt tnttatntcg tntgatttct tgtgttttat     420
ttgccaaaat gttaccaatc agtgaccaac cnagcacagc caaaaatcgg acntcngctt     480
tagtccgtct tcacacacag aataagaaaa cggcaaaccc accccacttt tnantttnat    540
```

```
tattactaan ttttttctgt tgggcaaaag aatctcagga acngccctgg ggccnccgta      600
ctanagttaa ccnagctagt tncatgaaaa atgatgggct ccncctcaat gggaaagcca      660 agaaaaagnc                                                              670

<210> SEQ ID NO 29
<211> LENGTH: 551
<212> TYPE: DNA
<213> ORGANISM: Homo sapien
<220> FEATURE:
<221> NAME/KEY: misc_feature
<222> LOCATION: (1)...(551)
<223> OTHER INFORMATION: n = A,T,C or G

<400> SEQUENCE: 29
actagtcctc cacagcctgt gaatccccct agacctttca agcatagtga gcggagaaga       60
agatctcagc gtttagccac cttacccatg cctgatgatt ctgtagaaaa ggtttcttct      120
ccctctccag ccactgatgg gaaagtattc tccatcagtt ctcaaaatca gcaagaatct      180
tcagtaccag aggtgcctga tgttgcacat ttgccacttg agaagctggg accctgtctc      240
cctcttgact taagtcgtgg ttcagaagtt acagcaccgg tagcctcaga ttcctcttac      300
cgtaatgaat gtcccagggc agaaaaagag gatacncaga tgcttccaaa tccttcttcc      360
aaagcaatag ctgatgggaa gaggagctcc agcagcagca ggaatatcga aacagaaaa       420 aaaagtgaaa ttgggaagac aaaagctcaa cagcatttgg taaggagaaa aganaagatg      480
aggaaggaag agagaagaga gacnaagatc nctacggacc gnnncggaag aagaagaagn      540
aaaaaanaaa a                                                           551

<210> SEQ ID NO 30
<211> LENGTH: 684
<212> TYPE: DNA
<213> ORGANISM: Homo sapien
<220> FEATURE:
<221> NAME/KEY: misc_feature
<222> LOCATION: (1)...(684)
<223> OTHER INFORMATION: n = A,T,C or G

<400> SEQUENCE: 30
actagttcta tctggaaaaa gcccgggttg aagaagctg tggagagtgc gtgtgcaatg        60
cgagactcat ttcttggaag catccctggc aaaaatgcag ctgagtacaa ggttatcact      120
gtgatagaac ctggactgct ttttgagata atagagatgc tgcagtctga agagacttcc      180
agcacctctc agttgaatga attaatgatg gcttctgagt caactttact ggctcaggaa      240
ccacgagaga tgactgcaga tgtaatcgag cttaaaggga aattcctcat caacttagaa      300
ggtggtgata ttcgtgaaga gtcttcctat aaagtaattg tcatgccgac tacgaaagaa      360
aaatgccccc gttgttggaa gtatacagcg ggagtcttca gatacactgt gtcctcgatg      420
tgcagaagtt gtcagtggga aaatagtatt aacagctcac tcgagcaaga accctcctga      480
cagtactggg ctagaagttt ggatggatta tttacaatat aggaaagaaa gccagaatt      540 aggtnatgag tggatgagta aatggtggan gatggggaat tcaaatcaga attatggaag      600
aagttnttcc tgttactata gaaggaatt atgtttattt acatgcagaa aatatanatg       660
tgtggtgtgt accgtggatg gaan                                             684

<210> SEQ ID NO 31
<211> LENGTH: 654
<212> TYPE: DNA
```

<213> ORGANISM: Homo sapien
<220> FEATURE:
<221> NAME/KEY: misc_feature
<222> LOCATION: (1)...(654)
<223> OTHER INFORMATION: n = A,T,C or G

<400> SEQUENCE: 31

| | | | | |
|---|---|---|---|---|
| gcgcagaaaa | ggaaccaata | tttcagaaac | aagcttaata | ggaacagctg | cctgtacatc | 60 |
| aacatcttct | cagaatgacc | cagaagttat | catcgtggga | gctggcgtgc | ttggctctgc | 120 |
| tttggcagct | gtgctttcca | gagatggaag | aaaggtgaca | gtcattgaga | gagacttaaa | 180 |
| agagcctgac | agaatagttg | agaattcct | gcagccgggt | ggttatcatg | ttctcaaaga | 240 |
| ccttggtctt | ggagatacag | tggaaggtct | tgatgcccag | gttgtaaatg | gttacatgat | 300 |
| tcatgatcag | ggaaagcaaa | tcagangttc | agattcctta | ccctctgtca | gaaaacaatc | 360 |
| aagtgcagag | tggaagagct | ttccatcacg | gaagattcat | catgagtctc | cggaaagcag | 420 |
| ctatggcaga | gcccaatgca | aagtttattg | aaggtgttgt | gttacagtta | ttagaggaag | 480 |
| atgatgttgt | gatgggagtt | cagtacaagg | ataaagagac | tgggagatat | caaggaactc | 540 |
| catgctccac | tgactgttgt | tgcagatggg | cttttctcca | anttcaggaa | aagcctggtc | 600 |
| tcaataaagt | ttctgtatca | ctcatttggt | tggcttctta | tgaagaatgc | nccc | 654 |

<210> SEQ ID NO 32
<211> LENGTH: 673
<212> TYPE: DNA
<213> ORGANISM: Homo sapien
<220> FEATURE:
<221> NAME/KEY: misc_feature
<222> LOCATION: (1)...(673)
<223> OTHER INFORMATION: n = A,T,C or G

<400> SEQUENCE: 32

| | | | | |
|---|---|---|---|---|
| actagtgaag | aaaagaaat | tctgatacgg | gacaaaatg | ctcttcaaaa | catcattctt | 60 |
| tatcacctga | caccaggagt | tttcattgga | aaaggatttg | aacctggtgt | tactaacatt | 120 |
| ttaaagacca | cacaaggaag | caaaatcttt | ctgaaagaag | taaatgatac | acttctggtg | 180 |
| aatgaattga | atcaaaaga | atctgacatc | atgacaacaa | atggtgtaat | tcatgttgta | 240 |
| gataaactcc | tctatccagc | agacacacct | gttggaaatg | atcaactgct | ggaaatactt | 300 |
| aataaattaa | tcaaatacat | ccaaattaag | tttgttcgtg | gtagcacctt | caaagaaatc | 360 |
| cccgtgactg | tctatnagcc | aattattaaa | aaatacacca | aaatcattga | tgggagtgcc | 420 |
| tgtgggaaat | aactgaaaaa | gagaccgaga | agaacgaatc | attacaggtc | ctgaaataaa | 480 |
| atacctagga | tttctactgg | aggtggagaa | acagaagaac | tctgaagaaa | ttgttacaag | 540 |
| aagangtccc | aaggtcacca | aattcattga | aggtggtgat | ggtctttatt | tgaagatgaa | 600 |
| gaaattaaaa | gacgcttcag | ggagacnccc | catgaaggaa | ttgccagcca | caaaaaatt | 660 |
| cagggattag | aaa | | | | | 673 |

<210> SEQ ID NO 33
<211> LENGTH: 673
<212> TYPE: DNA
<213> ORGANISM: Homo sapien
<220> FEATURE:
<221> NAME/KEY: misc_feature
<222> LOCATION: (1)...(673)
<223> OTHER INFORMATION: n = A,T,C or G

<400> SEQUENCE: 33

| | | | | |
|---|---|---|---|---|
| actagttatt | tacttccctc | cgcttcagaa | ggttttcag | actgagagcc | taagcatact | 60 |

```
ggatctgttg tttcttttgg gtctcacctc atcagtgtgc atagtggcag aaattataaa      120
gaaggttgaa aggagcaggg aaaagatcca gaagcatgtt agttcgacat catcatcttt      180
tcttgaagta tgatgcatat tgcattattt tatttgcaaa ctaggaattg cagtctgagg      240
atcatttaga agggcaagtt caagaggata tgaagatttg agaactttt aactattcat       300 tgactaaaaa tgaacattaa tgttnaagac ttaagacttt aacctgctgg cagtcccaaa      360
tgaaattatg caactttgat atcatattcc ttgatttaaa ttgggctttt gtgattgant      420
gaaactttat aaagcatatg gtcagttatt tnattaaaaa ggcaaaacct gaaccacctt      480
ctgcacttaa agaagtctaa cagtacaaat acctatctat cttagatgga tntatttntt      540
tntattttta aatattgtac tatttatggt nggtggggct ttcttactaa tacacaaatn      600
aatttatcat ttcaanggca ttctatttgg gtttagaagt tgattccaag nantgcatat      660
ttcgctactg tnt                                                          673

<210> SEQ ID NO 34
<211> LENGTH: 684
<212> TYPE: DNA
<213> ORGANISM: Homo sapien
<220> FEATURE:
<221> NAME/KEY: misc_feature
<222> LOCATION: (1)...(684)
<223> OTHER INFORMATION: n = A,T,C or G

<400> SEQUENCE: 34
actagtttat tcaagaaaag aacttactga ttcctctgtt cctaaagcaa gagtggcagg       60
tgatcagggc tggtgtagca tccggttcct ttagtgcagc taactgcatt tgtcactgat      120
gaccaaggag gaaatcacta agacatttga gaagcagtgg tatgaacgtt cttggacaag      180
ccacagttct gagccttaac cctgtagttt gcacacaaga acgagctcca cctcccttc       240 ttcaggagga atctgtgcgg atagattggc tggacttttc aatggttctg ggttgcaagt      300
gggcactgtt atggctgggt atggagcgga cagccccagg aatcagagcc tcagcccggc      360
tgcctggttg gaaggtacag gtgttcagca ccttcggaaa aagggcataa agtngtgggg      420
gacaattctc agtccaagaa gaatgcattg accattgctg gctatttgct tnccctagtan     480 gaattggatn cattttttgac cangatnntt ctnctatgct ttnttgcaat gaaatcaaat     540
cccgcattat ctacaagtgg tatgaagtcc tgcnnccccc agagaggctg ttcaggcnat      600
gtcttccaag ggcagggtgg gttacaccat tttacctccc ctctcccccc agattatgna     660
cncagaagga atttntttcc tccc                                              684

<210> SEQ ID NO 35
<211> LENGTH: 614
<212> TYPE: DNA
<213> ORGANISM: Homo sapien
<220> FEATURE:
<221> NAME/KEY: misc_feature
<222> LOCATION: (1)...(614)
<223> OTHER INFORMATION: n = A,T,C or G

<400> SEQUENCE: 35
actagtccaa cgcgttngcn aatattcccc tggtagccta cttccttacc cccgaatatt       60
ggtaagatcg agcaatggct tcaggacatg ggttctcttc tcctgtgatc attcaagtgc      120
tcactgcatg aagactggct tgtctcagtg tntcaacctc accagggctg tctcttggtc      180
cacacctcgc tccctgttag tgccgtatga cagcccccat canatgacct tggccaagtc      240
```

-continued

| | |
|---|---|
| acggtttctc tgtggtcaat gttggtnggc tgattggtgg aaagtanggt ggaccaaagg | 300 |
| aagncncgtg agcagncanc nccagttctg caccagcagc gcctccgtcc tactngggtg | 360 |
| ttccngtttc tcctggccct gngtgggcta nggcctgatt cgggaanatg cctttgcang | 420 |
| gaaggganga taantgggat ctaccaattg attctggcaa aacnatntct aagattnttn | 480 |
| tgctttatgt ggganacana tctanctctc atttnntgct gnanatnaca ccctactcgt | 540 |
| gntcgancnc gtcttcgatt ttcggganaca cnccantnaa tactggcgtt ctgttgttaa | 600 |
| aaaaaaaaaa aaaa | 614 |

<210> SEQ ID NO 36
<211> LENGTH: 686
<212> TYPE: DNA
<213> ORGANISM: Homo sapien
<220> FEATURE:
<221> NAME/KEY: misc_feature
<222> LOCATION: (1)...(686)
<223> OTHER INFORMATION: n = A,T,C or G

<400> SEQUENCE: 36

| | |
|---|---|
| gtggctggcc cggttctccg cttctcccca tcccctactt tcctccctcc ctcccttcc | 60 |
| ctccctcgtc gactgttgct tgctggtcgc agactccctg accctccct cacccctccc | 120 |
| taacctcggt gccaccggat tgcccttctt ttcctgttgc ccagcccagc cctagtgtca | 180 |
| gggcggggc ctggagcagc ccgaggcact gcagcagaag ananaaaaga cacgacnaac | 240 |
| ctcagctcgc cagtccggtc gctngcttcc cgccgcatgg caatnagaca gacgccgctc | 300 |
| acctgctctg gcacacgcg acccgtggtt gatttggcct tcagtggcat caccccttatg | 360 |
| ggtatttctt aatcagcgct tgcaaagatg gttaacctat gctacgccag ggagatacag | 420 |
| gagactggat tggaacattt ttggggtcta aaggtctgtt tggggtgcaa cactgaataa | 480 |
| ggatgccacc aaagcagcta cagcagctgc agatttcaca gcccaagtgt gggatgctgt | 540 |
| ctcagganat naattgataa cctggctcat aacacattgt caagaatgtg gatttcccca | 600 |
| ggatattatt atttgtttac cgggggganag gataactgtt tcncntattt taattgaaca | 660 |
| aactnaaaca aaanctaagg aaatcc | 686 |

<210> SEQ ID NO 37
<211> LENGTH: 681
<212> TYPE: DNA
<213> ORGANISM: Homo sapien
<220> FEATURE:
<221> NAME/KEY: misc_feature
<222> LOCATION: (1)...(681)
<223> OTHER INFORMATION: n = A,T,C or G

<400> SEQUENCE: 37

| | |
|---|---|
| gagacanacn naacgtcang agaanaaaag angcatggaa cacaanccag gcncgatggc | 60 |
| caccttccca ccagcancca gcgcccccca gcngccccca ngnccggang accangactc | 120 |
| cancctgnat caatctgganc tctattcctg gcccatncct acctcggagg tggangccgn | 180 |
| aaaggtcgca cnnncagaga agctgctgcc ancaccancc gccccnnccc tgncgggctn | 240 |
| nataggaaac tggtgaccnn gctgcanaat tcatacagga gcacgcgang ggcacnnnct | 300 |
| cacactgagt tnnngatgan gcctnaccan ggacctnccc cagcnnattg annacnggac | 360 |
| tgcggaggaa ggaagacccc gnacnggatc ctggccggcn tgccaccccc ccacccctag | 420 |
| gattatnccc cttgactgag tctctgaggg gctacccgaa cccgcctcca ttccctacca | 480 |
| natnntgctc natcgggact gacangctgg ggatnggagg ggctatcccc cancatcccc | 540 |

```
tnanaccaac agcnacngan natngggget ccccngggtc ggngcaacnc tcctncaccc      600
cggcgcnggc cttcggtgnt gtcctccntc aacnaattcc naaanggcgg gcccccccngt    660 ggactcctcn ttgttccctc c                                               681
```

<210> SEQ ID NO 38
<211> LENGTH: 687
<212> TYPE: DNA
<213> ORGANISM: Homo sapien
<220> FEATURE:
<221> NAME/KEY: misc_feature
<222> LOCATION: (1)...(687)
<223> OTHER INFORMATION: n = A,T,C or G

<400> SEQUENCE: 38

```
canaaaaaaa aaaacatggc cgaaaccagn aagctgcgcg atggcgccac ggcccctctt     60
ctcccggcct gtgtccggaa ggtttccctc cgaggcgccc cggctcccgc aagcggagga   120
gagggcggga cntgccgggg ccggagctca naggccctgg ggccgctctg ctctcccgcc   180
atcgcaaggg cggcgctaac ctnaggcctc cccgcaaagg tccccnangc ggnggcggcg   240
gggggctgtg anaaccgcaa aaanaacgct gggcgcgcng cgaacccgtc cacccccgcg   300
aaggananac ttccacagan gcagcgtttc cacagcccan agccacnttt ctagggtgat   360
gcaccccagt aagttcctgn cggggaagct caccgctgtc aaaaaanctc ttcgctccac   420
cggcgcacna aggggangan ggcangangc tgccgcccgc acaggtcatc tgatcacgtc   480
gcccgcccta ntctgctttt gtgaatctcc actttgttca accccacccg ccgttctctc   540
ctccttgcgc cttcctctna ccttaanaac cagcttcctc tacccnatng tanttnctct   600
gcncnngtng aaattaattc ggtccnccgg aacctcttnc ctgtggcaac tgctnaaaga   660
aactgctgtt ctgnttactg cngtccc                                       687
```

<210> SEQ ID NO 39
<211> LENGTH: 695
<212> TYPE: DNA
<213> ORGANISM: Homo sapien
<220> FEATURE:
<221> NAME/KEY: misc_feature
<222> LOCATION: (1)...(695)
<223> OTHER INFORMATION: n = A,T,C or G

<400> SEQUENCE: 39

```
actagtctgg cctacaatag tgtgattcat gtaggacttc tttcatcaat tcaaacccc      60 tagaaaaacg tatacagatt atataagtag ggataagatt tctaacattt ctgggctctc   120 tgaccectgc gctagactgt ggaaagggag tattattata gtatacaaca ctgctgttgc   180
cttattagtt ataacatgat aggtgctgaa ttgtgattca caatttaaaa acactgtaat   240
ccaaactttt tttttaact gtagatcatg catgtgaatg ttaatgttaa tttgttcaan   300
gttgttatgg gtagaaaaaa ccacatgcct taaaatttta aaaagcaggg cccaaactta   360
ttagtttaaa attaggggta tgtttccagt ttgttattaa ntggttatag ctctgtttag   420
aanaaatcna ngaacangat ttngaaantt aagntgacat tatttnccag tgacttgtta   480
atttgaaatc anacacggca ccttccgttt tggtnctatt ggnntttgaa tccaancngg   540
ntccaaatct tnttggaaac ngtccnttta acttttttac nanatcttat ttttttattt   600
tggaatggcc ctatttaang ttaaaagggg ggggnnccac naccattcnt gaataaaact   660
naatatatat ccttggtccc ccaaaattta aggng                               695
```

<210> SEQ ID NO 40
<211> LENGTH: 674
<212> TYPE: DNA
<213> ORGANISM: Homo sapien
<220> FEATURE:
<221> NAME/KEY: misc_feature
<222> LOCATION: (1)...(674)
<223> OTHER INFORMATION: n = A,T,C or G

<400> SEQUENCE: 40

```
actagtagtc agttgggagt ggttgctata ccttgacttc atttatatga atttccactt     60
tattaaataa tagaaaagaa atcccggtg cttgcagtag agttatagga cattctatgc    120
ttacagaaaa tatagccatg attgaaatca aatagtaaag gctgttctgg cttttatct    180
tcttagctca tcttaaataa gtagtacact tgggatgcag tgcgtctgaa gtgctaatca   240
gttgtaacaa tagcacaaat cgaacttagg atgtgtttct tctcttctgt gtttcgattt   300
tgatcaattc tttaattttg ggaacctata atacagtttt cctattcttg gagataaaaa   360
ttaaatggat cactgatatt taagtcattc tgcttctcat ctnaatattc catattctgt   420
attagganaa antacctccc agcacagccc cctctcaaac cccacccaaa accaagcatt   480
tggaatgagt ctcctttatt tccgaantgt ggatggtata acccatatcn ctccaatttc   540
tgnttgggtt gggtattaat ttgaactgtg catgaaaagn ggnaatcttt nctttgggtc   600
aaantttncc ggttaatttg nctngncaaa tccaatttnc tttaagggtg tctttataaa   660
atttgctatt cngg                                                    674
```

<210> SEQ ID NO 41
<211> LENGTH: 657
<212> TYPE: DNA
<213> ORGANISM: Homo sapien
<220> FEATURE:
<221> NAME/KEY: misc_feature
<222> LOCATION: (1)...(657)
<223> OTHER INFORMATION: n = A,T,C or G

<400> SEQUENCE: 41

```
gaaacatgca agtaccacac actgtttgaa ttttgcacaa aaagtgactg tagggatcag    60
gtgatagccc cggaatgtac agtgtcttgg tgcaccaaga tgccttctaa aggctgacat   120
accttgggac cctaatgggg cagagagtat agccctagcc cagtggtgac atgaccactc   180
cctttgggag gctgaagtta aagggaatgg tatgtgtttt ctcatggaag cagcacatga   240
atnggtnaca ngatgttaaa ntaaggntct antttgggtg tcttgtcatt tgaaaaantg   300
acacactcct ancanctggt aaagggtgc tggaagccat ggaagaactc taaaaacatt   360
agcatgggct gatctgatta cttcctggca tcccgctcac ttttatggga agtcttatta   420
naaggatggg ananttttcc atatccttgc tgttggaact ctggaacact ctctaaattt   480
ccctctatta aaaatcactg nccttactac acttcctcct tganggaata gaaatggacc   540
tttctctgac ttagttcttg gcatgggganc cagcccaaat taaaatctga cttntccggt   600
ttctccngaa ctcacctact tgaattggta aaacctcctt tggaattagn aaaaacc      657
```

<210> SEQ ID NO 42
<211> LENGTH: 389
<212> TYPE: DNA
<213> ORGANISM: Homo sapien
<220> FEATURE:
<221> NAME/KEY: misc_feature
<222> LOCATION: (1)...(389)
<223> OTHER INFORMATION: n = A,T,C or G

<400> SEQUENCE: 42

| actagtgctg | aggaatgtaa | acaagtttgc | tgggccttgc | gagacttcac | caggttgttt | 60 |
| cgatagctca | cactcctgca | ctgtgcctgt | cacccaggaa | tgtctttttt | aattagaaga | 120 |
| caggaagaaa | acaaaaacca | gactgtgtcc | cacaatcaga | aacctccgtt | gtggcagang | 180 |
| ggccttcacc | gccaccaggg | tgtcccgcca | gacaggaga | gactccagcc | ttctgaggcc | 240 |
| atcctgaaga | attcctgttt | gggggttgtg | aaggaaaatc | acccggattt | aaaaagatgc | 300 |
| tgttgcctgc | ccgcgtngtn | gggaagggac | tggtttcctg | gtgaatttct | aaaagaaaa | 360 |
| atattttaag | ttaagaaaaa | aaaaaaaa | | | | 389 |

<210> SEQ ID NO 43
<211> LENGTH: 279
<212> TYPE: DNA
<213> ORGANISM: Homo sapien

<400> SEQUENCE: 43

| actagtgaca | agctcctggt | cttgagatgt | cttctcgtta | aggagatggg | ccttttggag | 60 |
| gtaaaggata | aaatgaatga | gttctgtcat | gattcactat | tctagaactt | gcatgacctt | 120 |
| tactgtgtta | gctcttttgaa | tgttcttgaa | attttagact | ttctttgtaa | acaaataata | 180 |
| tgtccttatc | attgtataaa | agctgttatg | tgcaacagtg | tggagatcct | tgtctgattt | 240 |
| aataaaatac | ttaaacactg | aaaaaaaaaa | aaaaaaaa | | | 279 |

<210> SEQ ID NO 44
<211> LENGTH: 449
<212> TYPE: DNA
<213> ORGANISM: Homo sapien
<220> FEATURE:
<221> NAME/KEY: misc_feature
<222> LOCATION: (1)...(449)
<223> OTHER INFORMATION: n = A,T,C or G

<400> SEQUENCE: 44

| actagtagca | tctttctac | aacgttaaaa | ttgcagaagt | agcttatcat | taaaaaacaa | 60 |
| caacaacaac | aataacaata | aatcctaagt | gtaaatcagt | tattctaccc | cctaccaagg | 120 |
| atatcagcct | gttttttccc | ttttttctcc | tgggaataat | tgtgggcttc | ttcccaaatt | 180 |
| tctacagcct | ctttcctctt | ctcatgcttg | agcttccctg | tttgcacgca | tgcgttgtgc | 240 |
| aagantgggc | tgtttngctt | ggantncggt | ccnagtggaa | ncatgctttc | ccttgttact | 300 |
| gttggaagaa | actcaaacct | tcnancccta | ggtgttncca | ttttgtcaag | tcatcactgt | 360 |
| attttttgtac | tggcattaac | aaaaaaagaa | atnaaatatt | gttccattaa | actttaataa | 420 |
| aactttaaaa | gggaaaaaaa | aaaaaaaa | | | | 449 |

<210> SEQ ID NO 45
<211> LENGTH: 559
<212> TYPE: DNA
<213> ORGANISM: Homo sapien
<220> FEATURE:
<221> NAME/KEY: misc_feature
<222> LOCATION: (1)...(559)
<223> OTHER INFORMATION: n = A,T,C or G

<400> SEQUENCE: 45

| actagtgtgg | gggaatcacg | gacacttaaa | gtcaatctgc | gaaataattc | ttttattaca | 60 |
| cactcactga | agtttttgag | tcccagagag | ccattctatg | tcaaacattc | caagtactct | 120 |

| | |
|---|---|
| ttgagagccc agcattacat caacatgccc gtgcagttca aaccgaagtc cgcaggcaaa | 180 |
| tttgaagctt tgcttgtcat tcaaacagat gaaggcaaga gtattgctat tcgactaatt | 240 |
| ggtgaagctc ttggaaaaaa ttnactagaa tacttttttgt gttaagttaa ttacataagt | 300 |
| tgtattttgt taactttatc tttctacact acaattatgc ttttgtatat atattttgta | 360 |
| tgatggatat ctataattgt agattttgtt tttacaagct aatactgaag actcgactga | 420 |
| aatattatgt atctagccca tagtattgta cttaactttt acagggtgaa aaaaaaattc | 480 |
| tgtgtttgca ttgattatga tattctgaat aaatatggga atatatttta atgtgggtaa | 540 |
| aaaaaaaaaa aaaaggaa | 559 |

<210> SEQ ID NO 46
<211> LENGTH: 731
<212> TYPE: DNA
<213> ORGANISM: Homo sapien
<220> FEATURE:
<221> NAME/KEY: misc_feature
<222> LOCATION: (1)...(731)
<223> OTHER INFORMATION: n = A,T,C or G

<400> SEQUENCE: 46

| | |
|---|---|
| actagttcta gtaccatggc tgtcatagat gcaaccatta tattccattt agtttcttcc | 60 |
| tcaggttccc taacaattgt tgaaactga atatatatgt ttatgtatgt gtgtgtgttc | 120 |
| actgtcatgt atatggtgta tatgggatgt gtgcagtttt cagttatata tatattcata | 180 |
| tatacatatg catatatatg tataatatac atatatacat gcatacactt gtataatata | 240 |
| catatatata cacatatatg cacacatatn atcactgagt tccaaagtga gtctttattt | 300 |
| ggggcaattg tattctctcc ctctgtctgc tcactgggcc tttgcaagac atagcaattg | 360 |
| cttgatttcc tttggataag agtcttatct tcggcactct tgactctagc cttaacttta | 420 |
| gatttctatt ccagaatacc tctcatatct atcttaaaac ctaaganggg taaagangtc | 480 |
| ataagattgt agtatgaaag antttgctta gttaaattat atctcaggaa actcattcat | 540 |
| ctacaaatta aattgtaaaa tgatggtttg ttgtatctga aaaatgttt agaacaagaa | 600 |
| atgtaactgg gtacctgtta tatcaaagaa cctcnattta ttaagtctcc tcatagccan | 660 |
| atccttatat ngccctctct gacctgantt aatananact tgaataatga atagttaatt | 720 |
| taggnttggg c | 731 |

<210> SEQ ID NO 47
<211> LENGTH: 640
<212> TYPE: DNA
<213> ORGANISM: Homo sapien
<220> FEATURE:
<221> NAME/KEY: misc_feature
<222> LOCATION: (1)...(640)
<223> OTHER INFORMATION: n = A,T,C or G

<400> SEQUENCE: 47

| | |
|---|---|
| tgcgngccgg tttggccctt ctttgtanga cactttcatc cgccctgaaa tcttcccgat | 60 |
| cgttaataac tcctcaggtc cctgcctgca cagggttttt tcttantttg ttgcctaaca | 120 |
| gtacaccaaa tgtgacatcc tttcaccaat atngattnct tcataccaca tcntcnatgg | 180 |
| anacgactnc aacatttttt tgatnacccn aaanactggg ggctnnaana agtacantct | 240 |
| ggagcagcat ggacctgtcn gcnactaang gaacaaanagt nntgaacatt tacacaacct | 300 |
| ttggtatgtc ttactgaaag anagaaacat gcttctnncc ctagaccacg aggncaaccg | 360 |
| caganattgc caatgccaag tccgagcggt tagatcaggt aatacattcc atggatgcat | 420 |

```
tacatacntt gtccccgaaa nanaagatgc cctaanggct tcttcanact ggtccngaaa        480
acanctacac ctggtgcttg ganaacanac tctttggaag atcatctggc acaagttccc        540
cccagtgggt tttnccttgg cacctanctt accanatcna ttcggaancc attctttgcc        600
ntggcnttnt nttgggacca ntcttctcac aactgnaccc                              640
```

<210> SEQ ID NO 48
<211> LENGTH: 257
<212> TYPE: DNA
<213> ORGANISM: Homo sapien

<400> SEQUENCE: 48

```
actagtatat gaaaatgtaa atatcacttg tgtactcaaa caaaagttgg tcttaagctt         60
ccaccttgag cagccttgga aacctaacct gcctcttta gcataatcac atttctaaa         120 tgattttctt tgttcctgaa aaagtgattt gtattagttt tacatttgtt ttttggaaga        180
ttatatttgt atatgtatca tcataaaata tttaaataaa aagtatcttt agagtgaaaa        240
aaaaaaaaaa aaaaaaa                                                      257
```

<210> SEQ ID NO 49
<211> LENGTH: 652
<212> TYPE: DNA
<213> ORGANISM: Homo sapien
<220> FEATURE:
<221> NAME/KEY: misc_feature
<222> LOCATION: (1)...(652)
<223> OTHER INFORMATION: n = A,T,C or G

<400> SEQUENCE: 49

```
actagttcag atgagtggct gctgaagggg cccccttgtc attttcatta tacccaatt         60 tccacttatt tgaactctta agtcataaat gtataatgac ttatgaatta gcacagttaa       120
gttgacacta gaaactgccc atttctgtat tacactatca aataggaaac attggaaaga      180
tggggaaaaa aatcttattt taaaatggct tagaaagttt tcagattact ttgaaaattc      240
taaacttctt tctgtttcca aaacttgaaa atatgtagat ggactcatgc attaagactg      300
ttttcaaagc tttcctcaca ttttaaagt gtgattttcc ttttaatata catatttatt       360
ttctttaaag cagctatatc ccaacccatg actttggaga tatacctatn aaaccaatat     420
aacagcangg ttattgaagc agctttctca atgttgctt cagatgtgca agttgcaaat      480
tttattgtat ttgtanaata caattttttgt tttaaactgt atttcaatct atttctccaa    540
gatgcttttc atatagagtg aaatatccca ngataactgc ttctgtgtcg tcgcatttga     600
cgcataactg cacaaatgaa cagtgtatac ctcttggttg tgcattnacc cc              652
```

<210> SEQ ID NO 50
<211> LENGTH: 650
<212> TYPE: DNA
<213> ORGANISM: Homo sapien
<220> FEATURE:
<221> NAME/KEY: misc_feature
<222> LOCATION: (1)...(650)
<223> OTHER INFORMATION: n = A,T,C or G

<400> SEQUENCE: 50

```
ttgcgctttg attttttag ggcttgtgcc ctgtttcact tatagggtct agaatgcttg         60
tgttgagtaa aaaggagatg cccaatattc aaagctgcta atgttctctt tgccataaa        120 gactccgtgt aactgtgtga acacttggga tttttctcct ctgtcccgag gtcgtcgtct      180
```

-continued

```
gctttctttt ttgggttctt tctagaagat tgagaaatgc atatgacagg ctgagancac      240
ctccccaaac acacaagctc tcagccacan gcagcttctc cacagcccca gcttcgcaca      300
ggctcctgga nggctgcctg ggggaggcag acatgggagt gccaaggtgg ccagatggtt      360
ccaggactac aatgtcttta tttttaactg tttgccactg ctgccctcac ccctgcccgg      420
ctctggagta ccgtctgccc canacaagtg ggantgaaat gggggtgggg gggaacactg      480
attcccantt aggggtgcc taactgaaca gtagggatan aaggtgtgaa cctgngaant       540
gcttttataa attatnttcc ttgttanatt tatttttaa tttaatctct gttnaactgc       600
ccngggaaaa gggaaaaaa aaaaaaaat tctntttaaa cacatgaaca                   650
```

<210> SEQ ID NO 51
<211> LENGTH: 545
<212> TYPE: DNA
<213> ORGANISM: Homo sapien
<220> FEATURE:
<221> NAME/KEY: misc_feature
<222> LOCATION: (1)...(545)
<223> OTHER INFORMATION: n = A,T,C or G

<400> SEQUENCE: 51

```
tggcgtgcaa ccagggtagc tgaagtttgg gtctgggact ggagattggc cattaggcct       60
cctganattc cagctcccct tccaccaagcc cagtcttgct acgtgcaca gggcaaacct      120 gactcccttt gggcctcagt ttcccctccc cttcatgana tgaaaagaat actactttt       180 cttgttggtc taacnttgct ggacncaaag tgtngtcatt attgttgtat tgggtgatgt      240
gtncaaaact gcagaagctc actgcctatg agaggaanta agagagatag tggatganag      300
ggacanaagg agtcattatt tggtatagat ccacccntcc caacctttct ctcctcagtc      360
cctgcncctc atgtntctgg tntggtgagt cctttgtgcc accanccatc atgctttgca      420
ttgctgccat cctgggaagg gggtgnatcg tctcacaact tgttgtcatc gtttganatg      480
catgctttct tnatnaaaca aanaaannaa tgtttgacag ngtttaaaat aaaaaanaaa      540
caaaa                                                                 545
```

<210> SEQ ID NO 52
<211> LENGTH: 678
<212> TYPE: DNA
<213> ORGANISM: Homo sapien
<220> FEATURE:
<221> NAME/KEY: misc_feature
<222> LOCATION: (1)...(678)
<223> OTHER INFORMATION: n = A,T,C or G

<400> SEQUENCE: 52

```
actagtagaa gaactttgcc gcttttgtgc ctctcacagg cgcctaaagt cattgccatg       60
ggaggaagac gatttggggg gggagggggg ggggcanggg tccgtggggc tttccctant      120
ntatctccat ntccantgnn cnntgtcgcc tcttccctcg tncattnga anttantccc       180 tggncccnn ncctctccn nctncncct cccccctccg ncncctccnn cttttttntan       240 ncttccccat ctccntcccc cctnanngtc ccaacnccgn cagcaatnnc ncacttnctc      300
nctccncncc tccnncgtt cttctntttct cnacntntnc ncnnntncn tgccnntnaa       360 annctctccc cnctgcaanc gattctctcc ctccncnnan ctntccactc cntncttctc      420
ncncgctcct nttcntcnnc ccacctctcn ccttcgncc cantacnctc nccncccttn      480
cgnntcnttn nnntcctcnn accncccncc tcccttcncc cctcttctcc ccggtntntc      540
tctctcccnc nncncnncct cnncccntcc nngcgnccnt ttccgccccn cnccnccntt      600
```
ccttcntcnc cantccatcn cntntnccat nctncctncc nctcacnccc gctncccccn    660
ntctctttca cacngtcc    678

<210> SEQ ID NO 53
<211> LENGTH: 502
<212> TYPE: DNA
<213> ORGANISM: Homo sapien
<220> FEATURE:
<221> NAME/KEY: misc_feature
<222> LOCATION: (1)...(502)
<223> OTHER INFORMATION: n = A,T,C or G

<400> SEQUENCE: 53
tgaagatcct ggtgtcgcca tgggccgccg ccccgcccgt tgttaccggt attgtaagaa    60
caagccgtac ccaaagtctc gcttctgccg aggtgtccct gatgccaaaa ttcgcatttt    120
tgacctgggg cggaaaaang caaaantgga tgagtctccg ctttgtggcc acatggtgtc    180
agatcaatat gagcagctgt cctctgaagc cctgnangct gcccgaattt gtgccaataa    240
gtacatggta aaaagtngtg gcnaagatgc ttccatatcc gggtgcggnt ccaccccttc    300
cacgtcatcc gcatcaacaa gatgttgtcc tgtgctgggg ctgacaggct cccaacaggc    360
atgcgaagtg cctttggaaa acccanggca ctgtggccag ggttcacatt gggccaattn    420
atcatgttca tccgcaccaa ctgcagaaca angaacntgt naattnaagc cctgcccagg    480
gncaanttca aatttcccgg cc    502

<210> SEQ ID NO 54
<211> LENGTH: 494
<212> TYPE: DNA
<213> ORGANISM: Homo sapien
<220> FEATURE:
<221> NAME/KEY: misc_feature
<222> LOCATION: (1)...(494)
<223> OTHER INFORMATION: n = A,T,C or G

<400> SEQUENCE: 54
actagtccaa gaaaaatatg cttaatgtat attacaaagg ctttgtatat gttaacctgt    60
tttaatgcca aaagtttgct ttgtccacaa tttccttaag acctcttcag aaagggattt    120
gtttgcctta atgaatactg ttgggaaaaa acacagtata atgagtgaaa agggcagaag    180
caagaaattt ctacatctta gcgactccaa gaagaatgag tatccacatt tagatggcac    240
attatgagga ctttaatctt tccttaaaca caataatgtt ttcttttttc ttttattcac    300
atgatttcta agtatatttt tcatgcagga cagttttttca accttgatgt acagtgactg    360
tgttaaattt ttctttcagt ggcaacctct ataatcttta aaatatggtg agcatcttgt    420
ctgttttgaa ngggatatga cnatnaatct atcagatggg aaatcctgtt tccaagttag    480
aaaaaaaaaa aaaa    494

<210> SEQ ID NO 55
<211> LENGTH: 606
<212> TYPE: DNA
<213> ORGANISM: Homo sapien
<220> FEATURE:
<221> NAME/KEY: misc_feature
<222> LOCATION: (1)...(606)
<223> OTHER INFORMATION: n = A,T,C or G

<400> SEQUENCE: 55
actagtaaaa agcagcattg ccaaataatc cctaattttc cactaaaaat ataatgaaat    60

```
gatgttaagc ttttttgaaaa gtttaggtta aacctactgt tgttagatta atgtatttgt      120
tgcttccctt tatctggaat gtggcattag ctttttattt ttaaccctct ttaattctta      180
ttcaattcca tgacttaagg ttggagagct aaacactggg attttttggat aacagactga     240 cagttttgca taattataat cggcattgta catagaaagg atatggctac cttttgttaa      300
atctgcactt tctaaatatc aaaaaaggga atgaagtat aaatcaattt ttgtataatc       360
tgtttgaaac atganttta tttgcttaat attanggctt tgcccttttc tgttagtctc       420
ttgggatcct gtgtaaaact gttctcatta acaccaaac agttaagtcc attctctggt       480
actagctaca aattccgttt catattctac ntaacaattt aaattaactg aaatatttct      540
anatggtcta cttctgtcnt ataaaaacna aacttgantt nccaaaaaaa aaaaaaaaa       600 aaaaaa                                                                 606

<210> SEQ ID NO 56
<211> LENGTH: 183
<212> TYPE: DNA
<213> ORGANISM: Homo sapien

<400> SEQUENCE: 56
actagtatat ttaaacttac aggcttattt gtaatgtaaa ccaccatttt aatgtactgt       60
aattaacatg gttataatac gtacaatcct tccctcatcc catcacacaa ctttttttgt      120
gtgtgataaa ctgattttgg tttgcaataa aaccttgaaa aataaaaaaa aaaaaaaaa       180 aaa                                                                    183

<210> SEQ ID NO 57
<211> LENGTH: 622
<212> TYPE: DNA
<213> ORGANISM: Homo sapien
<220> FEATURE:
<221> NAME/KEY: misc_feature
<222> LOCATION: (1)...(622)
<223> OTHER INFORMATION: n = A,T,C or G

<400> SEQUENCE: 57
actagtcact actgtcttct ccttgtagct aatcaatcaa tattcttccc ttgcctgtgg       60
gcagtggaga gtgctgctgg gtgtacgctg cacctgccca ctgagttggg gaaagaggat      120
aatcagtgag cactgttctg ctcagagctc ctgatctacc ccacccccta ggatccagga     180
ctgggtcaaa gctgcatgaa accaggccct ggcagcaacc tgggaatggc tggaggtggg     240
agagaacctg acttctcttt ccctctccct cctccaacat tactggaact ctatcctgtt     300
agggatcttc tgagcttgtt tccctgctgg gtgggacaga agacaaagga gaagggaggg     360
tctacaanaa gcagcccttc tttgtcctct ggggttaatg agcttgacct ananttcatg      420
gaganaccan aagcctctga tttttaattt ccntnaaatg tttgaagtnt atatntacat      480
atatatattt ctttnaatnt ttgagtcttt gatatgtctt aaaatccant ccctctgccn      540
gaaacctgaa ttaaaaccat gaanaaaaat gttnccctta agatgttan taattaattg       600 aaacttgaaa aaaaaaaaaa aa                                               622

<210> SEQ ID NO 58
<211> LENGTH: 433
<212> TYPE: DNA
<213> ORGANISM: Homo sapien

<400> SEQUENCE: 58
gaacaaattc tgattggtta tgtaccgtca aaagacttga agaaatttca tgattttgca       60
```

```
gtgtggaagc gttgaaaatt gaaagttact gcttttccac ttgctcatat agtaaaggga    120
tcctttcagc tgccagtgtt gaataatgta tcatccagag tgatgttatc tgtgacagtc    180
accagcttta agctgaacca ttttatgaat accaaataaa tagacctctt gtactgaaaa    240
catatttgtg actttaatcg tgctgcttgg atagaaatat ttttactggt tcttctgaat    300
tgacagtaaa cctgtccatt atgaatggcc tactgttcta ttatttgttt tgacttgaat    360
ttatccacca aagacttcat ttgtgtatca tcaataaagt tgtatgtttc aactgaaaaa    420
aaaaaaaaaa aaa                                                        433

<210> SEQ ID NO 59
<211> LENGTH: 649
<212> TYPE: DNA
<213> ORGANISM: Homo sapien
<220> FEATURE:
<221> NAME/KEY: misc_feature
<222> LOCATION: (1)...(649)
<223> OTHER INFORMATION: n = A,T,C or G

<400> SEQUENCE: 59
actagttatt atctgacttt cnggttataa tcattctaat gagtgtgaag tagcctctgg     60
tgtcatttgg atttgcattt ctctgatgag tgatgctatc aagcaccttt gctggtgctg    120
ttggccatat gtgtatgttc cctggagaag tgtctgtgct gagccttggc ccacttttta    180
attaggcgtn tgtcttttta ttactgagtt gtaaganttc tttatatatt ctggattcta    240 gaccottatc agatacatgg tttgcaaata ttttctccca ttctgtgggt tgtgttttca    300
ctttatcgat aatgtcctta gacatataat aaatttgtat tttaaagtg acttgatttg     360 ggctgtgcaa ggtgggctca cgcttgtaat cccagcactt gggagactg aggtgggtgg     420 atcatatgan gangctagga gttcgaggtc agcctggcca gcatagcgaa aacttgtctc    480
tacnaaaaat acaaaaatta gtcaggcatg gtggtgcacg tctgtaatac cagcttctca    540
ggangctgan gcacaaggat cacttgaacc ccagaangaa gangttgcag tganctgaag    600
atcatgccag ggcaacaaaa atgagaactt gtttaaaaaa aaaaaaaa                 649

<210> SEQ ID NO 60
<211> LENGTH: 423
<212> TYPE: DNA
<213> ORGANISM: Homo sapien
<220> FEATURE:
<221> NAME/KEY: misc_feature
<222> LOCATION: (1)...(423)
<223> OTHER INFORMATION: n = A,T,C or G

<400> SEQUENCE: 60
actagttcag gccttccagt tcactgacaa acatggggaa gtgtgcccag ctggctggaa     60
acctggcagt gataccatca agcctgatgt ccaaaagagc aaagaatatt tctccaagca    120
gaagtgagcg ctgggctgtt ttagtgccag gctgcggtgg gcagccatga gaacaaaacc    180
tcttctgtat ttttttttc cattagtana acacaagact cngattcagc cgaattgtgg    240
tgtcttacaa ggcagggctt tcctacaggg ggtgganaaa acagccttcc ttcctttggt    300
aggaatggcc tgagttggcg ttgtgggcag gctactggtt tgtatgatgt attagtagag    360
caacccatta atcttttgta gtttgtatna aacttganct gagaccttaa acaaaaaaaa    420
aaa                                                                  423

<210> SEQ ID NO 61
```

```
<211> LENGTH: 423
<212> TYPE: DNA
<213> ORGANISM: Homo sapien
<220> FEATURE:
<221> NAME/KEY: misc_feature
<222> LOCATION: (1)...(423)
<223> OTHER INFORMATION: n = A,T,C or G

<400> SEQUENCE: 61
cgggactgga atgtaaagtg aagttcggag ctctgagcac gggctcttcc cgccgggtcc      60
tccctcccca gacccagag  ggagaggccc accccgccca gccccgcccc agcccctgct     120
caggtctgag tatggctggg agtcgggggc cacaggcctc tagctgtgct gctcaagaag     180
actggatcag ggtanctaca agtggccggg ccttgccttt gggattctac cctgttccta     240
atttggtgtt ggggtgcggg gtccctggcc ccctttttcca cactncctcc ctccngacag    300
caacctccct tggggcaatt gggcctggnt ctccncccgn tgttgcnacc ctttgttggt     360
ttaaggncttt taaaaatgtt annttttccc ntgccngggt taaaaaagga aaaaactnaa    420
aaa                                                                   423

<210> SEQ ID NO 62
<211> LENGTH: 683
<212> TYPE: DNA
<213> ORGANISM: Homo sapien
<220> FEATURE:
<221> NAME/KEY: misc_feature
<222> LOCATION: (1)...(683)
<223> OTHER INFORMATION: n = A,T,C or G

<400> SEQUENCE: 62
gctggagagg ggtacggact ttcttggagt tgtcccaggt tggaatgaga ctgaactcaa      60
gaagagaccc taagagactg gggaatggtt cctgccttca ggaaagtgaa agacgcttag    120
gctgtcaaca cttaaaggaa gtccccttga agcccagagt ggacagacta gacccattga    180
tggggccact ggccatggtc cgtggacaag acattccngt gggccatggc acaccggggg    240
ggatcaaaat gtgtacttgt ggggtctcgc cccttgccaa aaccaaacca ntcccactcc    300
tgtcnttgga ctttcttccc attccctcct ccccaaatgc acttcccctc ctccctctgc    360
ccctcctgtg ttttttggaat tctgtttccc tcaaaattgt taatttttta nttttngacc   420
atgaacttat gtttggggtc nangttcccc ttnccaatgc atactaatat attaatggtt    480
atttatttt  gaaatatttt ttaatgaact tggaaaaaat tnntgaatt tccttncttc      540
cnttttnttt gggggggggtg ggggntggg ttaaaatttt tttggaancc cnatnggaaa   600
ttnttacttg gggcccccct naaaaaantn anttccaatt cttnnatngc ccctnttccn   660
ctaaaaaaaa ananannaaa aan                                            683

<210> SEQ ID NO 63
<211> LENGTH: 731
<212> TYPE: DNA
<213> ORGANISM: Homo sapien
<220> FEATURE:
<221> NAME/KEY: misc_feature
<222> LOCATION: (1)...(731)
<223> OTHER INFORMATION: n = A,T,C or G

<400> SEQUENCE: 63
actagtcata aagggtgtgc gcgtcttcga cgtggcggtc ttggcgccac tgctgcgaga     60
cccggccctg gacctcaagg tcatccactt ggtgcgtgat ccccgcgcgg tggcgagttc    120
acggatccgc tcgcgccacg gcctcatccg tgagagccta caggtggtgc gcagccgaga    180
```

```
ccgcgagctc accgcatgcc cttcttggag gccgcgggcc acaagcttgg cgcccanaaa      240
gaaggcgtng ggggcccgca aantaccacg ctctgggcgc tatggaangt cctcttgcaa      300
taatattggt tnaaaanctg canaanagcc cctgcanccc cctgaactgg gntgcagggc      360
cncttacctn gtttggntgc ggttacaaag aacctgttn ggaaaaccct nccnaaaacc      420
ttccgggaaa attntncaaa ttttnttgg ggaattnttg ggtaaacccc ccnaaatgg      480 gaaacntttt tgccctnnaa antaaaccat tnggttccgg gggcccccc ncaaaacct      540 tttttntttt tttntgcccc cantnnnccc ccggggcccc tttttttngg ggaaaanccc      600 ccccctncc nananttta aagggnggg anaatttttn nttncccccc gggnccccn      660 ggngntaaaa nggtttcncc ccccgaggg gngggggnnc ctcnnaaaacc cntntcnna      720 ccncntttn n                                                            731

<210> SEQ ID NO 64
<211> LENGTH: 313
<212> TYPE: DNA
<213> ORGANISM: Homo sapien
<220> FEATURE:
<221> NAME/KEY: misc_feature
<222> LOCATION: (1)...(313)
<223> OTHER INFORMATION: n = A,T,C or G

<400> SEQUENCE: 64
actagttgtg caaaccacga ctgaagaaag acgaaaagtg ggaaataact tgcaacgtct       60
gttagagatg gttgctacac atgttgggtc tgtagagaaa catcttgagg agcagattgc      120
taaagttgat agagaatatg aagaatgcat gtcagaagat ctctcggaaa atattaaaga      180
gattagagat aagtatgaga agaaagctac tctaattaag tcttctgaag aatgaagatn      240
aaatgttgat catgtatata tatccatagt gaataaaatt gtctcagtaa agttgtaaaa      300
aaaaaaaaaa aaa                                                         313

<210> SEQ ID NO 65
<211> LENGTH: 420
<212> TYPE: DNA
<213> ORGANISM: Homo sapien
<220> FEATURE:
<221> NAME/KEY: misc_feature
<222> LOCATION: (1)...(420)
<223> OTHER INFORMATION: n = A,T,C or G

<400> SEQUENCE: 65
actagttccc tggcaggcaa gggcttccaa ctgaggcagt gcatgtgtgg cagagagagg       60
caggaagctg gcagtggcag cttctgtgtc tagggagggg tgtggctccc tccttccctg      120
tctgggaggt tggagggaag aatctaggcc ttagcttgcc ctcctgccac ccttcccctt      180
gtagatactg ccttaacact ccctcctctc tcagctgtgt ctgccaccca agccaggttt      240
ctccgtgctc actaatttat ttccaggaaa ggtgtgtgga agacatgagc cgtgtataat      300
atttgtttta acattttcat tgcaagtatt gaccatcatc cttggttgtg tatcgttgta      360
acacaaatta atgatattaa aaagcatcca aacaaagccn annnnnaana nnannngaaa      420

<210> SEQ ID NO 66
<211> LENGTH: 676
<212> TYPE: DNA
<213> ORGANISM: Homo sapien
<220> FEATURE:
<221> NAME/KEY: misc_feature
<222> LOCATION: (1)...(676)
```

```
<223> OTHER INFORMATION: n = A,T,C or G

<400> SEQUENCE: 66
actagtttcc tatgatcatt aaactcattc tcagggttaa gaaaggaatg taaatttctg      60
cctcaatttg tacttcatca ataagttttt gaagagtgca gattttagt caggtcttaa      120 aaataaactc acaaatctgg atgcatttct aaattctgca aatgtttcct ggggtgactt     180
aacaaggaat aatcccacaa tatacctagc tacctaatac atggagctgg ggctcaaccc     240
actgttttta aggatttgcg cttacttgtg gctgaggaaa aataagtagt tccgagggaa     300 gtagtttta aatgtgagct tatagatngg aaacagaata tcaacttaat tatggaaatt     360
gttagaaacc tgttctcttg ttatctgaat cttgattgca attactattg tactggatag    420
actccagccc attgcaaagt ctcagatatc ttanctgtgt agttgaattc cttggaaatt    480 cttttaaga aaaattgga gtttnaaaga aataaacccc tttgttaaat gaagcttggc       540
tttttggtga aaanaatca tcccgcaggg cttattgttt aaaaanggaa ttttaagcct     600
ccctggaaaa anttgttaat taaatgggga aaatgntggg naaaaattat ccgttagggt    660
ttaaagggaa aactta                                                    676

<210> SEQ ID NO 67
<211> LENGTH: 620
<212> TYPE: DNA
<213> ORGANISM: Homo sapien
<220> FEATURE:
<221> NAME/KEY: misc_feature
<222> LOCATION: (1)...(620)
<223> OTHER INFORMATION: n = A,T,C or G

<400> SEQUENCE: 67
caccattaaa gctgcttacc aagaacttcc ccagcatttt gacttccttg tttgatagct     60
gaattgtgag caggtgatag aagagccttt ctagttgaac atacagataa tttgctgaat    120
acattccatt taatgaaggg gttacatctg ttacgaagct actaagaagg agcaagagca    180
taggggaaaa aaatctgatc agaacgcatc aaactcacat gtgcccctc tactacaaac     240 agattgtagt gctgtggtgg tttattccgt tgtgcagaac ttgcaagctg agtcactaaa    300
cccaaagaga ggaaattata ggttagttaa acattgtaat cccaggaact aagtttaatt    360 cactttttgaa gtgttttgtt tttattttt ggtttgtctg atttacttg ggggaaaang    420 ctaaaaaaaa agggatatca atctctaatt cagtgcccac taaaagttgt ccctaaaaag    480
tctttactgg aanttatggg acttttaag ctccaggtnt tttggtcctc caaattaacc    540
ttgcatgggc cccttaaaat tgttgaangg cattcctgcc tctaagtttg gggaaaattc    600
ccccnttttn aaaatttgga                                                620

<210> SEQ ID NO 68
<211> LENGTH: 551
<212> TYPE: DNA
<213> ORGANISM: Homo sapien
<220> FEATURE:
<221> NAME/KEY: misc_feature
<222> LOCATION: (1)...(551)
<223> OTHER INFORMATION: n = A,T,C or G

<400> SEQUENCE: 68
actagtagct ggtacataat cactgaggag ctatttctta acatgctttt atagaccatg     60
ctaatgctag accagtattt aagggctaat ctcacacctc cttagctgta agagtctggc    120
ttagaacaga cctctctgtg caataacttg tggccactgg aaatccctgg gccggcattt    180
```

```
gtattggggt tgcaatgact cccaagggcc aaaagagtta aaggcacgac tgggatttct    240
tctgagactg tggtgaaact ccttccaagg ctgaggggt cagtangtgc tctgggaggg    300
actcggcacc actttgatat tcaacaagcc acttgaagcc caattataaa attgttattt   360
tacagctgat ggaactcaat ttgaaccttc aaaactttgt tagtttatcc tattatattg    420
ttaaacctaa ttacatttgt ctagcattgg atttggttcc tgtngcatat gttttttttcn  480 cctatgtgct cccctccccc nnatcttaat ttaaaccnca attttgcnat tcnccnnnnn    540
nannnannna a                                                        551
```

<210> SEQ ID NO 69
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 69

```
cagaaatgga aagcagagtt ttcatttctg tttataaacg tctccaaaca aaaatggaaa    60
gcagagtttt cattaaatcc ttttacctt ttttttttctt ggtaatcccc tcaaataaca    120
gtatgtggga tattgaatgt taaagggata ttttttttcta ttatttttat aattgtacaa   180
aattaagcaa atgttaaaag ttttatatgc tttattaatg ttttcaaaag gtatnataca   240
tgtgatacat ttttaagct tcagttgctt gtcttctggt actttctgtt atgggctttt     300
ggggagccan aaaccaatct acnatctctt tttgtttgcc aggacatgca ataaaattta    360
aaaaataaat aaaactatt nagaaattga aaaaaa                              396
```

<210> SEQ ID NO 70
<211> LENGTH: 536
<212> TYPE: DNA
<213> ORGANISM: Homo sapien
<220> FEATURE:
<221> NAME/KEY: misc_feature
<222> LOCATION: (1)...(536)
<223> OTHER INFORMATION: n = A,T,C or G

<400> SEQUENCE: 70

```
actagtgcaa aagcaaatat aaacatcgaa aaggcgttcc tcacgttagc tgaagatatc    60
cttcgaaaga cccctgtaaa agagcccaac agtgaaaatg tagatatcag cagtggagga    120
ggcgtgacag gctggaagag caatgctgc tgagcattct cctgttccat cagttgccat     180
ccactacccc gttttctctt cttgctgcaa ataaaccac tctgtccatt tttaactcta     240
aacagatatt tttgtttctc atcttaacta tccaagccac ctattttatt tgttctttca    300
tctgtgactg cttgctgact ttatcataat tttcttcaaa caaaaaaatg tatagaaaaa    360
tcatgtctgt gacttcattt ttaaatgnta cttgctcagc tcaactgcat ttcagttgtt    420
ttatagtcca gttcttatca acattnaaac ctatngcaat catttcaaat ctattctgca    480
aattgtataa gaataaaagt tagaatttaa caattaaaaa aaaaaaaaaa aaaaaa        536
```

<210> SEQ ID NO 71
<211> LENGTH: 865
<212> TYPE: DNA
<213> ORGANISM: Homo sapien
<220> FEATURE:
<221> NAME/KEY: misc_feature
<222> LOCATION: (1)...(865)

<223> OTHER INFORMATION: n = A,T,C or G

<400> SEQUENCE: 71

| | | | | | |
|---|---|---|---|---|---|
| gacaaagcgt | taggagaaga | anagaggcag | ggaanactnc | ccaggcacga | tggccncctt | 60 |
| cccaccagca | accagcgccc | cccaccagcc | cccaggcccg | gacgacgaag | actccatcct | 120 |
| ggattaatct | nacctctntc | gcctgnccca | ttcctacctc | ggaggtggag | gccgaaagg | 180 |
| tcncaccaag | aganaanctg | ctgccaacac | caaccgcccc | agccctggcg | ggcacganag | 240 |
| gaaactggtg | accaatctgc | agaattctna | gaggaanaag | cnaggggccc | cgcgctnaga | 300 |
| cagagctgga | tatgangcca | gaccatggac | nctacncccn | ncaatncana | cgggactgcg | 360 |
| gaagatggan | gacccncgac | nngatcaggc | cngctnncca | nccccccacc | cctatgaatt | 420 |
| attcccgctg | aangaatctc | tganngggctt | ccannaaagc | gcctcccnc | cnaacgnaan | 480 |
| tncaacatng | ggattananng | ctgggaactg | naaggggcaa | ancctnnaat | atccccagaa | 540 |
| acaanctctc | ccnaanaaac | tggggcncct | catnggtggn | accaactatt | aactaaaccg | 600 |
| cacgccaagn | aantataaaa | gggggcccc | tccncggnng | acccccttttt | gtcccttaat | 660 |
| ganggttatc | cnccttgcgt | accatggtnc | ccnnttctgt | ntgnatgttt | ccnctcccct | 720 |
| ccncctatnt | cnagccgaac | tcnnatttnc | ccggggtgc | natcnantng | tncnccttttn | 780 |
| ttngttgncc | cngcccttttc | cgncggaacn | cgtttcccccg | ttantaacgg | cacccgggggn | 840 |
| aagggtgntt | ggcccccctcc | ctccc | | | | 865 |

<210> SEQ ID NO 72
<211> LENGTH: 560
<212> TYPE: DNA
<213> ORGANISM: Homo sapien
<220> FEATURE:
<221> NAME/KEY: misc_feature
<222> LOCATION: (1)...(560)
<223> OTHER INFORMATION: n = A,T,C or G

<400> SEQUENCE: 72

| | | | | | |
|---|---|---|---|---|---|
| cctggacttg | tcttggttcc | agaacctgac | gacccggcga | cggcgacgtc | tcttttgact | 60 |
| aaaagacagt | gtccagtgct | ccngcctagg | agtctacggg | gaccgcctcc | cgcgccgcca | 120 |
| ccatgcccaa | cttctctggc | aactggaaaa | tcatccgatc | ggaaaacttc | gangaattgc | 180 |
| tcnaantgct | gggggtgaat | gtgatgctna | ngaanattgc | tgtggctgca | gcgtccaagc | 240 |
| cagcagtgga | gatcnaacag | gagggagaca | ctttctacat | caaaacctcc | accaccgtgc | 300 |
| gcaccacaaa | gattaacttc | nnngttgggg | agganttttga | ggancaaact | gtggatngga | 360 |
| ngcctgtnaa | aacctggtga | aatgggagaa | tganaataaa | atggtctgtg | ancanaaact | 420 |
| cctgaaagga | gaaggccccc | anaactcctg | gaccngaaaa | actgaccccnc | cnatngggga | 480 |
| actgatnctt | gaaccctgaa | cgggcgggat | ganccttttt | tnttgccncc | naangggttc | 540 |
| tttccntttc | cccaaaaaaa | | | | | 560 |

<210> SEQ ID NO 73
<211> LENGTH: 379
<212> TYPE: DNA
<213> ORGANISM: Homo sapien
<220> FEATURE:
<221> NAME/KEY: misc_feature
<222> LOCATION: (1)...(379)
<223> OTHER INFORMATION: n = A,T,C or G

<400> SEQUENCE: 73

| | | | | | |
|---|---|---|---|---|---|
| ctggggancc | ggcggtnngc | nccatntcnn | gncgcgaagg | tggcaataaa | aanccnctga | 60 |

```
aaccgcncaa naaacatgcc naagatatgg acgaggaaga tngngctttc nngnacaanc     120
gnanngagga acanaacaaa ctcnangagc tctcaagcta atgccgcggg aaggggccc      180 ttggccacnn gtggaattaa gaaatctggc aaanngtann tgttccttgt gcctnangag     240
ataagngacc cttatttca tctgtattta aacctctctn ttccctgnca taacttcttt     300
tnccacgtan agntggaant anttgttgtc ttggactgtt gtncatttta gannaaactt    360
ttgttcaaaa aaaaaataa                                                  379
```

```
<210> SEQ ID NO 74
<211> LENGTH: 437
<212> TYPE: DNA
<213> ORGANISM: Homo sapien
<220> FEATURE:
<221> NAME/KEY: misc_feature
<222> LOCATION: (1)...(437)
<223> OTHER INFORMATION: n = A,T,C or G

<400> SEQUENCE: 74
actagttcag actgccacgc caaccccaga aaatacccca catgccagaa aagtgaagtc     60
ctaggtgttt ccatctatgt ttcaatctgt ccatctacca ggcctcgcga taaaaacaaa    120
acaaaaaaac gctgccaggt tttanaagca gttctggtct caaaaccatc aggatcctgc    180
caccagggtt cttttgaaat agtaccacat gtaaaggga atttggcttt cacttcatct     240
aatcactgaa ttgtcaggct ttgattgata attgtagaaa taagtagcct tctgttgtgg    300
gaataagtta taatcagtat tcatctcttt gttttttgtc actcttttct ctctnattgt    360
gtcatttgta ctgtttgaaa atatttctt ctataaaatt aaactaacct gccttaaaaa     420
aaaaaaaaaa aaaaaaa                                                    437
```

```
<210> SEQ ID NO 75
<211> LENGTH: 579
<212> TYPE: DNA
<213> ORGANISM: Homo sapien
<220> FEATURE:
<221> NAME/KEY: misc_feature
<222> LOCATION: (1)...(579)
<223> OTHER INFORMATION: n = A,T,C or G

<400> SEQUENCE: 75
ctccgtcgcc gccaagatga tgtgcggggc gccctccgcc acgcagccgg ccaccgccga     60
gacccagcac atcgccgacc aggtgaggtc ccagcttgaa gagaaagaaa acaagaagtt    120
ccctgtgttt aaggccgtgt cattcaagag ccaggtggtc gcggggacaa actacttcat    180
caaggtgcac gtcggcgacg aggacttcgt acacctgcga gtgttccaat ctctccctca    240
tgaaaacaag cccttgacct tatctaacta ccagaccaac aaagccaagc atgatgagct    300
gacctatttc tgatcctgac tttggacaag gcccttcagc cagaagactg acaaagtcat    360
cctccgtcta ccagagcgtg cacttgtgat cctaaaataa gcttcatctc cgggctgtgc    420
ccttggggtg aaggggcan gatctgcact gcttttgcat ttctcttcct aaatttcatt    480
gtgttgattc tttccttcca ataggtgatc ttnattactt tcagaatatt ttccaaatna    540
gatatatttt naaatccctt aaaaaaaaaa aaaaaaaa                             579
```

```
<210> SEQ ID NO 76
<211> LENGTH: 666
<212> TYPE: DNA
<213> ORGANISM: Homo sapien
<220> FEATURE:
```

<221> NAME/KEY: misc_feature
<222> LOCATION: (1)...(666)
<223> OTHER INFORMATION: n = A,T,C or G

<400> SEQUENCE: 76

| | | |
|---|---|---|
| gtttatccta tctctccaac cagattgtca gctccttgag ggcaagagcc acagtatatt | 60 |
| tccctgtttc ttccacagtg cctaataata ctgtggaact aggttttaat aatttttaa | 120 |
| ttgatgttgt tatgggcagg atggcaacca gaccattgtc tcagagcagg tgctggctct | 180 |
| ttcctggcta ctccatgttg gctagcctct ggtaacctct tacttattat cttcaggaca | 240 |
| ctcactacag ggaccaggga tgatgcaaca tccttgtctt tttatgacag gatgtttgct | 300 |
| cagcttctcc aacaataaaa agcacgtggt aaaacacttg cggatattct ggactgtttt | 360 |
| taaaaaatat acagtttacc gaaaatcata ttatcttaca atgaaaagga ntttatagat | 420 |
| cagccagtga acaacctttt cccaccatac aaaaattcct tttcccgaan gaaaanggct | 480 |
| ttctcaataa ncctcactt cttaanatct tacaagatag ccccganatc ttatcgaaac | 540 |
| tcattttagg caaatatgan ttttattgtn cgttacttgt ttcaaaattt ggtattgtga | 600 |
| atatcaatta ccaccccat ctcccatgaa anaaanggga aanggtgaan ttcntaancg | 660 |
| cttaaa | 666 |

<210> SEQ ID NO 77
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 77

| | | |
|---|---|---|
| ctgcagcccg ggggatccac taatctacca nggttatttg gcagctaatt ctanatttgg | 60 |
| atcattgccc aaagttgcac ttgctggtct cttgggatt ggccttggaa aggtatcata | 120 |
| catanganta tgccanaata aattccattt ttttgaaaat canctccntg gggctggttt | 180 |
| tggtccacag cataacangc actgcctcct tacctgtgag gaatgcaaaa taaagcatgg | 240 |
| attaagtgag aagggagact ctcagccttc agcttcctaa attctgtgtc tgtgactttc | 300 |
| gaagttttt aaacctctga atttgtacac atttaaaatt tcaagtgtac tttaaaataa | 360 |
| aatacttcta atgggaacaa aaaaaaaaaa aaaaaa | 396 |

<210> SEQ ID NO 78
<211> LENGTH: 793
<212> TYPE: DNA
<213> ORGANISM: Homo sapien
<220> FEATURE:
<221> NAME/KEY: misc_feature
<222> LOCATION: (1)...(793)
<223> OTHER INFORMATION: n = A,T,C or G

<400> SEQUENCE: 78

| | | |
|---|---|---|
| gcatcctagc cgccgactca cacaaggcag gtgggtgagg aaatccagag ttgccatgga | 60 |
| gaaaattcca gtgtcagcat tcttgctcct tgtggccctc tcctcactc tggccagaga | 120 |
| taccacagtc aaacctggag ccaaaaagga cacaaggac tctcgaccca aactgcccca | 180 |
| gaccctctcc agaggttggg gtgaccaact catctggact cagacatatg aagaagctct | 240 |
| atataaatcc aagacaagca acaaaccctt gatgattatt catcacttgg atgagtgccc | 300 |
| acacagtcna gctttaaaga aagtgtttgc tgaaaataaa gaaatccaga aattggcaga | 360 |

```
gcagtttgtc ctcctcaatc tggtttatga acaactgac aaacacctttt ctcctgatgg      420 ccagtatgtc ccaggattat gtttgttgac ccatctctga cagttgaagc cgatatcctg      480
ggaagatatt cnaaccgtct ctatgcttac aaactgcaga tacgctctgt tgcttgacac      540
atgaaaaagc tctcaagttg ctnaaaatga attgtaagaa aaaaaatctc cagccttctg      600
tctgtcggct tgaaaattga aaccagaaaa atgtgaaaaa tggctattgt ggaacanatn      660
gacacctgat taggttttgg ttatgttcac cactattttt aanaaaanan nttttaaaat      720
ttggttcaat tntctttttn aaacaatntg tttctacntt ngnanctgat ttctaaaaaa      780
aataatnttt ggc                                                        793
```

<210> SEQ ID NO 79
<211> LENGTH: 456
<212> TYPE: DNA
<213> ORGANISM: Homo sapien
<220> FEATURE:
<221> NAME/KEY: misc_feature
<222> LOCATION: (1)...(456)
<223> OTHER INFORMATION: n = A,T,C or G

<400> SEQUENCE: 79

```
actagtatgg ggtgggaggc cccaccttc tcccctaggc gctgttcttg ctccaaaggg       60
ctccgtggag agggactggc agagctgang ccacctgggg ctgggatcc cactcttctt      120 gcagctgttg agcgcaccta accactggtc atgcccccac cctgctctc cgcacccgct      180 tcctcccgac cccangacca ggctacttct cccctcctct tgcctccctc ctgcccctgc      240
tgcctctgat cgtangaatt gangantgtc ccgccttgtg gctganaatg gacagtggca      300
ggggctggaa atgggtgtgt gtgtgtgtgt gtgtgtgtgt gtgtgtgtgt gcnccccccc      360
tgcaagaccg agattgaggg aaancatgtc tgctgggtgt gaccatgttt cctctccata      420 aantnccct gtgacnctca naaaaaaaaa aaaaaa                                456
```

<210> SEQ ID NO 80
<211> LENGTH: 284
<212> TYPE: DNA
<213> ORGANISM: Homo sapien
<220> FEATURE:
<221> NAME/KEY: misc_feature
<222> LOCATION: (1)...(284)
<223> OTHER INFORMATION: n = A,T,C or G

<400> SEQUENCE: 80

```
ctttgtacct ctagaaaaga taggtattgt gtcatgaaac ttgagtttaa atttatata       60 taaaactaaa agtaatgctc actttagcaa cacatactaa aattggaacc atactgagaa     120
gaatagcatg acctccgtgc aaacaggaca agcaaatttg tgatgtgttg attaaaaga      180 aataaataaa tgtgtatatg tgtaacttgt atgtttatgt ggaatacaga ttgggaaata     240
aaatgtattt cttactgtga aaaaaaaaa aaaaaaaaa aana                        284
```

<210> SEQ ID NO 81
<211> LENGTH: 671
<212> TYPE: DNA
<213> ORGANISM: Homo sapien
<220> FEATURE:
<221> NAME/KEY: misc_feature
<222> LOCATION: (1)...(671)
<223> OTHER INFORMATION: n = A,T,C or G

<400> SEQUENCE: 81

-continued

| | |
|---|---|
| gccaccaaca ttccaagcta ccctgggtac ctttgtgcag tagaagctag tgagcatgtg | 60 |
| agcaagcggt gtgcacacgg agactcatcg ttataattta ctatctgcca agagtagaaa | 120 |
| gaaaggctgg ggatatttgg gttggcttgg ttttgatttt ttgcttgttt gtttgttttg | 180 |
| tactaaaaca gtattatctt ttgaatatcg tagggacata agtatataca tgttatccaa | 240 |
| tcaagatggc tagaatggtg cctttctgag tgtctaaaac ttgacacccc tggtaaatct | 300 |
| ttcaacacac ttccactgcc tgcgtaatga agttttgatt cattttaac cactggaatt | 360 |
| tttcaatgcc gtcattttca gttagatnat tttgcacttt gagattaaaa tgccatgtct | 420 |
| atttgattag tcttattttt ttattttac aggcttatca gtctcactgt tggctgtcat | 480 |
| tgtgacaaag tcaaataaac ccccnaggac aacacacagt atgggatcac atattgtttg | 540 |
| acattaagct ttggccaaaa aatgttgcat gtgttttacc tcgacttgct aaatcaatan | 600 |
| canaaaggct ggctnataat gttggtggtg aaataattaa tnantaacca aaaaaaaaan | 660 |
| aaaaaaaaaa a | 671 |

<210> SEQ ID NO 82
<211> LENGTH: 217
<212> TYPE: DNA
<213> ORGANISM: Homo sapien
<220> FEATURE:
<221> NAME/KEY: misc_feature
<222> LOCATION: (1)...(217)
<223> OTHER INFORMATION: n = A,T,C or G

<400> SEQUENCE: 82

| | |
|---|---|
| ctgcagatgt ttcttgaatg ctttgtcaaa ttaanaaagt taaagtgcaa taatgtttga | 60 |
| agacaataag tggtggtgta tcttgtttct aataagataa acttttttgt ctttgcttta | 120 |
| tcttattagg gagttgtatg tcagtgtata aaacatactg tgtggtataa caggcttaat | 180 |
| aaattcttta aaggaaaaa aaaaaaaaaa aaaaaaa | 217 |

<210> SEQ ID NO 83
<211> LENGTH: 460
<212> TYPE: DNA
<213> ORGANISM: Homo sapien
<220> FEATURE:
<221> NAME/KEY: misc_feature
<222> LOCATION: (1)...(460)
<223> OTHER INFORMATION: n = A,T,C or G

<400> SEQUENCE: 83

| | |
|---|---|
| cgcgagtggg agcaccagga tctcgggctc ggaacgagac tgcacggatt gttttaagaa | 60 |
| aatggcagac aaaccagaca tgggggaaat cgccagcttc gatnaggcca agctgaanaa | 120 |
| aacggagacg caggagaaga acaccctgcc gaccaaagag accattgagc angagaagcg | 180 |
| gagtgaaatt tcctaagatc ctggaggatt tcctaccccc gtcctcttcg agaccccagt | 240 |
| cgtgatgtgg aggaagagcc acctgcaaga tggacacgag ccacaagctg cactgtgaac | 300 |
| ctgggcactc cgcgccgatg ccaccggcct gtgggtctct gaaggggccc ccccaatcg | 360 |
| gactgccaaa ttctccggtt tgccccggga tattatacaa nattatttgt atgaataatg | 420 |
| annataaaac acacctcgtg gcancaaana aaaaaaaaa | 460 |

<210> SEQ ID NO 84
<211> LENGTH: 323
<212> TYPE: DNA
<213> ORGANISM: Homo sapien
<220> FEATURE:
<221> NAME/KEY: misc_feature

```
<222> LOCATION: (1)...(323)
<223> OTHER INFORMATION: n = A,T,C or G

<400> SEQUENCE: 84
tggtggatct tggctctgtg gagctgctgg gacgggatct aaaagactat tctggaagct    60
gtggtccaan gcattttgct ggcttaacgg gtcccggaac aaaggacacc agctctctaa   120
aattgaagtt tacccganat aacaatcttt tgggcagaga tgcctatttt aacaaacncc   180
gtccctgcgc aacaacnaac aatctctggg aaataccggc catgaacntg ctgtctcaat   240
cnancatctc tctagctgac cgatcatatc gtcccagatt actacanatc ataataattg   300
atttcctgta naaaaaaaaa aaa                                           323

<210> SEQ ID NO 85
<211> LENGTH: 771
<212> TYPE: DNA
<213> ORGANISM: Homo sapien
<220> FEATURE:
<221> NAME/KEY: misc_feature
<222> LOCATION: (1)...(771)
<223> OTHER INFORMATION: n = A,T,C or G

<400> SEQUENCE: 85
aaactgggta ctcaacactg agcagatctg ttctttgagc taaaaccat gtgctgtacc     60 aanagtttgc tcctggctgc tttgatgtca gtgctgctac tccacctctg cggcgaatca   120
gaagcaagca actttgactg ctgtcttgga tacacagacc gtattcttca tcctaaattt   180
attgtgggct tcacacggca gctggccaat gaaggctgtg acatcaatgc tatcatcttt   240
cacacaaaga aaaagttgtc tgtgtgcgca atccaaaac agacttgggt gaaatatatt    300
gtgcgtctcc tcagtaaaaa agtcaagaac atgtaaaaac tgtggctttt ctggaatgga   360
attggacata gcccaagaac agaaagaact tgctggggtt ggaggtttca cttgcacatc   420
atgganggtt tagtgcttat cttatttgtg cctcctggac ttgtccaatt natgaagtta   480
atcatattgc atcatantt gctttgttta acatcacatt naaattaaac tgtattttat    540
gttatttata gctntaggtt ttctgtgttt aacttttttat acnaantttc ctaaactatt   600
ttggtntant gcaanttaaa aattatattt ggggggggaa taaatattgg antttctgca   660
gccacaagct tttttaaaa aaccantaca nccnngttaa atggtnggtc ccnaatggtt    720
tttgcttttn antagaaaat ttnttagaac natttgaaaa aaaaaaaaaa a            771

<210> SEQ ID NO 86
<211> LENGTH: 628
<212> TYPE: DNA
<213> ORGANISM: Homo sapien
<220> FEATURE:
<221> NAME/KEY: misc_feature
<222> LOCATION: (1)...(628)
<223> OTHER INFORMATION: n = A,T,C or G

<400> SEQUENCE: 86
actagtttgc tttacatttt tgaaaagtat tatttttgtc caagtgctta tcaactaaac    60
cttgtgttag gtaagaatgg aatttattaa gtgaatcagt gtgaccttc ttgtcataag   120 attatcttaa agctgaagcc aaaatatgct tcaaaagaaa angactttat tgttcattgt   180
agttcataca ttcaaagcat ctgaactgta gtttctatag caagccaatt acatccataa   240
gtggagaaag aaatagatta atgtcnaagt atgattggtg gagggagcaa ggttgaagat   300
aatctggggt tgaaattttc tagttttcat tctgtacatt tttagttnga catcagattt   360
```

-continued

| | |
|---|---|
| gaaatattaa tgtttaccttt tcaatgtgtg gtatcagctg gactcantaa caccccttc | 420 |
| ttccctngggg gatggggaat ggattattgg aaaatggaaa gaaaaagta cttaaagcct | 480 |
| tcctttcnca gtttctggct cctaccctac tgatttaacc agaataagaa aacatttat | 540 |
| catcntctgc tttattccca ttaatnaant tttgatgaat aaatctgctt ttatgcnnac | 600 |
| ccaaggaatt nagtggnttc ntcnttgt | 628 |

<210> SEQ ID NO 87
<211> LENGTH: 518
<212> TYPE: DNA
<213> ORGANISM: Homo sapien
<220> FEATURE:
<221> NAME/KEY: misc_feature
<222> LOCATION: (1)...(518)
<223> OTHER INFORMATION: n = A,T,C or G

<400> SEQUENCE: 87

| | |
|---|---|
| tttttattt ttttagaga gtagttcagc ttttatttat aaatttattg cctgttttat | 60 |
| tataacaaca ttatactgtt tatggtttaa tacatatggt tcaaaatgta taatacatca | 120 |
| agtagtacag ttttaaaatt ttatgcttaa aacaagtttt gtgtaaaaaa tgcagataca | 180 |
| ttttacatgg caaatcaatt tttaagtcat cctaaaaatt gatttttttt tgaaatttaa | 240 |
| aaacacattt aatttcaatt tctctcttat ataacctta ttactatagc atggtttcca | 300 |
| ctacagttta acaatgcagc aaaattccca tttcacggta aattgggttt taagcggcaa | 360 |
| ggttaaaatg ctttgaggat cctnaatacc ctttgaactt caaatgaagg ttatggttgt | 420 |
| naatttaacc ctcatgccat aagcagaagc acaagtttag ctgcatttg ctctaaactg | 480 |
| taaaancgag cccccgttg aaaagcaaa agggaccc | 518 |

<210> SEQ ID NO 88
<211> LENGTH: 1844
<212> TYPE: DNA
<213> ORGANISM: Homo sapien

<400> SEQUENCE: 88

| | |
|---|---|
| gagacagtga atcctagtat caaggatttt ttggcctcag aaaaagttgt tgattatttt | 60 |
| tattttattt tattttttcga gactccgtct caaaaaaaaa aaaaaaaaaa agaatcacaa | 120 |
| ggtatttgct aaagcatttt gagctgcttg gaaaagggga agtagttgca gtagagtttc | 180 |
| ttccatcttc ttggtgctgg gaagccatat atgtgtcttt tactcaagct aaggggtata | 240 |
| agcttatgtg ttgaatttgc tacatctata tttcacatat tctcacaata agagaatttt | 300 |
| gaaatagaaa tatcatagaa catttaagaa agtttagtat aaataatatt ttgtgtgttt | 360 |
| taatcccttt gaagggatct atccaaagaa aatattttac actgagctcc ttcctacacg | 420 |
| tctcagtaac agatcctgtg ttagtctttg aaaatagctc attttttaaa tgtcagtgag | 480 |
| tagatgtagc atacatatga tgtataatga cgtgtattat gttaacaatg tctgcagatt | 540 |
| ttgtaggaat acaaaacatg gcctttttta taagcaaaac gggccaatga ctagaataac | 600 |
| acatagggca atctgtgaat atgtattata agcagcattc cagaaaagta gttggtgaaa | 660 |
| taattttcaa gtcaaaaagg gatatggaaa gggaattatg agtaacctct attttttaag | 720 |
| ccttgctttt aaattaaacg ctacagccat ttaagccttg aggataataa agcttgagag | 780 |
| taataatgtt aggttagcaa aggtttagat gtatcacttc atgcatgcta ccatgatagt | 840 |
| aatgcagctc ttcgagtcat ttctggtcat tcaagatatt cacccttttg cccatagaaa | 900 |
| gcaccctacc tcacctgctt actgacattg tcttagctga tcacaagatc attatcagcc | 960 |

```
tccattattc cttactgtat ataaaataca gagtttttata ttttcctttc ttcgttttc      1020 accatattca aaacctaaat ttgttttttgc agatggaatg caaagtaatc aagtgttcgt     1080
gctttcacct agaagggtgt ggtcctgaag gaaagaggtc cctaaatatc ccccaccctg     1140
ggtgctcctc cttccctggt accctgacta ccagaagtca ggtgctagag cagctggaga    1200
agtgcagcag cctgtgcttc cacagatggg ggtgctgctg caacaaggct ttcaatgtgc    1260
ccatcttagg gggagaagct agatcctgtg cagcagcctg gtaagtcctg aggaggttcc    1320
attgctcttc ctgctgctgt cctttgcttc tcaacggggc tcgctctaca gtctagagca    1380
catgcagcta acttgtgcct ctgcttatgc atgagggtta aattaacaac cataaccttc    1440
atttgaagtt caaaggtgta ttcaggatcc tcaaagcatt ttaaccttgc cgcttaaaac    1500
ccaatttacc gtgaaatggg aattttgctg cattgttaaa ctgtagtgga accatgcta    1560 tagtaataaa ggttatataa gagagaaatt gaaattaaat gtgttttttaa atttcaaaaa    1620 aaaatcaatc tttaggatga cttaaaaatt gatttgccat gtaaaatgta tctgcatttt    1680
ttacacaaaa cttgttttaa gcataaaatt ttaaaactgt actacttgat gtattataca    1740
ttttgaacca tatgtattaa accataaaca gtataatgtt gttataataa aacaggcaat    1800
aaatttataa ataaaagctg aaaaaaaaaa aaaaaaaaa aaaa                       1844

<210> SEQ ID NO 89
<211> LENGTH: 523
<212> TYPE: DNA
<213> ORGANISM: Homo sapien
<220> FEATURE:
<221> NAME/KEY: misc_feature
<222> LOCATION: (1)...(523)
<223> OTHER INFORMATION: n = A,T,C or G

<400> SEQUENCE: 89 ttttttttt tttttttagt caatccacat ttattgatca cttattatgt accaggcact       60
gggataaaga tgactgttag tcactcacag taaggaagaa aactagcaaa taagacgatt     120
acaatatgat gtagaaaatg ctaagccaga gatatagaaa ggtcctattg ggtccttctg     180
tcaccttgtc tttccacatc cctacccttc acaggccttc cctccagctt cctgcccccg     240
ctccccactg cagatcccct gggattttgc ctagagctaa acgagganat gggccccctg     300
gccctggcat gacttgaacc caaccacaga ctgggaaagg gagcctttcg anagtggatc     360
actttgatna gaaaacacat agggaattga agagaaantc cccaaatggc cacccgtgct     420
ggtgctcaag aaaagtttgc agaatggata aatgaaggat caagggaatt aatanatgaa     480
taattgaatg gtggctcaat aagaatgact ncnttgaatg acc                       523

<210> SEQ ID NO 90
<211> LENGTH: 604
<212> TYPE: DNA
<213> ORGANISM: Homo sapien
<220> FEATURE:
<221> NAME/KEY: misc_feature
<222> LOCATION: (1)...(604)
<223> OTHER INFORMATION: n = A,T,C or G

<400> SEQUENCE: 90
ccagtgtggt ggaatgcaaa gattaccccg gaagctttcg agaagctggg attccctgca       60
gcaaaggaaa tagccaatat gtgtcgtttc tatgaaatga agccagaccg agatgtcaat     120
ctcacccacc aactaaatcc caaagtcaaa agcttcagcc agtttatctc agagaaccag     180
```

-continued

```
gggagccttc aagggcatgt agaaaatcag ctgttcagat aggcctctgc accacacagc      240
ctctttcctc tctgatcctt ttcctcttta cggcacaaca ttcatgtttg acagaacatg      300
ctggaatgca attgtttgca acaccgaagg atttcctgcg gtcgcctctt cagtaggaag      360
cactgcattg gtgataggac acggtaattt gattcacatt taacttgcta gttagtgata      420
aggggtggta cacctgtttg gtaaaatgag aagcctcgga aacttgggag cttctctcct      480
accactaatg gggagggcag attattactg ggatttctcc tggggtgaat taatttcaag      540
ccctaattgc tgaaattccc ctnggcaggc tccagttttc tcaactgcat tgcaaaattc      600
cccc                                                                   604
```

<210> SEQ ID NO 91
<211> LENGTH: 858
<212> TYPE: DNA
<213> ORGANISM: Homo sapien
<220> FEATURE:
<221> NAME/KEY: misc_feature
<222> LOCATION: (1)...(858)
<223> OTHER INFORMATION: n = A,T,C or G

<400> SEQUENCE: 91

```
ttttttttt ttttttttta tgattattat ttttttatt gatctttaca tcctcagtgt        60
tggcagagtt tctgatgctt aataaacatt tgttctgatc agataagtgg aaaaaattgt      120
catttcctta ttcaagccat gcttttctgt gatattctga tcctagttga acatacagaa      180
ataaatgtct aaaacagcac ctcgattctc gtctataaca ggactaagtt cactgtgatc      240
ttaaataagc ttggctaaaa tgggacatga gtggaggtag tcacacttca gcgaagaaag      300
agaatctcct gtataatctc accaggagat tcaacgaatt ccaccacact ggactagtgg      360
atcccccggg ctgcaggaat tcgatatcaa gcttatcgat accgtcgacc tcgagggggg      420
gcccggtacc caattcgccc tatagtgagt cgtattacgc gcgctcactg gccgtcgttt      480
tacaacgtcg tgactgggaa aaccctggcg ttacccaact taatcgcctt gcagcacatc      540 ccccttcgc cagctggcgt aatagcgaan agcccgcacc gatcgccctt naacagttg      600 cgcagcctga atggcgaatg ggacgcgccc tgtagcggcg cattaaagcg ggcngggtg      660 tggnggntcc cccacgtgac cgntacactt ggcagcgcct tacgccggtc nttcgctttc      720
ttcccttcct ttctcgcacc gttcgccggg tttccccgnn agctnttaat cggggggnctc      780 cctttanggg tncnaattaa nggnttacng gaccttngan cccaaaaact ttgattaggg      840
ggaaggtccc cgaagggg                                                    858
```

<210> SEQ ID NO 92
<211> LENGTH: 585
<212> TYPE: DNA
<213> ORGANISM: Homo sapien
<220> FEATURE:
<221> NAME/KEY: misc_feature
<222> LOCATION: (1)...(585)
<223> OTHER INFORMATION: n = A,T,C or G

<400> SEQUENCE: 92

```
gttgaatctc ctggtgagat tatacaggag attctctttc ttcgctgaag tgtgactacc       60
tccactcatg tcccatttta gccaagctta tttaagatca cagtgaactt agtcctgtta      120
tagacgagaa tcgaggtgct gttttagaca tttatttctg tatgttcaac taggatcaga      180
atatcacaga aaagcatggc ttgaataagg aaatgacaat ttttccact tatctgatca       240 gaacaaatgt ttattaagca tcagaaactc tgccaacact gaggatgtaa agatcaataa      300
```

```
aaaaaataat aatcatnann naaanannan nngaagggcg gccgccaccg cggtggagct    360
ccagcttttg ttccctttag tgagggttaa ttgcgcgctt ggcgttaatc atggtcatag    420
ctgtttcctg tgtgaaattg ttatccggct cacaattccn cncaacatac gagccgggaa    480
gcntnangtg taaaagcctg ggggtgccta attgagtgag ctnactcaca ttaattgngt    540
tgcgctccac ttgcccgctt ttccantccg ggaaacctgt tcgnc                   585
```

<210> SEQ ID NO 93
<211> LENGTH: 567
<212> TYPE: DNA
<213> ORGANISM: Homo sapien
<220> FEATURE:
<221> NAME/KEY: misc_feature
<222> LOCATION: (1)...(567)
<223> OTHER INFORMATION: n = A,T,C or G

<400> SEQUENCE: 93

```
cggcagtgtt gctgtctgcg tgtccacctt ggaatctggc tgaactggct gggaggacca     60
agactgcggc tggggtgggc anggaaggga accgggggct gctgtgaagg atcttggaac    120
ttccctgtac ccaccttccc cttgcttcat gtttgtanag gaaccttgtg ccggccaagc    180
ccagtttcct tgtgtgatac actaatgtat ttgcttttt tgggaaatan anaaaaatca    240
attaaattgc tantgtttct ttgaannnnn nnnnnnnnnn nnnnnnnggg ggggncgccc    300
ccncggngga aacnccccct tttgttccct ttaattgaaa ggttaattng cncncntggc    360
gttaanccnt gggccaaanc tngttncccg tgntgaaatt gttatcccc tcccaaattc     420 cccccnncc ttccaaaccc ggaaanccnn annntgttna ncccgggggg gttgcctaan    480
ngnaattnaa ccnaaccccc ntttaaatng nntttgcncn ccacnngccc cnctttccca    540
nttcggggaa aaccctntcc gtgccca                                       567
```

<210> SEQ ID NO 94
<211> LENGTH: 620
<212> TYPE: DNA
<213> ORGANISM: Homo sapien
<220> FEATURE:
<221> NAME/KEY: misc_feature
<222> LOCATION: (1)...(620)
<223> OTHER INFORMATION: n = A,T,C or G

<400> SEQUENCE: 94

```
actagtcaaa aatgctaaaa taatttggga gaaatatttt ttaagtagt gttatagttt      60 catgtttatc ttttattatg ttttgtgaag ttgtgtcttt tcactaatta cctatactat    120
gccaatattt ccttatatct atccataaca tttatactac atttgtaana naatatgcac    180
gtgaaactta acactttata aggtaaaaat gaggtttcca anatttaata atctgatcaa    240
gttcttgtta tttccaaata gaatggactt ggtctgttaa gggctaagga gaagaggaag    300
ataaggttaa aagttgttaa tgaccaaaca ttctaaaaga aatgcaaaaa aaaagttttat   360 tttcaagcct tcgaactatt taaggaaagc aaaatcattt cctaaatgca tatcatttgt    420
gagaatttct cattaatatc ctgaatcatt catttcacta aggctcatgt tnactccgat    480
atgtctctaa gaaagtacta tttcatggtc caaacctggt tgccatantt gggtaaaggc    540
tttcccttaa gtgtgaaant atttaaaatg aaattttcct ctttttaaaa attctttana   600
agggttaagg gtgttgggga                                               620
```

<210> SEQ ID NO 95

<211> LENGTH: 470
<212> TYPE: DNA
<213> ORGANISM: Homo sapien
<220> FEATURE:
<221> NAME/KEY: misc_feature
<222> LOCATION: (1)...(470)
<223> OTHER INFORMATION: n = A,T,C or G

<400> SEQUENCE: 95

| | | | | | |
|---|---|---|---|---|---|
| ctcgaccttc | tctgcacagc | ggatgaaccc | tgagcagctg | aagaccagaa | aagccactat | 60 |
| nactttntgc | ttaattcang | agcttacang | attcttcaaa | gagtgngtcc | agcatccttt | 120 |
| gaaacatgag | ttcttaccag | cagaagcaga | cctttacccc | accacctcag | cttcaacagc | 180 |
| agcaggtgaa | acaacccatc | cagcctccac | ctnaggaaat | atttgttccc | acaaccaagg | 240 |
| agccatgcca | ctcaaaggtt | ccacaacctg | naaacacaaa | nattccagag | ccaggctgta | 300 |
| ccaaggtccc | tgagccaggg | ctgtaccaan | gtccctgagc | caggttgtac | caangtccct | 360 |
| gagccaggat | gtaccaaggt | ccctgancca | ggttgtccaa | ggtccctgag | ccaggctaca | 420 |
| ccaagggcct | gngccaggca | gcatcaangt | ccctgaccaa | ggcttatcaa | | 470 |

<210> SEQ ID NO 96
<211> LENGTH: 660
<212> TYPE: DNA
<213> ORGANISM: Homo sapien
<220> FEATURE:
<221> NAME/KEY: misc_feature
<222> LOCATION: (1)...(660)
<223> OTHER INFORMATION: n = A,T,C or G

<400> SEQUENCE: 96

| | | | | | |
|---|---|---|---|---|---|
| tttttttttt | tttttttttt | ggaattaaaa | gcaatttaat | gagggcagag | caggaaacat | 60 |
| gcatttcttt | tcattcgaat | cttcagatga | accctgagca | gccgaagacc | agaaaagcca | 120 |
| tgaagacttt | ctgcttaatt | caggggctta | caggattctt | cagagtgtgt | gtgaacaaaa | 180 |
| gctttatagt | acgtattttt | aggatacaaa | taagagagag | actatggctt | ggggtgagaa | 240 |
| tgtactgatt | acaaggtcta | cagacaatta | agacacagaa | acagatggga | agagggtgnc | 300 |
| cagcatctgg | nggttggctt | ctcaagggct | tgtctgtgca | ccaaattact | tctgcttggn | 360 |
| cttctgctga | gctgggcctg | gagtgaccgt | tgaaggacat | ggctctggta | cctttgtgta | 420 |
| gcctgncaca | ggaactttgg | tgtatccttg | ctcaggaact | ttgatggcac | ctggctcagg | 480 |
| aaacttgatg | aagccttggt | caagggacct | tgatgcttgc | tggctcaggg | accttggngn | 540 |
| ancctgggct | canggaccct | tgncncaacc | ttggcttcaa | gggacccttg | gnacatcctg | 600 |
| gcnnagggac | ccttgggncc | aaccctgggc | ttnagggacc | ctttggntnc | nanccttggc | 660 |

<210> SEQ ID NO 97
<211> LENGTH: 441
<212> TYPE: DNA
<213> ORGANISM: Homo sapien
<220> FEATURE:
<221> NAME/KEY: misc_feature
<222> LOCATION: (1)...(441)
<223> OTHER INFORMATION: n = A,T,C or G

<400> SEQUENCE: 97

| | | | | | |
|---|---|---|---|---|---|
| gggaccatac | anagtattcc | tctcttcaca | ccaggaccag | ccactgttgc | agcatgagtt | 60 |
| cccagcagca | gaagcagccc | tgcatcccac | cccctcagct | tcagcagcag | caggtgaaac | 120 |
| agccttgcca | gcctccacct | caggaaccat | gcatcccaa | aaccaaggag | ccctgccacc | 180 |
| ccaaggtgcc | tgagccctgc | caccccaaag | tgcctgagcc | ctgccagccc | aaggttccag | 240 |

| agccatgcca cccccaaggtg cctgagccct gcccttcaat agtcactcca gcaccagccc | 300 |
| agcagaanac caagcagaag taatgtggtc cacagccatg cccttgagga gccggccacc | 360 |
| agatgctgaa tccctatcc cattctgtgt atgagtccca tttgccttgc aattagcatt | 420 |
| ctgtctcccc caaaaaaaaa a | 441 |

```
<210> SEQ ID NO 98
<211> LENGTH: 600
<212> TYPE: DNA
<213> ORGANISM: Homo sapien
<220> FEATURE:
<221> NAME/KEY: misc_feature
<222> LOCATION: (1)...(600)
<223> OTHER INFORMATION: n = A,T,C or G

<400> SEQUENCE: 98
```

| gtattcctct cttcacacca ggaccagcca ctgttgcagc atgagttccc agcagcagaa | 60 |
| gcagccctgc atcccacccc ctcagcttca gcagcagcag gtgaaacagc cttgccagcc | 120 |
| tccacctcag gaaccatgca tccccaaaac caaggagccc tgccaccccca aggtgcctga | 180 |
| gccctgccac cccaaagtgc ctgagccctg ccagcccaag gttccagagc catgccaccc | 240 |
| caaggtgcct gagccctgcc cttcaatagt cactccagca ccagcccagc agaanaccaa | 300 |
| gcagaagtaa tgtggtccac agccatgccc ttgaggagcc ggccaccana tgctgaatcc | 360 |
| cctatcccat tctgtgtatg agtcccattt gccttgcaat tagcattctg tctccccccaa | 420 |
| aaaagaatgt gctatgaagc tttctttcct acacactctg agtctctgaa tgaagctgaa | 480 |
| ggtcttaant acaganctag ttttcagctg ctcagaattc tctgaagaaa agatttaaga | 540 |
| tgaaaggcaa atgattcagc tccttattac cccattaaat tcnctttcaa ttccaaaaaa | 600 |

```
<210> SEQ ID NO 99
<211> LENGTH: 667
<212> TYPE: DNA
<213> ORGANISM: Homo sapien
<220> FEATURE:
<221> NAME/KEY: misc_feature
<222> LOCATION: (1)...(667)
<223> OTHER INFORMATION: n = A,T,C or G

<400> SEQUENCE: 99
```

| actagtgact gagttcctgg caaagaaatt tgacctggac cagttgataa ctcatgtttt | 60 |
| accatttaaa aaaatcagtg aaggatttga gctgctcaat tcaggacaaa gcattcgaac | 120 |
| ggtcctgacg ttttgagatc caaagtggca ggaggtctgt gttgtcatgg tgaactggag | 180 |
| tttctcttgt gagagttccc tcatctgaaa tcatgtatct gtctcacaaa tacaagcata | 240 |
| agtagaagat tgttgaaga catagaaccc ttataaagaa ttattaacct ttataaacat | 300 |
| ttaaagtctt gtgagcacct gggaattagt ataataacaa tgttnatatt tttgatttac | 360 |
| attttgtaag gctataattg tatctttta gaaaacatac cttggatttc tatgttgaaa | 420 |
| tggagatttt taagagtttt aaccagctgc tgcagatata ttactcaaaa cagatatagc | 480 |
| gtataaagat atagtaaatg catctcctag agtaatattc acttaacaca ttggaaacta | 540 |
| ttattttta gatttgaata tnaatgttat tttttaaaca cttgttatga gttacttggg | 600 |
| attacatttt gaaatcagtt cattccatga tgcanattac tgggattaga ttaagaaaga | 660 |
| cggaaaa | 667 |

```
<210> SEQ ID NO 100
```

<211> LENGTH: 583
<212> TYPE: DNA
<213> ORGANISM: Homo sapien
<220> FEATURE:
<221> NAME/KEY: misc_feature
<222> LOCATION: (1)...(583)
<223> OTHER INFORMATION: n = A,T,C or G

<400> SEQUENCE: 100

| | | | | | |
|---|---|---|---|---|---|
| gttttgtttg | taagatgatc | acagtcatgt | tacactgatc | taaaggacat | atatataacc | 60 |
| ctttaaaaaa | aaaatcactg | cctcattctt | atttcaagat | gaatttctat | acagactaga | 120 |
| tgttttctg | aagatcaatt | agacattttg | aaaatgattt | aaagtgtttt | ccttaatgtt | 180 |
| ctctgaaaac | aagtttcttt | tgtagtttta | accaaaaaag | tgcccttttt | gtcactggat | 240 |
| tctcctagca | ttcatgattt | ttttttcata | caatgaaatt | aaaattgcta | aaatcatgga | 300 |
| ctggctttct | ggttggattt | caggtaagat | gtgtttaagg | ccagagcttt | tctcagtatt | 360 |
| tgattttttt | ccccaatatt | tgattttta | aaaatataca | catnggtgct | gcatttatat | 420 |
| ctgctggttt | aaaattctgt | catatttcac | ttctagcctt | ttagttatgg | caaatcatat | 480 |
| tttactttta | cttaaagcat | ttggtnattt | ggantatctg | gttctannct | aaaaaaanta | 540 |
| attctatnaa | ttgaantttt | ggtactcnnc | catatttgga | tcc | | 583 |

<210> SEQ ID NO 101
<211> LENGTH: 592
<212> TYPE: DNA
<213> ORGANISM: Homo sapien
<220> FEATURE:
<221> NAME/KEY: misc_feature
<222> LOCATION: (1)...(592)
<223> OTHER INFORMATION: n = A,T,C or G

<400> SEQUENCE: 101

| | | | | | |
|---|---|---|---|---|---|
| gtggagacgt | acaaagagca | gccgctcaag | acacctggga | agaaaagaa | aggcaagccc | 60 |
| gggaaacgca | aggagcagga | aaagaaaaaa | cggcgaactc | gctctgcctg | gttagactct | 120 |
| ggagtgactg | ggagtgggct | agaagggac | cacctgtctg | acacctccac | aacgtcgctg | 180 |
| gagctcgatt | cacggaggca | ttgaaatttt | cagcaganac | cttccaagga | catattgcag | 240 |
| gattctgtaa | tagtgaacat | atggaaagta | ttagaaatat | ttattgtctg | taaatactgt | 300 |
| aaatgcattg | gaataaaact | gtctcccca | ttgctctatg | aaactgcaca | ttggtcattg | 360 |
| tgaatatttt | tttttttgcc | aaggctaatc | caattattat | tatcacattt | accataattt | 420 |
| attttgtcca | ttgatgtatt | tatttgtaa | atgtatcttg | gtgctgctga | atttctatat | 480 |
| tttttgtaca | taatgcnttt | anatataacct | atcaagtttg | ttgataaatg | acncaatgaa | 540 |
| gtgncncnan | ttggnggttg | aatttaatga | atgcctaatt | ttattatccc | aa | 592 |

<210> SEQ ID NO 102
<211> LENGTH: 587
<212> TYPE: DNA
<213> ORGANISM: Homo sapien
<220> FEATURE:
<221> NAME/KEY: misc_feature
<222> LOCATION: (1)...(587)
<223> OTHER INFORMATION: n = A,T,C or G

<400> SEQUENCE: 102

| | | | | | |
|---|---|---|---|---|---|
| cgtcctaagc | acttagacta | catcagggaa | gaacacagac | cacatccctg | tcctcatgcg | 60 |
| gcttatgttt | tctggaagaa | agtggagacc | nagtccttgg | ctttagggct | ccccggctgg | 120 |
| gggctgtgca | ntccggtcag | ggcgggaagg | gaaatgcacc | gctgcatgtg | aacttacagc | 180 |

```
ccaggcggat gccccttccc ttagcactac ctggcctcct gcatccctc gcctcatgtt      240 cctcccacct tcaaanaatg aanaacccca tgggcccagc cccttgccct ggggaaccaa     300
ggcagccttc caaaactcag gggctgaagc anactattag ggcaggggct gactttgggt    360
gacactgccc attccctctc agggcagctc angtcacccn ggnctcttga acccagcctg    420
ttcctttgaa aaagggcaaa actgaaaagg cttttccta naaaagaaa accagggaa       480 ctttgccagg gcttcnntnt taccaaaacn ncttctcnng gattttaat tccccattng     540 gcctccactt accnggggcn atgccccaaa attaanaatt tcccatc                  587

<210> SEQ ID NO 103
<211> LENGTH: 496
<212> TYPE: DNA
<213> ORGANISM: Homo sapien
<220> FEATURE:
<221> NAME/KEY: misc_feature
<222> LOCATION: (1)...(496)
<223> OTHER INFORMATION: n = A,T,C or G

<400> SEQUENCE: 103
anaggactgg ccctacntgc tctctctcgt cctacctatc aatgcccaac atggcagaac     60
ctgcanccct tggncactgc anatggaaac ctctcagtgt cttgacatca ccctacccnt   120
gcggtgggtc tccaccacaa ccactttgac tctgtggtcc ctgnanggtg gnttctcctg   180
actggcagga tggaccttan ccnacatatc cctctgttcc ctctgctnag anaaagaatt   240
cccttaacat gatataatcc acccatgcaa ntngctactg gcccagctac catttaccat   300
ttgcctacag aatttcattc agtctacact ttggcattct ctctggcgat agagtgtggc   360
tgggctgacc gcaaaaggtg ccttacacac tggcccccac cctcaaccgt tgacncatca   420
gangcttgcc tcctccttct gattnncccc catgttggat atcagggtgc tcnagggatt   480
ggaaaagaaa caaaac                                                    496

<210> SEQ ID NO 104
<211> LENGTH: 575
<212> TYPE: DNA
<213> ORGANISM: Homo sapien
<220> FEATURE:
<221> NAME/KEY: misc_feature
<222> LOCATION: (1)...(575)
<223> OTHER INFORMATION: n = A,T,C or G

<400> SEQUENCE: 104
gcacctgctc tcaatccnnc tctcaccatg atcctccgcc tgcanaaact cctctgccaa     60
ctatggangt ggtttcnggg gtggctcttg ccaactggga agaagccgtg gtgtctctac   120
ctgttcaact cngtttgtgt ctgggggatc aactngggc tatggaagcg gctnaactgt    180
tgttttggtg gaagggctgg taattggctt tgggaagtng cttatngaag ttggcctngg   240
gaagttgcta ttgaaagtng ccntggaagt ngntttggtg gggggttttg ctggtggcct   300
ttgttnaatt tgggtgcttt gtnaatggcg gcccctcnc ctgggcaatg aaaaaaatca    360
ccnatgcngn aaacctcnac nnaacagcct gggcttccct cacctcgaaa aagttgctc    420 ccccccaaa aaaggncaan ccctcaann tggaangttg aaaaaatcct cgaatgggga    480
ncccnaaaac aaaaanccc ccntttccn gnaanggggg aaataccncc cccccactta    540
cnaaacccct tntaaaaaac ccccgggaa aaaaa                                575

<210> SEQ ID NO 105
```

```
<211> LENGTH: 619
<212> TYPE: DNA
<213> ORGANISM: Homo sapien
<220> FEATURE:
<221> NAME/KEY: misc_feature
<222> LOCATION: (1)...(619)
<223> OTHER INFORMATION: n = A,T,C or G

<400> SEQUENCE: 105
cactagtagg atagaaacac tgtgtcccga gagtaaggag agaagctact attgattaga      60
gcctaaccca ggttaactgc aagaagaggc gggatacttt cagctttcca tgtaactgta     120
tgcataaagc caatgtagtc cagtttctaa gatcatgttc caagctaact gaatcccact     180
tcaatacaca ctcatgaact cctgatggaa caataacagg cccaagcctg tggtatgatg     240
tgcacacttg ctagactcan aaaaaatact actctcataa atgggtggga gtattttggt     300
gacaacctac tttgcttggc tgagtgaagg aatgatattc atatattcat ttattccatg     360
gacatttagt tagtgctttt tataccag gcatgatgct gagtgacact cttgtgtata      420
tttccaaatt tttgtacagt cgctgcacat atttgaaatc atatattaag acttccaaaa     480
aatgaagtcc ctggttttc atggcaactt gatcagtaaa ggattcncct ctgtttggta     540
cttaaaacat ctactatatn gttnanatga aattccttt cccncctcc cgaaaaaana      600
aagtggtggg gaaaaaaaa                                                  619

<210> SEQ ID NO 106
<211> LENGTH: 506
<212> TYPE: DNA
<213> ORGANISM: Homo sapien
<220> FEATURE:
<221> NAME/KEY: misc_feature
<222> LOCATION: (1)...(506)
<223> OTHER INFORMATION: n = A,T,C or G

<400> SEQUENCE: 106
cattggtnct ttcatttgct ntggaagtgt nnatctctaa cagtggacaa agttcccngt      60
gccttaaact ctgtnacact tttgggaant gaaaanttng tantatgata ggttattctg     120
angtanagat gttctggata ccattanatn tgcccccngt gtcagaggct catattgtgt     180
tatgtaaatg gtatntcatt cgctactatn antcaattng aaatanggtc tttgggttat     240
gaatantnng cagcncanct nanangctgt ctgtngtatt cattgtggtc atagcacctc     300
acancattgt aacctcnatc nagtgagaca nactagnaan ttcctagtga tggctcanga     360
ttccaaatgg nctcatntcn aatgtttaaa agttanttaa gtgtaagaaa tacagactgg     420
atgttccacc aactagtacc tgtaatgacn ggcctgtccc aacacatctc ccttttccat     480
gactgtggta ncccgcatcg gaaaaa                                          506

<210> SEQ ID NO 107
<211> LENGTH: 452
<212> TYPE: DNA
<213> ORGANISM: Homo sapien
<220> FEATURE:
<221> NAME/KEY: misc_feature
<222> LOCATION: (1)...(452)
<223> OTHER INFORMATION: n = A,T,C or G

<400> SEQUENCE: 107
gttgagtctg tactaaacag taagatatct caatgaacca taaattcaac tttgtaaaaa      60
tcttttgaag catagataat attgtttggt aaatgtttct tttgtttggt aaatgtttct     120
tttaaagacc ctcctattct ataaaactct gcatgtagag gcttgtttac ctttctctct     180
```

```
ctaaggttta caataggagt ggtgatttga aaaatataaa attatgagat tggttttcct      240
gtggcataaa ttgcatcact gtatcatttt ctttttttaac cggtaagant ttcagtttgt     300
tggaaagtaa ctgtganaac ccagtttccc gtccatctcc cttagggact acccatagaa      360
catgaaaagg tccccacnga agcaagaaga taagtctttc atggctgctg gttgcttaaa     420
ccactttaaa accaaaaaat tccccttgga aa                                    452

<210> SEQ ID NO 108
<211> LENGTH: 502
<212> TYPE: DNA
<213> ORGANISM: Homo sapien
<220> FEATURE:
<221> NAME/KEY: misc_feature
<222> LOCATION: (1)...(502)
<223> OTHER INFORMATION: n = A,T,C or G

<400> SEQUENCE: 108
atcttcttcc cttaattagt tnttatttat ntattaaatt ttattgcatg tcctggcaaa      60
caaaaagaga ttgtagattg gcttctggct ccccaaaagc ccataacaga agtaccaca      120 agaccncaac tgaagcttaa aaaatctatc acatgtataa tacctttnga agaacattaa    180
tanagcatat aaaactttta acatntgctt aatgttgtnc aattataaaa ntaatngaaa     240
aaaatgtccc tttaacatnc aatatcccac atagtgttat ttnagggat taccnngnaa     300 naaaaaaagg gtagaaggga tttaatgaaa actctgcttn ccatttctgt ttanaaacgt   360
ctccagaaca aaaacttntc aantctttca gctaaccgca tttgagctna ggccactcaa   420
aaactccatt agncccactt tctaanggtc tctanagctt actaanccctt ttgacccctt   480 accctggnta ctcctgccct ca                                             502

<210> SEQ ID NO 109
<211> LENGTH: 1308
<212> TYPE: DNA
<213> ORGANISM: Homo sapien

<400> SEQUENCE: 109
acccgaggtc tcgctaaaat catcatggat tcacttggcg ccgtcagcac tcgacttggg    60
tttgatcttt tcaaagagct gaagaaaaca aatgatggca acatcttctt ttcccctgtg   120
ggcatcttga ctgcaattgg catggtcctc ctggggaccc gaggagccac cgcttcccag   180
ttggaggagg tgtttcactc tgaaaaagag acgaagagct caagaataaa ggctgaagaa   240
aaagaggtga ttgagaacac agaagcagta catcaacaat tccaaaagtt tttgactgaa   300
ataagcaaac tcactaatga ttatgaactg aacataacca acaggctgtt tggagaaaaa   360
acatacctct tccttcaaaa atacttagat tatgttgaaa aatattatca tgcatctctg   420
gaacctgttg attttgtaaa tgcagccgat gaaagtcgaa agaagattaa ttcctgggtt   480
gaaagcaaaa caaatgaaaa aatcaaggac ttgttcccag atggctctat tagtagctct   540
accaagctgg tgctggtgaa catggtttat tttaaagggc aatgggacag ggagtttaag   600
aaagaaaata ctaaggaaga gaaattttgg atgaataaga gcacaagtaa atctgtacag   660
atgatgacac agagccattc ctttagcttc acttttcctgg aggacttgca ggccaaaatt   720
ctagggattc catataaaaa caacgaccta agcatgtttg tgcttctgcc caacgacatc   780
gatggcctgg agaagataat agataaaata agtcctgaga aattggtaga gtggactagt    840
ccagggcata tggaagaaag aaaggtgaat ctgcacttgc cccggtttga ggtggaggac    900
```

-continued

```
agttacgatc tagaggcggt cctggctgcc atggggatgg gcgatgcctt cagtgagcac    960
aaagccgact actcgggaat gtcgtcaggc tccgggttgt acgcccagaa gttcctgcac   1020
agttcctttg tggcagtaac tgaggaaggc accgaggctg cagctgccac tggcataggc   1080
tttactgtca catccgcccc aggtcatgaa atgttcact gcaatcatcc cttcctgttc    1140
ttcatcaggc acaatgaatc caacagcatc ctcttcttcg gcagattttc ttctccttaa   1200
gatgatcgtt gccatggcat tgctgctttt agcaaaaaac aactaccagt gttactcata   1260
tgattatgaa aatcgtccat tcttttaaat ggtggctcac ttgcattt                1308
```

<210> SEQ ID NO 110
<211> LENGTH: 391
<212> TYPE: PRT
<213> ORGANISM: Homo sapien

<400> SEQUENCE: 110

```
Met Asp Ser Leu Gly Ala Val Ser Thr Arg Leu Gly Phe Asp Leu Phe
 1               5                  10                  15

Lys Glu Leu Lys Lys Thr Asn Asp Gly Asn Ile Phe Phe Ser Pro Val
                20                  25                  30

Gly Ile Leu Thr Ala Ile Gly Met Val Leu Leu Gly Thr Arg Gly Ala
            35                  40                  45

Thr Ala Ser Gln Leu Glu Glu Val Phe His Ser Glu Lys Glu Thr Lys
        50                  55                  60

Ser Ser Arg Ile Lys Ala Glu Lys Glu Val Ile Glu Asn Thr Glu
65                  70                  75                  80

Ala Val His Gln Gln Phe Gln Lys Phe Leu Thr Glu Ile Ser Lys Leu
                85                  90                  95

Thr Asn Asp Tyr Glu Leu Asn Ile Thr Asn Arg Leu Phe Gly Glu Lys
            100                 105                 110

Thr Tyr Leu Phe Leu Gln Lys Tyr Leu Asp Tyr Val Glu Lys Tyr Tyr
        115                 120                 125

His Ala Ser Leu Glu Pro Val Asp Phe Val Asn Ala Ala Asp Glu Ser
    130                 135                 140

Arg Lys Lys Ile Asn Ser Trp Val Glu Ser Lys Thr Asn Glu Lys Ile
145                 150                 155                 160

Lys Asp Leu Phe Pro Asp Gly Ser Ile Ser Ser Thr Lys Leu Val
                165                 170                 175

Leu Val Asn Met Val Tyr Phe Lys Gly Gln Trp Asp Arg Glu Phe Lys
            180                 185                 190

Lys Glu Asn Thr Lys Glu Glu Lys Phe Trp Met Asn Lys Ser Thr Ser
        195                 200                 205

Lys Ser Val Gln Met Met Thr Gln Ser His Ser Phe Ser Phe Thr Phe
    210                 215                 220

Leu Glu Asp Leu Gln Ala Lys Ile Leu Gly Ile Pro Tyr Lys Asn Asn
225                 230                 235                 240

Asp Leu Ser Met Phe Val Leu Leu Pro Asn Asp Ile Asp Gly Leu Glu
                245                 250                 255

Lys Ile Ile Asp Lys Ile Ser Pro Glu Lys Leu Val Glu Trp Thr Ser
            260                 265                 270

Pro Gly His Met Glu Glu Arg Lys Val Asn Leu His Leu Pro Arg Phe
        275                 280                 285

Glu Val Glu Asp Ser Tyr Asp Leu Glu Ala Val Leu Ala Ala Met Gly
    290                 295                 300
```

```
Met Gly Asp Ala Phe Ser Glu His Lys Ala Asp Tyr Ser Gly Met Ser
305                 310                 315                 320

Ser Gly Ser Gly Leu Tyr Ala Gln Lys Phe Leu His Ser Ser Phe Val
            325                 330                 335

Ala Val Thr Glu Glu Gly Thr Glu Ala Ala Ala Thr Gly Ile Gly
                340                 345                 350

Phe Thr Val Thr Ser Ala Pro Gly His Glu Asn Val His Cys Asn His
            355                 360                 365

Pro Phe Leu Phe Phe Ile Arg His Asn Glu Ser Asn Ser Ile Leu Phe
        370                 375                 380

Phe Gly Arg Phe Ser Ser Pro
385                 390

<210> SEQ ID NO 111
<211> LENGTH: 1419
<212> TYPE: DNA
<213> ORGANISM: Homo sapien

<400> SEQUENCE: 111
ggagaactat aaattaagga tcccagctac ttaattgact tatgcttcct agttcgttgc      60
ccagccacca ccgtctctcc aaaaacccga ggtctcgcta aaatcatcat ggattcactt    120
ggcgccgtca gcactcgact tgggtttgat cttttcaaag agctgaagaa aacaaatgat    180
ggcaacatct tctttccccc tgtgggcatc ttgactgcaa ttggcatggt cctcctgggg    240
acccgaggag ccaccgcttc ccagttggag gaggtgtttc actctgaaaa agagacgaag    300
agctcaagaa taaaggctga gaaaaagag gtggtaagaa taaaggctga aggaaaagag    360
attgagaaca cagaagcagt acatcaacaa ttccaaaagt ttttgactga ataagcaaa    420 ctcactaatg attatgaact gaacataacc aacaggctgt ttggagaaaa aacatacctc    480
ttccttcaaa aatacttaga ttatgttgaa aaatattatc atgcatctct ggaacctgtt    540
gattttgtaa atgcagccga tgaaagtcga aagaagatta attcctgggt tgaaagcaaa    600
acaaatgaaa aaatcaagga cttgttccca gatggctcta ttagtagctc taccaagctg    660
gtgctggtga acatggttta ttttaaaggg caatgggaca gggagtttaa gaaagaaaat    720
actaaggaag agaaattttg gatgaataag agcacaagta atctgtaca gatgatgaca    780 cagagccatt cctttagctt cactttcctg gaggacttgc aggccaaaat tctagggatt    840
ccatataaaa acaacgacct aagcatgttt gtgcttctgc ccaacgacat cgatggcctg    900
gagaagataa tagataaaat aagtcctgag aaattggtag agtggactag tccagggcat    960
atggaagaaa gaaggtgaa tctgcacttg ccccggtttg aggtggagga cagttacgat   1020
ctagaggcgg tcctggctgc catggggatg ggcgatgcct tcagtgagca caaagccgac   1080
tactcgggaa tgtcgtcagg ctccggggttg tacgcccaga agttcctgca cagttccttt   1140
gtggcagtaa ctgaggaagg caccgaggct gcagctgcca ctggcatagg ctttactgtc   1200
acatccgccc caggtcatga aaatgttcac tgcaatcatc ccttcctgtt cttcatcagg   1260
cacaatgaat ccaacagcat cctcttcttc ggcagatttt cttctcctta agatgatcgt   1320
tgccatggca ttgctgcttt tagcaaaaaa caactaccag tgttactcat atgattatga   1380
aaatcgtcca ttctttttaaa tggtggctca cttgcatt                          1419

<210> SEQ ID NO 112
<211> LENGTH: 400
<212> TYPE: PRT
<213> ORGANISM: Homo sapien
```

-continued

<400> SEQUENCE: 112

```
Met Asp Ser Leu Gly Ala Val Ser Thr Arg Leu Gly Phe Asp Leu Phe
  1               5                  10                  15
Lys Glu Leu Lys Lys Thr Asn Asp Gly Asn Ile Phe Phe Ser Pro Val
             20                  25                  30
Gly Ile Leu Thr Ala Ile Gly Met Val Leu Leu Gly Thr Arg Gly Ala
         35                  40                  45
Thr Ala Ser Gln Leu Glu Glu Val Phe His Ser Glu Lys Glu Thr Lys
 50                  55                  60
Ser Ser Arg Ile Lys Ala Glu Lys Glu Val Val Arg Ile Lys Ala
 65                  70                  75                  80
Glu Gly Lys Glu Ile Glu Asn Thr Glu Ala Val His Gln Gln Phe Gln
                 85                  90                  95
Lys Phe Leu Thr Glu Ile Ser Lys Leu Thr Asn Asp Tyr Glu Leu Asn
            100                 105                 110
Ile Thr Asn Arg Leu Phe Gly Glu Lys Thr Tyr Leu Phe Leu Gln Lys
        115                 120                 125
Tyr Leu Asp Tyr Val Glu Lys Tyr Tyr His Ala Ser Leu Glu Pro Val
130                 135                 140
Asp Phe Val Asn Ala Ala Asp Glu Ser Arg Lys Lys Ile Asn Ser Trp
145                 150                 155                 160
Val Glu Ser Lys Thr Asn Glu Lys Ile Lys Asp Leu Phe Pro Asp Gly
                165                 170                 175
Ser Ile Ser Ser Ser Thr Lys Leu Val Leu Val Asn Met Val Tyr Phe
            180                 185                 190
Lys Gly Gln Trp Asp Arg Glu Phe Lys Lys Glu Asn Thr Lys Glu Glu
        195                 200                 205
Lys Phe Trp Met Asn Lys Ser Thr Ser Lys Ser Val Gln Met Met Thr
210                 215                 220
Gln Ser His Ser Phe Ser Phe Thr Phe Leu Glu Asp Leu Gln Ala Lys
225                 230                 235                 240
Ile Leu Gly Ile Pro Tyr Lys Asn Asn Asp Leu Ser Met Phe Val Leu
                245                 250                 255
Leu Pro Asn Asp Ile Asp Gly Leu Glu Lys Ile Ile Asp Lys Ile Ser
            260                 265                 270
Pro Glu Lys Leu Val Glu Trp Thr Ser Pro Gly His Met Glu Glu Arg
        275                 280                 285
Lys Val Asn Leu His Leu Pro Arg Phe Glu Val Glu Asp Ser Tyr Asp
290                 295                 300
Leu Glu Ala Val Leu Ala Ala Met Gly Met Gly Asp Ala Phe Ser Glu
305                 310                 315                 320
His Lys Ala Asp Tyr Ser Gly Met Ser Ser Gly Ser Gly Leu Tyr Ala
                325                 330                 335
Gln Lys Phe Leu His Ser Ser Phe Val Ala Val Thr Glu Glu Gly Thr
            340                 345                 350
Glu Ala Ala Ala Ala Thr Gly Ile Gly Phe Thr Val Thr Ser Ala Pro
        355                 360                 365
Gly His Glu Asn Val His Cys Asn His Pro Phe Leu Phe Phe Ile Arg
370                 375                 380
His Asn Glu Ser Asn Ser Ile Leu Phe Phe Gly Arg Phe Ser Ser Pro
385                 390                 395                 400
```

<210> SEQ ID NO 113
<211> LENGTH: 957
<212> TYPE: DNA
<213> ORGANISM: Homo sapien

<400> SEQUENCE: 113

```
ctcgaccttc tctgcacagc ggatgaaccc tgagcagctg aagaccagaa aagccactat      60
gactttctgc ttaattcagg agcttacagg attcttcaaa gagtgtgtcc agcatccttt     120
gaaacatgag ttcttaccag cagaagcaga cctttacccc accacctcag cttcaacagc     180
agcaggtgaa acaacccagc cagcctccac ctcaggaaat atttgttccc acaaccaagg     240
agccatgcca ctcaaaggtt ccacaacctg aaacacaaa gattccagag ccaggctgta     300
ccaaggtccc tgagccaggc tgtaccaagg tccctgagcc aggttgtacc aaggtccctg     360
agccaggatg taccaaggtc cctgagccag gttgtaccaa ggtccctgag ccaggctaca     420
ccaaggtccc tgagccaggc agcatcaagg tccctgacca aggcttcatc aagtttcctg     480
agccaggtgc catcaaagtt cctgagcaag atacaccaa agttcctgtg ccaggctaca     540
caaaggtacc agagccatgt ccttcaacgg tcactccagg cccagctcag cagaagacca     600
agcagaagta atttggtgca cagacaagcc cttgagaagc caaccaccag atgctggaca     660
ccctcttccc atctgtttct gtgtcttaat tgtctgtaga ccttgtaatc agtacattct     720
cacccaagc catagtctct ctcttatttg tatcctaaaa atacggtact ataaagcttt     780
tgttcacaca cactctgaag aatcctgtaa gcccctgaat taagcagaaa gtcttcatgg     840
cttttctggt cttcggctgc tcagggttca tctgaagatt cgaatgaaaa gaaatgcatg     900
tttcctgctc tgccctcatt aaattgcttt taattccaaa aaaaaaaaaa aaaaaaa       957
```

<210> SEQ ID NO 114
<211> LENGTH: 161
<212> TYPE: PRT
<213> ORGANISM: Homo sapien

<400> SEQUENCE: 114

Met Ser Ser Tyr Gln Gln Lys Gln Thr Phe Thr Pro Pro Gln Leu
1               5                   10                  15

Gln Gln Gln Gln Val Lys Gln Pro Ser Gln Pro Pro Gln Glu Ile
                20                  25                  30

Phe Val Pro Thr Thr Lys Glu Pro Cys His Ser Lys Val Pro Gln Pro
            35                  40                  45

Gly Asn Thr Lys Ile Pro Glu Pro Gly Cys Thr Lys Val Pro Glu Pro
        50                  55                  60

Gly Cys Thr Lys Val Pro Glu Pro Gly Cys Thr Lys Val Pro Glu Pro
65                  70                  75                  80

Gly Cys Thr Lys Val Pro Glu Pro Gly Cys Thr Lys Val Pro Glu Pro
                85                  90                  95

Gly Tyr Thr Lys Val Pro Glu Pro Gly Ser Ile Lys Val Pro Asp Gln
                100                 105                 110

Gly Phe Ile Lys Phe Pro Glu Pro Gly Ala Ile Lys Val Pro Glu Gln
            115                 120                 125

Gly Tyr Thr Lys Val Pro Val Pro Gly Tyr Thr Lys Val Pro Glu Pro
        130                 135                 140

Cys Pro Ser Thr Val Thr Pro Gly Pro Ala Gln Gln Lys Thr Lys Gln
145                 150                 155                 160

Lys

<210> SEQ ID NO 115
<211> LENGTH: 506
<212> TYPE: DNA
<213> ORGANISM: Homo sapien
<220> FEATURE:
<221> NAME/KEY: misc_feature
<222> LOCATION: (1)...(506)
<223> OTHER INFORMATION: n = A,T,C or G

<400> SEQUENCE: 115

| | | | | | |
|---|---|---|---|---|---|
| cattggtnct | ttcatttgct | ntggaagtgt | nnatctctaa | cagtggacaa | agttcccngt | 60 |
| gccttaaact | ctgtnacact | tttgggaant | gaaaanttng | tantatgata | ggttattctg | 120 |
| angtanagat | gttctggata | ccattanatn | tgcccccngt | gtcagaggct | catattgtgt | 180 |
| tatgtaaatg | gtatntcatt | cgctactatn | antcaattng | aaatanggtc | tttgggttat | 240 |
| gaatantnng | cagcncanct | nanangctgt | ctgtngtatt | cattgtggtc | atagcacctc | 300 |
| acancattgt | aacctcnatc | nagtgagaca | nactagnaan | ttcctagtga | tggctcanga | 360 |
| ttccaaatgg | nctcatntcn | aatgtttaaa | agttantttaa | gtgtaagaaa | tacagactgg | 420 |
| atgttccacc | aactagtacc | tgtaatgacn | ggcctgtccc | aacacatctc | cctttccat | 480 |
| gactgtggta | ncccgcatcg | gaaaaa | | | | 506 |

<210> SEQ ID NO 116
<211> LENGTH: 3079
<212> TYPE: DNA
<213> ORGANISM: Homo sapien

<400> SEQUENCE: 116

| | | | | | |
|---|---|---|---|---|---|
| ggatccccgg | gtttcctaaa | ccccccacag | agtcctgccc | aggccaaaga | gcaaggaaaa | 60 |
| ggtcaaaggg | cagaaaaaat | gctgagttag | gaggagctat | ggaaggataa | acctggcctt | 120 |
| aaagaggtca | aagtggttta | taggggggcgc | tgagggcttc | ccacattctc | tggcctaaac | 180 |
| cttgcaggca | gatctgccca | gtgggctctg | ggatagctgt | gccttcccta | acaaaaaaat | 240 |
| tgtgcacaaa | aggatgaaac | tctatttttcc | ctctagcaca | taaccaagaa | tataaggcta | 300 |
| cagattgcct | ttcccagagg | gaaaaccctg | cagcaacctg | ctgcctggaa | aagtgtaaga | 360 |
| gcagatcact | ggggaatcgt | ttgccccccg | ctgatgggaca | gcttcccccaa | gctccaaggg | 420 |
| caggtgctca | gcatgtaccg | tactgggatg | gttgtcaata | ctcctggtcc | tgtaagagtc | 480 |
| ccaggacact | gccatgccaa | tgcccccctca | gttcctggca | tccttttttgg | gctgctcaca | 540 |
| gccccagcct | ctatggtgaa | gacatacttg | ctagcagcgt | caccaacttg | ttgccaagag | 600 |
| atcagtgctc | gaaggcaagg | ttatttctaa | ctgagcagag | cctgccagga | agaaagcgtt | 660 |
| tgcaccccac | accactgtgc | aggtgtgacc | ggtgagctca | cagctgcccc | ccaggcatgc | 720 |
| ccagcccact | taatcatcac | agctcgacag | ctctctcgcc | cagcccagtt | ctggaaggga | 780 |
| taaaaggggg | catcaccgtt | cctgggtaac | agagccacct | tctgcgtcct | gctgagctct | 840 |
| gttctctcca | gcacctccca | acccactagt | gcctggttct | cttgctccac | caggaacaag | 900 |
| ccaccatgtc | tcgccagtca | agtgtgtctt | ccggagcggg | gggcagtcgt | agcttcagca | 960 |
| ccgcctctgc | catcaccccg | tctgtctccc | gcaccagctt | cacctccgtg | tcccggtccg | 1020 |
| ggggtggcgg | tggtggtggc | ttcggcaggg | tcagccttgc | gggtgcttgt | ggagtgggtg | 1080 |
| gctatggcag | ccggagcctc | tacaacctgg | ggggctccaa | gaggatatcc | atcagcacta | 1140 |
| gtggtggcag | cttcaggaac | cggtttggtg | ctggtgctgg | aggcggctat | ggctttggag | 1200 |
| gtggtgccgg | tagtggattt | ggtttcggcg | gtggagctgg | tggtggcttt | gggctcggtg | 1260 |

```
gcggagctgg ctttggaggt ggcttcggtg gccctggctt tcctgtctgc cctcctggag   1320
gtatccaaga ggtcactgtc aaccagagtc tcctgactcc cctcaacctg caaatcgacc   1380
ccagcatcca gagggtgagg accgaggagc gcgagcagat caagaccctc aacaataagt   1440
ttgcctcctt catcgacaag gtgcggttcc tggagcagca gaacaaggtt ctggaaacaa   1500
agtggaccct gctgcaggag cagggcacca agactgtgag gcagaacctg gagccgttgt   1560
tcgagcagta catcaacaac ctcaggaggc agctggacag catcgtgggg gaacggggcc   1620
gcctggactc agagctgaga aacatgcagg acctggtgga agacttcaag aacaagtatg   1680
aggatgaaat caacaagcgt accactgctg agaatgagtt tgtgatgctg aagaaggatg   1740
tagatgctgc ctacatgaac aaggtggagc tggaggccaa ggttgatgca ctgatggatg   1800
agattaactt catgaagatg ttctttgatg cggagctgtc ccagatgcag acgcatgtct   1860 ctgacaccctc agtggtcctc tccatggaca caaccgcaa cctggacctg gatagcatca   1920
tcgctgaggt caaggcccag tatgaggaga ttgccaaccg cagccggaca gaagccgagt   1980
cctggtatca gaccaagtat gaggagctgc agcagacagc tggccggcat ggcgatgacc   2040
tccgcaacac caagcatgag atctctgaga tgaaccggat gatccagagg ctgagagccg   2100
agattgacaa tgtcaagaaa cagtgcgcca atctgcagaa cgccattgcg gatgccgagc   2160
agcgtgggga gctggccctc aaggatgcca ggaacaagct ggccgagctg gaggaggccc   2220
tgcagaaggc caagcaggac atggcccggc tgctgcgtga gtaccaggag ctcatgaaca   2280
ccaagctggc cctggacgtg gagatcgcca cttaccgcaa gctgctggag ggcgaggaat   2340
gcagactcag tggagaagga gttggaccag tcaacatctc tgttgtcaca agcagtgttt   2400
cctctggata tggcagtggc agtggctatg gcggtggcct cggtggaggt cttggcggcg   2460
gcctcggtgg aggtcttgcc ggaggtagca gtggaagcta ctactccagc agcagtgggg   2520
gtgtcggcct aggtggtggg ctcagtgtgg ggggctctgg cttcagtgca agcagtagcc   2580
gagggctggg ggtgggcttt ggcagtggcg ggggtagcag ctccagcgtc aaatttgtct   2640
ccaccacctc ctcctcccgg aagagcttca agagctaaga acctgctgca agtcactgcc   2700
ttccaagtgc agcaacccag cccatggaga ttgcctcttc taggcagttg ctcaagccat   2760
gttttatcct tttctggaga gtagtctaga ccaagccaat tgcagaacca cattctttgg   2820
ttcccaggag agccccattc ccagcccctg gtctcccgtg ccgcagttct atattctgct   2880
tcaaatcagc cttcaggttt cccacagcat ggcccctgct gacacgagaa cccaaagttt   2940
tcccaaatct aaatcatcaa aacagaatcc ccaccccaat cccaattttt gttttggttc   3000
taactacctc cagaatgtgt tcaataaaat gttttataat ataagctggt gtgcagaatt   3060
gttttttttt tctacccaa                                                3079
```

<210> SEQ ID NO 117
<211> LENGTH: 6921
<212> TYPE: DNA
<213> ORGANISM: Homo sapien

<400> SEQUENCE: 117

```
gaattctgac tgtccactca aaacttctat tccgatcaaa gctatctgtg actacagaca     60
aattgagata accattttaca aagacgatga atgtgttttg gcgaataact ctcatcgtgc   120
taaatggaag gtcattagtc ctactgggaa tgaggctatg gtcccatctg tgtgcttcac   180
cgttcctcca ccaaacaaag aagcggtgga ccttgccaac agaattgagc aacagtatca   240
```

```
gaatgtcctg actctttggc atgagtctca cataaacatg aagagtgtag tatcctggca    300
ttatctcatc aatgaaattg atagaattcg agctagcaat gtggcttcaa taaagacaat    360
gctacctggt gaacatcagc aagttctaag taatctacaa tctcgttttg aagattttct    420
ggaagatagc caggaatccc aagtcttttc aggctcagat ataacacaac tggaaaagga    480
ggttaatgta tgtaagcagt attatcaaga acttcttaaa tctgcagaaa gagaggagca    540
agaggaatca gtttataatc tctacatctc tgaagttcga acattagac ttcggttaga     600 gaactgtgaa gatcggctga ttagacagat tcgaactccc ctggaaagag atgatttgca    660
tgaaagtgtg ttcagaatca cagaacagga gaaactaaag aaagagctgg aacgacttaa    720
agatgatttg ggaacaatca caaataagtg tgaggagttt ttcagtcaag cagcagcctc    780
ttcatcagtc cctaccctac gatcagagct taatgtggtc cttcagaaca tgaaccaagt    840
ctattctatg tcttccactt acatagataa gttgaaaact gttaacttgg tgttaaaaaa    900
cactcaagct gcagaagccc tcgtaaaact ctatgaaact aaactgtgtg aagaagaagc    960
agttatagct gacaagaata atattgagaa tctaataagt actttaaagc aatggagatc    1020
tgaagtagat gaaaagagac aggtattcca tgccttagag gatgagttgc agaaagctaa    1080
agccatcagt gatgaaatgt ttaaaacgta taagaacgg gaccttgatt ttgactggca    1140
caaagaaaaa gcagatcaat tagttgaaag gtggcaaaat gttcatgtgc agattgacaa    1200
caggttacgg gacttagagg gcattggcaa atcactgaag tactacagag acacttacca    1260
tcctttagat gattggatcc agcaggttga aactactcag agaaagattc aggaaaatca    1320
gcctgaaaat agtaaaaccc tagccacaca gttgaatcaa cagaagatgc tggtgtccga    1380
aatagaaatg aaacagagca aaatggacga gtgtcaaaaa tatgcagaac agtactcagc    1440
tacagtgaag gactatgaat tacaaacaat gacctaccgg gccatggtag attcacaaca    1500
aaaatctcca gtgaaacgcc gaagaatgca gagttcagca gatctcatta ttcaagagtt    1560
catggaccta aggactcgat atactgccct ggtcactctc atgacacaat atattaaatt    1620
tgctggtgat tcattgaaga ggctggaaga ggaggagatt aaaaggtgta aggagacttc    1680
tgaacatggg gcatattcag atctgcttca gcgtcagaag gcaacagtgc ttgagaatag    1740
caaacttaca ggaaagataa gtgagttgga agaatggta gctgaactaa agaaacaaaa    1800
gtcccgagta gaggaagaac ttccgaaggt cagggaggct gcagaaaatg aattgagaaa    1860
gcagcagaga aatgtagaag atatctctct gcagaagata agggctgaaa gtgaagccaa    1920
gcagtaccgc agggaacttg aaaccattgt gagagagaag gaagccgctg aaagagaact    1980
ggagcgggta aggcagctca ccatagaggc cgaggctaaa agagctgccg tggaagagaa    2040
cctcctgaat tttcgcaatc agttggagga aaacaccttt accagacgaa cactggaaga    2100
tcatcttaaa agaaagatt taagtctcaa tgatttggag caacaaaaaa ataaattaat     2160
ggaagaatta agaagaaaga gagacaatga ggaagaactc ttgaagctga taagcagat     2220 ggaaaaagac cttgcatttc agaaacaggt agcagagaaa cagttgaaag aaaagcagaa    2280
aattgaattg gaagcaagaa gaaaaataac tgaaattcag tatacatgta gagaaaatgc    2340
attgccagtg tgtccgatca cacaggctac atcatgcagg gcagtaacgg gtctccagca    2400
agaacatgac aagcagaaag cagaagaact caaacagcag gtagatgaac taacagctgc    2460
caatagaaag gctgaacaag acatgagaga gctgacatat gaacttaatg ccctccagct    2520
tgaaaaaacg tcatctgagg aaaaggctcg tttgctaaaa gataaactag atgaaacaaa    2580
taatacactc agatgcctta agttggagct ggaaaggaag gatcaggcgg agaaagggta    2640
```

```
ttctcaacaa ctcagagagc ttggtaggca attgaatcaa accacaggta aagctgaaga    2700
agccatgcaa gaagctagtg atctcaagaa aataaagcgc aattatcagt tagaattaga    2760
atctcttaat catgaaaaag ggaaactaca aagagaagta gacagaatca caagggcaca    2820
tgctgtagct gagaagaata ttcagcattt aaattcacaa attcattctt ttcgagatga    2880
gaaagaatta gaaagactac aaatctgcca gagaaaatca gatcatctaa aagaacaatt    2940
tgagaaaagc catgagcagt tgcttcaaaa tatcaaagct gaaaagaaaa ataatgataa    3000
aatccaaagg ctcaatgaag aattggagaa aagtaatgag tgtgcagaga tgctaaaaca    3060
aaaagtagag gagcttacta ggcagaataa tgaaaccaaa ttaatgatgc agagaattca    3120
ggcagaatca gagaatatag ttttagagaa acaaactatc cagcaaagat gtgaagcact    3180
gaaaattcag gcagatggtt ttaaagatca gctacgcagc acaaatgaac acttgcataa    3240
acagacaaaa acagagcagg attttcaaag aaaaattaaa tgcctagaag aagacctggc    3300
gaaaagtcaa aatttggtaa gtgaatttaa gcaaaagtgt gaccaacaga acattatcat    3360
ccagaatacc aagaaagaag ttagaaatct gaatgcggaa ctgaatgctt ccaaagaaga    3420
gaagcgacgc ggggagcaga aagttcagct acaacaagct caggtgcaag agttaaataa    3480
caggttgaaa aaagtacaag acgaattaca cttaaagacc atagaggagc agatgaccca    3540
cagaaagatg gttctgtttc aggaagaatc tggtaaattc aaacaatcag cagaggagtt    3600
tcggaagaag atggaaaaat taatggagtc caaagtcatc actgaaaatg atatttcagg    3660
cattaggctt gactttgtgt ctcttcaaca agaaaactct agagcccaag aaaatgctaa    3720
gctttgtgaa acaaacatta aagaacttga agcagcagctt caacagtatc gtgaacaaat    3780
gcagcaaggg cagcacatgg aagcaaatca ttaccaaaaa tgtcagaaac ttgaggatga    3840
gctgatagcc cagaagcgtg aggttgaaaa cctgaagcaa aaaatggacc aacagatcaa    3900
agagcatgaa catcaattag ttttgctcca gtgtgaaatt caaaaaaaga gcacagccaa    3960
agactgtacc ttcaaaccag atttttgagat gacagtgaag gagtgccagc actctggaga    4020
gctgtcctct agaaacactg gacaccttca cccaacaccc agatcccctc tgttgagatg    4080
gactcaagaa ccacagccat tggaagagaa gtggcagcat cgggttgttg aacagatacc    4140
caaagaagtc caattccagc caccaggggc tccactcgag aaagagaaaa gccagcagtg    4200
ttactctgag tacttttctc agacaagcac cgagttacag ataactttg atgagacaaa    4260 ccccattaca agactgtctg aaattgagaa gataagagac caagccctga caattctag    4320 accacctgtt aggtatcaag ataacgcatg tgaaatggaa ctggtgaagg ttttgacacc    4380
cttagagata gctaagaaca agcagtatga tatgcataca gaagtcacaa cattaaaaca    4440
agaaaagaac ccagttccca gtgctgaaga atggatgctt gaagggtgca gagcatctgg    4500
tggactcaag aaagggggatt tccttaagaa gggcttagaa ccagagacct tccagaactt    4560
tgatggtgat catgcatgtt cagtcaggga tgatgaattt aaattccaag ggcttaggca    4620
cactgtgact gccaggcagt tggtggaagc taagcttctg gacatgagaa caattgagca    4680
gctgcgactc ggtcttaaga ctgttgaaga agttcagaaa actcttaaca agtttctgac    4740
gaaagccacc tcaattgcag ggcttttacct agaatctaca aaagaaaaga tttcatttgc    4800
ctcagcggcc gagagaatca taatagacaa aatggtggct ttggcatttt tagaagctca    4860
ggctgcaaca ggttttataa ttgatcccat ttcaggtcag acatattctg ttgaagatgc    4920
agttcttaaa ggagttgttg accccgaatt cagaattagg cttcttgagg cagagaaggc    4980
```

-continued

```
agctgtggga tattcttatt cttctaagac attgtcagtg tttcaagcta tggaaaatag      5040
aatgcttgac agacaaaaag gtaaacatat cttggaagcc cagattgcca gtggggtgt      5100 cattgaccct gtgagaggca ttcgtgttcc tccagaaatt gctctgcagc aggggttgtt      5160
gaataatgcc atcttacagt ttttacatga gccatccagc aacacaagag ttttccctaa      5220
tcccaataac aagcaagctc tgtattactc agaattactg cgaatgtgtg tatttgatgt      5280
agagtcccaa tgctttctgt ttccatttgg ggagaggaac atttccaatc tcaatgtcaa      5340
gaaaacacat agaatttctg tagtagatac taaaacagga tcagaattga ccgtgtatga      5400
ggctttccag agaaacctga ttgagaaaag tatatatctt gaactttcag ggcagcaata      5460
tcagtggaag gaagctatgt tttttgaatc ctatgggcat tcttctcata tgctgactga      5520
tactaaaaca ggattacact tcaatattaa tgaggctata gagcagggaa caattgacaa      5580
agccttggtc aaaaagtatc aggaaggcct catcacactt acagaacttg ctgattcttt      5640
gctgagccgg ttagtcccca agaaagattt gcacagtcct gttgcagggt attggctgac      5700
tgctagtggg gaaaggatct ctgtactaaa agcctcccgt agaaatttgg ttgatcggat      5760
tactgccctc cgatgccttg aagcccaagt cagtacaggg ggcataattg atcctcttac      5820
tggcaaaaag taccgggtgg ccgaagcttt gcatagaggc ctggttgatg aggggtttgc      5880
ccagcagctg cgacagtgtg aattagtaat cacagggatt ggccatccca tcactaacaa      5940
aatgatgtca gtggtggaag ctgtgaatgc aaatattata ataaggaaa tgggaatccg      6000 atgtttggaa tttcagtact tgacaggagg gttgatagag ccacaggttc actctcggtt      6060
atcaatagaa gaggctctcc aagtaggtat tatagatgtc ctcattgcca caaaactcaa      6120
agatcaaaag tcatatgtca gaaatataat atgccctcag acaaaaagaa agttgacata      6180
taaagaagcc ttagaaaaag ctgattttga tttccacaca ggacttaaac tgttagaagt      6240
atctgagccc ctgatgacag gaatttctag cctctactat tcttcctaat gggacatgtt      6300
taaataactg tgcaagggggt gatgcaggct ggttcatgcc acttttcag agtatgatga      6360 tatcggctac atatgcagtc tgtgaattat gtaacatact ctatttcttg agggctgcaa      6420
attgctaagt gctcaaaata gagtaagttt taaattgaaa attacataag atttaatgcc      6480
cttcaaatgg tttcatttag ccttgagaat ggttttttga aacttggcca cactaaaatg      6540 ttttttttt tttacgtaga atgtgggata aacttgatga actccaagtt cacagtgtca      6600
tttcttcaga actcccttc attgaatagt gatcatttat taaatgataa attgcactcg      6660
ctgaaagagc acgtcatgaa gcaccatgga atcaaagaga aagatataaa ttcgttccca      6720
cagccttcaa gctgcagtgt tttagattgc ttcaaaaat gaaaagttt tgccttttc       6780 gatatagtga ccttctttgc atattaaaat gtttaccaca atgtcccatt tctagttaag      6840
tcttcgcact tgaaagctaa cattatgaat attatgtgtt ggaggagggg aaggattttc      6900
ttcattctgt gtattttccg g                                                6921
```

<210> SEQ ID NO 118
<211> LENGTH: 946
<212> TYPE: DNA
<213> ORGANISM: Homo sapien

<400> SEQUENCE: 118

```
cttctgactg ggctcaggct gacaggtaga gctcaccatg gcttcttgtg tccttgtccc       60
ctccccatca cagctgtggt gcagtccacc gtctccagtg gctatggcgg tgccagtggt      120
gtcggcagtg gcttaggcct gggtggagga agcagctact cctatggcag tggtcttggc      180
```

| | |
|---|---|
| gttggaggtg gcttcagttc cagcagtggc agagccattg ggggtggcct cagctctgtt | 240 |
| ggaggcggca gttccaccat caagtacacc accacctcct cctccagcag gaagagctat | 300 |
| aagcactaaa gtgcgtctgc tagctctcgg tcccacagtc ctcaggcccc tctctggctg | 360 |
| cagagccctc tcctcaggtt gcctgtcctc tcctggcctc cagtctcccc tgctgtccca | 420 |
| ggtagagctg gggatgaatg cttagtgccc tcacttcttc tctctctctc tataccatct | 480 |
| gagcacccat tgctcaccat cagatcaacc tctgatttta catcatgatg taatcaccac | 540 |
| tggagcttca ctgttactaa attattaatt tcttgcctcc agtgttctat ctctgaggct | 600 |
| gagcattata agaaaatgac ctctgctcct tttcattgca gaaaattgcc aggggcttat | 660 |
| ttcagaacaa cttccactta ctttccactg gctctcaaac tctctaactt ataagtgttg | 720 |
| tgaaccccca cccaggcagt atccatgaaa gcacaagtga ctagtcctat gatgtacaaa | 780 |
| gcctgtatct ctgtgatgat ttctgtgctc ttcactgttt gcaattgcta aataaagcag | 840 |
| atttataata catatattct tttactttgc cttgctttgg ggccaaagtt ttgggcttaa | 900 |
| acttttttat ctgataagtg aatagttgtt tttaaaagat aatcta | 946 |

<210> SEQ ID NO 119
<211> LENGTH: 8948
<212> TYPE: DNA
<213> ORGANISM: Homo sapien

<400> SEQUENCE: 119

| | |
|---|---|
| tcaacagccc ctgctccttg ggcccctcca tgccatgccg taatctctcc caccccgacca | 60 |
| acaccaacac ccagctccga cgcagctcct ctgcgcccct tgccgcccctcc gagccacagc | 120 |
| tttcctcccg ctcctgcccc cggcccgtcg ccgtctccgc gctcgcagcg gcctcgggag | 180 |
| ggcccaggta gcgagcagcg acctcgcgag ccttccgcac tcccgcccgg ttccccggcc | 240 |
| gtccgcctat ccttggcccc ctccgctttc tccgcgccgg cccgcctcgc ttatgcctcg | 300 |
| gcgctgagcc gctctcccga ttgcccgccg acatgagctg caacgaggc tcccacccgc | 360 |
| ggatcaacac tctgggccgc atgatccgcg ccgagtctgg cccggacctg cgctacgagg | 420 |
| tgaccagcgg cggcgggggc accagcagga tgtactattc tcggcgcggc gtgatcaccg | 480 |
| accagaactc ggacggctac tgtcaaaccg gcacgatgtc caggcaccag aaccagaaca | 540 |
| ccatccagga gctgctgcag aactgctccg actgcttgat gcgagcagag ctcatcgtgc | 600 |
| agcctgaatt gaagtatgga gatggaatac aactgactcg gagtcgagaa ttggatgagt | 660 |
| gttttgccca ggccaatgac caaatggaaa tcctcgacag cttgatcaga gagatgcggc | 720 |
| agatgggcca gccctgtgat gcttaccaga aaaggcttct tcagctccaa gagcaaatgc | 780 |
| gagccctta taaagccatc agtgtccctc gagtccgcag ggccagctcc aagggtggtg | 840 |
| gaggctacac ttgtcagagt ggctctggct gggatgagtt caccaaacat gtcaccagtg | 900 |
| aatgtttggg gtggatgagg cagcaaaggg cggagatgga catggtggcc tggggtgtgg | 960 |
| acctggcctc agtggagcag cacattaaca gccaccgggg catccacaac tccatcggcg | 1020 |
| actatcgctg gcagctggac aaaatcaaag ccgacctgcg cgagaaatct gcgatctacc | 1080 |
| agttggagga ggagtatgaa aacctgctga aagcgtcctt tgagaggatg gatcacctgc | 1140 |
| gacagctgca gaacatcatt caggccacgt ccagggagat catgtggatc aatgactgcg | 1200 |
| aggaggagga gctgctgtac gactggagcg acaagaacac caacatcgct cagaaacagg | 1260 |
| aggccttctc catacgcatg agtcaactgg aagttaaaga aaaagagctc aataagctga | 1320 |

```
aacaagaaag tgaccaactt gtcctcaatc agcatccagc ttcagacaaa attgaggcct    1380
atatggacac tctgcagacg cagtggagtt ggattcttca gatcaccaag tgcattgatg    1440
ttcatctgaa agaaaatgct gcctactttc agttttttga agaggcgcag tctactgaag    1500
catacctgaa ggggctccag gactccatca ggaagaagta ccctgcgac aagaacatgc     1560 ccctgcagca cctgctggaa cagatcaagg agctggagaa agaacgagag aaaatccttg    1620
aatacaagcg tcaggtgcag aacttggtaa acaagtctaa gaagattgta cagctgaagc    1680
ctcgtaaccc agactacaga agcaataaac ccattattct cagagctctc tgtgactaca    1740
aacaagatca gaaaatcgtg cataagggg atgagtgtat cctgaaggac aacaacgagc     1800
gcagcaagtg gtacgtgacg ggcccgggag gcgttgacat gcttgttccc tctgtggggc    1860
tgatcatccc tcctccgaac ccactggccg tggacctctc ttgcaagatt gagcagtact    1920
acgaagccat cttggctctg tggaaccagc tctacatcaa catgaagagc ctggtgtcct    1980
ggcactactg catgattgac atagagaaga tcagggccat gacaatcgcc aagctgaaaa    2040
caatgcggca ggaagattac atgaagacga tagccgacct tgagttacat taccaagagt    2100
tcatcagaaa tagccaaggc tcagagatgt ttggagatga tgacaagcgg aaaatacagt    2160
ctcagttcac cgatgcccag aagcattacc agaccctggt cattcagctc cctggctatc    2220
cccagcacca gacagtgacc acaactgaaa tcactcatca tggaacctgc caagatgtca    2280
accataataa agtaattgaa accaacagag aaaatgacaa gcaagaaaca tggatgctga    2340
tggagctgca gaagattcgc aggcagatag agcactgcga gggcaggatg actctcaaaa    2400
acctccctct agcagaccag gggtcttctc accacatcac agtgaaaatt aacgagctta    2460
agagtgtgca gaatgattca caagcaattg ctgaggttct caaccagctt aaagatatgc    2520
ttgccaactt cagaggttct gaaaagtact gctatttaca gaatgaagta tttggactat    2580
ttcagaaact ggaaaatatc aatggtgtta cagatggcta cttaaatagc ttatgcacag    2640
taagggcact gctccaggct attctccaaa cagaagacat gttaaaggtt tatgaagcca    2700
ggctcactga ggaggaaact gtctgcctgg acctggataa agtggaagct taccgctgtg    2760
gactgaagaa aataaaaaat gacttgaact tgaagaagtc gttgttggcc actatgaaga    2820
cagaactaca gaaagcccag cagatccact ctcagacttc acagcagtat ccactttatg    2880
atctggactt gggcaagttc ggtgaaaaag tcacacagct gacagaccgc tggcaaagga    2940
tagataaaca gatcgacttt agattatggg acctggagaa acaaatcaag caattgagga    3000
attatcgtga taactatcag gctttctgca gtggctcta tgatcgtaaa cgccgccagg     3060
attccttaga atccatgaaa tttggagatt ccaacacagt catgcggttt ttgaatgagc    3120
agaagaactt gcacagtgaa atatctggca aacgagacaa atcagaggaa gtacaaaaaa    3180
ttgctgaact ttgcgccaat tcaattaagg attatgagct ccagctggcc tcatacacct    3240
caggactgga aactctgctg aacataccta tcaagaggac catgattcag tcccttctg     3300 gggtgattct gcaagaggct gcagatgttc atgctcggta cattgaacta cttacaagat    3360
ctggagacta ttacaggttc ttaagtgaga tgctgaagag tttggaagat ctgaagctga    3420
aaaataccaa gatcgaagtt ttggaagagg agctcagact ggcccgagat gccaactcgg    3480
aaaactgtaa taagaacaaa ttcctggatc agaacctgca gaaataccag gcagagtgtt    3540
cccagttcaa agcgaagctt gcgagcctgg aggagctgaa gagacaggct gagctggatg    3600
ggaagtcggc taagcaaaat ctagacagt gctacggcca aataaagaa ctcaatgaga      3660 agatcacccg actgacttat gagattgaag atgaaaagag aagaagaaaa tctgtggaag    3720
```

```
acagatttga ccaacagaag aatgactatg accaactgca gaaagcaagg caatgtgaaa    3780
aggagaacct tggttggcag aaattagagt ctgagaaagc catcaaggag aaggagtacg    3840
agattgaaag gttgagggtt ctactgcagg aagaaggcac ccggaagaga gaatatgaaa    3900
atgagctggc aaaggtaaga aaccactata tgaggagat gagtaattta aggaacaagt    3960
atgaaacaga gattaacatt acgaagacca ccatcaagga gatatccatg caaaaagagg    4020
atgattccaa aaatcttaga aaccagcttg atagactttc aagggaaaat cgagatctga    4080
aggatgaaat tgtcaggctc aatgacagca tcttgcaggc cactgagcag cgaaggcgag    4140
ctgaagaaaa cgcccttcag caaaaggcct gtggctctga gataatgcag aagaagcagc    4200
atctggagat agaactgaag caggtcatgc agcagcgctc tgaggacaat gcccggcaca    4260
agcagtccct ggaggaggct gccaagacca ttcaggacaa aaataaggag atcgagagac    4320
tcaaagctga gtttcaggag gaggccaagc gccgctggga atatgaaaat gaactgagta    4380
aggtaagaaa caattatgat gaggagatca ttagcttaaa aaatcagttt gagaccgaga    4440
tcaacatcac caagaccacc atccaccagc tcaccatgca gaaggaagag gataccagtg    4500
gctaccgggc tcagatagac aatctcaccc gagaaaacag gagcttatct gaagaaataa    4560
agaggctgaa gaacactcta acccagacca cagagaatct caggagggtg gaagaagaca    4620
tccaacagca aaaggccact ggctctgagg tgtctcagag gaaacagcag ctggaggttg    4680
agctgagaca agtcactcag atgcgaacag aggagagcgt aagatataag caatctctg    4740 atgatgctgc caaaaccatc caggataaaa acaaggagat agaaaggtta aaacaactga    4800
tcgacaaaga aacaaatgac cggaaatgcc tggaagatga aaacgcgaga ttacaaaggg    4860
tccagtatga cctgcagaaa gcaaacagta gtgcgacgga gacaataaac aaactgaagg    4920
ttcaggagca agaactgaca cgcctgagga tcgactatga aagggtttcc caggagagga    4980
ctgtgaagga ccaggatatc acgcggttcc agaactctct gaaagagctg cagctgcaga    5040
agcagaaggt ggaagaggag ctgaatcggc tgaagaggac cgcgtcagaa gactcctgca    5100
agaggaagaa gctggaggaa gagctggaag gcatgaggag gtcgctgaag gagcaagcca    5160
tcaaaatcac caacctgacc cagcagctgg agcaggcatc cattgttaag aagaggagtg    5220
aggatgacct ccggcagcag agggacgtgc tggatggcca cctgagggaa aagcagagga    5280
cccaggaaga gctgaggagg ctctcttctg aggtcgaggc cctgaggcgg cagttactcc    5340
aggaacagga aagtgtcaaa caagctcact tgaggaatga gcatttccag aaggcgatag    5400
aagataaaag cagaagctta aatgaaagca aaatagaaat tgagaggctg cagtctctca    5460
cagagaacct gaccaaggag cacttgatgt tagaagaaga actgcggaac ctgaggctgg    5520
agtacgatga cctgaggaga ggacgaagcg aagcggacag tgataaaaat gcaaccatct    5580
tggaactaag gagccagctg cagatcagca caaccggac cctggaactg caggggctga    5640
ttaatgattt acagagagag agggaaaatt tgagacagga aattgagaaa ttccaaaagc    5700
aggctttaga ggcatctaat aggattcagg aatcaaagaa tcagtgtact caggtggtac    5760
aggaaagaga gagccttctg gtgaaaatca agtcctgga gcaagacaag gcaaggctgc    5820
agaggctgga ggatgagctg aatcgtgcaa aatcaactct agaggcagaa accagggtga    5880
aacagcgcct ggagtgtgag aaacagcaaa ttcagaatga cctgaatcag tggaagactc    5940
aatattcccg caaggaggag gctattagga agatagaatc ggaaagagaa aagagtgaga    6000
gagagaagaa cagtcttagg agtgagatcg aaagactcca agcagagatc aagagaattg    6060
```

-continued

```
aagagaggtg caggcgtaag ctggaggatt ctaccaggga gacacagtca cagttagaaa    6120
cagaacgctc ccgatatcag agggagattg ataaactcag acagcgccca tatgggtccc    6180
atcgagagac ccagactgag tgtgagtgga ccgttgacac ctccaagctg gtgtttgatg    6240
ggctgaggaa gaaggtgaca gcaatgcagc tctatgagtg tcagctgatc gacaaaacaa    6300
ccttggacaa actattgaag gggaagaagt cagtggaaga agttgcttct gaaatccagc    6360
cattccttcg gggtgcagga tctatcgctg gagcatctgc ttctcctaag gaaaaatact    6420
ctttggtaga ggccaagaga aagaaattaa tcagcccaga atccacagtc atgcttctgg    6480
aggcccaggc agctacaggt ggtataattg atccccatcg gaatgagaag ctgactgtcg    6540
acagtgccat agctcgggac ctcattgact tcgatgaccg tcagcagata tatgcagcag    6600
aaaaagctat cactggtttt gatgatccat tttcaggcaa gacagtatct gtttcagaag    6660
ccatcaagaa aaatttgatt gatagagaaa ccggaatgcg cctgctggaa gcccagattg    6720
cttcagggggg tgtagtagac cctgtgaaca gtgtctttttt gccaaaagat gtcgccttgg    6780
cccgggggct gattgataga gatttgtatc gatccctgaa tgatccccga gatagtcaga    6840
aaaactttgt ggatccagtc accaaaaaga aggtcagtta cgtgcagctg aaggaacggt    6900
gcagaatcga accacatact ggtctgctct tgctttcagt acagaagaga agcatgtcct    6960
tccaaggaat cagacaacct gtgaccgtca ctgagctagt agattctggt atattgagac    7020
cgtccactgt caatgaactg gaatctggtc agatttctta tgacgaggtt ggtgagagaa    7080
ttaaggactt cctccaggg tcaagctgca tagcaggcat atacaatgag accacaaaac    7140
agaagcttgg catttatgag gccatgaaaa ttggcttagt ccgacctggt actgctctgg    7200
agttgctgga agcccaagca gctactggct ttatagtgga tcctgttagc aacttgaggt    7260
taccagtgga ggaagcctac aagagaggtc tggtgggcat tgagttcaaa gagaagctcc    7320
tgtctgcaga acgagctgtc actgggtata atgatcctga acaggaaaac atcatctctt    7380
tgttccaagc catgaataag gaactcatcg aaaagggcca cggtattcgc ttattagaag    7440
cacagatcgc aaccgggggg atcattgacc caaggagag ccatcgttta ccagttgaca    7500
tagcatataa gagggctat ttcaatgagg aactcagtga gattctctca gatccaagtg    7560
atgataccaa aggatttttt gaccccaaca ctgaagaaaa tcttacctat ctgcaactaa    7620
aagaaagatg cattaaggat gaggaaacag ggctctgtct tctgcctctg aaagaaaaga    7680
agaaacaggt gcagacatca caaaagaata ccctcaggaa gcgtagagtg gtcatagttg    7740
acccagaaac caataaagaa atgtctgttc aggaggccta caagaagggc ctaattgatt    7800
atgaaaccTt caaagaactg tgtgagcagg aatgtgaatg ggaagaaata accatcacgg    7860
gatcagatgg ctccaccagg gtggtcctgg tagatagaaa gacaggcagt cagtatgata    7920
ttcaagatgc tattgacaag ggccttgttg acaggaagtt cttggatcag taccgatccg    7980
gcagcctcag cctcactcaa tttgctgaca tgatctcctt gaaaaatggt gtcggcacca    8040
gcagcagcat gggcagtggt gtcagcgatg atgttttag cagctcccga catgaatcag    8100
taagtaagat ttccaccata tccagcgtca ggaatttaac cataaggagc agctcttttt    8160
cagacaccct ggaagaatcg agccccattg cagccatctt tgacacagaa aacctggaga    8220
aaatctccat tacagaaggt atagagcggg gcatcgttga cagcatcacg ggtcagaggc    8280
ttctggaggc tcaggcctgc acaggtggca tcatccaccc aaccacgggc cagaagctgt    8340
cacttcagga cgcagtctcc cagggtgtga ttgaccaaga catggccacc agcgtgaagc    8400
ctgctcagaa agccttcata ggcttcgagg gtgtgaaggg aaagaagaag atgtcagcag    8460
```

| | |
|---|---|
| cagaggcagt gaaagaaaaa tggctcccgt atgaggctgg ccagcgcttc ctggagttcc | 8520 |
| agtacctcac gggaggtctt gttgacccgg aagtgcatgg gaggataagc accgaagaag | 8580 |
| ccatccggaa ggggttcata gatggccgcg ccgcacagag gctgcaagac accagcagct | 8640 |
| atgccaaaat cctgacctgc cccaaaacca aattaaaaat atcctataag gatgccataa | 8700 |
| atcgctccat ggtagaagat atcactgggc tgcgccttct ggaagccgcc tccgtgtcgt | 8760 |
| ccaagggctt acccagccct acaacatgt cttcggctcc gggtcccgc tccggctccc | 8820 |
| gctcgggatc tcgctccgga tctcgctccg gtcccgcag tgggtcccgg agaggaagct | 8880 |
| ttgacgccac agggaattct tcctactctt attcctactc atttagcagt agttctattg | 8940 |
| ggcactag | 8948 |

<210> SEQ ID NO 120
<211> LENGTH: 587
<212> TYPE: DNA
<213> ORGANISM: Homo sapien
<220> FEATURE:
<221> NAME/KEY: misc_feature
<222> LOCATION: (1)...(587)
<223> OTHER INFORMATION: n = A,T,C or G

<400> SEQUENCE: 120

| | |
|---|---|
| cgtcctaagc acttagacta catcagggaa gaacacagac cacatccctg tcctcatgcg | 60 |
| gcttatgttt tctggaagaa agtggagacc nagtccttgg ctttagggct ccccggctgg | 120 |
| gggctgtgca ntccggtcag ggcgggaagg gaaatgcacc gctgcatgtg aacttacagc | 180 |
| ccaggcggat gccccttccc ttagcactac ctggcctcct gcatcccctc gcctcatgtt | 240 |
| cctcccacct tcaaanaatg aanaacccca tgggcccagc cccttgccct ggggaaccaa | 300 |
| ggcagccttc caaaactcag gggctgaagc anactattag ggcaggggct gactttgggt | 360 |
| gacactgccc attccctctc agggcagctc angtcaccen ggnctcttga acccagcctg | 420 |
| ttcctttgaa aaagggcaaa actgaaaagg gcttttccta naaaaagaaa accagggaa | 480 |
| ctttgccagg gcttcnntnt taccaaaacn ncttctcnng gattttaat tccccattng | 540 |
| gcctccactt accngggggcn atgccccaaa attaanaatt tcccatc | 587 |

<210> SEQ ID NO 121
<211> LENGTH: 619
<212> TYPE: DNA
<213> ORGANISM: Homo sapien
<220> FEATURE:
<221> NAME/KEY: misc_feature
<222> LOCATION: (1)...(619)
<223> OTHER INFORMATION: n = A,T,C or G

<400> SEQUENCE: 121

| | |
|---|---|
| cactagtagg atagaaacac tgtgtcccga gagtaaggag agaagctact attgattaga | 60 |
| gcctaaccca ggttaactgc aagaagaggc gggatacttt cagctttcca tgtaactgta | 120 |
| tgcataaagc caatgtagtc cagtttctaa gatcatgttc caagctaact gaatcccact | 180 |
| tcaatacaca ctcatgaact cctgatggaa caataacagg cccaagcctg tggtatgatg | 240 |
| tgcacacttg ctagactcan aaaaaatact actctcataa atgggtggga gtattttggt | 300 |
| gacaacctac tttgcttggc tgagtgaagg aatgatattc atatattcat ttattccatg | 360 |
| gacatttagt tagtgctttt tatataccag gcatgatgct gagtgacact cttgtgtata | 420 |
| tttccaaatt tttgtacagt cgctgcacat atttgaaatc atatattaag acttccaaaa | 480 |

-continued

| aatgaagtcc ctggtttttc atggcaactt gatcagtaaa ggattcncct ctgtttggta | 540 |
| cttaaaacat ctactatatn gttnanatga aattccttttt ccccnctcc cgaaaaaana | 600 |
| aagtggtggg gaaaaaaaa | 619 |

<210> SEQ ID NO 122
<211> LENGTH: 1475
<212> TYPE: DNA
<213> ORGANISM: Homo sapien

<400> SEQUENCE: 122

| tccacctgtc cccgcagcgc cggctcgcgc cctcctgccg cagccaccga gccgccgtct | 60 |
| agcgccccga cctcgccacc atgagagccc tgctggcgcg cctgcttctc tgcgtcctgg | 120 |
| tcgtgagcga ctccaaaggc agcaatgaac ttcatcaagt tccatcgaac tgtgactgtc | 180 |
| taaatggagg aacatgtgtg tccaacaagt acttctccaa cattcactgg tgcaactgcc | 240 |
| caaagaaatt cggagggcag cactgtgaaa tagataagtc aaaaacctgc tatgagggga | 300 |
| atggtcactt ttaccgagga aaggccagca ctgacaccat gggccggccc tgcctgccct | 360 |
| ggaactctgc cactgtcctt cagcaaacgt accatgccca cagatctgat gctcttcagc | 420 |
| tgggcctggg gaaacataat tactgcagga acccagacaa ccggaggcga ccctggtgct | 480 |
| atgtgcaggt gggcctaaag ccgcttgtcc aagagtgcat ggtgcatgac tgcgcagatg | 540 |
| gaaaaaagcc ctcctctcct ccagaagaat taaaatttca gtgtggccaa aagactctga | 600 |
| ggccccgctt taagattatt gggggagaat tcaccaccat cgagaaccag ccctggtttg | 660 |
| cggccatcta caggaggcac cgggggggct ctgtcaccta cgtgtgtgga ggcagcctca | 720 |
| tcagcccttg ctgggtgatc agcgccacac actgcttcat tgattaccca aagaaggagg | 780 |
| actacatcgt ctacctgggt cgctcaaggc ttaactccaa cacgcaaggg gagatgaagt | 840 |
| ttgaggtgga aaacctcatc ctacacaagg actacagcgc tgacacgctt gctcaccaca | 900 |
| acgacattgc cttgctgaag atccgttcca aggagggcag gtgtgcgcag ccatcccgga | 960 |
| ctatacagac catctgcctg ccctcgatgt ataacgatcc ccagtttggc acaagctgtg | 1020 |
| agatcactgg cttttggaaaa gagaattcta ccgactatct ctatccggag cagctgaaga | 1080 |
| tgactgttgt gaagctgatt tccaccgggg agtgtcagca gccccactac tacggctctg | 1140 |
| aagtcaccac caaaatgctg tgtgctgctg acccacagtg gaaaacagat tcctgccagg | 1200 |
| gagactcagg ggaccccctc gtctgttccc tccaaggccg catgacttttg actggaattg | 1260 |
| tgagctgggg ccgtggatgt gccctgaagg acaagccagg cgtctacacg agagtctcac | 1320 |
| acttcttacc ctggatccgc agtcacacca aggaagagaa tggcctggcc ctctgagggt | 1380 |
| ccccagggag gaaacgggca ccacccgctt tcttgctggt tgtcatttttt gcagtagagt | 1440 |
| catctccatc agctgtaaga agagactggg aagat | 1475 |

<210> SEQ ID NO 123
<211> LENGTH: 2294
<212> TYPE: DNA
<213> ORGANISM: Homo sapien

<400> SEQUENCE: 123

| cagcgccggc tcgcgccctc ctgccgcagc caccgagccg ccgtctagcg ccccgacctc | 60 |
| gccaccatga gagccctgct ggcgcgcctg cttctctgcg tcctggtcgt gagcgactcc | 120 |
| aaaggcagca atgaacttca tcaagttcca tcgaactgtg actgtctaaa tggaggaaca | 180 |
| tgtgtgtcca acaagtactt ctccaacatt cactggtgca actgcccaaa gaaattcgga | 240 |

```
gggcagcact gtgaaataga taagtcaaaa acctgctatg aggggaatgg tcacttttac    300
cgaggaaagg ccagcactga caccatgggc cggccctgcc tgccctggaa ctctgccact    360
gtccttcagc aaacgtacca tgcccacaga tctgatgctc ttcagctggg cctggggaaa    420
cataattact gcaggaaccc agacaaccgg aggcgaccct ggtgctatgt gcaggtgggc    480
ctaaagccgc ttgtccaaga gtgcatggtg catgactgcg cagatggaaa aaagccctcc    540
tctcctccag aagaattaaa atttcagtgt ggccaaaaga ctctgaggcc ccgctttaag    600
attattgggg gagaattcac caccatcgag aaccagccct ggtttgcggc catctacagg    660
aggcaccggg ggggctctgt cacctacgtg tgtggaggca gcctcatcag cccttgctgg    720
gtgatcagcg ccacacactg cttcattgat tacccaaaga aggaggacta catcgtctac    780
ctgggtcgct caaggcttaa ctccaacacg caagggagga tgaagtttga ggtggaaaac    840
ctaatcctac acaaggacta cagcgctgac acgcttgctc accacaacga cattgccttg    900
ctgaagatcc gttccaagga gggcaggtgt gcgcagccat cccggactat acagaccatc    960
tgcctgccct cgatgtataa cgatccccag tttggcacaa gctgtgagat cactggcttt   1020
ggaaaagaga attctaccga ctatctctat ccggagcagc tgaaaatgac tgttgtgaag   1080
ctgatttccc accgggagtg tcagcagccc cactactacg gctctgaagt caccaccaaa   1140
atgctgtgtg ctgctgaccc acagtggaaa acagattcct gccagggaga ctcaggggga   1200
cccctcgtct gttccctcca aggccgcatg actttgactg gaattgtgag ctggggccgt   1260
ggatgtgccc tgaaggacaa gccaggcgtc tacacgagag tctcacactt cttaccctgg   1320
atccgcagtc acaccaagga agagaatggc ctggccctct gagggtcccc agggaggaaa   1380
cgggcaccac ccgctttctt gctggttgct attttgcagt agagtcatct ccatcagctg   1440
taagaagagc tgggaatata ggctctgcac agatggattt gcctgtgcca ccaccagggc   1500
gaacgacaat agctttaccc tcaggcatag gcctgggtgc tggctgccca gacccctctg   1560
gccaggatgg agggtggtc ctgactcaac atgttactga ccagcaactt gtcttttct    1620
ggactgaagc ctgcaggagt taaaaagggc agggcatctc ctgtgcatgg gctcgaaggg   1680
agagccagct cccccgaccg gtgggcattt gtgaggccca tggttgagaa atgaataatt   1740
tcccaattag gaagtgtaag cagctgaggt ctcttgaggg agcttagcca atgtgggagc   1800
agcggtttgg ggagcagaga cactaacgac ttcagggcag ggctctgata ttccatgaat   1860
gtatcaggaa atatatatgt gtgtgtatgt ttgcacactt gtgtgtgggc tgtgagtgta   1920
agtgtgagta agagctggtg tctgattgtt aagtctaaat atttccttaa actgtgtgga   1980
ctgtgatgcc acacagagtg gtcttttctgg agaggttata ggtcactcct ggggcctctt   2040
gggtcccca cgtgacagtg cctgggaatg tattattctg cagcatgacc tgtgaccagc   2100
actgtctcag tttcactttc acatagatgt ccctttcttg gccagttatc ccttcctttt   2160
agcctagttc atccaatcct cactgggtgg ggtgaggacc actcctgtac actgaatatt   2220
tatatttcac tattttttatt tatatttttg taattttaaa taaagtgat caataaaatg    2280
tgattttct gatg                                                       2294
```

<210> SEQ ID NO 124
<211> LENGTH: 956
<212> TYPE: DNA
<213> ORGANISM: Homo sapien

<400> SEQUENCE: 124

```
gatgagttcc gcaccaagtt tgagacagac caggccctgc gcctgagtgt ggaggccgac    60
atcaatggcc tgcgcagggt gctggatgag ctgaccctgg ccagagccga cctggagatg   120
cagattgaga acctcaagga ggagctggcc tacctgaaga agaaccacga ggaggagatg   180
aacgccctgc gaggccaggt gggtggtgag atcaatgtgg agatggacgc tgccccaggc   240
gtggacctga gccgcatcct caacgagatg cgtgaccagt atgagaagat ggcagagaag   300
aaccgcaagg atgccgagga ttggttcttc agcaagacag aggaactgaa ccgcgaggtg   360
gccaccaaca gtgagctggt gcagagtggc aagagtgaga tctcggagct ccggcgcacc   420
atgcaggcct tggagataga gctgcagtcc cagctcagca tgaaagcatc cctggagggc   480
aacctggcgg agacagagaa ccgctactgc gtgcagctgt cccagatcca ggggctgatt   540
ggcagcgtgg aggagcagct ggcccagctt cgctgcgaga tggagcagca gaaccaggaa   600
tacaaaatcc tgctggatgt gaagacgcgg ctggagcagg agattgccac ctaccgccgc   660
ctgctggagg gagaggatgc ccacctgact cagtacaaga agaaccggt gaccacccgt   720 caggtgcgta ccattgtgga agaggtccag gatggcaagg tcatctcctc ccgcgagcag   780
gtccaccaga ccacccgctg aggactcagc taccccggcc ggccacccag gaggcaggga   840
cgcagccgcc ccatctgccc cacagtctcc ggcctctcca gcctcagccc cctgcttcag   900
tcccttcccc atgcttcctt gcctgatgac aataaaagct tgttgactca gctatg      956

<210> SEQ ID NO 125
<211> LENGTH: 486
<212> TYPE: DNA
<213> ORGANISM: Homo sapien
<220> FEATURE:
<221> NAME/KEY: misc_feature
<222> LOCATION: (1)...(486)
<223> OTHER INFORMATION: n = A,T,C or G

<400> SEQUENCE: 125
aaattatata tagtgnttca gctcccattg tggtgttcat agtcttctag gaacagataa    60
acttaagtat tcaattcact cttggcattt tttctttaat ataggctttt tagcctattt   120
ttggaaaact gcttttcttc tgagaacctt attctgaatg tcatcaactt taccaaacct   180
tctaagtcca gagctaactt agtactgttt aagttactat tgactgaatt ttcttcattt   240
tctgtttagc cagtgttacc aaggtaagct ggggaatgaa gtataccaac ttctttcaga   300 gcatttttagg acattatggc agctttagaa ggctgtcttg tttctagcca agggagagcc   360
agcgcaggtt ttggatacta gagaaagtca tttgcttgta ctattgccat tttagaaagc   420
tctgatgtga attcaaattt tacctctgtt acttaaagcc aacaattta aggcagtagt   480 tttact                                                             486

<210> SEQ ID NO 126
<211> LENGTH: 3552
<212> TYPE: DNA
<213> ORGANISM: Homo sapien

<400> SEQUENCE: 126
cggcaggcag gtctcgtctc ggcaccctcc cggcgcccgc gttctcctgg ccctgcccgg    60
catcccgatg gccgccgctg ggccccggcg ctccgtgcgc ggagccgtct gcctgcatct   120
gctgctgacc ctcgtgatct tcagtcgtgc tggtgaagcc tgcaaaaagg tgatacttaa   180
tgtaccttct aaactagagg cagacaaaat aattggcaga gttaatttgg aagagtgctt   240
caggtctgca gacctcatcc ggtcaagtga tcctgatttc agagttctaa atgatgggtc   300
```

```
agtgtacaca gccagggctg ttgcgctgtc tgataagaaa agatcattta ccatatggct      360
ttctgacaaa aggaaacaga cacagaaaga ggttactgtg ctgctagaac atcagaagaa      420
ggtatcgaag acaagacaca ctagagaaac tgttctcagg cgtgccaaga ggagatgggc      480
acctattcct tgctctatgc aagagaattc cttgggccct ttcccattgt ttcttcaaca      540
agttgaatct gatgcagcac agaactatac tgtcttctac tcaataagtg gacgtggagt      600
tgataaagaa cctttaaatt tgttttatat agaaagagac actggaaatc tattttgcac      660
tcggcctgtg gatcgtgaag aatatgatgt ttttgatttg attgcttatg cgtcaactgc      720
agatggatat tcagcagatc tgcccctccc actacccatc agggtagagg atgaaaatga      780
caaccaccct gttttcacag aagcaattta aattttgaa gttttggaaa gtagtagacc       840
tggtactaca gtgggggtgg tttgtgccac agacagagat gaaccggaca caatgcatac      900
gcgcctgaaa tacagcattt tgcagcagac accaaggtca cctgggctct tttctgtgca      960
tcccagcaca ggcgtaatca ccacagtctc tcattatttg gacagagagg ttgtagacaa     1020
gtactcattg ataatgaaag tacaagacat ggatggccag ttttttggat tgataggcac     1080
atcaacttgt atcataacag taacagattc aaatgataat gcacccactt tcagacaaaa     1140
tgcttatgaa gcatttgtag aggaaaatgc attcaatgtg gaaatcttac gaataccat     1200 agaagataag gatttaatta acactgccaa ttggagagtc aattttacca ttttaagggg     1260
aaatgaaaat ggacatttca aaatcagcac agacaaagaa actaatgaag gtgttctttc     1320
tgttgtaaag ccactgaatt atgaagaaaa ccgtcaagtg aacctggaaa ttggagtaaa     1380
caatgaagcg ccatttgcta gagatattcc cagagtgaca gccttgaaca gagccttggt     1440
tacagttcat gtgagggatc tggatgaggg gcctgaatgc actcctgcag cccaatatgt     1500
gcggattaaa gaaaacttag cagtgggtc aaagatcaac ggctataagg catatgaccc      1560
cgaaaataga aatggcaatg gtttaaggta caaaaaattg catgatccta aggttggat      1620 caccattgat gaaatttcag ggtcaatcat aacttccaaa atcctggata gggaggttga     1680
aactcccaaa atgagttgt ataatattac agtcctggca atagacaaag atgatagatc      1740
atgtactgga acacttgctg tgaacattga agatgtaaat gataatccac cagaaatact     1800
tcaagaatat gtagtcattt gcaaaccaaa atgggggtat accgacattt tagctgttga     1860
tcctgatgaa cctgtccatg gagctccatt ttatttcagt ttgcccaata cttctccaga     1920
aatcagtaga ctgtggagcc tcaccaaagt taatgataca gctgcccgtc tttcatatca     1980
gaaaaatgct ggatttcaag aatataccat tcctattact gtaaaagaca gggccggcca     2040
agctgcaaca aaattattga gagttaatct gtgtgaatgt actcatccaa ctcagtgtcg     2100
tgcgacttca aggagtacag gagtaatact tggaaaatgg gcaatccttg caatattact     2160
gggtatagca ctgctctttt ctgtattgct aactttagta tgtggagttt ttggtgcaac     2220
taaagggaaa cgttttcctg aagatttagc acagcaaaac ttaattatat caaacacaga     2280
agcacctgga gacgatagag tgtgctctgc caatggattt atgacccaaa ctaccaacaa     2340
ctctagccaa ggttttttgtg gtactatggg atcaggaatg aaaaatggag gcaggaaac     2400 cattgaaatg atgaaaggag gaaaccgac cttggaatcc tgccgggggg ctgggcatca    2460 tcatacctg gactcctgca ggggaggaca cacggaggtg gacaactgca gatacactta     2520
ctcggagtgg cacagtttta ctcaacccg tctcggtgaa aaattgcatc gatgtaatca     2580
gaatgaagac cgcatgccat cccaagatta tgtcctcact tataactatg agggaagagg     2640
```

```
atctccagct ggttctgtgg gctgctgcag tgaaaagcag gaagaagatg gccttgactt    2700
tttaaataat ttggaaccca aatttattac attagcagaa gcatgcacaa agagataatg    2760
tcacagtgct acaattaggt ctttgtcaga cattctggag gtttccaaaa ataatattgt    2820
aaagttcaat ttcaacatgt atgtatatga tgattttttt ctcaattttg aattatgcta    2880
ctcaccaatt tatatttta aagcaagttg ttgcttatct tttccaaaaa gtgaaaaatg    2940
ttaaaacaga caactggtaa atctcaaact ccagcactgg aattaaggtc tctaaagcat    3000
ctgctctttt tttttttttac agatatttta gtaataaata tgctggataa atattagtcc    3060
aacaatagct aagttatgct aatatcacat tattatgtat tcactttaag tgatagttta    3120
aaaaataaac aagaaatatt gagtatcact atgtgaagaa agttttggaa agaaacaat    3180 gaagactgaa ttaaattaaa aatgttgcag ctcataaaga attggactca cccctactgc    3240
actaccaaat tcatttgact ttggaggcaa aatgtgttga agtgccctat gaagtagcaa    3300
ttttctatag gaatatagtt ggaaataaat gtgtgtgtgt atattattat taatcaatgc    3360
aatatttaaa tgaaatgaga acaaagagga aaatggtaaa aacttgaaat gaggctgggg    3420
tatagtttgt cctacaatag aaaaaagaga gagcttccta ggcctgggct cttaaatgct    3480
gcattataac tgagtctatg aggaaatagt tcctgtccaa tttgtgtaat ttgtttaaaa    3540
ttgtaaataa at                                                        3552
```

<210> SEQ ID NO 127
<211> LENGTH: 754
<212> TYPE: DNA
<213> ORGANISM: Homo sapien

<400> SEQUENCE: 127

```
ttttttttt ttgtcattgt tcattgattt taatgagaaa gctaagagag gaaataagta     60
gcctttcaaa ggtcacacag aagtaagtga cagatccagg attcatatcc aagcattctg    120
gctctagtgt ccatgcttct caaccattat gacccaatat tcaaccaaat caatactgaa    180
ggacacgtga aatgtatccg gtattttact attacaaaca aaaatccaat gaacattctt    240
gaagacatac acaaaaataa tggttacaat agaagttact ggaattgaaa ttttggttca    300
acctatatta aaatgtaagg cttttgatat agctaataga ttttttgaaat gatcagtctt    360 aacgtttgta gggagcaca ctcctgcatg gggaaaagat tcactgtgaa gcacagagca    420
cctttatggt tggatcatct tgtcattaaa gttcaggcgt tatctatcct gtaagtggca    480
gaatcaagac tgcaatatcg cctgcttttc tttttaactc atgttttccc ttgactacac    540
tggtcctcaa agtaaaaccc ctgtgtcagt gtactattca tggaatactc tgcaattata    600
accaccttct aatactttta atacccaatc aaaatttatt atacatatgt atcatagata    660
ctcatctgta aagctgtgct tcaaaatagt gatctcttcc caacattaca atatatatta    720
atgatgtcga acctgcccgg gcggccgctc gaag                                754
```

<210> SEQ ID NO 128
<211> LENGTH: 374
<212> TYPE: DNA
<213> ORGANISM: Homo sapien

<400> SEQUENCE: 128

```
aggttttgat taaaaaggca aatgatttta ttgttcgata atcttttaaa aaaataagag     60
gaaggagtaa aattaaagat gaaagatgat ttttatttcc ttgtgacctc tatatccccc    120
ttcccctgcc cttggtaagt aactcttgat ggagaaagga ttaaagactc ttatttaacc    180
```

```
aaaaaacaga gccagctaat catttccaaa ggttagtatc tccctgctga cctcttcttt    240
ggtttaattg aataaaacta tatgttcata tatgtattaa aacaactcag aataacatct    300
tttcttcctt agttaaggca ttataagggc tatactatca tccataataa ccaaggcaat    360
aacttaaaaa gctg                                                      374
```

<210> SEQ ID NO 129
<211> LENGTH: 546
<212> TYPE: DNA
<213> ORGANISM: Homo sapien

<400> SEQUENCE: 129

```
agtgtgatgg atatctgcag aattcgggct aagcgtggtc gcggcccgag gtctggaact     60
tcccagcacy tgaaaaggag cctcctgagc tgactcggct aaagccccac tttcgctcct    120
cctcatttct gcctactgat ttccttggag cattcatctg aatattaccg tttgctgtgt    180
aacctggtac atacatagca tgactccctg aatagagtg gctggggtg cttatgctgg      240 gagagtgatt gacatgcact ttcaagctat atctaccatt tgcagcaaag gagaaaaaat    300
acctcgagta aattccatca tttttttataa catcagcacc tgctccatca tcaaggagtc   360
tcagcgtaac aggatctcca gtctctggct caactgtggc agtgacagtg cattaagaa     420 tgggataaaa tccctgtttc acattggcat aaatcatcac aggatgagga aaatggaggc    480
tgtctctttc cacaaaggct tccacagtgg ctgggggcac agacctgccc gggcggccgc    540
tcgaaa                                                              546
```

<210> SEQ ID NO 130
<211> LENGTH: 5156
<212> TYPE: DNA
<213> ORGANISM: Homo sapien

<400> SEQUENCE: 130

```
accaaccgag gcgccgggca gcgacccctg cagcggagac agagactgag cggcccggca     60
ccgccatgcc tgcgctctgg ctgggctgct gcctctgctt gtcgctcctc ctgcccgcag    120
cccgggccac ctccaggagg gaagtctgtg attgcaatgg gaagtccagg cagtgtatct    180
ttgatcggga acttcacaga caaactggta atggattccg ctgcctcaac tgcaatgaca    240
acactgatgg cattcactgc gagaagtgca agaatggctt ttaccggcac agagaaaggg    300
accgctgttt gccctgcaat tgtaactcca aggttctct tagtgctcga tgtgacaact    360
ccggacggtg cagctgtaaa ccaggtgtga caggagccag atgcgaccga tgtctgccag    420
gcttccacat gctcacggat gcggggtgca cccaagacca gagactgcta gactccaagt    480
gtgactgtga cccagctggc atcgcagggc cctgtgacgc gggccgctgt gtctgcaagc    540
cagctgtcac tggagaacgc tgtgataggt gtcgatcagg ttactataat ctggatgggg    600
ggaaccctga gggctgtacc cagtgtttct gctatgggca ttcagccagc tgccgcagct    660
ctgcagaata cagtgtccat aagatcacct ctacctttca tcaagatgtt gatggctgga    720
aggctgtcca acgaaatggg tctcctgcaa agctccaatg gtcacagcgc atcaagatg     780 tgtttagctc agcccaacga ctagaccctg tctattttgt ggctcctgcc aaatttcttg    840
ggaatcaaca ggtgagctat ggtcaaagcc tgtcctttga ctaccgtgtg gacagaggag    900
gcagacaccc atctgcccat gatgtgattc tggaaggtgc tggtctacgg atcacagctc    960
ccttgatgcc acttggcaag acactgcctt gtgggctcac caagacttac acattcaggt   1020
```

```
taaatgagca tccaagcaat aattggagcc cccagctgag ttactttgag tatcgaaggt   1080
tactgcggaa tctcacagcc ctccgcatcc gagctacata tggagaatac agtactgggt   1140
acattgacaa tgtgaccctg atttcagccc gccctgtctc tggagcccca gcaccctggg   1200
ttgaacagtg tatatgtcct gttgggtaca agggcaatt  ctgccaggat tgtgcttctg   1260
gctacaagag agattcagcg agactggggc cttttggcac ctgtattcct tgtaactgtc   1320 aaggggagg  ggcctgtgat ccagacacag gagattgtta ttcaggggat gagaatcctg   1380
acattgagtg tgctgactgc ccaattggtt tctacaacga tccgcacgac ccccgcagct   1440
gcaagccatg tccctgtcat aacgggttca gctgctcagt gatgccggag acggaggagg   1500
tggtgtgcaa taactgccct cccggggtca ccggtgcccg ctgtgagctc tgtgctgatg   1560
gctactttgg ggacccctt  ggtgaacatg cccagtgag  gccttgtcag ccctgtcaat   1620
gcaacaacaa tgtggacccc agtgcctctg gaattgtga  ccggctgaca ggcaggtgtt   1680
tgaagtgtat ccacaacaca gccggcatct actgcgacca gtgcaaagca ggctacttcg   1740
gggacccatt ggctcccaac ccagcagaca agtgtcgagc ttgcaactgt aaccccatgg   1800
gctcagagcc tgtaggatgt cgaagtgatg gcacctgtgt ttgcaagcca ggatttggtg   1860
gccccaactg tgagcatgga gcattcagct gtccagcttg ctataatcaa gtgaagattc   1920
agatggatca gtttatgcag cagcttcaga gaatggaggc cctgatttca aaggctcagg   1980
gtggtgatgg agtagtacct gatacagagc tggaaggcag gatgcagcag gctgagcagg   2040
cccttcagga cattctgaga gatgcccaga tttcagaagg tgctagcaga tcccttggtc   2100
tccagttggc caaggtgagg agccaagaga acagctacca gagccgcctg gatgacctca   2160
agatgactgt ggaaagagtt cgggctctgg gaagtcagta ccagaaccga gttcgggata   2220
ctcacaggct catcactcag atgcagctga gcctggcaga aagtgaagct tccttgggaa   2280
acactaacat tcctgcctca gaccactacg tggggccaaa tggctttaaa agtctggctc   2340
aggaggccac aagattagca gaaagccacg ttgagtcagc cagtaacatg gagcaactga   2400
caagggaaac tgaggactat tccaaacaag ccctctcact ggtgcgcaag gccctgcatg   2460
aaggagtcgg aagcggaagc ggtagcccgg acggtgctgt ggtgcaaggg cttgtggaaa   2520
aattggagaa aaccaagtcc ctggcccagc agttgacaag ggaggccact caagcggaaa   2580
ttgaagcaga taggtcttat cagcacagtc tccgcctcct ggattcagtg tctcggcttc   2640
agggagtcag tgatcagtcc tttcaggtgg aagaagcaaa gaggatcaaa caaaaagcgg   2700
attcactctc aagcctggta accaggcata tggatgagtt caagcgtaca cagaagaatc   2760
tgggaaactg gaaagaagaa gcacagcagc tcttacagaa tggaaaaagt gggagagaga   2820
aatcagatca gctgctttcc cgtgccaatc ttgctaaaag cagagcacaa gaagcactga   2880
gtatgggcaa tgccactttt tatgaagttg agagcatcct taaaaacctc agagagtttg   2940
acctgcaggt ggacaacaga aaagcagaag ctgaagaagc catgaagaga ctctcctaca   3000
tcagccagaa ggtttcagat gccagtgaca agacccagca agcagaaaga gccctgggga   3060
gcgctgctgc tgatgcacag agggcaaaga tggggccgg  ggaggccctg gaaatctcca   3120
gtgagattga acaggagatt gggagtctga acttggaagc caatgtgaca gcagatggag   3180
ccttggccat ggaaaaggga ctggcctctc tgaagagtga gatgagggaa gtggaaggag   3240
agctggaaag gaaggagctg gagtttgaca cgaatatgga tgcagtacag atggtgatta   3300
cagaagccca gaaggttgat accagagcca agaacgctgg ggttacaatc caagacacac   3360
```

-continued

```
tcaacacatt agacggcctc ctgcatctga tggaccagcc tctcagtgta gatgaagagg    3420
ggctggtctt actggagcag aagctttccc gagccaagac ccagatcaac agccaactgc    3480
ggcccatgat gtcagagctg aagagaggg cacgtcagca gaggggccac ctccatttgc     3540
tggagacaag catagatggg attctggctg atgtgaagaa cttggagaac attagggaca    3600
acctgccccc aggctgctac aatacccagg ctcttgagca acagtgaagc tgccataaat    3660
atttctcaac tgaggttctt gggatacaga tctcagggct cgggagccat gtcatgtgag    3720
tgggtgggat ggggacattt gaacatgttt aatgggtatg ctcaggtcaa ctgacctgac    3780
cccattcctg atcccatggc caggtggttg tcttattgca ccatactcct tgcttcctga    3840
tgctgggcaa tgaggcagat agcactgggt gtgagaatga tcaaggatct ggaccccaaa    3900
gaatagactg gatggaaaga caaactgcac aggcagatgt ttgcctcata atagtcgtaa    3960
gtggagtcct ggaatttgga caagtgctgt tgggatatag tcaacttatt ctttgagtaa    4020
tgtgactaaa ggaaaaaact ttgactttgc ccaggcatga aattcttcct aatgtcagaa    4080
cagagtgcaa cccagtcaca ctgtggccag taaaatacta ttgcctcata ttgtcctctg    4140
caagcttctt gctgatcaga gttcctccta cttacaaccc agggtgtgaa catgttctcc    4200
attttcaagc tggaagaagt gagcagtgtt ggagtgagga cctgtaaggc aggcccattc    4260
agagctatgg tgcttgctgg tgcctgccac cttcaagttc tggacctggg catgacatcc    4320
tttcttttaa tgatgccatg gcaacttaga gattgcattt ttattaaagc atttcctacc    4380
agcaaagcaa atgttgggaa agtatttact ttttcggttt caaagtgata gaaaagtgtg    4440
gcttgggcat tgaaagaggt aaaattctct agatttatta gtcctaattc aatcctactt    4500
ttagaacacc aaaaatgatg cgcatcaatg tattttatct tattttctca atctcctctc    4560
tctttcctcc acccataata agagaatgtt cctactcaca cttcagctgg gtcacatcca    4620
tccctccatt catccttcca tccatctttc catccattac ctccatccat ccttccaaca    4680
tatatttatt gagtacctac tgtgtgccag gggctggtgg gacagtggtg acatagtctc    4740
tgccctcata gagttgattg tctagtgagg aagacaagca ttttttaaaaa ataaatttaa    4800 acttacaaac tttgtttgtc acaagtggtg tttattgcaa taaccgcttg gtttgcaacc    4860
tctttgctca acagaacata tgttgcaaga ccctcccatg ggggcacttg agttttggca    4920
aggctgacag agctctgggt tgtgcacatt tctttgcatt ccagctgtca ctctgtgcct    4980
ttctacaact gattgcaaca gactgttgag ttatgataac accagtggga attgctggag    5040
gaaccagagg cacttccacc ttggctggga agactatggt gctgccttgc ttctgtattt    5100
ccttggattt tcctgaaagt gttttttaaat aaagaacaat tgttagaaaa aaaaaa       5156
```

<210> SEQ ID NO 131  
<211> LENGTH: 671  
<212> TYPE: DNA  
<213> ORGANISM: Homo sapien

<400> SEQUENCE: 131

```
aggtctggag ggcccacagc cggatgtggg acaccgggaa aaagtggtca tagcacacat      60
ttttgcatcc cggttgcagt gtgttgcaga cgaagtcctc ttgctcgtca ccccacactt     120
cctgggcagc caycacgagg atcatgactc ggaaaataaa gatgactgtg atccacacct     180
tcccgatgct ggtggagtgt ttgttgacac ccccgatgaa agtgtgcagc gtcccccaat     240
ccattgcgct ggtttatccc tgagtcctgt ttccaacgac tgccagtgtt tcagacccaa     300
```

-continued

| | | |
|---|---|---|
| agaatgaggg caagatccct ctgcgagggt ttcagacctc cttctcctac cccactggag | 360 |
| tgcctagaag ccaatgggtg cacagtgatg atacgaatgt caatctttgc tcggtcagtg | 420 |
| aggatgtcgc ctggaatatt caaattgaat tacagatgca tgaagagggc gtacaagtta | 480 |
| gaattttcct ttcgccatac agaaattgtt tagccagatc ttctgtactt cttttccttc | 540 |
| cctgacccct tcctgctccc aggaagggag gtcagccccg tttgcaaaac acaggatgcc | 600 |
| cgtgacaccg gagacaggtc ttcttcaccg acaggaagtg ccttctggtg cctgcacgtt | 660 |
| ttaactgcta t | 671 |

<210> SEQ ID NO 132
<211> LENGTH: 590
<212> TYPE: DNA
<213> ORGANISM: Homo sapien

<400> SEQUENCE: 132

| | | |
|---|---|---|
| ctgaatggaa aagcttatgg ctctgtgatg atattagtga ccagcggaga tgataagctt | 60 |
| cttggcaatt gcttacccac tgtgctcagc agtggttcaa caattcactc cattgccctg | 120 |
| ggttcatctg cagccccaaa tctggaggaa ttatcacgtc ttacaggagg tttaaagttc | 180 |
| tttgttccag atatatcaaa ctccaatagc atgattgatg ctttcagtag aatttcctct | 240 |
| ggaactggag acattttcca gcaacatatt cagcttgaaa gtacaggtga aaatgtcaaa | 300 |
| cctcaccatc aattgaaaaa cacagtgact gtggataata ctgtgggcaa cgacactatg | 360 |
| tttctagtta cgtggcaggc cagtggtcct cctgagatta tattatttga tcctgatgga | 420 |
| cgaaaatact acacaaataa ttttatcacc aatctaactt ttcggacagc tagtctttgg | 480 |
| attccaggaa cagctaagcc tgggcactgg acttacaccc tgaacaatac ccatcattct | 540 |
| ctgcaagccc tgaaagtgac agtgacctct cgcgcctcca actcagacct | 590 |

<210> SEQ ID NO 133
<211> LENGTH: 581
<212> TYPE: DNA
<213> ORGANISM: Homo sapien

<400> SEQUENCE: 133

| | | |
|---|---|---|
| aggtcctgtc cgggggcact gagaactccc tctggaattc ttgggggggtg ttggggagag | 60 |
| actgtgggcc tggagataaa acttgtctcc tctaccacca ccctgtaccc tagcctgcac | 120 |
| ctgtcctcat ctctgcaaag ttcagcttcc ttccccaggt ctctgtgcac tctgtcttgg | 180 |
| atgctctggg gagctcatgg gtggaggagt ctccaccaga gggaggctca ggggactggt | 240 |
| tgggccaggg atgaatattt gagggataaa aattgtgtaa gagccaaaga attggtagta | 300 |
| gggggagaac agagaggagc tgggctatgg gaaatgattt gaataatgga gctgggaata | 360 |
| tggctggata tctggtacta aaaaagggtc tttaagaacc tacttcctaa tctcttcccc | 420 |
| aatccaaacc atagctgtct gtccagtgct ctcttcctgc ctccagctct gccccaggct | 480 |
| cctcctagac tctgtccctg ggctaggcga ggggaggagg gagagcaggg ttgggggaga | 540 |
| ggctgaggag agtgtgacat gtggggagag gaccagacct c | 581 |

<210> SEQ ID NO 134
<211> LENGTH: 4797
<212> TYPE: DNA
<213> ORGANISM: Homo sapien
<220> FEATURE:
<221> NAME/KEY: misc_feature
<222> LOCATION: (1)...(4797)

<223> OTHER INFORMATION: n = A,T,C or G

<400> SEQUENCE: 134

| | | | | | |
|---|---|---|---|---|---:|
| cctgggacca | aagtgctgcc | cagagctgag | ggtcctggag | ccacatgaga | aggcttctcc | 60 |
| ctgtgtacct | gtgcagcaca | gggtagggtg | agtccactca | gctgtctagg | agaggaccca | 120 |
| ggagcagcag | agacncgcca | agcctttact | cataccatat | tctgatcctt | ttccagcaaa | 180 |
| ttgtggctac | taatttgccc | cctgaagatc | aagatggctc | tggggatgac | tctgacaact | 240 |
| tctccggctc | aggtgcaggt | gaggttgtca | tgggggcccc | ccccacccaa | gacggcaaca | 300 |
| ggtcatgcct | gggggcagtg | gtcaggcagt | ctcctgtgtt | tactgagcat | gtactgagtg | 360 |
| caccctgcct | gccctgtctc | cacccagctg | gctccaaagg | gcaatgctga | ggagaggaat | 420 |
| ggggtcgtga | gctgctgtta | aggagagctc | atgcttggag | gtgaggtgaa | ggctgtgagc | 480 |
| tccagaaggc | cccagggcgc | nctgctgcac | gcaggctcat | attcactagg | aatagcttta | 540 |
| ctcactaaga | aacctctgga | acccccttca | gaaggttatt | tgactcctga | gcctctattt | 600 |
| tctcatctgc | aaaatgggaa | taataccttg | acctgataag | cttgtggagc | tgtaaggcag | 660 |
| cacagagcca | gctgggtgt | agctcttcca | tccaagctcc | cttccttact | tcccctttcc | 720 |
| tgtggggact | gggggagaga | agtccctgag | ctggaggtgg | tcagggaagc | ttcacagagg | 780 |
| aggtggctct | tgagtggacc | tcaggaagag | gggtgagaga | gctaaggaag | gaggctgagg | 840 |
| tcatccctgg | ggaagtgacc | tagcggaggc | ctgagagctg | caaggtagga | tatctgttgt | 900 |
| tggaagtgtc | tgttgttgga | agtggggggcc | ttttttcag | ggagggtggg | gccagagaag | 960 |
| tgtgtgccct | gggataagta | ggataaccac | agtagttatg | ccctaaggg | atgcccaccc | 1020 |
| caccctgtg | gtcacagaaa | agctttccca | ggtggcctag | gcacctgtct | cgtggctcca | 1080 |
| gagacaggct | gcacctgaca | cacacaatgg | aaggacagct | ctccttgtcc | attttccaag | 1140 |
| gagcttagcc | tcagctgcct | tgtccaggta | ctagcctccc | tcatagcctg | agcttggcca | 1200 |
| gcccaggtgc | tctggagcct | ccccgaccc | acccaacaca | ctctgcttct | ggtcctcccc | 1260 |
| accccccacc | tccccaacac | actctgcttc | tggtcctgca | ggtgctttgc | aagatatcac | 1320 |
| cttgtcacag | cagaccccct | ccacttggaa | ggacacgcag | ctcctgacgg | ctattcccac | 1380 |
| gtctccagaa | cccaccggcc | tggaggctac | agctgcctcc | acctccaccc | tgccggctgg | 1440 |
| agagggccc | aaggagggag | aggctgtagt | cctgccagaa | gtggagcctg | gcctcaccgc | 1500 |
| ccgggagcag | gaggccaccc | cccgacccag | ggagaccaca | cagctcccga | ccactcatca | 1560 |
| ggcctcaacg | accacagcca | ccacggccca | ggagcccgcc | acctcccacc | cccacaggga | 1620 |
| catgcagcct | ggccaccatg | agacctcaac | ccctgcagga | cccagccaag | ctgaccttca | 1680 |
| cactccccac | acagaggatg | gaggtccttc | tgccaccgag | agggctgctg | aggatggagc | 1740 |
| ctccagtcag | ctcccagcag | cagagggctc | tggggagcag | gtgagtggcc | tctgcattcc | 1800 |
| ttgggaaatt | gagtgggttg | gtcctaatgc | ctggcacttg | gcaggcccta | cacctgtgcc | 1860 |
| ctgcgcgatc | tcgtattcct | caccaggaag | acagggcaca | ggggccgcct | tcccctaccc | 1920 |
| ccagggcctc | gcagagcagg | acagactaac | tatgagatca | gagcagaagc | acccttaaag | 1980 |
| atcacccaag | agagggctcc | caaactcaca | atccaaactt | gcagccctcg | tcgaagagtg | 2040 |
| aacgttatac | cagtcatttt | atttatagct | tcgtggattt | acgcttacac | taaatagtct | 2100 |
| gctattcata | caaaatgtgt | gctttgtatc | acttttttgtg | atatccatgc | catggtccag | 2160 |
| ccagggtccg | gagttgatgt | ggcaagaagg | cctggctttc | gggccctgtg | cgatcctggt | 2220 |
| ttgggtgcat | ctgagtgggt | ggtggcaaag | atcagggagg | caggagctgc | ttctgggtct | 2280 |

```
gtagtggagc tggttgctgc tgctggcggt gacctggcca acccaatctg cccctgccct    2340
cccacaggac ttcacctttg aaacctcggg ggagaatacg gctgtagtgg ccgtggagcc    2400
tgaccgccgg aaccagtccc cagtggatca gggggccacg ggggcctcac agggcctcct    2460
ggacaggaaa gaggtgctgg gaggtgagtt ttctttcagg ggggtagttt ggggtgaatt    2520
gctgctgtgg ggtcagggtg gggctgacca cagccaaggc cactgctttg ggagggtctg    2580
cacgagagcc caaggagccg ctgagctgag ctggccccgt ctacctgccc taggggtcat    2640
tgccggaggc ctcgtggggc tcatctttgc tgtgtgcctg gtgggtttca tgctgtaccg    2700
catgaagaag aaggacgaag gcagctactc cttggaggag ccgaaacaag ccaacggcgg    2760
ggcctaccag aagcccacca acaggaggag attctatgcc tgacgcggga gccatgcgcc    2820
ccctccgccc tgccactcac taggcccca cttgcctctt ccttgaagaa ctgcaggccc     2880
tggcctcccc tgccaccagg ccacctcccc agcattccag cccctctggt cgctcctgcc    2940
cacggagtcg tgggtgtgct gggagctcca ctctgcttct ctgacttctg cctggagact    3000
tagggcacca ggggtttctc gcataggacc tttccaccac agccagcacc tggcatcgca    3060
ccattctgac tcggtttctc caaactgaag cagcctctcc ccaggtccag ctctggaggg    3120
gagggggatc cgactgcttt ggacctaaat ggcctcatgt ggctggaaga tcctgcgggt    3180
ggggcttggg gctcacacac ctgtagcact tactggtagg accaagcatc ttgggggggt    3240
ggccgctgag tggcagggga caggagtcac tttgtttcgt ggggaggtct aatctagata    3300
tcgacttgtt tttgcacatg tttcctctag ttctttgttc atagcccagt agaccttgtt    3360
acttctgagg taagttaagt aagttgattc ggtatccccc catcttgctt ccctaatcta    3420
tggtcgggag acagcatcag ggttaagaag acttttttttt tttttttaa actaggagaa    3480
ccaaatctgg aagccaaaat gtaggcttag tttgtgtgtt gtctcttgag tttgtcgctc    3540
atgtgtgcaa cagggtatgg actatctgtc tggtggcccc gttctggtgg tctgttggca    3600
ggctggccag tccaggctgc cgtgggggccg ccgcctcttt caagcagtcg tgcctgtgtc    3660
catgcgctca gggccatgct gaggcctggg ccgctgccac gttggagaag cccgtgtgag    3720
aagtgaatgc tgggactcag ccttcagaca gagaggactg tagggagggc ggcaggggcc    3780
tggagatcct cctgcaggct cacgcccgtc ctcctgtggc gccgtctcca ggggctgctt    3840
cctcctggaa attgacgagg ggtgtcttgg gcagagctgg ctctgagcgc ctccatccaa    3900
ggccaggttc tccgttagct cctgtggccc caccctgggc cctgggctgg aatcaggaat    3960
attttccaaa gagtgatagt cttttgcttt tggcaaaact ctacttaatc caatgggttt    4020
ttccctgtac agtagatttt ccaaatgtaa taaactttaa tataaagtag tctgtgaatg    4080
ccactgcctt cgcttcttgc ctctgtgctg tgtgtgacgt gaccggactt ttctgcaaac    4140
accaacatgt tgggaaactt ggctcgaatc tctgtgcctt cgtctttccc atggggaggg    4200
attctggttc cagggtccct ctgtgtattt gcttttttgt tttggctgaa attctcctgg    4260
aggtcggtag gttcagccaa ggttttataa ggctgatgtc aatttctgtg ttgccaagct    4320
ccaagcccat cttctaaatg gcaaaggaag gtggatggcc ccagcacagc ttgacctgag    4380
gctgtggtca cagcggaggt gtggagccga ggcctacccc ncagacacct ggacatcct     4440
cctcccaccc ggctgcagag gccaganncc agcccagggt cctgcactta cttgcttatt    4500
tgacaacgtt tcagcgactc cgttggccac tccgagagtg ggccagtctg tggatcagag    4560
atgcaccacc aagccaaggg aacctgtgtc cggtattcga tactgcgact ttctgcctgg    4620
```

-continued

```
agtgtatgac tgcacatgac tcggggtgg ggaaagggt cggctgacca tgctcatctg    4680
ctggtccgtg ggacggtncc caagccagag gtgggttcat ttgtgtaacg acaataaacg    4740
gtacttgtca tttcgggcaa cggctgctgt ggtggtggtt gagtctcttc ttggcct      4797
```

<210> SEQ ID NO 135
<211> LENGTH: 2856
<212> TYPE: DNA
<213> ORGANISM: Homo sapien

<400> SEQUENCE: 135

```
tagtcgcggg tccccgagtg agcacgccag ggagcaggag accaaacgac ggggtcgga      60 gtcagagtcg cagtgggagt ccccggaccg agcacgagc ctgagcggga gagcgccgct    120
cgcacgcccg tcgccacccg cgtacccggc gcagccagag ccaccagcgc agcgctgcca    180
tggagcccag cagcaagaag ctgacgggtc gcctcatgct ggctgtggga ggagcagtgc    240
ttggctccct gcagtttggc tacaacactg gagtcatcaa tgcccccag aaggtgatcg    300 aggagttcta caaccagaca tgggtccacc gctatgggga gagcatcctg cccaccacgc    360
tcaccacgct ctggtccctc tcagtggcca tcttttctgt tgggggcatg attggctcct    420
tctctgtggg ccttttcgtt aaccgctttg gccggcggaa ttcaatgctg atgatgaacc    480
tgctggcctt cgtgtccgcc gtgctcatgg gcttctcgaa actgggcaag tcctttgaga    540
tgctgatcct gggccgcttc atcatcggtg tgtactgcgg cctgaccaca ggcttcgtgc    600
ccatgtatgt gggtgaagtg tcacccacag cctttcgtgg ggccctgggc accctgcacc    660
agctgggcat cgtcgtcggc atcctcatcg cccaggtgtt cggcctggac tccatcatgg    720
gcaacaagga ccctgtgggc cctgctgctga gcatcatctt catcccggcc ctgctgcagt    780
gcatcgtgct gcccttctgc cccgagagtc cccgcttcct gctcatcaac cgcaacgagg    840
agaaccgggc caagagtgtg ctaaagaagc tgcgcgggac agctgacgtg acccatgacc    900
tgcaggagat gaaggaagag agtcggcaga tgatgcggga agaaggtc accatcctgg    960 agctgttccg ctcccccgcc taccgccagc ccatcctcat cgctgtggtg ctgcagctgt   1020
cccagcagct gtctggcatc aacgctgtct tctattactc cacgagcatc ttcgagaagg   1080
cgggggtgca gcagcctgtg tatgccacca ttggctccgg tatcgtcaac acggccttca   1140
ctgtcgtgtc gctgtttgtg gtggagcgag caggccggcg gaccctgcac ctcataggcc   1200
tcgctggcat ggcgggttgt gccatactca tgaccatcgc gctagcactg ctggagcagc   1260
taccctggat gtcctatctg agcatcgtgg ccatctttgg ctttgtggcc ttctttgaag   1320
tgggtcctgg ccccatccca tggttcatcg tggctgaact cttcagccag ggtccacgtc   1380
cagctgccat tgccgttgca ggcttctcca actggaccte aaatttcatt gtgggcatgt   1440
gcttccagta tgtggagcaa ctgtgtggtc cctacgtctt catcatcttc actgtgctcc   1500
tggttctgtt cttcatcttc acctacttca agttcctga gactaaaggc cggaccttcg   1560
atgagatcgc ttccggcttc cggcagggg gagccagcca aagtgataag acacccgagg   1620
agctgttcca tccccctgggg gctgattccc aagtgtgagt cgccccagat caccagcccg   1680
gcctgctccc agcagcccta aggatctctc aggagcacag gcagctggat gagacttcca   1740
aacctgacag atgtcagccg agccgggcct ggggctcctt tctccagcca gcaatgatgt   1800
ccagaagaat attcaggact taacggctcc aggattttaa caaaagcaag actgttgctc   1860
aaatctattc agacaagcaa caggttttat aatttttta ttactgattt tgttattttt   1920
atatcagcct gagtctcctg tgcccacatc ccaggcttca ccctgaatgg ttccatgcct   1980
```

```
gagggtggag actaagccct gtcgagacac ttgccttctt cacccagcta atctgtaggg    2040
ctggacctat gtcctaagga cacactaatc gaactatgaa ctacaaagct tctatcccag    2100
gaggtggcta tggccacccg ttctgctggc ctggatctcc ccactctagg ggtcaggctc    2160
cattaggatt tgcccttcc catctcttcc tacccaacca ctcaaattaa tctttcttta    2220
cctgagacca gttgggagca ctggagtgca gggaggagag gggaagggcc agtctgggct    2280
gccgggttct agtctccttt gcactgaggg ccacactatt accatgagaa gagggcctgt    2340
gggagcctgc aaactcactg ctcaagaaga catggagact cctgccctgt tgtgtataga    2400
tgcaagatat ttatatatat ttttggttgt caatattaaa tacagacact aagttatagt    2460
atatctggac aagccaactt gtaaatacac cacctcactc ctgttactta cctaaacaga    2520
tataaatggc tggtttttag aaacatggtt ttgaaatgct tgtggattga gggtaggagg    2580
tttggatggg agtgagacag aagtaagtgg ggttgcaacc actgcaacgg cttagacttc    2640
gactcaggat ccagtccctt acacgtacct ctcatcagtg tcctcttgct caaaaatctg    2700
tttgatccct gttacccaga gaatatatac attcttatc ttgacattca aggcatttct    2760
atcacatatt tgatagttgg tgttcaaaaa aacactagtt ttgtgccagc cgtgatgctc    2820
aggcttgaaa tcgcattatt ttgaatgtga agggaa                              2856

<210> SEQ ID NO 136
<211> LENGTH: 356
<212> TYPE: DNA
<213> ORGANISM: Homo sapien

<400> SEQUENCE: 136
ggtggagcca aatgaagaaa atgaagatga aagagacaga cacctcagtt tttctggatc     60
aggcattgat gatgatgaag attttatctc cagcaccatt tcaaccacac cacgggcttt    120
tgaccacaca aaacagaacc aggactggac tcagtggaac ccaagccatt caaatccgga    180
agtgctactt cagacaacca caaggatgac tgatgtagac agaaatggca ccactgctta    240
tgaaggaaac tggaacccag aagcacaccc tcccctcatt caccatgagc atcatgagga    300
agaagagacc ccacattcta caagcacaat ccaggcaact cctagtagta caacgg        356

<210> SEQ ID NO 137
<211> LENGTH: 356
<212> TYPE: DNA
<213> ORGANISM: Homo sapien
<220> FEATURE:
<221> NAME/KEY: misc_feature
<222> LOCATION: (1)...(356)
<223> OTHER INFORMATION: n = A,T,C or G

<400> SEQUENCE: 137
gcaggtggag aagacatttt attgttcctg gggtctctgg aggcccattg gtggggctgg     60
gtcactggct gcccccggaa cagggcgctg ctccatggct ctgcttgtgg tagtctgtgg    120
ctatgtctcc cagcaaggac agaaactcag aaaaatcaat cttcttatcc tcattcttgt    180 ccttttctc aaagacatcg gcgaggtaat ttgtgcccct tttacctcgg cccgcgacca    240
cgctaaggcc aaanttccag acanayggcc gggccggtnc natagggan cccaacttgg    300 ggacccaaac tctggcgcgg aaacacangg gcataagctt gnttcctgtg gggaaa        356

<210> SEQ ID NO 138
<211> LENGTH: 353
<212> TYPE: DNA
```

<213> ORGANISM: Homo sapien

<400> SEQUENCE: 138

| aggtccagtc ctccacttgg cctgatgaga gtggggagtg gcaagggacg tttctcctgc | 60 |
| aatagacact tagatttctc tcttgtggga agaaaccacc tgtccatcca ctgactcttc | 120 |
| tacattgatg tggaaattgc tgctgctacc accacctcct gaagaggctt ccctgatgcc | 180 |
| aatgccagcc atcttggcat cctggccctc gagcaggctg cggtaagtag cgatctcctg | 240 |
| ctccagccgt gtctttatgt caagcagcat cttgtactcc tggttctgag cctccatctc | 300 |
| gcatcggagc tcactcagac ctcgsccgsg mssmcgctam gccgaattcc agc | 353 |

<210> SEQ ID NO 139
<211> LENGTH: 371
<212> TYPE: DNA
<213> ORGANISM: Homo sapien

<400> SEQUENCE: 139

| agcgtggtcg cggccgaggt ccatccgaag caagattgca gatggcagtg tgaagagaga | 60 |
| agacatattc tacacttcaa agctttggtg caattcccat cgaccagagt tggtccgacc | 120 |
| agccttggaa aggtcactga aaaatcttca attggattat gttgacctct accttattca | 180 |
| ttttccagtg tctgtaaagc caggtgagga agtgatccca aaagatgaaa atggaaaaat | 240 |
| actatttgac acagtggatc tctgtgccac gtgggaggcc gtggagaagt gtaaagatgc | 300 |
| aggattggac ctgcccgggc ggccgctcga agccgaattc cagcacact ggcggccgtt | 360 |
| actagtggat c | 371 |

<210> SEQ ID NO 140
<211> LENGTH: 370
<212> TYPE: DNA
<213> ORGANISM: Homo sapien

<400> SEQUENCE: 140

| tagcgtggtc gcggccgagg tccatctccc tttgggaact aggggggctgc tggtgggaaa | 60 |
| tgggagccag ggcagatgtt gcattccttt gtgtccctgt aaatgtggga ctacaagaag | 120 |
| aggagctgcc tgagtggtac tttctcttcc tggtaatcct ctggcccagc tcatggcag | 180 |
| aatagaggta ttttaggct attttgtaa tatggcttct ggtcaaaatc cctgtgtagc | 240 |
| tgaattccca agccctgcat tgtacagccc cccactcccc tcaccaccta ataaggaat | 300 |
| agttaacact caaaaaaaaa aaaaaacctg cccgggcggc cgctcgaaag ccgaattcca | 360 |
| gcacactggc | 370 |

<210> SEQ ID NO 141
<211> LENGTH: 371
<212> TYPE: DNA
<213> ORGANISM: Homo sapien

<400> SEQUENCE: 141

| tagcgtggtc gcggccgagg tcctctgtgc tgcctgtcac agcccgatgg taccagcgca | 60 |
| gggtgtaggc agtgcaggag ccctcatcca gtggcaggga acaggggtca tcactatccc | 120 |
| aaggagcttc agggtcctgg tactcctcca cagaatactc ggagtattca gagtactcat | 180 |
| catcctcagg gggtacccgc tcttcctcct ctgcatgaga gacgcggagc acaggcacag | 240 |
| catgagctg ggagccggca gtgtctgcag cataactagg gagggtcgt gatccagatg | 300 |
| cgatgaactg gccctggcag gcacagtgct gactcatctc ttggcgacct gcccgggcgg | 360 |

```
ccgctcgaag c                                                     371
```

<210> SEQ ID NO 142
<211> LENGTH: 343
<212> TYPE: DNA
<213> ORGANISM: Homo sapien

<400> SEQUENCE: 142

```
cgttttgag gccaatggtg taaaaggaaa tatcttcaca taaaaactag atggaagcat    60
gtcagaaac ctctttgtga tgtttgcttt caactcacag agttgaacat tccttttcat   120
gagcagttt tgaaacactc ttttgtagaa tttgcaagcg atgattgga tcgctatgag    180
tcttcattg gaaacgggat acctttacat aaaaactaga cagtagcatt ctcagaaatt   240
ctttgggat gtgggcattc aacccacaga ggagaacttc atttgataga gcagttttga   300
acacccttt ttgtagaatc tacaggtgga catttagagt gct                    343
```

<210> SEQ ID NO 143
<211> LENGTH: 354
<212> TYPE: DNA
<213> ORGANISM: Homo sapien

<400> SEQUENCE: 143

```
ggtctgatg gcagaaaaac tcagactgtc tgcaacttta cagatggtgc attggttcag    60
atcaggagt gggatgggaa ggaaagcaca ataacaagaa aattgaaaga tgggaaatta   120
tggtggagt gtgtcatgaa caatgtcacc tgtactcgga tctatgaaaa agtagaataa   180
aattccatc atcactttgg acaggagtta attaagagaa tgaccaagct cagttcaatg   240
gcaaatctc catactgttt ctttcttttt tttttcatta ctgtgttcaa ttatctttat   300
ataaacatt ttacatgcag ctatttcaaa gtgtgttgga ttaattagga tcat         354
```

<210> SEQ ID NO 144
<211> LENGTH: 353
<212> TYPE: DNA
<213> ORGANISM: Homo sapien

<400> SEQUENCE: 144

```
gtcaaggac ctgggggacc cccaggtcca gcagccacat gattctgcag cagacaggga    60
ctagagcac atctggatct cagccccacc cctggcaacc tgcctgccta gagaactccc   120
agatgacag actaagtagg attctgccat ttagaataat tctggtatcc tgggcgttgc   180
ttaagttgc ttaactttca ttctgtctta cgatagtctt cagaggtggg aacagatgaa   240
aaaccatgc cccagagaag gttaagtgac ttcctcttta tggagccagt gttccaacct   300
ggtttgcct gataccagac ctgtggcccc acctcccatg caggtctctg tgg          353
```

<210> SEQ ID NO 145
<211> LENGTH: 371
<212> TYPE: DNA
<213> ORGANISM: Homo sapien

<400> SEQUENCE: 145

```
caggtctgtc ataaactggt ctggagtttc tgacgactcc ttgttcacca aatgcaccat    60
ttcctgagac ttgctggcct ctccgttgag tccacttggc tttctgtcct ccacagctcc   120
attgccactg ttgatcacta gcttttttctt ctgcccacac cttcttcgac tgttgactgc   180
aatgcaaact gcaagaatca aagccaaggc caagagggat gccaagatga tcagccattc   240
```

```
tggaatttgg ggtgtcctta taggaccaga ggttgtgttt gctccacctt cttgactccc    300
atgtgagacc tcggccgcga ccacgctaag ccgaattcca gcacactggc ggcccgttac    360
tagtggatcc g                                                         371
```

<210> SEQ ID NO 146
<211> LENGTH: 355
<212> TYPE: DNA
<213> ORGANISM: Homo sapien

<400> SEQUENCE: 146

```
gtcctccgt cctcttccca gaggtgtcgg ggcttggccc cagcctccat cttcgtctct     60 aggatggcg agtagcagcg gctccaaggc tgaattcatt gtcggaggga aatataaact    120 gtacggaag atcgggtctg gctccttcgg ggacatctat ttggcgatca acatcaccaa    180 ggcgaggaa gtggcagtga agctagaatc tcagaaggcc aggcatcccc agttgctgta    240 gagagcaag ctctataaga ttcttcaagg tggggttggc atcccccaca tacggtggta    300 ggtcaggaa aaagactaca atgtactagt catggatctt ctgggaccta gcctc         355
```

<210> SEQ ID NO 147
<211> LENGTH: 355
<212> TYPE: DNA
<213> ORGANISM: Homo sapien

<400> SEQUENCE: 147

```
gtctgttac aaaatgaaga cagacaacac aacatttact ctgtggagat atcctactca     60 actatgcac gtgctgtgat tttgaacata actcgtccca aaaacttgtc acgatcatcc    120 gactttta ggttggctga tccatcaatc ttgcactcaa ctgttacttc tttcccagtg    180 tgttaggag caaagctgac ctgaacagca accaatggct gtagataccc aacatgcagt    240 ttttcccat aatatgggaa atattttaag tctatcattc cattatgagg ataaactgct    300 catttggta tatcttcatt ctttgaaaca caatctatcc ttggcactcc ttcag         355
```

<210> SEQ ID NO 148
<211> LENGTH: 369
<212> TYPE: DNA
<213> ORGANISM: Homo sapien

<400> SEQUENCE: 148

```
aggtctctct cccctctcc ctctcctgcc agccaagtga agacatgctt acttcccctt     60
caccttcctt catgatgtgg gaagagtgct gcaacccagc cctagccaac accgcatgag   120
agggagtgtg ccgagggctt ctgagaaggt ttctctcaca tctagaaaga agcgcttaag   180
atgtggcagc ccctcttctt caagtggctc ttgtcctgtt gccctgggag ttctcaaatt   240
gctgcagcag cctccatcca gcctgaggat gacatcaata cacagaggaa gaagagtcag   300
gaaaagatga gagaagttac agactctcct gggcgacccc gagagcttac cattcctcag   360
acttcttca                                                           369
```

<210> SEQ ID NO 149
<211> LENGTH: 620
<212> TYPE: DNA
<213> ORGANISM: Homo sapien
<220> FEATURE:
<221> NAME/KEY: misc_feature
<222> LOCATION: (1)...(620)
<223> OTHER INFORMATION: n = A,T,C or G

```
<400> SEQUENCE: 149
actagtcaaa aatgctaaaa taatttggga gaaatatttt tttaagtagt gttatagttt      60
catgtttatc ttttattatg ttttgtgaag ttgtgtcttt tcactaatta cctatactat     120
gccaatattt ccttatatct atccataaca tttatactac atttgtaana naatatgcac     180
gtgaaactta acactttata aggtaaaaat gaggtttcca anatttaata atctgatcaa     240
gttcttgtta tttccaaata gaatggactt ggtctgttaa gggctaagga gaagaggaag     300
ataaggttaa aagttgttaa tgaccaaaca ttctaaaaga aatgcaaaaa aaagtttat      360
tttcaagcct tcgaactatt taaggaaagc aaaatcattt cctaaatgca tatcatttgt     420
gagaatttct cattatatc ctgaatcatt catttcacta aggctcatgt tnactccgat      480
atgtctctaa gaaatacta tttcatggtc caaacctggt tgccatantt gggtaaaggc      540
tttcccttaa gtgtaaant atttaaaatg aattttcct cttttttaaaa attctttana      600
agggttaagg gtgtgggga                                                   620

<210> SEQ ID NO150
<211> LENGTH: 371
<212> TYPE: DNA
<213> ORGANISM: Homo sapien

<400> SEQUENCE: 150
ggtccgatca aaacctgcta cctccccaag actttactag tgccgataaa ctttctcaaa      60
gagcaaccag tatcacttcc ctgtttataa aacctctaac catctctttg ttctttgaac     120
atgctgaaaa ccacctggtc tgcatgtatg cccgaatttg yaattctttt ctctcaaatg     180
aaaatttaat tttagggatt catttctata ttttcacata tgtagtatta ttatttcctt     240
atatgtgtaa ggtgaaattt atggtatttg agtgtgcaag aaaatatatt tttaaagctt     300
tcatttttcc cccagtgaat gatttagaat tttttatgta aatatacaga atgttttttc     360
ttacttttat a                                                          371

<210> SEQ ID NO 151
<211> LENGTH: 4655
<212> TYPE: DNA
<213> ORGANISM: Homo sapien

<400> SEQUENCE: 151
gggacttgag ttctgttatc ttcttaagta gattcatatt gtaagggtct cggggtgggg      60
gggttggcaa aatcctggag ccagaagaaa ggacagcagc attgatcaat cttacagcta     120
acatgttgta cctggaaaac aatgcccaga ctcaatttag tgagccacag tacacgaacc     180
tggggctcct gaacagcatg gaccagcaga ttcagaacgg ctcctcgtcc accagtccct     240
ataacacaga ccacgcgcag aacagcgtca cggcgccctc gccctacgca cagcccagct     300
ccaccttcga tgctctctct ccatcacccg ccatcccctc caacaccgac tacccaggcc     360
cgcacagttt cgacgtgtcc ttccagcagt cgagcaccgc caagtcggcc acctggacgt     420
attccactga actgaagaaa ctctactgcc aaattgcaaa gacatgcccc atccagatca     480
aggtgatgac cccacctcct caggagctg ttatccgcgc catgcctgtc tacaaaaaag     540
ctgagcacgt cacggaggtg gtgaagcggt gccccaacca tgagctgagc cgtgaattca     600
acgagggaca gattgcccct yctagtcatt tgattcgagt agaggggaac agccatgccc     660
agtatgtaga agatccatc acaggaagac agagtgtgct ggtaccttat gagccacccc     720
aggttggcac tgaattcacg acagtcttgt acaatttcat gtgtaacagc agttgtgttg     780
```

```
                                      -continued gagggatgaa ccgccgtcca attttaatca ttgttactct ggaaaccaga gatgggcaag    840
tcctgggccg acgctgcttt gaggcccgga tctgtgcttg cccaggaaga dacaggaagg    900
cggatgaaga tagcatcaga aagcagcaag tttcggacag tacaaagaac ggtgatggta    960
cgaagcgccc gtttcgtcag aacacacatg gtatccagat gacatccatc aagaaacgaa   1020
gatccccaga tgatgaactg gtatacttac cagtgagggg ccgtgagact tatgaaatgc   1080
tggtgaagat caaagagtcc ctggaactca tgcagtacct tcttcagcac acaattgaaa   1140
cgtacaggca acagcaacag cagcagcacc agcacttact tcagaaacag acctcaatac   1200
agtctccatc ttcatatggt aacagctccc cacctctgaa caaaatgaac agcatgaaca   1260
agctgccttc tgtgagccag cttatcaacc ctcagcagcg caacgccctc actcctacaa   1320
ccattcctga tggcatggga gccaacattc ccatgatggg cacccacatg ccaatggctg   1380
gagacatgaa tggactcagc cccacccagg cactccctcc cccactctcc atgccatcca   1440
cctcccactg cacaccccca cctccgtatc ccacagattg cagcattgtc agtttcttag   1500
cgaggttggg ctgttcatca tgtctggact atttcacgac ccaggggctg accaccatct   1560
atcagattga gcattactcc atggatgatc tggcaagtct gaaaatccct gagcaatttc   1620
gacatgcgat ctggaaggdc atcctggacc accggcagct ccacgaattc tcctcccctt   1680
ctcatctcct gcggacccca agcagtgcct ctacagtcag tgtgggctcc agtgagaccc   1740
ggggtgagcg tgttattgat gctgtgcgat tcaccctccg ccagaccatc tctttcccac   1800
cccgagatga gtggaatgac ttcaactttg acatggatgc tcgccgcaat aagcaacagc   1860
gcatcaaaga ggaggggggag tgagcctcac catgtgagct cttcctatcc ctctcctaac   1920
tgccagcccc ctaaaagcac tcctgcttaa tcttcaaagc cttctcccta gctcctcccc   1980
ttcctcttgt ctgatttctt aggggaagga gaagtaagag gcttacttct taccctaacc   2040
atctgacctg gcatctaatt ctgattctgg ctttaagcct tcaaaactat agcttgcaga   2100
actgtagctt gccatggcta ggtagaagtg agcaaaaaag agttgggtgt ctccttaagc   2160
tgcagagatt tctcattgac ttttataaag catgttcacc cttatagtct aagactatat   2220
atataaatgt ataaatatac agtatagatt tttgggtggg gggcattgag tattgtttaa   2280
aatgtaattt aaatgaaaga aaattgagtt gcacttattg accattttt aatttacttg    2340 ttttggatgg cttgtctata ctccttccct taagggtat catgtatggt gataggtatc    2400
tagagcttaa tgctacatgt gagtgacgat gatgtacaga ttctttcagt tctttggatt   2460
ctaaatacat gccacatcaa acctttgagt agatccattt ccattgctta ttatgtaggt   2520
aagactgtag atatgtattc ttttctcagt gttggtatat tttatattac tgacatttct   2580
tctagtgatg atggttcacg ttggggtgat ttaatccagt tataagaaga agttcatgtc   2640
caaacgtcct ctttagtttt tggttgggaa tgaggaaaat tcttaaaagg cccatagcag   2700
ccagttcaaa acacccgac gtcatgtatt tgagcatatc agtaacccc ttaaatttaa      2760 taccagatac cttatcttac aatattgatt gggaaaacat ttgctgccat tacagaggta   2820
ttaaaactaa atttcactac tagattgact aactcaaata cacatttgct actgttgtaa   2880
gaattctgat tgatttgatt gggatgaatg ccatctatct agttctaaca gtgaagtttt   2940
actgtctatt aatattcagg gtaaatagga atcattcaga aatgttgagt ctgtactaaa   3000
cagtaagata tctcaatgaa ccataaattc aactttgtaa aaatcttttg aagcatagat   3060
aatattgttt ggtaaatgtt tcttttgttt ggtaaatgtt tcytttaaag accctcctat   3120
```

-continued

```
tctataaaac tctgcatgta gaggcttgtt tacctttctc tctctaaggt ttacaatagg     3180
agtggtgatt tgaaaaatat aaaattatga gattggtttt cctgtggcat aaattgcatc     3240
actgtatcat tttctttttt aaccggtaag agtttcagtt tgttggaaag taactgtgag     3300
aacccagttt cccgtccatc tcccttaggg actacccata gacatgaaag gtccccacag     3360
agcaagagat aagtctttca tggctgctgt tgcttaaacc acttaaacga agagttccct     3420
tgaaactttg ggaaaacatg ttaatgacaa tattccagat cttttcagaaa tataacacat     3480 ttttttgcat gcatgcaaat gagctctgaa atcttcccat gcattctggt caagggctgt     3540
cattgcacat aagcttccat tttaatttta aagtgcaaaa gggccagcgt ggctctaaaa     3600
ggtaatgtgt ggattgcctc tgaaaagtgt gtatatattt tgtgtgaaat tgcatacttt     3660
gtattttgat tattttttt ttcttcttgg gatagtggga tttccagaac cacacttgaa     3720
accttttttt atcgtttttg tattttcatg aaaataccat ttagtaagaa taccacatca     3780
aataagaaat aatgctacaa ttttaagagg ggagggaagg gaaagttttt tttttatta     3840 tttttttaaa attttgtatg ttaaagagaa tgagtccttg atttcaaagt tttgttgtac     3900
ttaaatggta ataagcactg taaacttctg caacaagcat gcagctttgc aaacccatta     3960
aggggaagaa tgaaagctgt tccttggtcc tagtaagaag acaaactgct tcccttactt     4020
tgctgagggt ttgaataaac ctaggacttc cgagctatgt cagtactatt caggtaacac     4080
tagggccttg gaaatccctg tactgtgtct catggatttg gcactagcca aagcgaggca     4140 cccccttactg gcttacctcc tcatggcagc ctactctcct tgagtgtatg agtagccagg     4200
gtaaggggta aaaggatagt aagcatagaa accactagaa agtgggctta atggagttct     4260
tgtggcctca gctcaatgca gttagctgaa gaattgaaaa gttttgtttt ggagacgttt     4320
ataaacagaa atggaaagca gagttttcat taaatccttt tacctttttt ttttcttggt     4380
aatcccctaa aataacagta tgtgggatat tgaatgttaa agggatattt ttttctatta     4440
tttttataat tgtacaaaat taagcaaatg ttaaaagttt tatatgcttt attaatgttt     4500
tcaaaaggta ttatacatgt gatacatttt ttaagcttca gttgcttgtc ttctggtact     4560
ttctgttatg ggcttttggg gagccagaag ccaatctaca atctcttttt gtttgccagg     4620
acatgcaata aaatttaaaa aataaataaa aacta                                4655
```

<210> SEQ ID NO 152
<211> LENGTH: 586
<212> TYPE: PRT
<213> ORGANISM: Homo sapien

<400> SEQUENCE: 152

```
Met Leu Tyr Leu Glu Asn Asn Ala Gln Thr Gln Phe Ser Glu Pro Gln
 1               5                  10                  15

Tyr Thr Asn Leu Gly Leu Leu Asn Ser Met Asp Gln Gln Ile Gln Asn
            20                  25                  30

Gly Ser Ser Ser Thr Ser Pro Tyr Asn Thr Asp His Ala Gln Asn Ser
        35                  40                  45

Val Thr Ala Pro Ser Pro Tyr Ala Gln Pro Ser Ser Thr Phe Asp Ala
    50                  55                  60

Leu Ser Pro Ser Pro Ala Ile Pro Ser Asn Thr Asp Tyr Pro Gly Pro
65                  70                  75                  80

His Ser Phe Asp Val Ser Phe Gln Gln Ser Ser Thr Ala Lys Ser Ala
                85                  90                  95

Thr Trp Thr Tyr Ser Thr Glu Leu Lys Lys Leu Tyr Cys Gln Ile Ala
```

-continued

```
                100                 105                 110
Lys Thr Cys Pro Ile Gln Ile Lys Val Met Thr Pro Pro Gln Gly
            115                 120                 125
Ala Val Ile Arg Ala Met Pro Val Tyr Lys Lys Ala Glu His Val Thr
            130                 135                 140
Glu Val Val Lys Arg Cys Pro Asn His Glu Leu Ser Arg Glu Phe Asn
145                 150                 155                 160
Glu Gly Gln Ile Ala Pro Ser Ser His Leu Ile Arg Val Glu Gly Asn
                165                 170                 175
Ser His Ala Gln Tyr Val Glu Asp Pro Ile Thr Gly Arg Gln Ser Val
            180                 185                 190
Leu Val Pro Tyr Glu Pro Pro Gln Val Gly Thr Glu Phe Thr Thr Val
            195                 200                 205
Leu Tyr Asn Phe Met Cys Asn Ser Ser Cys Val Gly Gly Met Asn Arg
            210                 215                 220
Arg Pro Ile Leu Ile Ile Val Thr Leu Glu Thr Arg Asp Gly Gln Val
225                 230                 235                 240
Leu Gly Arg Arg Cys Phe Glu Ala Arg Ile Cys Ala Cys Pro Gly Arg
                245                 250                 255
Asp Arg Lys Ala Asp Glu Asp Ser Ile Arg Lys Gln Gln Val Ser Asp
            260                 265                 270
Ser Thr Lys Asn Gly Asp Gly Thr Lys Arg Pro Phe Arg Gln Asn Thr
            275                 280                 285
His Gly Ile Gln Met Thr Ser Ile Lys Lys Arg Arg Ser Pro Asp Asp
            290                 295                 300
Glu Leu Val Tyr Leu Pro Val Arg Gly Arg Glu Thr Tyr Glu Met Leu
305                 310                 315                 320
Val Lys Ile Lys Glu Ser Leu Glu Leu Met Gln Tyr Leu Leu Gln His
                325                 330                 335
Thr Ile Glu Thr Tyr Arg Gln Gln Gln Gln Gln His Gln His Leu
            340                 345                 350
Leu Gln Lys Gln Thr Ser Ile Gln Ser Pro Ser Ser Tyr Gly Asn Ser
            355                 360                 365
Ser Pro Pro Leu Asn Lys Met Asn Ser Met Asn Lys Leu Pro Ser Val
            370                 375                 380
Ser Gln Leu Ile Asn Pro Gln Gln Arg Asn Ala Leu Thr Pro Thr Thr
385                 390                 395                 400
Ile Pro Asp Gly Met Gly Ala Asn Ile Pro Met Met Gly Thr His Met
                405                 410                 415
Pro Met Ala Gly Asp Met Asn Gly Leu Ser Pro Thr Gln Ala Leu Pro
            420                 425                 430
Pro Pro Leu Ser Met Pro Ser Thr Ser His Cys Thr Pro Pro Pro
            435                 440                 445
Tyr Pro Thr Asp Cys Ser Ile Val Ser Phe Leu Ala Arg Leu Gly Cys
            450                 455                 460
Ser Ser Cys Leu Asp Tyr Phe Thr Thr Gln Gly Leu Thr Thr Ile Tyr
465                 470                 475                 480
Gln Ile Glu His Tyr Ser Met Asp Asp Leu Ala Ser Leu Lys Ile Pro
                485                 490                 495
Glu Gln Phe Arg His Ala Ile Trp Lys Gly Ile Leu Asp His Arg Gln
            500                 505                 510
Leu His Glu Phe Ser Ser Pro Ser His Leu Leu Arg Thr Pro Ser Ser
            515                 520                 525
```

```
Ala Ser Thr Val Ser Val Gly Ser Ser Glu Thr Arg Gly Glu Arg Val
        530                 535                 540

Ile Asp Ala Val Arg Phe Thr Leu Arg Gln Thr Ile Ser Phe Pro Pro
545                 550                 555                 560

Arg Asp Glu Trp Asn Asp Phe Asn Phe Asp Met Asp Ala Arg Arg Asn
                565                 570                 575

Lys Gln Gln Arg Ile Lys Glu Glu Gly Glu
                580                 585

<210> SEQ ID NO 153
<211> LENGTH: 2007
<212> TYPE: DNA
<213> ORGANISM: Homo sapien

<400> SEQUENCE: 153
gaattcgtcg ctgctccagg gaaagttctg ttactccact gactctctct tttcctgata      60
acatggccag caagaaagta attacagtgt ttggagcaac aggagctcaa ggtggctctg     120
tggccagggc aatttggag agcaaaaaat ttgcagtgag agcagtgacc agggatgtga     180
cttgaccaaa tgccctggag ctccagcgcc ttggagctga ggtggtcaaa ggtgacctga     240
atgataaagc atcggtggac agtgccttaa aaggtgtcta tggggccttc ttggtgacca     300
acttctggga ccctctcaac aagataagg aagtgtgtcg ggggaagctg gtggcagact     360
ccgccaagca cctgggtctg aagcacgtgg tgtacagcgg cctggagaac gtcaagcgac     420
tgacggatgg caagctggag gtgccgcact ttgacagcaa gggcgaggtg gaggagtact     480
tctggtccat tggcatcccc atgaccagtg tccgcgtggc ggcctacttt gaaaactttc     540
tcgcggcgtg gcggcccgtg aaagcctctg atggagatta ctacaccttg gctgtaccga     600
tgggagatgt accaatggat ggtatctctg ttgctgatat tggagcagcc gtctctagca     660
tttttaattc tccagaggaa ttttttaggca aggccgtggg gctcagtgca gaagcactaa     720
caatacagca atatgctgat gttttgtcca aggctttggg gaaagaagtc cgagatgcaa     780
agattacccc ggaagctttc gagaagctgg gattccctgc agcaaaggaa atagccaata     840
tgtgtcgttt ctatgaaatg aagccagacc gagatgtcaa tctcacccac caactaaatc     900
ccaaagtcaa aagcttcagc cagtttatct cagagaacca gggagccttc aagggcatgt     960
agaaaatcag ctgttcagat aggcctctgc accacacagc ctctttcctc tctgatcctt    1020
ttcctcttta cggcacaaca ttcatgttga cagaacatgc tggaatgcaa ttgtttgcaa    1080
caccgaagga tttcctgcgg tcgcctcttc agtaggaagc actgcattgg tgataggaca    1140
cggtaatttg attcacattt aacttgctag ttagtgataa gggtggtaca actgtttggt    1200
aaaatgagaa gcctcggaac ttggagcttc tctcctacca ctaatgggag gcagattat    1260
actgggattt ctcctgggtg agtaatttca agccctaatg ctgaaattcc ctaggcagc    1320
tccagttttc tcaactgcat tgcaaaattc ccagtgaact tttaagtact tttaacttaa    1380
aaaaatgaac atctttgtag agaattttct ggggaacatg gtgttcaatg aacaagcaca    1440
agcattggaa atgctaaaat tcagttttgc ctcaagattg aagtttatt ttctgactca    1500
ttcatgaagt catctattga gccaccattc aattattcat ctattaattc cttgatcctt    1560
catttatcca ttctgcaaac ttttcttgag caccagcacg ggtggccatt tgtggacttc    1620
tcttcattcc tatgtgtttt cttatcaaag tgatccactc tcgaaaggct cctttccagt    1680
ctgtggttgg gttcaagtca tgccagggcc agggggccca tctcctcgtt tagctctagg    1740
```

```
caaaatccag gggatctgca gtggggagcg ggggcaggaa gctggaggga aggcctgtga    1800
agggtaggga tgtggaaaga caaggtgaca gaaggaccca ataggacctt tctatatctc    1860
tggcttagca ttttctacat catattgtaa tcgtcttatt tgctagtttt cttccttact    1920
gtgagtgact aacagtcatc tttatcccag tgcctggtac ataataagtg atcaataaat    1980
gttgattgac taaaaaaaaa aaaaaaa                                        2007

<210> SEQ ID NO 154
<211> LENGTH: 2148
<212> TYPE: DNA
<213> ORGANISM: Homo sapien

<400> SEQUENCE: 154
gaattcgtcg ctgctccagg gaaagttctg ttactccact gactctctct tttcctgata      60
acatggccag caagaaagta attacagtgt ttggagcaac aggagctcaa ggtggctctg     120
tggccagggc aattttggag agcaaaaaat ttgcagtgag agcagtgacc agggatgtga     180
cttgaccaaa tgccctggag ctccagcgcc ttggagctga ggtggtcaaa ggtgacctga     240
atgataaagc atcggtggac agtgccttaa aaggggaagc tggtggcaga ctccgccaag     300
cacctgggtc tgaagcacgt ggtgtacagc ggcctggaga acgtcaagcg actgacggat     360
ggcaagctgg aggtgccgca ctttgacagc aagggcgagg tggaggagta cttctggtcc     420
attggcatcc ccatgaccag tgtccgcgtg gcggcctact ttgaaaactt tctcgcggcg     480
tggcggcccg tgaaagcctc tgatggagat tactacacct tggctgtacc gatgggagat     540
gtaccaatgg atggtatctc tgttgctgat attggagcag ccgtctctag cattttttaat    600 tctccagagg aattttttagg caaggccgtg gggctcagtg cagaagcact aacaatacag     660
caatatgctg atgttttgtc caaggctttg gggaagaag tccgagatgc aaagactatc      720
tgtgctatag atgaccagaa acagtggaa gaaggtttca tggaagacgt gggcttgagt      780
tggtccttga gggaacatga ccatgtatag acagaggagg catcaagaag gctggcctgg     840
ctaattctgg aataaacacg acaaaccaga ggcagtacgg gaaggaggca aattctggct     900
ctgcctctat ccttgattac cccggaagct ttcgagaagc tgggattccc tgcagcaaag     960
gaaatagcca atatgtgtcg tttctatgaa atgaagccag accgagatgt caatctcacc    1020
caccaactaa atcccaaagt caaaagcttc agccatttta tctcagagaa ccagggagcc    1080
ttcaagggca tgtagaaaat cagctgttca gataggcctc tgcaccacac agcctctttc    1140
ctctctgatc ctttttcctct ttacggcaca acattcatgt tgacagaaca tgctggaatg    1200
caattgtttg caacaccgaa ggatttcctg cggtcgcctc ttcagtagga agcactgcat    1260
tggtgatagg acacggtaat ttgattcaca tttaacttgc tagttagtga taagggtggt    1320
acaactgttt ggtaaaatga gaagcctcgg aacttggagc ttctctccta ccactaatgg    1380
gagggcagat tatactggga tttctcctgg gtgagtaatt tcaagcccta atgctgaaat    1440 tccctaggc agctccagtt ttctcaactg cattgcaaaa ttcccagtga acttttaagt     1500
acttttaact taaaaaaatg aacatctttg tagagaattt tctgggggaac atggtgttca    1560 atgaacaagc acaagcattg gaaatgctaa aattcagttt tgcctcaaga ttggaagttt    1620 atttctgac tcattcatga agtcatctat tgagccacca ttcaattatt catctattaa     1680
ttccttgatc cttcatttat ccattctgca aacttttctt gagcaccagc acgggtggcc    1740
atttgtggac ttctcttcat tcctatgtgt tttcttatca aagtgatcca ctctcgaaag    1800 gctccttttcc agtctgtggt tgggttcaag tcatgccagg gccaggggggc ccatctcctc   1860
```

```
gtttagctct aggcaaaatc cagggatct gcagtgggga gcgggggcag gaagctggag    1920
ggaaggcctg tgaagggtag ggatgtggaa agacaaggtg acagaaggac ccaataggac    1980 cttctctatat ctctggctta gcattttcta catcatattg taatcgtctt atttgctagt   2040
tttcttcctt actgtgagtg actaacagtc atctttatcc cagtgcctgg tacataataa    2100
gtgatcaata aatgttgatt gactaaatga aaaaaaaaaa aaaaaaaa                 2148
```

<210> SEQ ID NO 155
<211> LENGTH: 153
<212> TYPE: PRT
<213> ORGANISM: Homo sapien

<400> SEQUENCE: 155

```
Met Thr Ser Val Arg Val Ala Ala Tyr Phe Glu Asn Phe Leu Ala Ala
1               5                   10                  15

Trp Arg Pro Val Lys Ala Ser Asp Gly Asp Tyr Tyr Thr Leu Ala Val
            20                  25                  30

Pro Met Gly Asp Val Pro Met Asp Gly Ile Ser Val Ala Asp Ile Gly
        35                  40                  45

Ala Ala Val Ser Ser Ile Phe Asn Ser Pro Glu Glu Phe Leu Gly Lys
    50                  55                  60

Ala Val Gly Leu Ser Ala Glu Ala Leu Thr Ile Gln Gln Tyr Ala Asp
65                  70                  75                  80

Val Leu Ser Lys Ala Leu Gly Lys Glu Val Arg Asp Ala Lys Ile Thr
                85                  90                  95

Pro Glu Ala Phe Glu Lys Leu Gly Phe Pro Ala Ala Lys Glu Ile Ala
            100                 105                 110

Asn Met Cys Arg Phe Tyr Glu Met Lys Pro Asp Arg Asp Val Asn Leu
        115                 120                 125

Thr His Gln Leu Asn Pro Lys Val Lys Ser Phe Ser Gln Phe Ile Ser
    130                 135                 140

Glu Asn Gln Gly Ala Phe Lys Gly Met
145                 150
```

<210> SEQ ID NO 156
<211> LENGTH: 128
<212> TYPE: PRT
<213> ORGANISM: Homo sapien

<400> SEQUENCE: 156

```
Met Thr Ser Val Arg Val Ala Ala Tyr Phe Glu Asn Phe Leu Ala Ala
1               5                   10                  15

Trp Arg Pro Val Lys Ala Ser Asp Gly Asp Tyr Tyr Thr Leu Ala Val
            20                  25                  30

Pro Met Gly Asp Val Pro Met Asp Gly Ile Ser Val Ala Asp Ile Gly
        35                  40                  45

Ala Ala Val Ser Ser Ile Phe Asn Ser Pro Glu Glu Phe Leu Gly Lys
    50                  55                  60

Ala Val Gly Leu Ser Ala Glu Ala Leu Thr Ile Gln Gln Tyr Ala Asp
65                  70                  75                  80

Val Leu Ser Lys Ala Leu Gly Lys Glu Val Arg Asp Ala Lys Thr Ile
                85                  90                  95

Cys Ala Ile Asp Asp Gln Lys Thr Val Glu Glu Gly Phe Met Glu Asp
            100                 105                 110

Val Gly Leu Ser Trp Ser Leu Arg Glu His Asp His Val Ala Gly Ala
```

```
                   115                 120                 125
```

<210> SEQ ID NO 157
<211> LENGTH: 424
<212> TYPE: DNA
<213> ORGANISM: Homo sapien
<220> FEATURE:
<221> NAME/KEY: misc_feature
<222> LOCATION: (1)...(424)
<223> OTHER INFORMATION: n = A,T,C or G

<400> SEQUENCE: 157

| | | | |
|---|---|---|---|
| ctgcagcccg gggatccac tagtccagtg tggtggaatt cattggtctt tacaagactt | | | 60 |
| gatacatta cagcagacat ggaaatataa ttttaaaaaa tttctctcca acctccttca | | | 120 |
| attcagtca ccactgttat attaccttct ccaggaaccc tccagtgggg aaggctgcga | | | 180 |
| attagattt ccttgtatgc aaagtttttg ttgaaagctg tgctcagagg aggtgagagg | | | 240 |
| gaggaagga gaaaactgca tcataacttt acagaattga atctagagtc ttccccgaaa | | | 300 |
| gcccagaaa cttctctgcn gnatctggct tgtccatctg gtctaaggtg gctgcttctt | | | 360 |
| cccagccat cgagtcagtt tgtgcccatg aataatacac gacctgctat ttcccatgac | | | 420 |
| gct | | | 424 |

<210> SEQ ID NO 158
<211> LENGTH: 2099
<212> TYPE: DNA
<213> ORGANISM: Homo sapien

<400> SEQUENCE: 158

| | | | |
|---|---|---|---|
| ccgcggttaa aaggcgcagc aggtgggagc cggggccttc acccgaaacc cgacgagagc | | | 60 |
| ccgacagccg gcggcgcccg agcccgacct gcctgcccag ccggagcgaa gggcgccgcc | | | 120 |
| ccgcgcagag cccgcgccag ggccgccggc cgcagagcag ttaaaacgtg caggcaccag | | | 180 |
| aaggcacttc ctgtcggtga agaagacctg tctccggtgt cacgggcatc ctgtgttttg | | | 240 |
| caaacggggc tgacctccct tcctggggag caggaagggt cagggaagga aaagaagtac | | | 300 |
| agaagatctg gctaaacaat ttctgtatgg cgaaagaaaa attctaactt gtacgccctc | | | 360 |
| ttcatgcatc tttaattcaa tttgaatatt ccaggcgaca tcctcactga ccgagcaaag | | | 420 |
| attgacattc gtatcatcac tgtgcaccat ggcttctag gcactccagt ggggtaggag | | | 480 |
| aaggaggtct gaaaccctcg cagagggatc ttgccctcat tctttgggtc tgaaacactg | | | 540 |
| gcagtcgttg gaaacaggac tcaggataa ccagcgcaa tggattgggg gacgctgcac | | | 600 |
| actttcatcg ggggtgtcaa caaacactcc accagcatcg ggaaggtgtg gatcacagtc | | | 660 |
| atctttatt tccgagtcat gatcctcgtg gtggctgccc aggaagtgtg gggtgacgag | | | 720 |
| caagaggact tcgtctgcaa cacactgcaa ccgggatgca aaaatgtgtg ctatgaccac | | | 780 |
| tttttcccgg tgtcccacat ccggctgtgg gccctccagc tgatcttcgt ctccacccca | | | 840 |
| gcgctgctgg tggccatgca tgtggcctac acaggcacg aaaccactcg caagttcagg | | | 900 |
| cgaggagaga agaggaatga tttcaaagac atagaggaca ttaaaaagca gaaggttcgg | | | 960 |
| atagaggggt cgctgtggtg gacgtacacc agcagcatct ttttccgaat catctttgaa | | | 1020 |
| gcagccttta tgtatgtgtt ttacttcctt tacaatgggt accacctgcc ctgggtgttg | | | 1080 |
| aaatgtggga ttgacccctg ccccaacctt gttgactgct ttatttctag gccaacagag | | | 1140 |
| aagaccgtgt ttaccatttt tatgatttct gcgtctgtga tttgcatgct gcttaacgtg | | | 1200 |
| gcagagttgt gctacctgct gctgaaagtg tgttttagga gatcaaagag agcacagacg | | | 1260 |

-continued

```
caaaaaaatc accccaatca tgccctaaag gagagtaagc agaatgaaat gaatgagctg    1320
atttcagata gtggtcaaaa tgcaatcaca ggttcccaag ctaaacattt caaggtaaaa    1380
tgtagctgcg tcataaggag acttctgtct tctccagaag gcaataccaa cctgaaagtt    1440
ccttctgtag cctgaagagt ttgtaaatga cttttcataat aaatagacac ttgagttaac    1500
tttttgtagg atacttgctc cattcataca caacgtaatc aaatatgtgg tccatctctg    1560
aaaacaagag actgcttgac aaaggagcat tgcagtcact ttgacaggtt cctttaagt    1620 ggactctctg acaaagtggg tactttctga aaatttatat aactgttgtt gataaggaac    1680
atttatccag gaattgatac gtttattagg aaaagatatt tttataggct tggatgtttt    1740
tagttctgac tttgaattta tataaagtat ttttataatg actggtcttc cttacctgga    1800
aaaacatgcg atgttagttt tagaattaca ccacaagtat ctaaatttgg aacttacaaa    1860
gggtctatct tgtaaatatt gttttgcatt gtctgttggc aaatttgtga actgtcatga    1920
tacgcttaag gtggaaagtg ttcattgcac aatatatttt tactgctttc tgaatgtaga    1980
cggaacagtg tggaagcaga aggctttttt aactcatccg tttgccaatc attgcaaaca    2040
actgaaatgt ggatgtgatt gcctcaataa agctcgtccc cattgcttaa aaaaaaaaa    2099
```

<210> SEQ ID NO 159
<211> LENGTH: 291
<212> TYPE: PRT
<213> ORGANISM: Homo sapien

<400> SEQUENCE: 159

```
Met Asp Trp Gly Thr Leu His Thr Phe Ile Gly Gly Val Asn Lys His
  1               5                  10                  15

Ser Thr Ser Ile Gly Lys Val Trp Ile Thr Val Ile Phe Ile Phe Arg
             20                  25                  30

Val Met Ile Leu Val Val Ala Ala Gln Glu Val Trp Gly Asp Glu Gln
         35                  40                  45

Glu Asp Phe Val Cys Asn Thr Leu Gln Pro Gly Cys Lys Asn Val Cys
     50                  55                  60

Tyr Asp His Phe Phe Pro Val Ser His Ile Arg Leu Trp Ala Leu Gln
 65                  70                  75                  80

Leu Ile Phe Val Ser Thr Pro Ala Leu Leu Val Ala Met His Val Ala
                 85                  90                  95

Tyr Tyr Arg His Glu Thr Thr Arg Lys Phe Arg Arg Gly Glu Lys Arg
            100                 105                 110

Asn Asp Phe Lys Asp Ile Glu Asp Ile Lys Lys Gln Lys Val Arg Ile
        115                 120                 125

Glu Gly Ser Leu Trp Trp Thr Tyr Thr Ser Ser Ile Phe Phe Arg Ile
    130                 135                 140

Ile Phe Glu Ala Ala Phe Met Tyr Val Phe Tyr Leu Tyr Asn Gly
145                 150                 155                 160

Tyr His Leu Pro Trp Val Leu Lys Cys Gly Ile Asp Pro Cys Pro Asn
                165                 170                 175

Leu Val Asp Cys Phe Ile Ser Arg Pro Thr Glu Lys Thr Val Phe Thr
            180                 185                 190

Ile Phe Met Ile Ser Ala Ser Val Ile Cys Met Leu Leu Asn Val Ala
        195                 200                 205

Glu Leu Cys Tyr Leu Leu Leu Lys Val Cys Phe Arg Arg Ser Lys Arg
    210                 215                 220
```

```
Ala Gln Thr Gln Lys Asn His Pro Asn His Ala Leu Lys Glu Ser Lys
225                 230                 235                 240

Gln Asn Glu Met Asn Glu Leu Ile Ser Asp Ser Gly Gln Asn Ala Ile
            245                 250                 255

Thr Gly Ser Gln Ala Lys His Phe Lys Val Lys Cys Ser Cys Val Ile
        260                 265                 270

Arg Arg Leu Leu Ser Ser Pro Glu Gly Asn Thr Asn Leu Lys Val Pro
        275                 280                 285

Ser Val Ala
    290

<210> SEQ ID NO 160
<211> LENGTH: 3951
<212> TYPE: DNA
<213> ORGANISM: Homo sapien

<400> SEQUENCE: 160
```

| | | | | | | |
|---|---|---|---|---|---|---|
| tctgcatcca | tattgaaaac | ctgacacaat | gtatgcagca | ggctcagtgt | gagtgaactg | 60 |
| gaggcttctc | tacaacatga | cccaaaggag | cattgcaggt | cctatttgca | acctgaagtt | 120 |
| tgtgactctc | ctggttgcct | taagttcaga | actcccattc | ctgggagctg | gagtacagct | 180 |
| tcaagacaat | gggtataatg | gattgctcat | tgcaattaat | cctcaggtac | ctgagaatca | 240 |
| gaacctcatc | tcaaacatta | aggaaatgat | aactgaagct | tcattttacc | tatttaatgc | 300 |
| taccaagaga | gagtattttt | tcagaaatat | aaagatttta | atacctgcca | catggaaagc | 360 |
| taataataac | agcaaaataa | aacaagaatc | atatgaaaag | gcaaatgtca | tagtgactga | 420 |
| ctggtatggg | gcacatggag | atgatccata | caccctacaa | tacagagggt | gtggaaaaga | 480 |
| gggaaaatac | attcatttca | cacctaattt | cctactgaat | gataacttaa | cagctggcta | 540 |
| cggatcacga | ggccgagtgt | ttgtccatga | atgggcccac | ctccgttggg | gtgtgttcga | 600 |
| tgagtataac | aatgacaaac | ctttctacat | aaatgggcaa | aatcaaatta | aagtgacaag | 660 |
| gtgttcatct | gacatcacag | gcattttttgt | gtgtgaaaaa | ggtccttgcc | cccaagaaaa | 720 |
| ctgtattatt | agtaagcttt | ttaaagaagg | atgcacctttt | atctacaata | gcacccaaaa | 780 |
| tgcaactgca | tcaataatgt | tcatgcaaag | tttatcttct | gtggttgaat | tttgtaatgc | 840 |
| aagtacccac | aaccaagaag | caccaaacct | acagaaccag | atgtgcagcc | tcagaagtgc | 900 |
| atgggatgta | atcacagact | ctgctgactt | tcaccacagc | tttcccatga | acggactga | 960 |
| gcttccacct | cctcccacat | tctcgcttgt | agaggctggt | gacaaagtgg | tctgtttagt | 1020 |
| gctggatgtg | tccagcaaga | tggcagaggc | tgacagactc | cttcaactac | aacaagccgc | 1080 |
| agaatttttat | ttgatgcaga | ttgttgaaat | tcataccttc | gtgggcattg | ccagtttcga | 1140 |
| cagcaaagga | gagatcagag | cccagctaca | ccaaattaac | agcaatgatg | atcgaaagtt | 1200 |
| gctggtttca | tatctgccca | ccactgtatc | agctaaaaca | gacatcagca | tttgttcagg | 1260 |
| gcttaagaaa | ggatttgagg | tggttgaaaa | actgaatgga | aaagcttatg | ctctgtgat | 1320 |
| gatattagtg | accagcggag | atgataagct | tcttggcaat | tgcttaccca | ctgtgctcag | 1380 |
| cagtggttca | acaattcact | ccattgccct | gggttcatct | gcagccccaa | atctggagga | 1440 |
| attatcacgt | cttacaggag | gttttaaagtt | ctttgttcca | gatatatcaa | actccaatag | 1500 |
| catgattgat | gctttcagta | gaatttcctc | tggaactgga | gacatttttcc | agcaacatat | 1560 |
| tcagcttgaa | agtacaggtg | aaaatgtcaa | acctcaccat | caattgaaaa | acacagtgac | 1620 |
| tgtggataat | actgtgggca | acgacactat | gtttctagtt | acgtggcagg | ccagtggtcc | 1680 |

```
tcctgagatt atattatttg atcctgatgg acgaaaatac tacacaaata attttatcac    1740
caatctaact tttcggacag ctagtctttg gattccagga acagctaagc ctgggcactg    1800
gacttacacc ctgaacaata cccatcattc tctgcaagcc ctgaaagtga cagtgacctc    1860
tcgcgcctcc aactcagctg tgcccccagc cactgtggaa gcctttgtgg aaagagacag    1920
cctccatttt cctcatcctg tgatgattta tgccaatgtg aaacagggat tttatcccat    1980
tcttaatgcc actgtcactg ccacagttga gccagagact ggagatcctg ttacgctgag    2040
actccttgat gatggagcag gtgctgatgt tataaaaaat gatggaattt actcgaggta    2100
tttttttctcc tttgctgcaa atggtagata tagcttgaaa gtgcatgtca atcactctcc    2160
cagcataagc accccagccc actctattcc agggagtcat gctatgtatg taccaggtta    2220
cacagcaaac ggtaatattc agatgaatgc tccaaggaaa tcagtaggca gaaatgagga    2280
ggagcgaaag tggggcttta gccgagtcag ctcaggaggc tccttttcag tgctgggagt    2340
tccagctggc ccccaccctg atgtgtttcc accatgcaaa attattgacc tggaagctgt    2400
aaaagtagaa gaggaattga ccctatcttg gacagcacct ggagaagact ttgatcaggg    2460
ccaggctaca agctatgaaa taagaatgag taaaagtcta cagaatatcc aagatgactt    2520
taacaatgct attttagtaa atacatcaaa gcgaaatcct cagcaagctg gcatcaggga    2580
gatatttacg ttctcacccc aaatttccac gaatggacct gaacatcagc caaatggaga    2640
aacacatgaa agccacagaa tttatgttgc aatacgagca atggatagga actccttaca    2700
gtctgctgta tctaacattg cccaggcgcc tctgtttatt cccccaatt ctgatcctgt    2760
acctgccaga gattatctta tattgaaagg agttttaaca gcaatgggtt tgataggaat    2820
catttgcctt attatagttg tgacacatca tactttaagc aggaaaaaga gagcagacaa    2880
gaaagagaat ggaacaaaat tattataaat aaatatccaa agtgtcttcc ttcttagata    2940
taagacccat ggccttcgac tacaaaaaca tactaacaaa gtcaaattaa catcaaaact    3000
gtattaaaat gcattgagtt tttgtacaat acagataaga tttttacatg gtagatcaac    3060
aaaattcttt tgggggtaga ttagaaaacc cttacacttt ggctatgaac aaataataaa    3120
aattattctt taaagtaatg tctttaaagg caaagggaag ggtaaagtcg gaccagtgtc    3180
aaggaaagtt tgttttattg aggtggaaaa atagccccaa gcagagaaaa ggagggtagg    3240
tctgcattat aactgtctgt gtgaagcaat catttagtta ctttgattaa ttttttcttt    3300
ctccttatct gtgcagaaca ggttgcttgt ttacaactga agatcatgct atatttcata    3360
tatgaagccc ctaatgcaaa gctctttacc tcttgctatt ttgttatata tattacagat    3420
gaaatctcac tgctaatgct cagagatctt ttttcactgt aagaggtaac ctttaacaat    3480
atgggtatta cctttgtctc ttcataccgg ttttatgaca aaggtctatt gaatttattt    3540
gtttgtaagt ttctactccc atcaaagcag ctttttaagt tattgccttg gttattatgg    3600
atgatagtta tagcccttat aatgccttaa ctaaggaaga aaagatgtta ttctgagttt    3660
gttttaatac atatatgaac atatagtttt attcaattaa accaaagaag aggtcagcag    3720
ggagatacta acctttggaa atgattagct ggctctgttt tttggttaaa taagagtctt    3780
taatcctttc tccatcaaga gttacttacc aagggcaggg gaaggggggat atagaggtcc    3840
caaggaaata aaaatcatct ttcatctttca attttactcc ttcctcttat ttttttaaaa    3900
gattatcgaa caataaaatc atttgccttt ttaattaaaa acataaaaaa a             3951
```

<210> SEQ ID NO 161
<211> LENGTH: 943

-continued

```
<212> TYPE: PRT
<213> ORGANISM: Homo sapien

<400> SEQUENCE: 161

Met Thr Gln Arg Ser Ile Ala Gly Pro Ile Cys Asn Leu Lys Phe Val
 1               5                  10                  15

Thr Leu Val Ala Leu Ser Ser Glu Leu Pro Phe Leu Gly Ala Gly
             20                  25                  30

Val Gln Leu Gln Asp Asn Gly Tyr Asn Gly Leu Leu Ile Ala Ile Asn
             35                  40                  45

Pro Gln Val Pro Glu Asn Gln Asn Leu Ile Ser Asn Ile Lys Glu Met
         50                  55                  60

Ile Thr Glu Ala Ser Phe Tyr Leu Phe Asn Ala Thr Lys Arg Arg Val
 65                  70                  75                  80

Phe Phe Arg Asn Ile Lys Ile Leu Ile Pro Ala Thr Trp Lys Ala Asn
                 85                  90                  95

Asn Asn Ser Lys Ile Lys Gln Glu Ser Tyr Glu Lys Ala Asn Val Ile
                100                 105                 110

Val Thr Asp Trp Tyr Gly Ala His Gly Asp Asp Pro Tyr Thr Leu Gln
            115                 120                 125

Tyr Arg Gly Cys Gly Lys Glu Gly Lys Tyr Ile His Phe Thr Pro Asn
    130                 135                 140

Phe Leu Asn Asp Asn Leu Thr Ala Gly Tyr Gly Ser Arg Gly Arg
145                 150                 155                 160

Val Phe Val His Glu Trp Ala His Leu Arg Trp Gly Val Phe Asp Glu
                165                 170                 175

Tyr Asn Asn Asp Lys Pro Phe Tyr Ile Asn Gly Gln Asn Gln Ile Lys
                180                 185                 190

Val Thr Arg Cys Ser Ser Asp Ile Thr Gly Ile Phe Val Cys Glu Lys
            195                 200                 205

Gly Pro Cys Pro Gln Glu Asn Cys Ile Ile Ser Lys Leu Phe Lys Glu
    210                 215                 220

Gly Cys Thr Phe Ile Tyr Asn Ser Thr Gln Asn Ala Thr Ala Ser Ile
225                 230                 235                 240

Met Phe Met Gln Ser Leu Ser Ser Val Val Glu Phe Cys Asn Ala Ser
                245                 250                 255

Thr His Asn Gln Glu Ala Pro Asn Leu Gln Asn Gln Met Cys Ser Leu
                260                 265                 270

Arg Ser Ala Trp Asp Val Ile Thr Asp Ser Ala Asp Phe His His Ser
            275                 280                 285

Phe Pro Met Asn Gly Thr Glu Leu Pro Pro Pro Thr Phe Ser Leu
    290                 295                 300

Val Glu Ala Gly Asp Lys Val Val Cys Leu Val Leu Asp Val Ser Ser
305                 310                 315                 320

Lys Met Ala Glu Ala Asp Arg Leu Leu Gln Leu Gln Ala Ala Glu
                325                 330                 335

Phe Tyr Leu Met Gln Ile Val Glu Ile His Thr Phe Val Gly Ile Ala
                340                 345                 350

Ser Phe Asp Ser Lys Gly Glu Ile Arg Ala Gln Leu His Gln Ile Asn
            355                 360                 365

Ser Asn Asp Asp Arg Lys Leu Leu Val Ser Tyr Leu Pro Thr Thr Val
    370                 375                 380

Ser Ala Lys Thr Asp Ile Ser Ile Cys Ser Gly Leu Lys Lys Gly Phe
385                 390                 395                 400
```

-continued

```
Glu Val Val Glu Lys Leu Asn Gly Lys Ala Tyr Gly Ser Val Met Ile
            405                 410                 415
Leu Val Thr Ser Gly Asp Asp Lys Leu Leu Gly Asn Cys Leu Pro Thr
            420                 425                 430
Val Leu Ser Ser Gly Ser Thr Ile His Ser Ile Ala Leu Gly Ser Ser
            435                 440                 445
Ala Ala Pro Asn Leu Glu Glu Leu Ser Arg Leu Thr Gly Gly Leu Lys
            450                 455                 460
Phe Phe Val Pro Asp Ile Ser Asn Ser Asn Ser Met Ile Asp Ala Phe
465                 470                 475                 480
Ser Arg Ile Ser Ser Gly Thr Gly Asp Ile Phe Gln Gln His Ile Gln
            485                 490                 495
Leu Glu Ser Thr Gly Glu Asn Val Lys Pro His His Gln Leu Lys Asn
            500                 505                 510
Thr Val Thr Val Asp Asn Thr Val Gly Asn Asp Thr Met Phe Leu Val
            515                 520                 525
Thr Trp Gln Ala Ser Gly Pro Pro Glu Ile Ile Leu Phe Asp Pro Asp
            530                 535                 540
Gly Arg Lys Tyr Tyr Thr Asn Asn Phe Ile Thr Asn Leu Thr Phe Arg
545                 550                 555                 560
Thr Ala Ser Leu Trp Ile Pro Gly Thr Ala Lys Pro Gly His Trp Thr
            565                 570                 575
Tyr Thr Leu Asn Asn Thr His His Ser Leu Gln Ala Leu Lys Val Thr
            580                 585                 590
Val Thr Ser Arg Ala Ser Asn Ser Ala Val Pro Pro Ala Thr Val Glu
            595                 600                 605
Ala Phe Val Glu Arg Asp Ser Leu His Phe Pro His Pro Val Met Ile
            610                 615                 620
Tyr Ala Asn Val Lys Gln Gly Phe Tyr Pro Ile Leu Asn Ala Thr Val
625                 630                 635                 640
Thr Ala Thr Val Glu Pro Glu Thr Gly Asp Pro Val Thr Leu Arg Leu
            645                 650                 655
Leu Asp Asp Gly Ala Gly Ala Asp Val Ile Lys Asn Asp Gly Ile Tyr
            660                 665                 670
Ser Arg Tyr Phe Phe Ser Phe Ala Ala Asn Gly Arg Tyr Ser Leu Lys
            675                 680                 685
Val His Val Asn His Ser Pro Ser Ile Ser Thr Pro Ala His Ser Ile
            690                 695                 700
Pro Gly Ser His Ala Met Tyr Val Pro Gly Tyr Thr Ala Asn Gly Asn
705                 710                 715                 720
Ile Gln Met Asn Ala Pro Arg Lys Ser Val Gly Arg Asn Glu Glu Glu
            725                 730                 735
Arg Lys Trp Gly Phe Ser Arg Val Ser Ser Gly Gly Ser Phe Ser Val
            740                 745                 750
Leu Gly Val Pro Ala Gly Pro His Pro Asp Val Phe Pro Pro Cys Lys
            755                 760                 765
Ile Ile Asp Leu Glu Ala Val Lys Val Glu Glu Leu Thr Leu Ser
            770                 775                 780
Trp Thr Ala Pro Gly Glu Asp Phe Asp Gln Gly Gln Ala Thr Ser Tyr
785                 790                 795                 800
Glu Ile Arg Met Ser Lys Ser Leu Gln Asn Ile Gln Asp Asp Phe Asn
            805                 810                 815
```

```
Asn Ala Ile Leu Val Asn Thr Ser Lys Arg Asn Pro Gln Gln Ala Gly
                820                 825                 830

Ile Arg Glu Ile Phe Thr Phe Ser Pro Gln Ile Ser Thr Asn Gly Pro
            835                 840                 845

Glu His Gln Pro Asn Gly Glu Thr His Glu Ser His Arg Ile Tyr Val
    850                 855                 860

Ala Ile Arg Ala Met Asp Arg Asn Ser Leu Gln Ser Ala Val Ser Asn
865                 870                 875                 880

Ile Ala Gln Ala Pro Leu Phe Ile Pro Pro Asn Ser Asp Pro Val Pro
                885                 890                 895

Ala Arg Asp Tyr Leu Ile Leu Lys Gly Val Leu Thr Ala Met Gly Leu
            900                 905                 910

Ile Gly Ile Ile Cys Leu Ile Ile Val Val Thr His His Thr Leu Ser
        915                 920                 925

Arg Lys Lys Arg Ala Asp Lys Lys Glu Asn Gly Thr Lys Leu Leu
    930                 935                 940

<210> SEQ ID NO 162
<211> LENGTH: 498
<212> TYPE: DNA
<213> ORGANISM: Homo sapien

<400> SEQUENCE: 162
tggagaacca cgtggacagc accatgaaca tgttgggcgg gggaggcagt gctggccgga      60
agcccctcaa gtcgggtatg aaggagctgg ccgtgttccg ggagaaggtc actgagcagc     120
accggcagat gggcaagggt ggcaagcatc accttggcct ggaggagccc aagaagctgc     180 gaccacccc tgccaggact ccctgccaac aggaactgga ccaggtcctg gagcggatct     240
ccaccatgcg ccttccggat gagcggggcc ctctggagca cctctactcc ctgcacatcc     300
ccaactgtga caagcatggc ctgtacaacc tcaaacagtg gcaagatgtc tctgaacggg     360
cagcgtgggg agtgctggtg tgtgaacccc aacaccggga agctgatcca gggagccccc     420
accatccggg gggaccccga gtgtcatctc ttctacaatg agcagcagga ggctcgcggg     480
gtgcacaccc cagcggat                                                   498

<210> SEQ ID NO 163
<211> LENGTH: 1128
<212> TYPE: DNA
<213> ORGANISM: Homo sapien

<400> SEQUENCE: 163
gccacctggc cctcctgatc gacgacacac gcacttgaaa cttgttctca gggtgtgtgg      60
aatcaacttt ccggaagcaa ccagcccacc agaggaggtc ccgagcgcga gcggagacga     120
tgcagcggag actggttcag cagtggagcg tcgcggtgtt cctgctgagc tacgcggtgc     180
cctcctgcgg gcgctcggtg gagggtctca gccgccgcct caaaagagct gtgtctgaac     240
atcagctcct ccatgacaag gggaagtcca tccaagattt acggcgacga ttcttccttc     300
accatctgat cgcagaaatc cacacagctg aaatcagagc tacctcggag gtgtccccta     360
actccaagcc ctctcccaac acaaagaacc accccgtccg atttgggtct gatgatgagg     420 gcagataccct aactcaggaa actaacaagg tggagacgta caaagagcag ccgctcaaga     480
cacctgggaa gaaaagaaa ggcaagcccg ggaacgcaa ggagcaggaa aagaaaaaac     540
ggcgaactcg ctctgcctgg ttagactctg gagtgactga gagtgggcta aaggggacc     600 acctgtctga cacctccaca acgtcgctgg agctcgattc acggaggcat gaaatttttc     660
```

```
agcagagacc ttccaaggac atattgcagg attctgtaat agtgaacata tggaaagtat      720
tagaaatatt tattgtctgt aaatactgta aatgcattgg aataaaactg tctcccccat      780
tgctctatga aactgcacat tggtcattgt gaatatttt tttttgcca aggctaatcc       840 aattattatt atcacattta ccataattta ttttgtccat tgatgtattt attttgtaaa     900
tgtatcttgg tgctgctgaa tttctatatt ttttgtaaca taatgcactt tagatataca     960
tatcaagtat gttgataaat gacacaatga agtgtctcta ttttgtggtt gattttaatg    1020
aatgcctaaa tataattatc caaattgatt ttcctttgtg catgtaaaaa taacagtatt    1080
ttaaatttgt aaagaatgtc taataaaata taatctaatt acatcatg                 1128
```

<210> SEQ ID NO 164
<211> LENGTH: 1310
<212> TYPE: DNA
<213> ORGANISM: Homo sapien

<400> SEQUENCE: 164

```
gggcctggtt cgcaaagaag ctgacttcag aggggaaac tttcttcttt taggaggcgg      60
ttagccctgt tccacgaacc caggagaact gctggccaga ttaattagac attgctatgg    120
gagacgtgta aacacactac ttatcattga tgcatatata aaaccatttt attttcgcta    180
ttatttcaga ggaagcgcct ctgatttgtt tcttttttcc cttttgctc tttctggctg     240 tgtggtttgg agaaagcaca gttggagtag ccggttgcta aataagtccc gagcgcgagc    300
ggagacgatg cagcggagac tggttcagca gtggagcgtc gcggtgttcc tgctgagcta    360
cgcggtgccc tcctgcgggc gctcggtgga gggtctcagc cgccgcctca aaagagctgt    420
gtctgaacat cagctcctcc atgacaaggg gaagtccatc caagatttac ggcgacgatt    480
cttccttcac catctgatcg cagaaatcca cacagctgaa atcagagcta cctcggaggt    540
gtcccctaac tccaagccct ctcccaacac aaagaaccac cccgtccgat tgggtctga    600 tgatgagggc agatacctaa ctcaggaaac taacaaggtg gagacgtaca agagcagcc    660 gctcaagaca cctgggaaga aaagaaagg caagcccggg aaacgcaagg agcaggaaaa    720
gaaaaaacgg cgaactcgct ctgcctggtt agactctgga gtgactggga gtgggctaga    780
aggggaccac ctgtctgaca cctccacaac gtcgctggag ctcgattcac ggaggcattg    840
aaattttcag cagagacctt ccaaggacat attgcaggat tctgtaatag tgaacatatg    900
gaaagtatta gaaatattta ttgtctgtaa atactgtaaa tgcattggaa taaaactgtc    960
tcccccattg ctctatgaaa ctgcacattg gtcattgtga atatttttt ttttgccaag    1020 gctaatccaa ttattattat cacatttacc ataatttatt ttgtccattg atgtatttat   1080
tttgtaaatg tatcttggtg ctgctgaatt tctatatttt ttgtaacata atgcacttta   1140
gatatacata tcaagtatgt tgataaatga cacaatgaag tgtctctatt ttgtggttga   1200
ttttaatgaa tgcctaaata taattatcca aattgatttt cctttgtgcc cgtaaaaata   1260
acagtatttt aaatttgtaa agaatgtcta ataaaatata atctaattac               1310
```

<210> SEQ ID NO 165
<211> LENGTH: 177
<212> TYPE: PRT
<213> ORGANISM: Homo sapien

<400> SEQUENCE: 165

Met Gln Arg Arg Leu Val Gln Gln Trp Ser Val Ala Val Phe Leu Leu
1               5                   10                  15

Ser Tyr Ala Val Pro Ser Cys Gly Arg Ser Val Glu Gly Leu Ser Arg
            20                  25                  30

Arg Leu Lys Arg Ala Val Ser Glu His Gln Leu Leu His Asp Lys Gly
        35                  40                  45

Lys Ser Ile Gln Asp Leu Arg Arg Arg Phe Phe Leu His His Leu Ile
    50                  55                  60

Ala Glu Ile His Thr Ala Glu Ile Arg Ala Thr Ser Glu Val Ser Pro
65                  70                  75                  80

Asn Ser Lys Pro Ser Pro Asn Thr Lys Asn His Pro Val Arg Phe Gly
                85                  90                  95

Ser Asp Asp Glu Gly Arg Tyr Leu Thr Gln Glu Thr Asn Lys Val Glu
            100                 105                 110

Thr Tyr Lys Glu Gln Pro Leu Lys Thr Pro Gly Lys Lys Lys Lys Gly
        115                 120                 125

Lys Pro Gly Lys Arg Lys Glu Gln Glu Lys Lys Arg Arg Thr Arg
    130                 135                 140

Ser Ala Trp Leu Asp Ser Gly Val Thr Gly Ser Gly Leu Glu Gly Asp
145                 150                 155                 160

His Leu Ser Asp Thr Ser Thr Thr Ser Leu Glu Leu Asp Ser Arg Arg
                165                 170                 175

His

<210> SEQ ID NO 166
<211> LENGTH: 177
<212> TYPE: PRT
<213> ORGANISM: Homo sapien

<400> SEQUENCE: 166

Met Gln Arg Arg Leu Val Gln Gln Trp Ser Val Ala Val Phe Leu Leu
1               5                   10                  15

Ser Tyr Ala Val Pro Ser Cys Gly Arg Ser Val Glu Gly Leu Ser Arg
            20                  25                  30

Arg Leu Lys Arg Ala Val Ser Glu His Gln Leu Leu His Asp Lys Gly
        35                  40                  45

Lys Ser Ile Gln Asp Leu Arg Arg Arg Phe Phe Leu His His Leu Ile
    50                  55                  60

Ala Glu Ile His Thr Ala Glu Ile Arg Ala Thr Ser Glu Val Ser Pro
65                  70                  75                  80

Asn Ser Lys Pro Ser Pro Asn Thr Lys Asn His Pro Val Arg Phe Gly
                85                  90                  95

Ser Asp Asp Glu Gly Arg Tyr Leu Thr Gln Glu Thr Asn Lys Val Glu
            100                 105                 110

Thr Tyr Lys Glu Gln Pro Leu Lys Thr Pro Gly Lys Lys Lys Lys Gly
        115                 120                 125

Lys Pro Gly Lys Arg Lys Glu Gln Glu Lys Lys Arg Arg Thr Arg
    130                 135                 140

Ser Ala Trp Leu Asp Ser Gly Val Thr Gly Ser Gly Leu Glu Gly Asp
145                 150                 155                 160

His Leu Ser Asp Thr Ser Thr Thr Ser Leu Glu Leu Asp Ser Arg Arg
                165                 170                 175

His

<210> SEQ ID NO 167
<211> LENGTH: 3362

<212> TYPE: DNA
<213> ORGANISM: Homo sapien

<400> SEQUENCE: 167

| | | | | | |
|---|---|---|---|---|---|
| cacaatgtat | gcagcaggct | cagtgtgagt | gaactggagg | cttctctaca | acatgaccca | 60 |
| aaggagcatt | gcaggtccta | tttgcaacct | gaagtttgtg | actctcctgg | ttgccttaag | 120 |
| ttcagaactc | ccattcctgg | gagctggagt | acagcttcaa | gacaatgggt | ataatggatt | 180 |
| gctcattgca | attaatcctc | aggtacctga | gaatcagaac | ctcatctcaa | acattaagga | 240 |
| aatgataact | gaagcttcat | tttacctatt | taatgctacc | aagagaagag | tatttttcag | 300 |
| aaatataaag | attttaatac | ctgccacatg | gaaagctaat | aataacagca | aaataaaaca | 360 |
| agaatcatat | gaaaaggcaa | atgtcatagt | gactgactgg | tatggggcac | atggagatga | 420 |
| tccatacacc | ctacaataca | gagggtgtgg | aaagaggga | aaatacattc | atttcacacc | 480 |
| taatttccta | ctgaatgata | acttaacagc | tggctacgga | tcacgaggcc | gagtgtttgt | 540 |
| ccatgaatgg | gcccacctcc | gttggggtgt | gttcgatgag | tataacaatg | acaaaccttt | 600 |
| ctacataaat | gggcaaaatc | aaattaaagt | gacaaggtgt | tcatctgaca | tcacaggcat | 660 |
| ttttgtgtgt | gaaaaaggtc | cttgcccca | agaaaactgt | attattagta | agcttttttaa | 720 |
| agaaggatgc | acctttatct | acaatagcac | ccaaaatgca | actgcatcaa | taatgttcat | 780 |
| gcaaagttta | tcttctgtgg | ttgaattttg | taatgcaagt | acccacaacc | aagaagcacc | 840 |
| aaacctacag | aaccagatgt | gcagcctcag | aagtgcatgg | gatgtaatca | cagactctgc | 900 |
| tgactttcac | cacagctttc | ccatgaacgg | gactgagctt | ccacctcctc | ccacattctc | 960 |
| gcttgtagag | gctggtgaca | aagtggtctg | tttagtgctg | gatgtgtcca | gcaagatggc | 1020 |
| agaggctgac | agactccttc | aactacaaca | agccgcagaa | ttttatttga | tgcagattgt | 1080 |
| tgaaattcat | accttcgtgg | gcattgccag | tttcgacagc | aaaggagaga | tcagagccca | 1140 |
| gctacaccaa | attaacagca | atgatgatcg | aaagttgctg | gtttcatatc | tgcccaccac | 1200 |
| tgtatcagct | aaaacagaca | tcagcatttg | ttcagggctt | aagaaaggat | ttgaggtggt | 1260 |
| tgaaaaactg | aatggaaaag | cttatggctc | tgtgatgata | ttagtgacca | gcggagatga | 1320 |
| taagcttctt | ggcaattgct | tacccactgt | gctcagcagt | ggttcaacaa | ttcactccat | 1380 |
| tgccctgggt | tcatctgcag | ccccaaatct | ggaggaatta | tcacgtctta | caggaggttt | 1440 |
| aaagttcttt | gttccagata | tatcaaactc | caatagcatg | attgatgctt | tcagtagaat | 1500 |
| ttcctctgga | actggagaca | ttttccagca | acatattcag | cttgaaagta | caggtgaaaa | 1560 |
| tgtcaaacct | caccatcaat | tgaaaaacac | agtgactgtg | gataatactg | tgggcaacga | 1620 |
| cactatgttt | ctagttacgt | ggcaggccag | tggtcctcct | gagattatat | tatttgatcc | 1680 |
| tgatggacga | aaatactaca | caaataattt | tatcaccaat | ctaacttttc | ggacagctag | 1740 |
| tctttggatt | ccaggaacag | ctaagcctgg | gcactggact | tacaccctga | tgtgtttcca | 1800 |
| ccatgcaaaa | ttattgacct | ggaagctgta | aaagtagaag | aggaattgac | cctatcttgg | 1860 |
| acagcacctg | gagaagactt | tgatcagggc | caggctacaa | gctatgaaat | aagaatgagt | 1920 |
| aaaagtctac | agaatatcca | agatgacttt | aacaatgcta | ttttagtaaa | tacatcaaag | 1980 |
| cgaaatcctc | agcaagctgg | catcaggag | atatttacgt | tctcaccca | aatttccacg | 2040 |
| aatggacctg | aacatcagcc | aaatggagaa | acacatgaaa | gccacagaat | ttatgttgca | 2100 |
| atacgagcaa | tggataggaa | ctccttacag | tctgctgtat | ctaacattgc | ccaggcgcct | 2160 |
| ctgtttattc | ccccaattc | tgatcctgta | cctgccagag | attatcttat | attgaaagga | 2220 |

-continued

```
gttttaacag caatgggttt gataggaatc atttgcctta ttatagttgt gacacatcat    2280
actttaagca ggaaaaagag agcagacaag aaagagaatg gaacaaaatt attataaata    2340
aatatccaaa gtgtcttcct tcttagatat aagacccatg gccttcgact acaaaaacat    2400
actaacaaag tcaaattaac atcaaaactg tattaaaatg cattgagttt ttgtacaata    2460
cagataagat ttttacatgg tagatcaaca aattctttt gggggtagat tagaaaaccc     2520
ttacactttg gctatgaaca ataataaaa attattcttt aaagtaatgt ctttaaaggc     2580
aaagggaagg gtaaagtcgg accagtgtca aggaaagttt gttttattga ggtggaaaaa    2640
tagccccaag cagagaaaag gagggtaggt ctgcattata actgtctgtg tgaagcaatc    2700
atttagttac tttgattaat ttttcttttc tccttatctg tgcagaacag gttgcttgtt    2760
tacaactgaa gatcatgcta tatttcatat atgaagcccc taatgcaaag ctctttacct    2820
cttgctattt tgttatatat attacagatg aaatctcact gctaatgctc agagatcttt    2880
tttcactgta agaggtaacc tttaacaata tgggtattac cttttgtctct tcataccggt   2940 tttatgacaa aggtctattg aatttatttg tttgtaagtt tctactccca tcaaagcagc    3000
tttctaagtt attgccttgg ttattatgga tgatagttat agcccttata atgccttaac    3060
taaggaagaa aagatgttat tctgagtttg ttttaataca tatatgaaca tatagttta    3120 ttcaattaaa ccaaagaaga ggtcagcagg gagatactaa cctttggaaa tgattagctg    3180
gctctgtttt ttggttaaat aagagtcttt aatcctttct ccatcaagag ttacttacca    3240
agggcagggg aaggggggata tagaggtcac aaggaaataa aaatcatctt tcatctttaa    3300
ttttactcct tcctcttatt ttttttaaaag attatcgaac aataaaatca tttgccttt    3360 tt                                                                    3362
```

<210> SEQ ID NO 168
<211> LENGTH: 2784
<212> TYPE: DNA
<213> ORGANISM: Homo sapien

<400> SEQUENCE: 168

```
tctgcatcca tattgaaaac ctgacacaat gtatgcagca ggctcagtgt gagtgaactg     60
gaggcttctc tacaacatga cccaaaggag cattgcaggt cctatttgca acctgaagtt    120
tgtgactctc ctggttgcct taagttcaga actcccattc ctgggagctg gagtacagct    180
tcaagacaat gggtataatg gattgctcat tgcaattaat cctcaggtac ctgagaatca    240
gaacctcatc tcaaacatta aggaaatgat aactgaagct tcatttttacc tatttaatgc    300 taccaagaga agagtatttt tcagaaatat aaagatttta atacctgcca catggaaagc    360
taataataac agcaaaataa aacaagaatc atatgaaaag gcaaatgtca tagtgactga    420
ctggtatggg gcacatggag atgatccata caccctacaa tacagagggt gtggaaaaga    480
gggaaaatac attcatttca cacctaattt cctactgaat gataacttaa cagctggcta    540
cggatcacga ggccgagtgt ttgtccatga atgggcccac ctccgttggg gtgtgttcga    600
tgagtataac aatgacaaac ctttctacat aaatgggcaa atcaaatta aagtgacaag    660 gtgttcatct gacatcacag gcattttttgt gtgtgaaaaa ggtccttgcc cccaagaaaa    720
ctgtattatt agtaagcttt ttaaagaagg atgcaccttt atctacaata gcacccaaaa    780
tgcaactgca tcaataatgt tcatgcaaag tttatcttct gtggttgaat tttgtaatgc    840
aagtacccac aaccaagaag caccaaaacct acagaaccag atgtgcagcc tcagaagtgc    900
atgggatgta atcacagact ctgctgactt tcaccacagc tttcccatga acgggactga    960
```

-continued

```
gcttccacct cctcccacat tctcgcttgt agaggctggt gacaaagtgg tctgtttagt    1020
gctggatgtg tccagcaaga tggcagaggc tgacagactc cttcaactac aacaagccgc    1080
agaattttat ttgatgcaga ttgttgaaat tcataccttc gtgggcattg ccagtttcga    1140
cagcaaagga gagatcagag cccagctaca ccaaattaac agcaatgatg atcgaaagtt    1200
gctggtttca tatctgccca ccactgtatc agctaaaaca gacatcagca tttgttcagg    1260
gcttaagaaa ggatttgagg tggttgaaaa actgaatgga aaagcttatg ctctgtgat     1320 gatattagtg accagcggag atgataagct tcttggcaat tgcttaccca ctgtgctcag    1380
cagtggttca acaattcact ccattgccct gggttcatct gcagcccaa atctggagga     1440 attatcacgt cttacaggag gtttaaagtt ctttgttcca gatatatcaa actccaatag    1500
catgattgat gctttcagta gaatttcctc tggaactgga gacattttcc agcaacatat    1560
tcagcttgaa agtacaggtg aaaatgtcaa acctcaccat caattgaaaa acacagtgac    1620
tgtggataat actgtgggca cgacactat gtttctagtt acgtggcagg ccagtggtcc     1680
tcctgagatt atattatttg atcctgatgg acgaaaatac tacacaaata attttatcac    1740
caatctaact tttcggacag ctagtctttg gattccagga acagctaagc ctgggcactg    1800
gacttacacc ctgaacaata cccatcattc tctgcaagcc ctgaaagtga cagtgacctc    1860
tcgcgcctcc aactcagctg tgcccccagc cactgtggaa gcctttgtgg aaagagacag    1920
cctccatttt cctcatcctg tgatgattta tgccaatgtg aaacagggat ttatccccat    1980
tcttaatgcc actgtcactg ccacagttga gccagagact ggagatcctg ttacgctgag    2040
actccttgat gatggagcag gtgctgatgt tataaaaaat gatggaattt actcgaggta    2100
ttttttctcc tttgctgcaa atggtagata tagcttgaaa gtgcatgtca atcactctcc    2160
cagcataagc accccagccc actctattcc agggagtcat gctatgtatg taccaggtta    2220
cacagcaaac ggtaatattc agatgaatgc tccaaggaaa tcagtaggca gaaatgagga    2280
ggagcgaaag tggggctta gccgagtcag ctcaggaggc tcctttttcag tgctgggagt     2340 tccagctggc ccccaccctg atgtgtttcc accatgcaaa attattgacc tggaagctgt    2400 aatagaaga ggaattgacc ctatcttgga cagcacctgg agaagacttt gatcagggcc     2460 ggctacaag ctatgaaata agaatgagta aaagtctaca gaatatccaa gatgacttta     2520 caatgctat tttagtaaat acatcaaagc gaaatcctca gcaagctggc atcagggaga    2580 atttacgtt ctcaccccaa atttccacga atggacctga acatcagcca aatggagaaa    2640 acatgaaag ccacagaatt tatgttgcaa tacgagcaat ggataggaac tccttacagt     2700 tgctgtatc taacattgcc caggcgcctc tgtttattcc ccccaattct gatcctgtac     2760 tgccagaga ttatcttata ttga                                            2784
```

<210> SEQ ID NO 169
<211> LENGTH: 592
<212> TYPE: PRT
<213> ORGANISM: Homo sapien

<400> SEQUENCE: 169

```
Met Thr Gln Arg Ser Ile Ala Gly Pro Ile Cys Asn Leu Lys Phe Val
 1               5                  10                  15

Thr Leu Leu Val Ala Leu Ser Ser Glu Leu Pro Phe Leu Gly Ala Gly
             20                  25                  30

Val Gln Leu Gln Asp Asn Gly Tyr Asn Gly Leu Leu Ile Ala Ile Asn
         35                  40                  45
```

```
Pro Gln Val Pro Glu Asn Gln Asn Leu Ile Ser Asn Ile Lys Glu Met
 50                  55                  60

Ile Thr Glu Ala Ser Phe Tyr Leu Phe Asn Ala Thr Lys Arg Arg Val
 65                  70                  75                  80

Phe Phe Arg Asn Ile Lys Ile Leu Ile Pro Ala Thr Trp Lys Ala Asn
                 85                  90                  95

Asn Asn Ser Lys Ile Lys Gln Glu Ser Tyr Glu Lys Ala Asn Val Ile
            100                 105                 110

Val Thr Asp Trp Tyr Gly Ala His Gly Asp Asp Pro Tyr Thr Leu Gln
            115                 120                 125

Tyr Arg Gly Cys Gly Lys Glu Gly Lys Tyr Ile His Phe Thr Pro Asn
        130                 135                 140

Phe Leu Leu Asn Asp Asn Leu Thr Ala Gly Tyr Gly Ser Arg Gly Arg
145                 150                 155                 160

Val Phe Val His Glu Trp Ala His Leu Arg Trp Gly Val Phe Asp Glu
                165                 170                 175

Tyr Asn Asn Asp Lys Pro Phe Tyr Ile Asn Gly Gln Asn Gln Ile Lys
            180                 185                 190

Val Thr Arg Cys Ser Ser Asp Ile Thr Gly Ile Phe Val Cys Glu Lys
        195                 200                 205

Gly Pro Cys Pro Gln Glu Asn Cys Ile Ile Ser Lys Leu Phe Lys Glu
    210                 215                 220

Gly Cys Thr Phe Ile Tyr Asn Ser Thr Gln Asn Ala Thr Ala Ser Ile
225                 230                 235                 240

Met Phe Met Gln Ser Leu Ser Ser Val Val Glu Phe Cys Asn Ala Ser
                245                 250                 255

Thr His Asn Gln Glu Ala Pro Asn Leu Gln Asn Gln Met Cys Ser Leu
            260                 265                 270

Arg Ser Ala Trp Asp Val Ile Thr Asp Ser Ala Asp Phe His His Ser
        275                 280                 285

Phe Pro Met Asn Gly Thr Glu Leu Pro Pro Pro Thr Phe Ser Leu
    290                 295                 300

Val Glu Ala Gly Asp Lys Val Val Cys Leu Val Leu Asp Val Ser Ser
305                 310                 315                 320

Lys Met Ala Glu Ala Asp Arg Leu Leu Gln Leu Gln Gln Ala Ala Glu
                325                 330                 335

Phe Tyr Leu Met Gln Ile Val Glu Ile His Thr Phe Val Gly Ile Ala
            340                 345                 350

Ser Phe Asp Ser Lys Gly Glu Ile Arg Ala Gln Leu His Gln Ile Asn
        355                 360                 365

Ser Asn Asp Asp Arg Lys Leu Leu Val Ser Tyr Leu Pro Thr Thr Val
370                 375                 380

Ser Ala Lys Thr Asp Ile Ser Ile Cys Ser Gly Leu Lys Lys Gly Phe
385                 390                 395                 400

Glu Val Val Glu Lys Leu Asn Gly Lys Ala Tyr Gly Ser Val Met Ile
                405                 410                 415

Leu Val Thr Ser Gly Asp Asp Lys Leu Leu Gly Asn Cys Leu Pro Thr
            420                 425                 430

Val Leu Ser Ser Gly Ser Thr Ile His Ser Ile Ala Leu Gly Ser Ser
        435                 440                 445

Ala Ala Pro Asn Leu Glu Glu Leu Ser Arg Leu Thr Gly Gly Leu Lys
    450                 455                 460
```

```
Phe Phe Val Pro Asp Ile Ser Asn Ser Asn Ser Met Ile Asp Ala Phe
465                 470                 475                 480

Ser Arg Ile Ser Ser Gly Thr Gly Asp Ile Phe Gln Gln His Ile Gln
                485                 490                 495

Leu Glu Ser Thr Gly Glu Asn Val Lys Pro His His Gln Leu Lys Asn
            500                 505                 510

Thr Val Thr Val Asp Asn Thr Val Gly Asn Asp Thr Met Phe Leu Val
        515                 520                 525

Thr Trp Gln Ala Ser Gly Pro Pro Glu Ile Ile Leu Phe Asp Pro Asp
    530                 535                 540

Gly Arg Lys Tyr Tyr Thr Asn Asn Phe Ile Thr Asn Leu Thr Phe Arg
545                 550                 555                 560

Thr Ala Ser Leu Trp Ile Pro Gly Thr Ala Lys Pro Gly His Trp Thr
                565                 570                 575

Tyr Thr Leu Met Cys Phe His His Ala Lys Leu Leu Thr Trp Lys Leu
            580                 585                 590
```

<210> SEQ ID NO 170
<211> LENGTH: 791
<212> TYPE: PRT
<213> ORGANISM: Homo sapien

<400> SEQUENCE: 170

```
Met Thr Gln Arg Ser Ile Ala Gly Pro Ile Cys Asn Leu Lys Phe Val
1               5                   10                  15

Thr Leu Leu Val Ala Leu Ser Ser Glu Leu Pro Phe Leu Gly Ala Gly
                20                  25                  30

Val Gln Leu Gln Asp Asn Gly Tyr Asn Gly Leu Leu Ile Ala Ile Asn
            35                  40                  45

Pro Gln Val Pro Glu Asn Gln Asn Leu Ile Ser Asn Ile Lys Glu Met
50                  55                  60

Ile Thr Glu Ala Ser Phe Tyr Leu Phe Asn Ala Thr Lys Arg Arg Val
65                  70                  75                  80

Phe Phe Arg Asn Ile Lys Ile Leu Ile Pro Ala Thr Trp Lys Ala Asn
                85                  90                  95

Asn Asn Ser Lys Ile Lys Gln Glu Ser Tyr Glu Lys Ala Asn Val Ile
                100                 105                 110

Val Thr Asp Trp Tyr Gly Ala His Gly Asp Asp Pro Tyr Thr Leu Gln
            115                 120                 125

Tyr Arg Gly Cys Gly Lys Glu Gly Lys Tyr Ile His Phe Thr Pro Asn
130                 135                 140

Phe Leu Leu Asn Asp Asn Leu Thr Ala Gly Tyr Gly Ser Arg Gly Arg
145                 150                 155                 160

Val Phe Val His Glu Trp Ala His Leu Arg Trp Gly Val Phe Asp Glu
                165                 170                 175

Tyr Asn Asn Asp Lys Pro Phe Tyr Ile Asn Gly Gln Asn Gln Ile Lys
            180                 185                 190

Val Thr Arg Cys Ser Ser Asp Ile Thr Gly Ile Phe Val Cys Glu Lys
        195                 200                 205

Gly Pro Cys Pro Gln Glu Asn Cys Ile Ile Ser Lys Leu Phe Lys Glu
    210                 215                 220

Gly Cys Thr Phe Ile Tyr Asn Ser Thr Gln Asn Ala Thr Ala Ser Ile
225                 230                 235                 240

Met Phe Met Gln Ser Leu Ser Ser Val Val Glu Phe Cys Asn Ala Ser
                245                 250                 255
```

```
Thr His Asn Gln Glu Ala Pro Asn Leu Gln Asn Gln Met Cys Ser Leu
            260                 265                 270

Arg Ser Ala Trp Asp Val Ile Thr Asp Ser Ala Asp Phe His His Ser
        275                 280                 285

Phe Pro Met Asn Gly Thr Glu Leu Pro Pro Pro Thr Phe Ser Leu
    290                 295                 300

Val Glu Ala Gly Asp Lys Val Val Cys Leu Val Leu Asp Val Ser Ser
305                 310                 315                 320

Lys Met Ala Glu Ala Asp Arg Leu Leu Gln Leu Gln Gln Ala Ala Glu
                325                 330                 335

Phe Tyr Leu Met Gln Ile Val Glu Ile His Thr Phe Val Gly Ile Ala
                340                 345                 350

Ser Phe Asp Ser Lys Gly Glu Ile Arg Ala Gln Leu His Gln Ile Asn
        355                 360                 365

Ser Asn Asp Asp Arg Lys Leu Leu Val Ser Tyr Leu Pro Thr Thr Val
        370                 375                 380

Ser Ala Lys Thr Asp Ile Ser Ile Cys Ser Gly Leu Lys Lys Gly Phe
385                 390                 395                 400

Glu Val Val Glu Lys Leu Asn Gly Lys Ala Tyr Gly Ser Val Met Ile
                405                 410                 415

Leu Val Thr Ser Gly Asp Asp Lys Leu Leu Gly Asn Cys Leu Pro Thr
                420                 425                 430

Val Leu Ser Ser Gly Ser Thr Ile His Ser Ile Ala Leu Gly Ser Ser
                435                 440                 445

Ala Ala Pro Asn Leu Glu Glu Leu Ser Arg Leu Thr Gly Gly Leu Lys
            450                 455                 460

Phe Phe Val Pro Asp Ile Ser Asn Ser Asn Ser Met Ile Asp Ala Phe
465                 470                 475                 480

Ser Arg Ile Ser Ser Gly Thr Gly Asp Ile Phe Gln Gln His Ile Gln
                485                 490                 495

Leu Glu Ser Thr Gly Glu Asn Val Lys Pro His His Gln Leu Lys Asn
            500                 505                 510

Thr Val Thr Val Asp Asn Thr Val Gly Asn Asp Thr Met Phe Leu Val
        515                 520                 525

Thr Trp Gln Ala Ser Gly Pro Pro Glu Ile Ile Leu Phe Asp Pro Asp
    530                 535                 540

Gly Arg Lys Tyr Tyr Thr Asn Asn Phe Ile Thr Asn Leu Thr Phe Arg
545                 550                 555                 560

Thr Ala Ser Leu Trp Ile Pro Gly Thr Ala Lys Pro Gly His Trp Thr
                565                 570                 575

Tyr Thr Leu Asn Asn Thr His His Ser Leu Gln Ala Leu Lys Val Thr
                580                 585                 590

Val Thr Ser Arg Ala Ser Asn Ser Ala Val Pro Pro Ala Thr Val Glu
            595                 600                 605

Ala Phe Val Glu Arg Asp Ser Leu His Phe Pro His Pro Val Met Ile
    610                 615                 620

Tyr Ala Asn Val Lys Gln Gly Phe Tyr Pro Ile Leu Asn Ala Thr Val
625                 630                 635                 640

Thr Ala Thr Val Glu Pro Glu Thr Gly Asp Pro Val Thr Leu Arg Leu
                645                 650                 655

Leu Asp Asp Gly Ala Gly Ala Asp Val Ile Lys Asn Asp Gly Ile Tyr
                660                 665                 670
```

```
Ser Arg Tyr Phe Phe Ser Phe Ala Ala Asn Gly Arg Tyr Ser Leu Lys
            675                 680                 685

Val His Val Asn His Ser Pro Ser Ile Ser Thr Pro Ala His Ser Ile
        690                 695                 700

Pro Gly Ser His Ala Met Tyr Val Pro Gly Tyr Thr Ala Asn Gly Asn
705                 710                 715                 720

Ile Gln Met Asn Ala Pro Arg Lys Ser Val Gly Arg Asn Glu Glu Glu
                725                 730                 735

Arg Lys Trp Gly Phe Ser Arg Val Ser Ser Gly Gly Ser Phe Ser Val
            740                 745                 750

Leu Gly Val Pro Ala Gly Pro His Pro Asp Val Phe Pro Pro Cys Lys
            755                 760                 765

Ile Ile Asp Leu Glu Ala Val Asn Arg Arg Gly Ile Asp Pro Ile Leu
        770                 775                 780

Asp Ser Thr Trp Arg Arg Leu
785                 790

<210> SEQ ID NO 171
<211> LENGTH: 1491
<212> TYPE: DNA
<213> ORGANISM: Homo sapien

<400> SEQUENCE: 171
cctcctgcca gccaagtgaa gacatgctta cttcccttc accttcttc atgatgtggg       60 aagagtgctg caacccagcc ctagccaacg ccgcatgaga gggagtgtgc cgagggcttc      120
tgagaaggtt tctctcacat ctagaaagaa gcgcttaaga tgtggcagcc cctcttcttc      180
aagtggctct tgtcctgttg ccctgggagt tctcaaattg ctgcagcagc tccacccag       240 cctgaggatg acatcaatac acagaggaag aagagtcagg aaaagatgag agaagttaca      300
gactctcctg ggcgaccccg agagcttacc attcctcaga cttcttcaca tggtgctaac      360
agatttgttc ctaaaagtaa agctctagag gccgtcaaat tggcaataga agccgggttc      420
caccatattg attctgcaca tgtttacaat aatgaggagc aggttggact ggccatccga      480
agcaagattg cagatggcag tgtgaagaga aagacatat tctacacttc aaagctttgg       540
agcaattccc atcgaccaga gttggtccga ccagccttgg aaaggtcact gaaaaatctt      600
caattggact atgttgacct ctatcttatt cattttccag tgtctgtaaa gccaggtgag      660
gaagtgatcc caaagatgaa aatggaaaa atactatttg acacagtgga tctctgtgcc      720
acatgggagg ccatggagaa gtgtaaagat gcaggattgg ccaagtccat cggggtgtcc      780
aacttcaacc acaggctgct ggagatgatc ctcaacaagc cagggctcaa gtacaagcct      840
gtctgcaacc aggtggaatg tcatccttac ttcaaccaga gaaaactgct ggatttctgc      900
aagtcaaaag acattgttct ggttgcctat agtgctctgg gatcccatcg agaagaacca      960
tgggtggacc cgaactcccc ggtgctcttg gaggacccag tcctttgtgc cttggcaaaa     1020
aagcacaagc gaaccccagc cctgattgcc ctgcgctacc agctgcagcg tggggttgtg     1080
gtcctggcca agagctacaa tgagcagcgc atcagacaga acgtgcaggt gtttgaattc     1140
cagttgactt cagaggagat gaaagccata gatggcctaa acagaaatgt gcgatatttg     1200
acccttgata tttttgctgg cccccctaat tatccatttt ctgatgaata ttaacatgga     1260
gggcattgca tgaggtctgc cagaaggccc tgcgtgtgga tggtgacaca gaggatggct     1320
ctatgctggt gactggacac atcgcctctg gttaaatctc tcctgcttgg cgacttcagt     1380
aagctacagc taagcccatc ggccggaaaa gaaagacaat aatttttgttt ttcattttga     1440
```
aaaaattaaa tgctctctcc taaagattct tcacctaaaa aaaaaaaaaa a         1491

<210> SEQ ID NO 172
<211> LENGTH: 364
<212> TYPE: PRT
<213> ORGANISM: Homo sapien

<400> SEQUENCE: 172

```
Met Trp Gln Pro Leu Phe Phe Lys Trp Leu Ser Cys Cys Pro Gly
 1               5                  10                  15

Ser Ser Gln Ile Ala Ala Ala Ser Thr Gln Pro Glu Asp Asp Ile
                20                  25                  30

Asn Thr Gln Arg Lys Lys Ser Gln Glu Lys Met Arg Glu Val Thr Asp
            35                  40                  45

Ser Pro Gly Arg Pro Arg Glu Leu Thr Ile Pro Gln Thr Ser Ser His
        50                  55                  60

Gly Ala Asn Arg Phe Val Pro Lys Ser Lys Ala Leu Glu Ala Val Lys
65                  70                  75                  80

Leu Ala Ile Glu Ala Gly Phe His His Ile Asp Ser Ala His Val Tyr
                85                  90                  95

Asn Asn Glu Glu Gln Val Gly Leu Ala Ile Arg Ser Lys Ile Ala Asp
            100                 105                 110

Gly Ser Val Lys Arg Glu Asp Ile Phe Tyr Thr Ser Lys Leu Trp Ser
        115                 120                 125

Asn Ser His Arg Pro Glu Leu Val Arg Pro Ala Leu Glu Arg Ser Leu
    130                 135                 140

Lys Asn Leu Gln Leu Asp Tyr Val Asp Leu Tyr Leu Ile His Phe Pro
145                 150                 155                 160

Val Ser Val Lys Pro Gly Glu Glu Val Ile Pro Lys Asp Glu Asn Gly
                165                 170                 175

Lys Ile Leu Phe Asp Thr Val Asp Leu Cys Ala Thr Trp Glu Ala Met
            180                 185                 190

Glu Lys Cys Lys Asp Ala Gly Leu Ala Lys Ser Ile Gly Val Ser Asn
        195                 200                 205

Phe Asn His Arg Leu Leu Glu Met Ile Leu Asn Lys Pro Gly Leu Lys
    210                 215                 220

Tyr Lys Pro Val Cys Asn Gln Val Glu Cys His Pro Tyr Phe Asn Gln
225                 230                 235                 240

Arg Lys Leu Leu Asp Phe Cys Lys Ser Lys Asp Ile Val Leu Val Ala
                245                 250                 255

Tyr Ser Ala Leu Gly Ser His Arg Glu Glu Pro Trp Val Asp Pro Asn
            260                 265                 270

Ser Pro Val Leu Leu Glu Asp Pro Val Leu Cys Ala Leu Ala Lys Lys
        275                 280                 285

His Lys Arg Thr Pro Ala Leu Ile Ala Leu Arg Tyr Gln Leu Gln Arg
    290                 295                 300

Gly Val Val Val Leu Ala Lys Ser Tyr Asn Glu Gln Arg Ile Arg Gln
305                 310                 315                 320

Asn Val Gln Val Phe Glu Phe Gln Leu Thr Ser Glu Glu Met Lys Ala
                325                 330                 335

Ile Asp Gly Leu Asn Arg Asn Val Arg Tyr Leu Thr Leu Asp Ile Phe
            340                 345                 350

Ala Gly Pro Pro Asn Tyr Pro Phe Ser Asp Glu Tyr
        355                 360
```

<210> SEQ ID NO 173
<211> LENGTH: 1988
<212> TYPE: DNA
<213> ORGANISM: Homo sapiens

<400> SEQUENCE: 173

| | | | | | |
|---|---|---|---|---|---|
| cgggagccgc | ctccccgcgg | cctcttcgct | tttgtggcgg | cgcccgcgct | cgcaggccac | 60 |
| tctctgctgt | cgcccgtccc | gcgcgctcct | ccgacccgct | ccgctccgct | ccgctcggcc | 120 |
| ccgcgccgcc | cgtcaacatg | atccgctgcg | gcctggcctg | cgagcgctgc | cgctggatcc | 180 |
| tgccctgct | cctactcagc | gccatcgcct | tcgacatcat | cgcgctggcc | ggccgcggct | 240 |
| ggttgcagtc | tagcgaccac | ggccagacgt | cctcgctgtg | gtggaaatgc | tcccaagagg | 300 |
| gcggcggcag | cgggtcctac | gaggagggct | gtcagagcct | catggagtac | gcgtggggtt | 360 |
| gagcagcggc | tgccatgctc | ttctgtggct | tcatcatcct | ggtgatctgt | ttcatcctcc | 420 |
| ccttcttcgc | cctctgtgga | ccccagatgc | ttgtcttcct | gagagtgatt | ggaggtctcc | 480 |
| ttgccttggc | tgctgtgttc | cagatcatct | ccctggtaat | ttaccccgtg | aagtacaccc | 540 |
| agaccttcac | ccttcatgcc | aaccctgctg | tcacttacat | ctataactgg | gcctacggct | 600 |
| tgggtgggc | agccacgatt | atcctgatcg | gctgtgcctt | cttcttctgc | tgcctcccca | 660 |
| actacgaaga | tgaccttctg | ggcaatgcca | agcccaggta | cttctacaca | tctgcctaac | 720 |
| ttgggaatga | atgtgggaga | aaatcgctgc | tgctgagatg | gactccagaa | gaagaaactg | 780 |
| tttctccagg | cgactttgaa | cccatttttt | ggcagtgttc | atattattaa | actagtcaaa | 840 |
| aatgctaaaa | taatttggga | gaaaatattt | tttaagtagt | gttatagttt | catgtttatc | 900 |
| ttttattatg | ttttgtgaag | ttgtgtcttt | tcactaatta | cctatactat | gccaatattt | 960 |
| ccttatatct | atccataaca | tttatactac | atttgtaaga | gaatatgcac | gtgaaactta | 1020 |
| acactttata | aggtaaaaat | gaggtttcca | agatttaata | atctgatcaa | gttcttgtta | 1080 |
| tttccaaata | gaatggactt | ggtctgttaa | gggctaagga | gaagaggaag | ataaggttaa | 1140 |
| aagttgttaa | tgaccaaaca | ttctaaaaga | aatgcaaaaa | aaagtttat | tttcaagcct | 1200 |
| tcgaactatt | taaggaaagc | aaaatcattt | cctaaatgca | tatcatttgt | gagaatttct | 1260 |
| cattaatatc | ctgaatcatt | catttcagct | aaggcttcat | gttgactcga | tatgtcatct | 1320 |
| aggaaagtac | tatttcatgg | tccaaacctg | ttgccatagt | tggtaaggct | ttcctttaag | 1380 |
| tgtgaaatat | ttagatgaaa | ttttctcttt | taaagttctt | tataggggta | gggtgtggga | 1440 |
| aaatgctata | ttaataaatc | tgtagtgttt | tgtgtttata | tgttcagaac | cagagtagac | 1500 |
| tggattgaaa | gatggactgg | gtctaattta | tcatgactga | tagatctggt | taagttgtgt | 1560 |
| agtaaagcat | taggagggtc | attcytgtca | caaaagtgcc | actaaaacag | cctcaggaga | 1620 |
| ataaatgact | tgcttttcta | aatctcaggt | ttatctgggc | tctatcatat | agacaggctc | 1680 |
| ctgatagttt | gcarctgtaa | gcagaaacct | acatatagtt | aaaatcctgg | tctttcttgg | 1740 |
| taaacagatt | ttaaatgtct | gatataaaac | atgccacagg | agaattcggg | gatttgagtt | 1800 |
| tctctgaata | gcatatatat | gatgcatcgg | ataggtcatt | atgattttt | accatttcga | 1860 |
| cttacataat | gaaaaccaat | tcattttaaa | tatcagatta | ttattttgta | agttgtggaa | 1920 |
| aaagctaatt | gtagttttca | ttatgaagtt | ttcccaataa | accaggtatt | ctaaaaaaaa | 1980 |
| aaaaaaaa | | | | | | 1988 |

<210> SEQ ID NO 174

```
<211> LENGTH: 238
<212> TYPE: PRT
<213> ORGANISM: Homo sapiens

<400> SEQUENCE: 174

Gly Ala Ala Ser Pro Arg Pro Leu Arg Phe Cys Gly Gly Ala Arg Ala
  1               5                  10                  15
Arg Arg Pro Leu Ser Ala Val Ala Arg Pro Ala Arg Ser Ser Asp Pro
             20                  25                  30
Leu Arg Ser Ala Pro Leu Gly Pro Ala Pro Val Asn Met Ile Arg
         35                  40                  45
Cys Gly Leu Ala Cys Glu Arg Cys Arg Trp Ile Leu Pro Leu Leu Leu
 50                  55                  60
Leu Ser Ala Ile Ala Phe Asp Ile Ile Ala Leu Ala Gly Arg Gly Trp
 65                  70                  75                  80
Leu Gln Ser Ser Asp His Gly Gln Thr Ser Ser Leu Trp Trp Lys Cys
                 85                  90                  95
Ser Gln Glu Gly Gly Gly Ser Gly Ser Tyr Glu Glu Gly Cys Gln Ser
            100                 105                 110
Leu Met Glu Tyr Ala Trp Gly Arg Ala Ala Ala Met Leu Phe Cys
        115                 120                 125
Gly Phe Ile Ile Leu Val Ile Cys Phe Ile Leu Ser Phe Phe Ala Leu
130                 135                 140
Cys Gly Pro Gln Met Leu Val Phe Leu Arg Val Ile Gly Gly Leu Leu
145                 150                 155                 160
Ala Leu Ala Ala Val Phe Gln Ile Ile Ser Leu Val Ile Tyr Pro Val
                165                 170                 175
Lys Tyr Thr Gln Thr Phe Thr Leu His Ala Asn Pro Ala Val Thr Tyr
            180                 185                 190
Ile Tyr Asn Trp Ala Tyr Gly Phe Gly Trp Ala Thr Ile Ile Leu
        195                 200                 205
Ile Gly Cys Ala Phe Phe Cys Cys Leu Pro Asn Tyr Glu Asp Asp
210                 215                 220
Leu Leu Gly Asn Ala Lys Pro Arg Tyr Phe Tyr Thr Ser Ala
225                 230                 235

<210> SEQ ID NO 175
<211> LENGTH: 4181
<212> TYPE: DNA
<213> ORGANISM: Homo sapiens
<220> FEATURE:
<221> NAME/KEY: misc_feature
<222> LOCATION: (1)...(4181)
<223> OTHER INFORMATION: n=A,T,C or G

<400> SEQUENCE: 175
ggtggatgcg tttgggttgt agctaggctt tttctttct ttctctttta aaacacatct      60
agacaaggaa aaacaagcc tcggatctga tttttcactc ctcgttcttg tgcttggttc     120
ttactgtgtt tgtgtatttt aaaggcgaga agacgagggg aacaaaacca gctggatcca     180
tccatcaccg tgggtggttt taatttttcg tttttttctcg ttattttttt ttaaacaacc     240
actcttcaca atgaacaaac tgtatatcgg aaacctcagc gagaacgccg cccctcgga     300
cctagaaagt atcttcaagg acgccaagat cccggtgtcg ggacccttcc tggtgaagac     360
tggctacgcg ttcgtggact gcccggacga gagctgggcc ctcaaggcca tcgaggcgct     420
ttcaggtaaa atagaactgc acgggaaacc catagaagtt gagcactcgg tcccaaaaag     480
```

-continued

```
gcaaaggatt cggaaacttc agatacgaaa tatcccgcct catttacagt gggaggtgct     540
ggatagttta ctagtccagt atggagtggt ggagagctgt gagcaagtga acactgactc     600
ggaaactgca gttgtaaatg taacctattc cagtaaggac caagctagac aagcactaga     660
caaactgaat ggatttcagt tagagaattt caccttgaaa gtagcctata tccctgatga     720
aatggccgcc cagcaaaacc ccttgcagca gccccgaggt cgccggggc ttgggcagag      780 gggctcctca aggcagggt ctccaggatc cgtatccaag cagaaaccat gtgatttgcc      840
tctgcgcctg ctggttccca cccaatttgt tggagccatc ataggaaaag aaggtgccac     900
cattcggaac atcaccaaac agacccagtc taaaatcgat gtccaccgta agaaaatgc      960 gggggctgct gagaagtcga ttactatcct ctctactcct gaaggcacct ctgcggcttg    1020
taagtctatt ctggagatta tgcataagga agctcaagat ataaaattca cagaagagat    1080 cccctgaag atttagctc ataataactt tgttggacgt cttattggta agaaggaag       1140 aaatcttaaa aaaattgagc aagacacaga cactaaaatc acgatatctc cattgcagga    1200
attgacgctg tataatccag aacgcactat tacagttaaa ggcaatgttg agacatgtgc    1260
caaagctgag gaggagatca tgaagaaaat cagggagtct tatgaaaatg atattgcttc    1320
tatgaatctt caagcacatt taattcctgg attaaatctg aacgccttgg gtctgttccc    1380
acccacttca gggatgccac ctcccacctc agggccccct tcagccatga ctcctcccta    1440
cccgcagttt gagcaatcag aaacggagac tgttcatcag tttatcccag ctctatcagt    1500
cggtgccatc atcggcaagc agggccagca catcaagcag ctttctcgct tgctggagc     1560 ttcaattaag attgctccag cggaagcacc agatgctaaa gtgaggatgg tgattatcac    1620
tggaccacca gaggctcagt tcaaggctca gggaagaatt tatggaaaaa ttaaagaaga    1680
aaactttgtt agtcctaaag aagaggtgaa acttgaagct catatcagag tgccatcctt    1740
tgctgctggc agagttattg gaaaggagg caaaacggtg aatgaacttc agaatttgtc     1800
aagtgcagaa gttgttgtcc ctcgtgacca gacacctgat gagaatgacc aagtggttgt    1860
caaaataact ggtcacttct atgcttgcca ggttgcccag agaaaaattc aggaaattct    1920
gactcaggta aagcagcacc aacaacagaa ggctctgcaa agtggaccac ctcagtcaag    1980
acggaagtaa aggctcagga acagcccac cacagaggca gatgccaaac caagacaga     2040 ttgcttaacc aacagatggg cgctgacccc ctatccagaa tcacatgcac aagttttac     2100 ctagccagtt gtttctgagg accaggcaac ttttgaactc ctgtctctgt gagaatgtat    2160
actttatgct ctctgaaatg tatgacaccc agctttaaaa caaacaaaca aacaaacaaa    2220
aaaagggtgg gggagggagg gaaagagaag agctctgcac ttcccttgt tgtagtctca     2280 cagtataaca gatattctaa ttcttcttaa tattccccca taatgccaga aattggctta    2340
atgatgcttt cactaaattc atcaaataga ttgctcctaa atccaattgt taaaattgga    2400
tcagaataat tatcacagga acttaaatgt taagccatta gcatagaaaa actgttctca    2460
gttttatttt tacctaacac taacatgagt aacctaaggg aagtgctgaa tggtgttggc    2520 agggtatta acgtgcatt tttactcaac tacctcaggt attcagtaat acaatgaaaa      2580
gcaaaattgt tcctttttt tgaaaatttt atatacttta taatgataga agtccaaccg    2640
ttttttaaaa aataaattta aatttaaca gcaatcagct aacaggcaaa ttaagatttt     2700
tacttctggc tggtgacagt aaagctggaa aattaatttc agggtttttt gaggcttttg    2760
acacagttat tagttaaatc aaatgttcaa aaatacggag cagtgcctag tatctggaga    2820
gcagcactac catttattct ttcatttata gttgggaaag ttttgacgg tactaacaaa     2880
```

```
gtggtcgcag gagattttgg aacggctggt ttaaatggct tcaggagact tcagttttt      2940 gtttagctac atgattgaat gcataataaa tgctttgtgc ttctgactat caataccta       3000 agaaagtgca tcagtgaaga gatgcaagac tttcaactga ctggcaaaaa gcaagcttta      3060
gcttgtctta taggatgctt agtttgccac tacacttcag accaatggga cagtcataga     3120
tggtgtgaca gtgtttaaac gcaacaaaag gctacatttc catggggcca gcactgtcat      3180
gagcctcact aagctatttt gaagattttt aagcactgat aaattaaaaa aaaaaaaaa       3240 aaattagact ccaccttaag tagtaaagta taacaggatt tctgtatact gtgcaatcag      3300
ttctttgaaa aaaagtcaa aagatagaga atacaagaaa agttttnggg atataatttg       3360
aatgactgtg aaaacatatg acctttgata acgaactcat ttgctcactc cttgacagca     3420
aagcccagta cgtacaattg tgttgggtgt gggtggtctc caaggccacg ctgctctctg     3480
aattgatttt ttgagttttg gnttgnaaga tgatcacagn catgttacac tgatcttnaa     3540
ggacatatnt tataacccctt taaaaaaaaa atccctgcc tcattcttat ttcgagatga      3600
atttcgatac agactagatg tctttctgaa gatcaattag acattntgaa aatgatttaa      3660
agtgttttcc ttaatgttct ctgaaaacaa gtttctttg tagttttaac caaaaagtg       3720 cccttttgt cactggtttc tcctagcatt catgatttt ttttcacaca atgaattaaa       3780
attgctaaaa tcatggactg gctttctggt tggatttcag gtaagatgtg tttaaggcca     3840 agctttct cagtatttga ttttttttccc caatatttga ttttttaaaa atatacacat      3900 ggagctgca tttaaaaacct gctggtttaa attctgtcan atttcacttc tagccttta      3960 tatggcnaa tcanaattta ctttactta agcatttgta atttggagta tctggtacta      4020 ctaagaaat aattcnataa ttgagttttg tactcnccaa anatgggtca ttcctcatgn      4080 taatgtncc cccaatgcag cttcattttc caganacctt gacgcaggat aaattttttc     4140 tcatttagg tccccaaaaa aaaaaaaaaa aaaaaaaaaa a                          4181
```

<210> SEQ ID NO 176
<211> LENGTH: 579
<212> TYPE: PRT
<213> ORGANISM: Homo sapiens

<400> SEQUENCE: 176

```
Met Asn Lys Leu Tyr Ile Gly Asn Leu Ser Glu Asn Ala Ala Pro Ser
              5                  10                  15

Asp Leu Glu Ser Ile Phe Lys Asp Ala Lys Ile Pro Val Ser Gly Pro
         20                  25                  30

Phe Leu Val Lys Thr Gly Tyr Ala Phe Val Asp Cys Pro Asp Glu Ser
     35                  40                  45

Trp Ala Leu Lys Ala Ile Glu Ala Leu Ser Gly Lys Ile Glu Leu His
 50                  55                  60

Gly Lys Pro Ile Glu Val Glu His Ser Val Pro Lys Arg Gln Arg Ile
 65                  70                  75                  80

Arg Lys Leu Gln Ile Arg Asn Ile Pro Pro His Leu Gln Trp Glu Val
                 85                  90                  95

Leu Asp Ser Leu Leu Val Gln Tyr Gly Val Val Glu Ser Cys Glu Gln
            100                 105                 110

Val Asn Thr Asp Ser Glu Thr Ala Val Val Asn Val Thr Tyr Ser Ser
        115                 120                 125

Lys Asp Gln Ala Arg Gln Ala Leu Asp Lys Leu Asn Gly Phe Gln Leu
    130                 135                 140
```

-continued

```
Glu Asn Phe Thr Leu Lys Val Ala Tyr Ile Pro Asp Glu Met Ala Ala
145                 150                 155                 160

Gln Gln Asn Pro Leu Gln Gln Pro Arg Gly Arg Arg Gly Leu Gly Gln
            165                 170                 175

Arg Gly Ser Ser Arg Gln Gly Ser Pro Gly Ser Val Ser Lys Gln Lys
        180                 185                 190

Pro Cys Asp Leu Pro Leu Arg Leu Leu Val Pro Thr Gln Phe Val Gly
    195                 200                 205

Ala Ile Ile Gly Lys Glu Gly Ala Thr Ile Arg Asn Ile Thr Lys Gln
210                 215                 220

Thr Gln Ser Lys Ile Asp Val His Arg Lys Glu Asn Ala Gly Ala Ala
225                 230                 235                 240

Glu Lys Ser Ile Thr Ile Leu Ser Thr Pro Glu Gly Thr Ser Ala Ala
            245                 250                 255

Cys Lys Ser Ile Leu Glu Ile Met His Lys Glu Ala Gln Asp Ile Lys
        260                 265                 270

Phe Thr Glu Glu Ile Pro Leu Lys Ile Leu Ala His Asn Asn Phe Val
    275                 280                 285

Gly Arg Leu Ile Gly Lys Glu Gly Arg Asn Leu Lys Lys Ile Glu Gln
290                 295                 300

Asp Thr Asp Thr Lys Ile Thr Ile Ser Pro Leu Gln Glu Leu Thr Leu
305                 310                 315                 320

Tyr Asn Pro Glu Arg Thr Ile Thr Val Lys Gly Asn Val Glu Thr Cys
            325                 330                 335

Ala Lys Ala Glu Glu Glu Ile Met Lys Lys Ile Arg Glu Ser Tyr Glu
        340                 345                 350

Asn Asp Ile Ala Ser Met Asn Leu Gln Ala His Leu Ile Pro Gly Leu
    355                 360                 365

Asn Leu Asn Ala Leu Gly Leu Phe Pro Pro Thr Ser Gly Met Pro Pro
370                 375                 380

Pro Thr Ser Gly Pro Pro Ser Ala Met Thr Pro Pro Tyr Pro Gln Phe
385                 390                 395                 400

Glu Gln Ser Glu Thr Glu Thr Val His Gln Phe Ile Pro Ala Leu Ser
            405                 410                 415

Val Gly Ala Ile Ile Gly Lys Gln Gly Gln His Ile Lys Gln Leu Ser
        420                 425                 430

Arg Phe Ala Gly Ala Ser Ile Lys Ile Ala Pro Ala Glu Ala Pro Asp
    435                 440                 445

Ala Lys Val Arg Met Val Ile Ile Thr Gly Pro Pro Glu Ala Gln Phe
450                 455                 460

Lys Ala Gln Gly Arg Ile Tyr Gly Lys Ile Lys Glu Glu Asn Phe Val
465                 470                 475                 480

Ser Pro Lys Glu Glu Val Lys Leu Glu Ala His Ile Arg Val Pro Ser
            485                 490                 495

Phe Ala Ala Gly Arg Val Ile Gly Lys Gly Gly Lys Thr Val Asn Glu
        500                 505                 510

Leu Gln Asn Leu Ser Ser Ala Glu Val Val Pro Arg Asp Gln Thr
    515                 520                 525

Pro Asp Glu Asn Asp Gln Val Val Lys Ile Thr Gly His Phe Tyr
530                 535                 540

Ala Cys Gln Val Ala Gln Arg Lys Ile Gln Glu Ile Leu Thr Gln Val
545                 550                 555                 560
```

Lys Gln His Gln Gln Lys Ala Leu Gln Ser Gly Pro Pro Gln Ser
            565                 570                 575

Arg Arg Lys

<210> SEQ ID NO 177
<211> LENGTH: 401
<212> TYPE: DNA
<213> ORGANISM: Homo sapiens

<400> SEQUENCE: 177

```
atgccccgta aatgtcttca gtgttcttca gggtagttgg gatctcaaaa gatttggttc      60
agatccaaac aaatacacat tctgtgtttt agctcagtgt tttctaaaaa agaaactgc     120
cacacagcaa aaaattgttt actttgttgg acaaaccaaa tcagttctca aaaaatgacc    180
ggtgcttata aaaagttata aatatcgagt agctctaaaa caaaccacct gaccaagagg    240
gaagtgagct tgtgcttagt atttacattg gatgccagtt ttgtaatcac tgacttatgt    300
gcaaactggt gcagaaattc tataaactct ttgctgtttt tgatacctgc ttttttgtttc   360
attttgtttt gttttgtaaa aatgataaaa cttcagaaaa t                         401
```

<210> SEQ ID NO 178
<211> LENGTH: 561
<212> TYPE: DNA
<213> ORGANISM: Homo sapiens

<400> SEQUENCE: 178

```
acgcctttca agggtgtacg caaagcactc attgataccc ttttggatgg ctatgaaaca     60
gcccgctatg ggacagggt ctttggccag aatgagtacc tacgctatca ggaggccctg    120
agtgagctgg ccactgcggt taaagcacga attgggagct ctcagcgaca tcaccagtca   180
gcagccaaag acctaactca gtcccctgag gtctccccaa caaccatcca ggtgacatac   240
ctcccctcca gtcagaagag taaacgtgcc aagcacttcc ttgaattgaa gagctttaag   300
gataactata acacattgga gagtactctg tgacggagct gaaggactct tgccgtagat   360
taagccagtc agttgcaatg tgcaagacag gctgcttgcc gggccgccct cggaacatct   420
ggcccagcag gcccagactg tatccatcca agttcccgtt gtatccagag ttcttagagc   480
ttgtgtctaa agggtaattc cccaacccct ccttatgagc attttttagaa cattggctaa  540
gactattttc ccccagtagc g                                              561
```

<210> SEQ ID NO 179
<211> LENGTH: 521
<212> TYPE: DNA
<213> ORGANISM: Homo sapiens

<400> SEQUENCE: 179

```
cccaacgcgt ttgcaaatat tccctggta gcctacttcc ttaccccga atattggtaa      60
gatcgagcaa tggcttcagg acatgggttc tcttctcctg tgatcattca agtgctcact   120
gcatgaagac tggcttgtct cagtgtttca acctcaccag ggctgtctct tggtccacac   180
ctcgctccct gttagtgccg tatgacagcc cccatcaaat gaccttggcc aagtcacggt   240
ttctctgtgg tcaaggttgg ttggctgatt ggtggaaagt agggtggacc aaaggaggcc   300
acgtgagcag tcagcaccag ttctgcacca gcagcgcctc cgtcctagtg ggtgttcctg   360
tttctccctgg ccctgggtgg gctagggcct gattcgggaa gatgcctttg cagggagggg  420
aggataagtg ggatctacca attgattctg gcaaaacaat ttctaagatt ttttttgcttt  480
```

```
atgtgggaaa cagatctaaa tctcatttta tgctgtattt t                   521
```

<210> SEQ ID NO 180
<211> LENGTH: 417
<212> TYPE: DNA
<213> ORGANISM: Homo sapiens

<400> SEQUENCE: 180

```
ggtggaattc gccgaagatg gcggaggtgc aggtcctggt gcttgatggt cgaggccatc    60
tcctgggccg cctggcggcc atcgtggcta acaggtact  gctgggccgg aaggtggtgg   120
tcgtacgctg tgaaggcatc aacatttctg gcaatttcta cagaaacaag ttgaagtacc   180
tggctttcct ccgcaagcgg atgaacacca acccttcccg aggcccctac cacttccggg   240
cccccagccg catcttctgg cggaccgtgc gaggtatgct gccccacaaa accaagcgag   300
gccaggccgc tctggaccgt ctcaaggtgt tgacggcat  cccaccgccc tacgacaaga   360
aaaagcggat ggtggttcct gctgccctca aggtcgtgcg tctgaagcct acaagaa      417
```

<210> SEQ ID NO 181
<211> LENGTH: 283
<212> TYPE: DNA
<213> ORGANISM: Homo sapiens
<220> FEATURE:
<221> NAME/KEY: misc_feature
<222> LOCATION: (1)...(283)
<223> OTHER INFORMATION: n=A,T,C or G

<400> SEQUENCE: 181

```
gatttcttct aaataggatg taaaacttct ttcanattac tcttcctcag tcctgcctgc    60
caagaactca agtgtaactg tgataaaata acctttccca ggtatattgg caggtatgtg   120
tgtaatctca gaatacacag gtgacataga tatgatatga caactggtaa tggtggattc   180
atttacattg tttacacttc tatgaccagg ccttaaggga aggtcagttt tttaaaaaac   240
caagtagtgt cttcctacct atctccagat acatgtcaaa aaa                    283
```

<210> SEQ ID NO 182
<211> LENGTH: 401
<212> TYPE: DNA
<213> ORGANISM: Homo sapiens

<400> SEQUENCE: 182

```
atattcttgc tgcttatgca gctgacattg ttgccctccc taaagcaacc aagtagcctt    60
tatttcccac agtgaaagaa aacgctggcc tatcagttac attacaaaag gcagatttca   120
agaggattga gtaagtagtt ggatggcttt cataaaaaca agaattcaag aagaggattc   180
atgctttaag aaacatttgt tatacattcc tcacaaatta tacctgggat aaaaactatg   240
tagcaggcag tgtgttttcc ttccatgtct ctctgcacta cctgcagtgt gtcctctgag   300
gctgcaagtc tgtcctatct gaattcccag cagaagcact aagaagctcc accctatcac   360
ctagcagata aaactatggg gaaaacttaa atctgtgcat a                      401
```

<210> SEQ ID NO 183
<211> LENGTH: 366
<212> TYPE: DNA
<213> ORGANISM: Homo sapiens
<220> FEATURE:
<221> NAME/KEY: misc_feature
<222> LOCATION: (1)...(366)
<223> OTHER INFORMATION: n=A,T,C or G

<400> SEQUENCE: 183

```
accgtgtcca agtttttaga acccttgtta gccagaccga ggtgtcctgg tcaccgtttc    60
accatcatgc tttgatgttc ccctgtcttt ctctcttctg ctctcaagag caaaggttaa   120
tttaaggaca aagatgaagt cactgtaaac taatctgtca ttgttttttac cttccttttc   180 tttttcagtg cagaaattaa aagtaagtat aaagcaccgt gattgggagt gttttttgcgt   240 gtgtcggaat cactggtaaa tgttggctga aacaatccc tccccttgca cttgtgaaaa    300
cactttgagc gctttaagag attanccctga gaataatta aatatctttt ctcttcaaaa   360
aaaaaa                                                                366

<210> SEQ ID NO 184
<211> LENGTH: 370
<212> TYPE: DNA
<213> ORGANISM: Homo sapiens

<400> SEQUENCE: 184
tcttacttca aagaaaaat aaacataaaa aataagttgc tggttcctaa caggaaaaat      60
tttaataatt gtactgagag aaactgctta cgtacacatt gcagatcaaa tatttggagt   120
taaaatgtta gtctacatag atgggtgatt gtaactttat tgccattaaa agatttcaaa   180
ttgcattcat gcttctgtgt acacataatg aaaaatgggc aaataatgaa gatctctcct   240
tcagtctgct ctgtttaatt ctgctgtctg ctcttctcta atgctgcgtc cctaattgta    300
cacagtttag tgatatctag gagtataaag ttgtcgccca tcaataaaaa tcacaaagtt   360
ggtttaaaaa                                                            370

<210> SEQ ID NO 185
<211> LENGTH: 107
<212> TYPE: DNA
<213> ORGANISM: Homo sapiens

<400> SEQUENCE: 185
ctcatattat tttcctttg agaaattgga aactctttct gttgctatta tattaataaa      60
gttggtgttt attttctggt agtcaccttc cccatttaaa aaaaaaa                  107

<210> SEQ ID NO 186
<211> LENGTH: 309
<212> TYPE: DNA
<213> ORGANISM: Homo sapiens

<400> SEQUENCE: 186
gaaaggatgg ctctggttgc cacagagctg ggacttcatg ttcttctaga gaggggccaca    60 agagggccac aggggtggcc gggagttgtc agctgatgcc tgctgagagg caggaattgt   120
gccagtgagt gacagtcatg agggagtgtc tcttcttggg gaggaaagaa ggtagagcct   180
ttctgtctga atgaaaggcc aaggctacag tacagggccc cgcccagcc aggtgtgttaa     240 tgcccacgta gtggaggcct ctggcagatc ctgcattcca aggtcactgg actgtacgtt   300
tttatggtt                                                            309

<210> SEQ ID NO 187
<211> LENGTH: 477
<212> TYPE: DNA
<213> ORGANISM: Homo sapiens

<400> SEQUENCE: 187
ttcagtccta gcaagaagcg agaattctga gatcctccag aaagtcgagc agcacccacc     60
```

-continued

| | |
|---|---|
| tccaacctcg ggccagtgtc ttcaggcttt actggggacc tgcgagctgg cctaatgtgg | 120 |
| tggcctgcaa gccaggccat ccctgggcgc cacagacgag ctccgagcca ggtcaggctt | 180 |
| cggaggccac aagctcagcc tcaggcccag gcactgattg tggcagaggg gccactaccc | 240 |
| aaggtctagc taggcccaag acctagttac ccagacagtg agaagcccct ggaaggcaga | 300 |
| aaagttggga gcatggcaga cagggaaggg aaacattttc agggaaaaga catgtatcac | 360 |
| atgtcttcag aagcaagtca ggtttcatgt aaccgagtgt cctcttgcgt gtccaaaagt | 420 |
| agcccagggc tgtagcacag gcttcacagt gattttgtgt tcagccgtga gtcacac | 477 |

<210> SEQ ID NO 188
<211> LENGTH: 220
<212> TYPE: DNA
<213> ORGANISM: Homo sapiens

<400> SEQUENCE: 188

| | |
|---|---|
| taaatatggt agatattaat attcctctta gatgaccagt gattccaatt gtcccaagtt | 60 |
| ttaaataagt accctgtgag tatgagataa attagtgaca atcagaacaa gtttcagtat | 120 |
| cagatgttca agaggaagtt gctattgcat tgatttttaat atttgtacat aaacactgat | 180 |
| ttttttgagc attattttgt atttgttgta ctttaatacc | 220 |

<210> SEQ ID NO 189
<211> LENGTH: 417
<212> TYPE: DNA
<213> ORGANISM: Homo sapiens
<220> FEATURE:
<221> NAME/KEY: misc_feature
<222> LOCATION: (1)...(417)
<223> OTHER INFORMATION: n=A,T,C or G

<400> SEQUENCE: 189

| | |
|---|---|
| accatcttga cagaggatac atgctcccaa aacgtttgtt accacactta aaaatcactg | 60 |
| ccatcattaa gcatcnnttt caaaattata gccattcatg atttactttt tccagatgac | 120 |
| tatcattatt ctagtccttt gaatttgtaa ggggaaaaaa aacaaaaaca aaaacttacg | 180 |
| atgcactttt ctccagcaca tcagatttca aattgaaaat taaagacatg ctatggtaat | 240 |
| gcacttgcta gtactacaca ctttgtacaa caaaaaacag aggcaagaaa caacggaaag | 300 |
| agaaaagcct tcctttgttg gcccttaaac tgagtcaaga tctgaaatgt agagatgatc | 360 |
| tctgacgata cctgtatgtt cttattgtgt aaataaaatt gctggtatga aatgaca | 417 |

<210> SEQ ID NO 190
<211> LENGTH: 497
<212> TYPE: DNA
<213> ORGANISM: Homo sapiens

<400> SEQUENCE: 190

| | |
|---|---|
| gcactgcggc gctctcccgt cccgcggtgg ttgctgctgc tgccgctgct gctgggcctg | 60 |
| aacgcaggag ctgtcattga ctggcccaca gaggagggca aggaagtatg ggattatgtg | 120 |
| acggtccgca aggatgccta catgttctgg tggctctatt atgccaccaa ctcctgcaag | 180 |
| aacttctcag aactgcccct ggtcatgtgg cttcagggcg gtccaggcgg ttctagcact | 240 |
| ggatttggaa actttgagga aattgggccc cttgacagtg atctcaaacc acggaaaacc | 300 |
| acctggctcc aggctgccag tctcctattt gtggataatc ccgtgggcac tgggttcagt | 360 |
| tatgtgaatg gtagtggtgc ctatgccaag gacctggcta tggtggcttc agacatgatg | 420 |
| gttctcctga agaccttctt cagttgccac aaagaattcc agacagttcc attctacatt | 480 |

```
ttctcagagt cctatgg                                                      497

<210> SEQ ID NO 191
<211> LENGTH: 175
<212> TYPE: DNA
<213> ORGANISM: Homo sapiens

<400> SEQUENCE: 191
atgttgaata ttttgcttat taactttgtt tattgtcttc tccctcgatt agaatattag        60
ctacttgagt acaaggattt gagcctgtta cattcactgc tgaattttag gctcctggaa      120
gatacccagc attcaataga gaccacacaa taaatatatg tcaaataaaa aaaaa           175

<210> SEQ ID NO 192
<211> LENGTH: 526
<212> TYPE: DNA
<213> ORGANISM: Homo sapiens

<400> SEQUENCE: 192
agtaaacatt attatttttt ttatatttgc aaaggaaaca tatctaatcc ttcctataga        60
aagaacagta ttgctgtaat tccttttctt ttcttcctca tttcctctgc cccttaaaag      120
attgaagaaa gagaaacttg tcaactcata tccacgttat ctagcaaagt acataagaat      180
ctatcactaa gtaatgtatc cttcagaatg tgttggttta ccagtgacac cccatattca      240
tcacaaaatt aaagcaagaa gtccatagta atttatttgc taatagtgga tttttaatgc      300
tcagagtttc tgaggtcaaa ttttatcttt tcacttacaa gctctatgat cttaaataat      360
ttacttaatg tattttggtg tatttttcctc aaattaaat tggtgttcaa gactatatct      420
aattcctctg atcactttga gaaacaaact tttattaaat gtaaggcact tttctatgaa      480
ttttaaatat aaaaataaat attgttctga ttattactga aaaaaa                     526

<210> SEQ ID NO 193
<211> LENGTH: 553
<212> TYPE: DNA
<213> ORGANISM: Homo sapiens
<220> FEATURE:
<221> NAME/KEY: misc_feature
<222> LOCATION: (1)...(553)
<223> OTHER INFORMATION: n=A,T,C or G

<400> SEQUENCE: 193
tccattgtgg tggaattcgc tctctggtaa aggcgtgcag gtgttggccg cggcctctga        60
gctgggatga gccgtgctcc cggtggaagc aagggagccc agccggagcc atggccagta      120
cagtggtagc agttggactg accattgctg ctgcaggatt tgcaggccgt tacgttttgc      180
aagccatgaa gcatatggag cctcaagtaa aacagttttt tcaaagccta ccaaaatctg      240
ccttcagtgg tggctattat agaggtgggt ttgaacccaa aatgacaaan cgggaagcan      300
cattaatact aggtgtaagc cctactgcca ataagggaa ataagagat gctcatcgac        360 gaattatgct tttaaatcat cctgacaaag gaggatctcc ttatatagca nccaaaatca      420
atgaagctaa agatttacta naaggtcaag ctaaaaaatg aagtaaatgt atgatgaatt      480
ttaagttcgt attagtttat gtatatgagt actaagtttt tataataaaa tgcctcagag      540
ctacaatttt aaa                                                        553

<210> SEQ ID NO 194
<211> LENGTH: 320
<212> TYPE: DNA
```

<213> ORGANISM: Homo sapiens

<400> SEQUENCE: 194

```
cccttcccaa tccatcagta aagacccat  ctgccttgtc catgccgttt cccaacaggg    60
atgtcacttg atatgagaat ctcaaatctc aatgccttat aagcattcct tcctgtgtcc   120
attaagactc tgataattgt ctcccctcca taggaatttc tcccaggaaa gaaatatatc   180
cccatctccg tttcatatca gaactaccgt ccccgatatt cccttcagag agattaaaga   240
ccagaaaaaa gtgagcctct tcatctgcac ctgtaatagt ttcagttcct attttcttcc   300
attgacccat atttatacct                                               320
```

<210> SEQ ID NO 195
<211> LENGTH: 320
<212> TYPE: DNA
<213> ORGANISM: Homo sapiens
<220> FEATURE:
<221> NAME/KEY: misc_feature
<222> LOCATION: (1)...(320)
<223> OTHER INFORMATION: n=A,T,C or G

<400> SEQUENCE: 195

```
aagcatgacc tggggaaatg gtcagacctt gtattgtgtt tttggccttg aaagtagcaa    60
gtgaccagaa tctgccatgg caacaggctt taaaaaagac ccttaaaaag acactgtctc   120
aactgtggtg ttagcaccag ccagctctct gtacatttgc tagcttgtag ttttctaaga   180
ctgagtaaac ttcttatttt tanaaagggg aggctggntt gtaactttcc ttgtacttaa   240
ttgggtaaaa gtcttttcca caaaccacca tctattttgt gaactttgtt agtcatcttt   300
tatttggtaa attatgaact                                               320
```

<210> SEQ ID NO 196
<211> LENGTH: 357
<212> TYPE: DNA
<213> ORGANISM: Homo sapiens
<220> FEATURE:
<221> NAME/KEY: misc_feature
<222> LOCATION: (1)...(357)
<223> OTHER INFORMATION: n=A,T,C or G

<400> SEQUENCE: 196

```
atataaaata atacgaaact ttaaaaagca ttggantgtc agtatgttga atcagtagtt    60
tcactttaac tgtaaacaat ttcttaggac accatttggg ctagtttctg tgtaagtgta   120
aatactacaa aaacttattt atactgttct tatgtcattt gttatattca tagatttata   180
tgatgatatg acatctggct aaaaagaaat tattgcaaaa ctaaccacta tgtactttt   240
tataaatact gtatggacaa aaaatggcat tttttatatt aaattgttta gctctggcaa   300
aaaaaaaaaa ttttaagagc tggtactaat aaaggattat tatgactgtt aaaaaaa     357
```

<210> SEQ ID NO 197
<211> LENGTH: 565
<212> TYPE: DNA
<213> ORGANISM: Homo sapiens
<220> FEATURE:
<221> NAME/KEY: misc_feature
<222> LOCATION: (1)...(565)
<223> OTHER INFORMATION: n=A,T,C or G

<400> SEQUENCE: 197

```
tcagctgagt accatcagga tatttanccc tttaagtgct gttttgggag tagaaaacta    60
aagcaacaat acttcctctt gacagctttg attggaatgg ggttattaga tcattcacct   120
```

```
tggtcctaca cttttttagga tgcttggtga acataacacc acttataatg aacatccctg      180
gttcctatat tttgggctat gtgggtagga attgttactt gttactgcag cagcagccct      240
agaaagtaag cccagggctt cagatctaag ttagtccaaa agctaaatga tttaaagtca      300
agttgtaatg ctaggcataa gcactctata atacattaaa ttataggccg agcaattagg      360
gaatgtttct gaaacattaa acttgtattt atgtcactaa aattctaaca caaacttaaa      420
aaatgtgtct catacatatg ctgtactagg cttcatcatg catttctaaa tttgtgtatg      480
atttgaatat atgaaagaat ttatacaaga gtgttattta aaattattaa aaataaatgt      540
atataatttg tacctattgt aaaaa                                              565
```

<210> SEQ ID NO 198
<211> LENGTH: 484
<212> TYPE: DNA
<213> ORGANISM: Homo sapiens

<400> SEQUENCE: 198

```
tatgtaagta ttggtgtctg cttttaaaaaa ggagacccag acttcacctg tccttttttaa     60 acatttgaga acagtgttac tctgagcagt tgggccacct tcaccttatc cgacagctga     120
ctgttggatg tgtccattgt cgccagtttg gctgttgccc ggacaggaca ggacctccat     180
tgggcgcagc agcaggtggc aggggtgtgg cttgaggtgg gtggcagcgt ctggtcctcc     240
tctctggtgc tttctgagag ggtctctaaa gcagagtgtg gttggcctgg gggaaggcag     300
agcacgtatt tctcccctct agtacctctg catttgtgag tgttccctct ggctttctga     360
agggcagcag actcttgagt atactgcaga ggacatgctt tatcagtagg tcctgagggc     420
tccaggggct caactgacca gtaacacag aagttggggt atgtggccta tttgggtcgg     480
aaac                                                                    484
```

<210> SEQ ID NO 199
<211> LENGTH: 429
<212> TYPE: DNA
<213> ORGANISM: Homo sapiens
<220> FEATURE:
<221> NAME/KEY: misc_feature
<222> LOCATION: (1)...(429)
<223> OTHER INFORMATION: n=A,T,C or G

<400> SEQUENCE: 199

```
gcttatgttt tttgttttaa cttttgtttt ttaacattta gaatattaca ttttgtatta     60
tacagtacct ttctcanaca ttttgtanaa ttcatttcgg cagctcacta ggattttgct     120
gaacattaaa aagngtgata gcgatattag ngccaatcaa atggaaaaaa ggtagtctta     180
ataaacaana cacaacgttt ttatacaaca tactttaaaa tattaanaaa actccttaat     240
attgtttcct attaagtatt attctttggg caanattttc tgatgctttt gattttctct     300
caatttagca tttgctttng gttttttttct ctatttagca ttctgttaag gcacaaaaac     360
tatgtactgt atgggaaatg ttgtaaatat taccttttcc acattttaaa cagacaactt     420
tgaatccaa                                                               429
```

<210> SEQ ID NO 200
<211> LENGTH: 279
<212> TYPE: DNA
<213> ORGANISM: Homo sapiens

<400> SEQUENCE: 200

-continued

```
gcttttttga ggaattacag ggaagctcct ggaattgtac atggatatct ttatccctag      60
ggggaaatca aggagctggg caccactaat tctttatgga agtgttaaa actatttaa       120 ttttattaca agtattacta gagtagtggt tctactctaa gatttcaaaa gtgcatttaa    180
aatcatacat gttcccgcct gcaaatatat tgttattttg gtggagaaaa aatagtata     240 ttctacataa aaaattaaag atattaacta agaaaaaaa                            279
```

<210> SEQ ID NO 201
<211> LENGTH: 569
<212> TYPE: DNA
<213> ORGANISM: Homo sapiens

<400> SEQUENCE: 201

```
taggtcagta ttttagaaa ctcttaatag ctcatactct tgataccaaa agcagccctg      60
attgttaaag cacacacctg cacaagaagc agtgatggtt gcatttacat ttcctgggtg    120
cacaaaaaaa aattctcaaa aagcaaggac ttacgctttt tgcaaagcct ttgagaagtt    180
actggatcat aggaagctta taacaagaat ggaagattct taaataactc actttctttg    240
gtatccagta acagtagatg ttcaaaatat gtagctgatt aataccagca ttgtgaacgc    300
tgtacaacct tgtggttatt actaagcaag ttactactag cttctgaaaa gtagcttcat    360
aattaatgtt atttatacac tgccttccat gactttact ttgccctaag ctaatctcca    420
aaatctgaaa tgctactcca atatcagaaa aaaggggga ggtggaatta tatttcctgt    480
gattttaaga gtacagagaa tcatgcacat ctctgattag ttcatatatg tctagtgtgt    540
aataaaagtc aaagatgaac tctcaaaaa                                       569
```

<210> SEQ ID NO 202
<211> LENGTH: 501
<212> TYPE: DNA
<213> ORGANISM: Homo sapiens

<400> SEQUENCE: 202

```
attaataggc ttaataattg ttggcaagga tccttttgct ttctttggca tgcaagctcc      60
tagcatctgg cagtggggcc aagaaaataa ggtttatgca tgtatgatgg ttttcttctt    120
gagcaacatg attgagaacc agtgtatgtc aacaggtgca tttgagataa ctttaaatga    180
tgtacctgtg tggtctaagc tggaatctgg tcaccttcca tccatgcaac aacttgttca    240
aattcttgac aatgaaatga agctcaatgt gcatatggat tcaatcccac accatcgatc    300
atagcaccac ctatcagcac tgaaaactct tttgcattaa gggatcattg caagagcagc    360
gtgactgaca ttatgaaggc ctgtactgaa gacagcaagc tgttagtaca gaccagatgc    420
tttcttggca ggctcgttgt acctcttgga aaacctcaat gcaagatagt gtttcagtgc    480
tggcatattt tggaattctg c                                              501
```

<210> SEQ ID NO 203
<211> LENGTH: 261
<212> TYPE: DNA
<213> ORGANISM: Homo sapiens
<220> FEATURE:
<221> NAME/KEY: misc_feature
<222> LOCATION: (1)...(261)
<223> OTHER INFORMATION: n=A,T,C or G

<400> SEQUENCE: 203

```
gacaagctcc tggtcttgag atgtcttctc gttaangaga tgggccttttt ggaggtaaag      60 gataaaatga atgagttctg tcatgattca ctattntata acttgcatga cctttactgt    120
```

```
gttagctctt tgaatgttct tgaaatttta gactttcttt gtaaacaaat gatatgtcct      180
tatcattgta taaaagctgt tatgtgcaac agtgtggaga ttccttgtct gatttaataa      240
aatacttaaa cactgaaaaa a                                                261
```

<210> SEQ ID NO 204
<211> LENGTH: 421
<212> TYPE: DNA
<213> ORGANISM: Homo sapiens

<400> SEQUENCE: 204

```
agcatctttt ctacaacgtt aaaattgcag aagtagctta tcattaaaaa acaacaacaa       60
caacaataac aataaatcct aagtgtaaat cagttattct accccctacc aaggatatca      120
gcctgttttt tcccttttt ctcctgggaa taattgtggg cttcttccca aatttctaca      180
gcctctttcc tcttctcatg cttgagcttc cctgtttgca cgcatgcgtg tgcaggactg      240
gcttgtgtgc ttggactcgg ctccaggtgg aagcatgctt tcccttgtta ctgttggaga      300
aactcaaacc ttcaagccct aggtgtagcc attttgtcaa gtcatcaact gtattttgt       360 actggcatta acaaaaaaag aagataaaat attgtaccat taaactttaa taaaacttta      420
a                                                                      421
```

<210> SEQ ID NO 205
<211> LENGTH: 460
<212> TYPE: DNA
<213> ORGANISM: Homo sapiens

<400> SEQUENCE: 205

```
tactctcaca atgaaggacc tggaatgaaa atctgtgtc taaacaagtc ctctttagat       60
tttagtgcaa atccagagcc agcgtcggtt gcctcgagta attctttcat gggtaccttt      120
ggaaaagctc tcaggagacc tcacctagat gcctattcaa gctttggaca gccatcagat      180
tgtcagccaa gagccttta tttgaaagct cattcttccc cagacttgga ctctgggtca      240
gaggaagatg ggaaagaaag gacagatttt caggaagaaa atcacatttg tacctttaaa      300
cagactttag aaaactacag gactccaaat tttcagtctt atgacttgga cacatagact      360
gaatgagacc aaaggaaaag cttaacatac tacctcaagg tgaactttta tttaaaagag      420
agagaatctt atgttttta aatggagtta tgaatttaa                              460
```

<210> SEQ ID NO 206
<211> LENGTH: 481
<212> TYPE: DNA
<213> ORGANISM: Homo sapiens

<400> SEQUENCE: 206

```
tgtggtggaa ttcgggacgc ccccagaccc tgacttttc ctgcgtgggc cgtctcctcc       60
tgcggaagca gtgacctctg accctggtg accttcgctt tgagtgcctt ttgaacgctg      120
gtcccgcggg acttggtttt tcaagctct gtctgtccaa agacgctccg gtcgaggtcc      180
cgcctgccct gggtggatac ttgaacccca gacgcccctc tgtgctgctg tgtccggagg      240
cggccttccc atctgcctgc ccaccccgag ctctttccgc cggcgcaggg tcccaagccc      300
acctcccgcc ctcagtcctg cggtgtgcgt ctgggcacgt cctgcacaca caatgcaagt      360
cctggcctcc gcgcccgccc gcccacgcga gccgtacccg ccgccaactc tgttatttat      420
ggtgtgaccc cctggaggtg ccctcggccc accggggcta tttattgttt aatttatttg      480
``` t 481

<210> SEQ ID NO 207
<211> LENGTH: 605
<212> TYPE: DNA
<213> ORGANISM: Homo sapiens

<400> SEQUENCE: 207

| acccttttg | gattcagggc | tcctcacaat | taaaatgagt | gtaatgaaac | aaggtgaaaa | 60 |
| tatagaagca | tcccttttgta | tactgttttg | ctacttacag | tgtacttggc | attgctttat | 120 |
| ctcactggat | tctcacggta | ggatttctga | gatcttaatc | taagctccaa | agttgtctac | 180 |
| ttttttgatc | ctagggtgct | ccttttgttt | tacagagcag | ggtcacttga | tttgctagct | 240 |
| ggtggcagaa | ttggcaccat | tacccaggtc | tgactgacca | ccagtcagag | gcactttatt | 300 |
| tgtatcatga | aatgatttga | aatcattgta | agcagcgaa | gtctgataat | gaatgccagc | 360 |
| tttccttgtg | ctttgataac | aaagactcca | aatattctgg | agaacctgga | taaaagtttg | 420 |
| aagggctaga | ttgggatttg | aagacaaaat | tgtaggaaat | cttacatttt | tgcaataaca | 480 |
| aacattaatg | aaagcaaaac | attataaaag | taattttaat | tcaccacata | cttatcaatt | 540 |
| tcttgatgct | tccaaatgac | atctaccaga | tatggttttg | tggacatctt | tttctgttta | 600 |
| cataa | | | | | | 605 |

<210> SEQ ID NO 208
<211> LENGTH: 655
<212> TYPE: DNA
<213> ORGANISM: Homo sapiens

<400> SEQUENCE: 208

| ggcgttgttc | tggattcccg | tcgtaactta | aagggaaact | ttcacaatgt | ccggagccct | 60 |
| tgatgtcctg | caaatgaagg | aggaggatgt | ccttaagttc | cttgcagcag | gaacccactt | 120 |
| agtggcacc | aatcttgact | tccagatgga | acagtacatc | tataaaagga | aaagtgatgg | 180 |
| catctatatc | ataaatctca | agaggacctg | ggagaagctt | ctgctggcag | ctcgtgcaat | 240 |
| tgttgccatt | gaaaaccctg | ctgatgtcag | tgttatatcc | tccaggaata | ctggccagag | 300 |
| ggctgtgctg | aagtttgctg | ctgccactgg | agccactcca | attgctggcc | gcttcactcc | 360 |
| tggaaccttc | actaaccaga | tccaggcagc | cttccgggag | ccacggcttc | ttgtggttac | 420 |
| tgaccccagg | gctgaccacc | agcctctcac | ggaggcatct | tatgttaacc | tacctaccat | 480 |
| tgcgctgtgt | aacacagatt | ctcctctgcg | ctatgtggac | attgccatcc | catgcaacaa | 540 |
| caagggagct | cactcagtgg | gtttgatgtg | gtggatgctg | gctcgggaag | ttctgcgcat | 600 |
| gcgtggcacc | atttcccgtg | aacacccatg | ggaggtcatg | cctgatctgt | acttc | 655 |

<210> SEQ ID NO 209
<211> LENGTH: 621
<212> TYPE: DNA
<213> ORGANISM: Homo sapiens

<400> SEQUENCE: 209

| catttagaac | atggttatca | tccaagacta | ctctaccctg | caacattgaa | ctcccaagag | 60 |
| caaatccaca | ttcctcttga | gttctgcagc | ttctgtgtaa | atagggcagc | tgtcgtctat | 120 |
| gccgtagaat | cacatgatct | gaggaccatt | catggaagct | gctaaatagc | ctagtctggg | 180 |
| gagtcttcca | taaagttttg | catggagcaa | acaaacagga | ttaaactagg | tttggttcct | 240 |

| | | |
|---|---|---|
| tcagccctct aaaagcatag ggcttagcct gcaggcttcc ttgggctttc tctgtgtgtg | 300 | |
| tagttttgta aacactatag catctgttaa gatccagtgt ccatggaaac cttcccacat | 360 | |
| gccgtgactc tggactatat cagttttggg aaagcagggt tcctctgcct gctaacaagc | 420 | |
| ccacgtggac cagtctgaat gtctttcctt tacacctatg tttttaaata gtcaaacttc | 480 | |
| aagaaacaat ctaaacaagt ttctgttgca tatgtgtttg tgaacttgta tttgtattta | 540 | |
| gtaggcttct atattgcatt taacttgttt ttgtaactcc tgattcttcc ttttcggata | 600 | |
| ctattgatga ataaagaaat t | 621 | |

<210> SEQ ID NO 210
<211> LENGTH: 533
<212> TYPE: DNA
<213> ORGANISM: Homo sapiens
<220> FEATURE:
<221> NAME/KEY: misc_feature
<222> LOCATION: (1)...(533)
<223> OTHER INFORMATION: n=A,T,C or G

<400> SEQUENCE: 210

| | | |
|---|---|---|
| cgccttgggg agccggcggn ngagtccggg acgtggagac ccggggtccc ggcagccggg | 60 | |
| nggcccgcgg gcccagggtg gggatgcacc gccgcggggt gggagctggc gccatcgcca | 120 | |
| agaagaaact tgcagaggcc aagtataagg agcgaggac ggtcttggct gaggaccagc | 180 | |
| tagcccagat gtcaaagcag ttggacatgt tcaagaccaa cctggaggaa tttgccagca | 240 | |
| aacacaagca ggagatccgg aagaatcctg agttccgtgt gcagttccag gacatgtgtg | 300 | |
| caaccattgg cgtggatccg ctggcctctg gaaaaggatt ttggtctgag atgctgggcg | 360 | |
| tgggggactt ctattacgaa ctaggtgtcc aaattatcga agtgtgcctg gcgctgaagc | 420 | |
| atcggaatgg aggtctgata actttggagg aactacatca acaggtgttg aagggaaggg | 480 | |
| gcaagttcgc ccaggatgtc agtcaagatg acctgatcag agccatcaag aaa | 533 | |

<210> SEQ ID NO 211
<211> LENGTH: 451
<212> TYPE: DNA
<213> ORGANISM: Homo sapiens

<400> SEQUENCE: 211

| | | |
|---|---|---|
| ttagcttgag ccgagaacga ggcgagaaag ctggagaccg aggagaccgc ctagagcgga | 60 | |
| gtgaacgggg aggggaccgt ggggaccggc ttgatcgtgc gcggacacct gctaccaagc | 120 | |
| ggagcttcag caaggaagtg gaggagcgga gtagagaacg gccctcccag cctgaggggc | 180 | |
| tgcgcaaggc agctagcctc acggaggatc gggaccgtgg gcgggatgcc gtgaagcgag | 240 | |
| aagctgccct accccagtg agccccctga aggcggctct ctctgaggag gagttagaga | 300 | |
| agaaatccaa ggctatcatt gaggaatatc tccatctcaa tgacatgaaa gaggcagtcc | 360 | |
| agtgcgtgca ggagctggcc tcaccctcct tgctcttcat ctttgtacgg catggtgtcg | 420 | |
| agtctacgct ggagcgcagt gccattgctc g | 451 | |

<210> SEQ ID NO 212
<211> LENGTH: 471
<212> TYPE: DNA
<213> ORGANISM: Homo sapiens
<220> FEATURE:
<221> NAME/KEY: misc_feature
<222> LOCATION: (1)...(471)
<223> OTHER INFORMATION: n=A,T,C or G

<400> SEQUENCE: 212

```
gtgattattc ttgatcaggg agaagatcat ttagatttgt tttgcattcc ttanaatgga      60
gggcaacatt ccacagctgc cctggctgtg atgagtgtcc ttgcaggggc cggagtagga     120
gcactggggt gggggcggaa ttggggttac tcgatgtaag ggattccttg ttgttgtgtt     180
gagatccagt gcagttgtga tttctgtgga tcccagcttg gttccaggaa ttttgtgtga     240
ttggcttaaa tccagttttc aatcttcgac agctgggctg gaacgtgaac tcagtagctg     300
aacctgtctg acccggtcac gttcttggat cctcagaact ctttgctctt gtcggggtgg     360
gggtgggaac tcacgtgggg agcggtggct gagaaaatgt aaggattctg gaatacatat     420
tccatgggac tttccttccc tctcctgctt cctcttttcc tgctccctaa c             471
```

<210> SEQ ID NO 213
<211> LENGTH: 511
<212> TYPE: DNA
<213> ORGANISM: Homo sapiens
<220> FEATURE:
<221> NAME/KEY: misc_feature
<222> LOCATION: (1)...(511)
<223> OTHER INFORMATION: n=A,T,C or G

<400> SEQUENCE: 213

```
ctaattagaa acttgctgta ctttttnttt tcttttaggg gtcaaggacc ctctttatag      60
ctnccatttg cctacaataa attattgcag cagtttgcaa tactaaaata tttttttatag    120 actttatatt tttccttttg ataaagggat gctgcatagt agagttggtg taattaaact     180
atctcagccg tttccctgct ttccttctg ctccatatgc ctcattgtcc ttccagggag      240
ctcttttaat cttaaagttc tacatttcat gctcttagtc aaattctgtt acctttttaa     300
taactcttcc cactgcatat ttccatcttg aattggnggt tctaaattct gaaactgtag     360
ttgagataca gctatttaat atttctggga gatgtgcatc cctcttcttt gtggttgccc     420
aaggttgttt tgcgtaactg anactccttg atatgcttca gagaatttag gcaaacactg     480
gccatggccg tgggagtact gggagtaaaa t                                    511
```

<210> SEQ ID NO 214
<211> LENGTH: 521
<212> TYPE: DNA
<213> ORGANISM: Homo sapiens

<400> SEQUENCE: 214

```
agcattgcca aataatccct aatttccac taaaaatata atgaaatgat gttaagcttt       60
ttgaaaagtt taggttaaac ctactgttgt tagattaatg tatttgttgc ttcccttttat    120 ctggaatgtg gcattagctt tttattttta accctcttta attcttattc aattccatga    180
cttaaggttg gagagctaaa cactgggatt tttggataac agactgacag ttttgcataa    240
ttataatcgg cattgtacat agaaaggata tggctaccttt tgttaaatc tgcactttct    300 aaatatcaaa aaagggaaat gaagtataaa tcaattttg tataatctgt ttgaaacatg    360
agttttattt gcttaatatt agggctttgc cccttttctg taagtctctt gggatcctgt    420
gtagaagctg ttctcattaa acaccaaaca gttaagtcca ttctctggta ctagctacaa    480
attcggtttc atattctact taacaattta aataaactga a                        521
```

<210> SEQ ID NO 215
<211> LENGTH: 381
<212> TYPE: DNA
<213> ORGANISM: Homo sapiens
<220> FEATURE:

<221> NAME/KEY: misc_feature
<222> LOCATION: (1)...(381)
<223> OTHER INFORMATION: n=A,T,C or G

<400> SEQUENCE: 215

| | |
|---|---|
| gagcggagag cggaccngtn agagccctga gcagccccac cgccgccgcc ggcctagttn | 60 |
| ncatcacacc ccgggaggag ccgcagctgc cgcagccggc cccagtcacc atcaccgcaa | 120 |
| ccatgagcag cgaggccgag acccagcagc cgcccgccgc cccccccgcc gccccgccc | 180 |
| tcagcgccgc cgacaccaag cccggcacta cgggcagcgg cgcagggagc ggtggcccgg | 240 |
| gcggcctcac atcggcggcg cctgccggcg gggacaagaa ggtcatcgca acgaaggttt | 300 |
| tgggaacagt aaaatggttc aatgtaagga acggatatgg tttcatcaac aggaatgaca | 360 |
| ccaangaaga tgtatttgta c | 381 |

<210> SEQ ID NO 216
<211> LENGTH: 425
<212> TYPE: DNA
<213> ORGANISM: Homo sapiens

<400> SEQUENCE: 216

| | |
|---|---|
| ttactaacta ggtcattcaa ggaagtcaag ttaacttaaa catgtcacct aaatgcactt | 60 |
| gatggtgttg aaatgtccac cttcttaaat ttttaagatg aacttagttc taagaagat | 120 |
| aacaggccaa tcctgaaggt actccctgtt tgctgcagaa tgtcagatat tttggatgtt | 180 |
| gcataagagt cctatttgcc ccagttaatt caacttttgt ctgcctgttt tgtggactgg | 240 |
| ctggctctgt tagaactctg tccaaaaagt gcatggaata taacttgtaa agcttcccac | 300 |
| aattgacaat atatatgcat gtgtttaaac caaatccaga aagcttaaac aatagagctg | 360 |
| cataatagta tttattaaag aatcacaact gtaaacatga gaataactta aggattctag | 420 |
| tttag | 425 |

<210> SEQ ID NO 217
<211> LENGTH: 181
<212> TYPE: DNA
<213> ORGANISM: Homo sapiens

<400> SEQUENCE: 217

| | |
|---|---|
| gagaaaccaa atgataggtt gtagagcctg atgactccaa acaaagccat cacccgcatt | 60 |
| cttcctcctt cttctggtgc tacagctcca agggcccttc accttcatgt ctgaaatgga | 120 |
| actttggctt tttcagtgga agaatatgtt gaaggtttca ttttgttcta gaaaaaaaaa | 180 |
| a | 181 |

<210> SEQ ID NO 218
<211> LENGTH: 405
<212> TYPE: DNA
<213> ORGANISM: Homo sapiens

<400> SEQUENCE: 218

| | |
|---|---|
| caggccttcc agttcactga caaacatggg gaagtgtgcc cagctggctg gaaacctggc | 60 |
| agtgatacca tcaagcctga tgtccaaaag agcaaagaat atttctccaa gcagaagtga | 120 |
| gcgctgggct gttttagtgc caggctgcgg tgggcagcca tgagaacaaa acctcttctg | 180 |
| tattttttt ttccattagt aaaacacaag acttcagatt cagccgaatt gtggtgtctt | 240 |
| acaaggcagg cctttcctac aggggtgga gagaccagcc tttcttcctt tggtaggaat | 300 |
| ggcctgagtt ggcgttgtgg gcaggctact ggtttgtatg atgtattagt agagcaaccc | 360 |

```
attaatctttt tgtagtttgt attaaacttg aactgagaaa aaaaa              405

<210> SEQ ID NO 219
<211> LENGTH: 216
<212> TYPE: DNA
<213> ORGANISM: Homo sapiens
<220> FEATURE:
<221> NAME/KEY: misc_feature
<222> LOCATION: (1)...(216)
<223> OTHER INFORMATION: n=A,T,C or G

<400> SEQUENCE: 219
actccaagag ttagggcagc agagtggagc gatttagaaa gaacatttta aaacaatcag    60
ttaatttacc atgtaaaatt gctgtaaatg ataatgtgta cagattttct gttcaaatat   120
tcaattgtaa acttcttgtt aagactgtta cgtttctatt gcttttgtat gggatattgc   180
aaaaataaaa aggaaagaac cctcttnaan aaaaaa                             216

<210> SEQ ID NO 220
<211> LENGTH: 380
<212> TYPE: DNA
<213> ORGANISM: Homo sapiens

<400> SEQUENCE: 220
cttacaaatt gcccccatgt gtagggaca cagaacccctt tgagaaaact tagattttg     60 tctgtacaaa gtctttgcct ttttccttct tcatttttt ccagtacatt aaatttgtca   120
atttcatctt tgagggaaac tgattagatg ggttgtgttt gtgttctgat ggagaaaaca   180
gcaccccaag gactcagaag atgattttaa cagttcagaa cagatgtgtg caatattggt   240
gcatgtaata atgttgagtg gcagtcaaaa gtcatgattt ttatcttagt tcttcattac   300
tgcattgaaa aggaaaacct gtctgagaaa atgcctgaca gtttaattta aaactatggt   360
gtaagtcttt gacaaaaaaa                                              380

<210> SEQ ID NO 221
<211> LENGTH: 398
<212> TYPE: DNA
<213> ORGANISM: Homo sapiens

<400> SEQUENCE: 221
ggttagtaag ctgtcgactt tgtaaaaaag ttaaaaatga aaaaaaagg aaaaatgaat     60 tgtatattta atgaatgaac atgtacaatt tgccactggg aggaggttcc ttttttgttgg  120 gtgagtctgc aagtgaattt cactgatgtt gatattcatt gtgtgtagtt ttatttcggt   180
cccagccccg tttccttta ttttggagct aatgccagct gcgtgtctag ttttgagtgc    240
agtaaaatag aatcagcaaa tcactcttat ttttcatcct tttccggtat tttttgggtt   300
gtttctgtgg gagcagtgta caccaactct tcctgtatat tgcctttttg ctggaaaatg   360
ttgtatgttg aataaaattt tctataaaaa ttaaaaaa                          398

<210> SEQ ID NO 222
<211> LENGTH: 301
<212> TYPE: DNA
<213> ORGANISM: Homo sapiens
<220> FEATURE:
<221> NAME/KEY: misc_feature
<222> LOCATION: (1)...(301)
<223> OTHER INFORMATION: n=A,T,C or G

<400> SEQUENCE: 222
```

-continued

```
ttcgataatt gatctcatgg gctttccctg gaggaaaggt ttttttttgnt gtttattttt      60 taanaacttg aaacttgtaa actgagatgt ctgtagcttt tttgcccatc tgtagtgtat     120
gtgaagattt caaaacctga gagcactttt tctttgttta gaattatgag aaaggcacta     180
gatgacttta ggatttgcat ttttccctt attgcctcat ttcttgtgac gccttgttgg      240
ggagggaaat ctgtttattt tttcctacaa ataaaaagct aagattctat atcgcaaaaa     300
a                                                                      301
```

<210> SEQ ID NO 223
<211> LENGTH: 200
<212> TYPE: DNA
<213> ORGANISM: Homo sapiens

<400> SEQUENCE: 223

```
gtaagtgctt aggaagaaac tttgcaaaca tttaatgagg atacactgtt catttttaaa      60
attccttcac actgtaattt aatgtgtttt atattctttt gtagtaaaac aacataactc     120
agatttctac aggagacagt ggttttattt ggattgtctt ctgtaatagg tttcaataaa     180
gctggatgaa cttaaaaaaa                                                  200
```

<210> SEQ ID NO 224
<211> LENGTH: 385
<212> TYPE: DNA
<213> ORGANISM: Homo sapiens

<400> SEQUENCE: 224

```
gaaaggtttg atccggactc aaagaaagca aggagtgtg agccgccatc tgctggagca       60
gctgtaactg caagacctgg acaagagatt cgtcagcgaa ctgcagctca agaaaccttt     120
tctccaacac cagcaagccc taaccagggc cctcctccac aagttccagt atctcctgga     180
ccaccaaagg acagttctgc ccctggtgga cccccagaaa ggactgttac tccagcccta     240
tcatcaaatg tgttaccaag acatcttgga tccctgcta cttcagtgcc tggaatgggt     300
aaacagagca cttaatgtta tttacagttt atattgtttt ctctggttac caataaaacg     360 ggccatttc agtgtaa aaaaa                                                 385
```

<210> SEQ ID NO 225
<211> LENGTH: 560
<212> TYPE: PRT
<213> ORGANISM: Homo sapien

<400> SEQUENCE: 225

```
Met Glu Cys Leu Tyr Tyr Phe Leu Gly Phe Leu Leu Ala Ala Arg
 1               5                  10                  15

Leu Pro Leu Asp Ala Ala Lys Arg Phe His Asp Val Leu Gly Asn Glu
                20                  25                  30

Arg Pro Ser Ala Tyr Met Arg Glu His Asn Gln Leu Asn Gly Trp Ser
            35                  40                  45

Ser Asp Glu Asn Asp Trp Asn Gly Lys Leu Tyr Pro Val Trp Lys Arg
        50                  55                  60

Gly Asp Met Arg Trp Lys Asn Ser Trp Lys Gly Gly Arg Val Gln Ala
    65                  70                  75                  80

Val Leu Thr Ser Asp Ser Pro Ala Leu Val Gly Ser Asn Ile Thr Phe
                85                  90                  95

Ala Val Asn Leu Ile Phe Pro Arg Cys Gln Lys Glu Asp Ala Asn Gly
                100                 105                 110
```

-continued

```
Asn Ile Val Tyr Glu Lys Asn Cys Arg Asn Glu Ala Gly Leu Ser Ala
    115                 120                 125

Asp Pro Tyr Val Tyr Asn Trp Thr Ala Trp Ser Glu Asp Ser Asp Gly
    130                 135                 140

Glu Asn Gly Thr Gly Gln Ser His His Asn Val Phe Pro Asp Gly Lys
145                 150                 155                 160

Pro Phe Pro His His Pro Gly Trp Arg Arg Trp Asn Phe Ile Tyr Val
                165                 170                 175

Phe His Thr Leu Gly Gln Tyr Phe Gln Lys Leu Gly Arg Cys Ser Val
            180                 185                 190

Arg Val Ser Val Asn Thr Ala Asn Val Thr Leu Gly Pro Gln Leu Met
        195                 200                 205

Glu Val Thr Val Tyr Arg Arg His Gly Arg Ala Tyr Val Pro Ile Ala
    210                 215                 220

Gln Val Lys Asp Val Tyr Val Val Thr Asp Gln Ile Pro Val Phe Val
225                 230                 235                 240

Thr Met Phe Gln Lys Asn Asp Arg Asn Ser Ser Asp Glu Thr Phe Leu
                245                 250                 255

Lys Asp Leu Pro Ile Met Phe Asp Val Leu Ile His Asp Pro Ser His
            260                 265                 270

Phe Leu Asn Tyr Ser Thr Ile Asn Tyr Lys Trp Ser Phe Gly Asp Asn
        275                 280                 285

Thr Gly Leu Phe Val Ser Thr Asn His Thr Val Asn His Thr Tyr Val
    290                 295                 300

Leu Asn Gly Thr Phe Ser Leu Asn Leu Thr Val Lys Ala Ala Ala Pro
305                 310                 315                 320

Gly Pro Cys Pro Pro Pro Pro Pro Pro Arg Pro Ser Lys Pro Thr
                325                 330                 335

Pro Ser Leu Gly Pro Ala Gly Asp Asn Pro Leu Glu Leu Ser Arg Ile
            340                 345                 350

Pro Asp Glu Asn Cys Gln Ile Asn Arg Tyr Gly His Phe Gln Ala Thr
        355                 360                 365

Ile Thr Ile Val Glu Gly Ile Leu Glu Val Asn Ile Gln Met Thr
    370                 375                 380

Asp Val Leu Met Pro Val Pro Trp Pro Glu Ser Ser Leu Ile Asp Phe
385                 390                 395                 400

Val Val Thr Cys Gln Gly Ser Ile Pro Thr Glu Val Cys Thr Ile Ile
                405                 410                 415

Ser Asp Pro Thr Cys Glu Ile Thr Gln Asn Thr Val Cys Ser Pro Val
            420                 425                 430

Asp Val Asp Glu Met Cys Leu Leu Thr Val Arg Arg Thr Phe Asn Gly
        435                 440                 445

Ser Gly Thr Tyr Cys Val Asn Leu Thr Leu Gly Asp Asp Thr Ser Leu
    450                 455                 460

Ala Leu Thr Ser Thr Leu Ile Ser Val Pro Asp Arg Asp Pro Ala Ser
465                 470                 475                 480

Pro Leu Arg Met Ala Asn Ser Ala Leu Ile Ser Val Gly Cys Leu Ala
                485                 490                 495

Ile Phe Val Thr Val Ile Ser Leu Leu Val Tyr Lys Lys His Lys Glu
            500                 505                 510

Tyr Asn Pro Ile Glu Asn Ser Pro Gly Asn Val Arg Ser Lys Gly
        515                 520                 525

Leu Ser Val Phe Leu Asn Arg Ala Lys Ala Val Phe Phe Pro Gly Asn
```

```
                530              535              540
Gln Glu Lys Asp Pro Leu Leu Lys Asn Gln Glu Phe Lys Gly Val Ser
545              550              555              560
```

<210> SEQ ID NO 226
<211> LENGTH: 9
<212> TYPE: PRT
<213> ORGANISM: Homo sapien

<400> SEQUENCE: 226

```
Ile Leu Ile Pro Ala Thr Trp Lys Ala
1               5
```

<210> SEQ ID NO 227
<211> LENGTH: 9
<212> TYPE: PRT
<213> ORGANISM: Homo sapien

<400> SEQUENCE: 227

```
Phe Leu Leu Asn Asp Asn Leu Thr Ala
1               5
```

<210> SEQ ID NO 228
<211> LENGTH: 9
<212> TYPE: PRT
<213> ORGANISM: Homo sapien

<400> SEQUENCE: 228

```
Leu Leu Gly Asn Cys Leu Pro Thr Val
1               5
```

<210> SEQ ID NO 229
<211> LENGTH: 10
<212> TYPE: PRT
<213> ORGANISM: Homo sapien

<400> SEQUENCE: 229

```
Lys Leu Leu Gly Asn Cys Leu Pro Thr Val
1               5                   10
```

<210> SEQ ID NO 230
<211> LENGTH: 10
<212> TYPE: PRT
<213> ORGANISM: Homo sapien

<400> SEQUENCE: 230

```
Arg Leu Thr Gly Gly Leu Lys Phe Phe Val
1               5                   10
```

<210> SEQ ID NO 231
<211> LENGTH: 9
<212> TYPE: PRT
<213> ORGANISM: Homo sapien

<400> SEQUENCE: 231

```
Ser Leu Gln Ala Leu Lys Val Thr Val
1               5
```

<210> SEQ ID NO 232
<211> LENGTH: 20
<212> TYPE: PRT
<213> ORGANISM: Homo sapiens

<400> SEQUENCE: 232

```
Ala Gly Ala Asp Val Ile Lys Asn Asp Gly Ile Tyr Ser Arg Tyr Phe
                 5                  10                  15

Phe Ser Phe Ala
            20

<210> SEQ ID NO 233
<211> LENGTH: 21
<212> TYPE: PRT
<213> ORGANISM: Homo sapiens

<400> SEQUENCE: 233

Phe Phe Ser Phe Ala Ala Asn Gly Arg Tyr Ser Leu Lys Val His Val
                 5                  10                  15

Asn His Ser Pro Ser
            20

<210> SEQ ID NO 234
<211> LENGTH: 20
<212> TYPE: PRT
<213> ORGANISM: Homo sapiens

<400> SEQUENCE: 234

Phe Leu Val Thr Trp Gln Ala Ser Gly Pro Pro Glu Ile Ile Leu Phe
                 5                  10                  15

Asp Pro Asp Gly
            20

<210> SEQ ID NO 235
<211> LENGTH: 20
<212> TYPE: PRT
<213> ORGANISM: Homo sapiens

<400> SEQUENCE: 235

Leu Gln Ser Ala Val Ser Asn Ile Ala Gln Ala Pro Leu Phe Ile Pro
                 5                  10                  15

Pro Asn Ser Asp
            20

<210> SEQ ID NO 236
<211> LENGTH: 20
<212> TYPE: PRT
<213> ORGANISM: Homo sapiens

<400> SEQUENCE: 236

Ile Gln Asp Asp Phe Asn Asn Ala Ile Leu Val Asn Thr Ser Lys Arg
                 5                  10                  15

Asn Pro Gln Gln
            20

<210> SEQ ID NO 237
<211> LENGTH: 21
<212> TYPE: PRT
<213> ORGANISM: Homo sapiens

<400> SEQUENCE: 237

Arg Asn Ser Leu Gln Ser Ala Val Ser Asn Ile Ala Gln Ala Pro Leu
                 5                  10                  15

Phe Ile Pro Pro Asn
            20

<210> SEQ ID NO 238
<211> LENGTH: 20
```

-continued

```
<212> TYPE: PRT
<213> ORGANISM: Homo sapiens

<400> SEQUENCE: 238

Thr His Glu Ser His Arg Ile Tyr Val Ala Ile Arg Ala Met Asp Arg
                 5                  10                  15

Asn Ser Leu Gln
            20

<210> SEQ ID NO 239
<211> LENGTH: 20
<212> TYPE: PRT
<213> ORGANISM: Homo sapiens

<400> SEQUENCE: 239

Arg Asn Pro Gln Gln Ala Gly Ile Arg Glu Ile Phe Thr Phe Ser Pro
                 5                  10                  15

Gln Ile Ser Thr
            20

<210> SEQ ID NO 240
<211> LENGTH: 21
<212> TYPE: PRT
<213> ORGANISM: Homo sapiens

<400> SEQUENCE: 240

Gly Gln Ala Thr Ser Tyr Glu Ile Arg Met Ser Lys Ser Leu Gln Asn
                 5                  10                  15

Ile Gln Asp Asp Phe
            20

<210> SEQ ID NO 241
<211> LENGTH: 20
<212> TYPE: PRT
<213> ORGANISM: Homo sapiens

<400> SEQUENCE: 241

Glu Arg Lys Trp Gly Phe Ser Arg Val Ser Ser Gly Gly Ser Phe Ser
                 5                  10                  15

Val Leu Gly Val
            20

<210> SEQ ID NO 242
<211> LENGTH: 20
<212> TYPE: PRT
<213> ORGANISM: Homo sapiens

<400> SEQUENCE: 242

Gly Ser His Ala Met Tyr Val Pro Gly Tyr Thr Ala Asn Gly Asn Ile
                 5                  10                  15

Gln Met Asn Ala
            20

<210> SEQ ID NO 243
<211> LENGTH: 20
<212> TYPE: PRT
<213> ORGANISM: Homo sapiens

<400> SEQUENCE: 243

Val Asn His Ser Pro Ser Ile Ser Thr Pro Ala His Ser Ile Pro Gly
                 5                  10                  15

Ser His Ala Met
```

20

<210> SEQ ID NO 244
<211> LENGTH: 20
<212> TYPE: PRT
<213> ORGANISM: Homo sapiens

<400> SEQUENCE: 244

Ala Val Pro Pro Ala Thr Val Glu Ala Phe Val Glu Arg Asp Ser Leu
                 5                  10                  15

His Phe Pro His
            20

<210> SEQ ID NO 245
<211> LENGTH: 20
<212> TYPE: PRT
<213> ORGANISM: Homo sapiens

<400> SEQUENCE: 245

Lys Pro Gly His Trp Thr Tyr Thr Leu Asn Asn Thr His His Ser Leu
                 5                  10                  15

Gln Ala Leu Lys
            20

<210> SEQ ID NO 246
<211> LENGTH: 20
<212> TYPE: PRT
<213> ORGANISM: Homo sapiens

<400> SEQUENCE: 246

Asn Leu Thr Phe Arg Thr Ala Ser Leu Trp Ile Pro Gly Thr Ala Lys
                 5                  10                  15

Pro Gly His Trp
            20

<210> SEQ ID NO 247
<211> LENGTH: 20
<212> TYPE: PRT
<213> ORGANISM: Homo sapiens

<400> SEQUENCE: 247

Leu His Phe Pro His Pro Val Met Ile Tyr Ala Asn Val Lys Gln Gly
                 5                  10                  15

Phe Tyr Pro Ile
            20

<210> SEQ ID NO 248
<211> LENGTH: 20
<212> TYPE: PRT
<213> ORGANISM: Homo sapiens

<400> SEQUENCE: 248

Pro Glu Thr Gly Asp Pro Val Thr Leu Arg Leu Leu Asp Asp Gly Ala
                 5                  10                  15

Gly Ala Asp Val
            20

<210> SEQ ID NO 249
<211> LENGTH: 20
<212> TYPE: PRT
<213> ORGANISM: Homo sapiens

<400> SEQUENCE: 249

```
Gly Phe Tyr Pro Ile Leu Asn Ala Thr Val Thr Ala Thr Val Glu Pro
                5                   10                  15

Glu Thr Gly Asp
            20

<210> SEQ ID NO 250
<211> LENGTH: 20
<212> TYPE: PRT
<213> ORGANISM: Homo sapiens

<400> SEQUENCE: 250

Phe Asp Pro Asp Gly Arg Lys Tyr Tyr Thr Asn Asn Phe Ile Thr Asn
                5                   10                  15

Leu Thr Phe Arg
            20

<210> SEQ ID NO 251
<211> LENGTH: 20
<212> TYPE: PRT
<213> ORGANISM: Homo sapiens

<400> SEQUENCE: 251

Leu Gln Ala Leu Lys Val Thr Val Thr Ser Arg Ala Ser Asn Ser Ala
                5                   10                  15

Val Pro Pro Ala
            20

<210> SEQ ID NO 252
<211> LENGTH: 153
<212> TYPE: PRT
<213> ORGANISM: Homo sapien

<400> SEQUENCE: 252

Met Ala Ser Val Arg Val Ala Ala Tyr Phe Glu Asn Phe Leu Ala Ala
 1               5                   10                  15

Trp Arg Pro Val Lys Ala Ser Asp Gly Asp Tyr Tyr Thr Leu Ala Val
                20                  25                  30

Pro Met Gly Asp Val Pro Met Asp Gly Ile Ser Val Ala Asp Ile Gly
            35                  40                  45

Ala Ala Val Ser Ser Ile Phe Asn Ser Pro Glu Glu Phe Leu Gly Lys
        50                  55                  60

Ala Val Gly Leu Ser Ala Glu Ala Leu Thr Ile Gln Gln Tyr Ala Asp
65                  70                  75                  80

Val Leu Ser Lys Ala Leu Gly Lys Glu Val Arg Asp Ala Lys Ile Thr
                85                  90                  95

Pro Glu Ala Phe Glu Lys Leu Gly Phe Pro Ala Ala Lys Glu Ile Ala
            100                 105                 110

Asn Met Cys Arg Phe Tyr Glu Met Lys Pro Asp Arg Asp Val Asn Leu
        115                 120                 125

Thr His Gln Leu Asn Pro Lys Val Lys Ser Phe Ser Gln Phe Ile Ser
    130                 135                 140

Glu Asn Gln Gly Ala Phe Lys Gly Met
145                 150

<210> SEQ ID NO 253
<211> LENGTH: 462
<212> TYPE: DNA
<213> ORGANISM: Homo sapien
```

```
<400> SEQUENCE: 253
atggccagtg tccgcgtggc ggcctacttt gaaaactttc tcgcggcgtg gcggcccgtg      60
aaagcctctg atggagatta ctacaccttg gctgtaccga tgggagatgt accaatggat     120
ggtatctctg ttgctgatat tggagcagcc gtctctagca tttttaattc tccagaggaa     180
tttttaggca aggccgtggg gctcagtgca aagcactaa caatacagca atatgctgat     240
gttttgtcca aggctttggg gaaagaagtc cgagatgcaa agattacccc ggaagctttc     300
gagaagctgg gattccctgc agcaaaggaa atagccaata tgtgtcgttt ctatgaaatg     360
aagccagacc gagatgtcaa tctcacccac caactaaatc ccaaagtcaa agcttcagc     420 cagtttatct cagagaacca gggagccttc aagggcatgt ag                       462

<210> SEQ ID NO 254
<211> LENGTH: 8031
<212> TYPE: DNA
<213> ORGANISM: Homo sapien

<400> SEQUENCE: 254
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta aatcggggggc tcccttaggg   180 gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aaccctatct cggtctattc     360
ttttgattta agggatttt tgccgatttc ggcctattgg ttaaaaaatg agctgattta      420
acaaaaattt aacgcgaatt ttaacaaaat attaacgttt acaatttcag gtggcacttt     480
tcggggaaat gtgcgcggaa ccctatttg tttatttttc taaatacatt caaatatgta     540
tccgctcatg aattaattct tagaaaaact catcgagcat caaatgaaac tgcaatttat     600
tcatatcagg attatcaata ccatatttt gaaaagccg tttctgtaat gaaggagaaa      660
actcaccgag gcagttccat aggatggcaa gatcctggta tcggtctgcg attccgactc    720
gtccaacatc aatacaacct attaatttcc cctcgtcaaa ataaggtta tcaagtgaga    780 aatcaccatg agtgacgact gaatccggtg agaatggcaa agtttatgc atttctttcc     840 agacttgttc aacaggccag ccattacgct cgtcatcaaa atcactcgca tcaaccaaac     900
cgttattcat tcgtgattgc gcctgagcga gacgaaatac gcgatcgctg ttaaaaggac     960
aattacaaac aggaatcgaa tgcaaccggc gcaggaacac tgccagcgca tcaacaatat    1020
tttcacctga atcaggatat tcttctaata cctggaatgc tgttttcccg gggatcgcag    1080
tggtgagtaa ccatgcatca tcaggagtac ggataaaatg cttgatggtc ggaagaggca    1140
taaattccgt cagccagttt agtctgacca tctcatctgt aacatcattg gcaacgctac    1200
ctttgccatg tttcagaaac aactctggcg catcgggctt cccatacaat cgatagattg    1260
tcgcacctga ttgcccgaca ttatcgcgag cccatttata cccatataaa tcagcatcca    1320
tgttggaatt taatcgcggc ctagagcaag acgtttcccg ttgaatatgg ctcataacac    1380
cccttgtatt actgtttatg taagcagaca gttttattgt tcatgaccaa atcccttaa     1440 cgtgagtttt cgttccactg agcgtcagac cccgtagaaa agatcaaagg atcttcttga    1500
gatccttttt ttctgcgcgt aatctgctgc ttgcaaacaa aaaaaccacc gctaccagcg    1560
gtggtttgtt tgccggatca agagctacca actcttttc cgaaggtaac tggcttcagc    1620
```

```
agagcgcaga taccaaatac tgtccttcta gtgtagccgt agttaggcca ccacttcaag    1680
aactctgtag caccgcctac atacctcgct ctgctaatcc tgttaccagt ggctgctgcc    1740
agtggcgata agtcgtgtct taccgggttg gactcaagac gatagttacc ggataaggcg    1800
cagcggtcgg gctgaacggg gggttcgtgc acacagccca gcttggagcg aacgacctac    1860
accgaactga gatacctaca gcgtgagcta tgagaaagcg ccacgcttcc cgaagggaga    1920
aaggcggaca ggtatccggt aagcggcagg gtcggaacag gagagcgcac gagggagctt    1980 ccaggggaa acgcctggta tctttatagt cctgtcgggt ttcgccacct ctgacttgag    2040
cgtcgatttt tgtgatgctc gtcagggggg cggagcctat ggaaaaacgc cagcaacgcg    2100
gcctttttac ggttcctggc cttttgctgg ccttttgctc acatgttctt tcctgcgtta    2160
tcccctgatt ctgtggataa ccgtattacc gcctttgagt gagctgatac cgctcgccgc    2220
agccgaacga ccgagcgcag cgagtcagtg agcgaggaag cggaagagcg cctgatgcgg    2280
tattttctcc ttacgcatct gtgcggtatt tcacaccgca tatatggtgc actctcagta    2340
caatctgctc tgatgccgca tagttaagcc agtatacact ccgctatcgc tacgtgactg    2400
ggtcatggct gcgccccgac acccgccaac acccgctgac gcgccctgac gggcttgtct    2460
gctcccggca tccgcttaca gacaagctgt gaccgtctcc gggagctgca tgtgtcagag    2520
gttttcaccg tcatcaccga aacgcgcgag gcagctgcgg taaagctcat cagcgtggtc    2580
gtgaagcgat tcacagatgt ctgcctgttc atccgcgtcc agctcgttga gtttctccag    2640
aagcgttaat gtctggcttc tgataaagcg ggccatgtta agggcggttt tttcctgttt    2700
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
```

-continued

```
tcggctgaat ttgattgcga gtgagatatt tatgccagcc agccgacgcg agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatataca tatgcagcat caccaccatc accacggagt    5100
acagcttcaa gacaatgggt ataatggatt gctcattgca attaatcctc aggtacctga    5160
gaatcagaac ctcatctcaa acattaagga aatgataact gaagcttcat tttacctatt    5220
taatgctacc aagagaagag tattttttcag aaatataaag atttttaatac ctgccacatg    5280 gaaagctaat aataacagca aaataaaaca agaatcatat gaaaaggcaa atgtcatagt    5340
gactgactgg tatggggcac atggagatga tccatacacc ctacaataca gagggtgtgg    5400
aaaagaggga aaatacattc atttcacacc taatttccta ctgaatgata acttaacagc    5460
tggctacgga tcacgaggcc gagtgtttgt ccatgaatgg gcccacctcc gttggggtgt    5520
gttcgatgag tataacaatg acaaaccttt ctacataaat gggcaaaatc aaattaaagt    5580
gacaaggtgt catctgacaa tcacaggcat ttttgtgtgt gaaaaaggtc cttgccccca    5640
agaaaactgt attattagta agcttttttaa agaaggatgc acctttatct acaatagcac    5700
ccaaaatgca actgcatcaa taatgttcat gcaaagttta tcttctgtgg ttgaattttg    5760
taatgcaagt acccacaacc aagaagcacc aaacctacag aaccagatgt gcagcctcag    5820
aagtgcatgg gatgtaatca cagactctgc tgactttcac cacagctttc ccatgaacgg    5880
gactgagctt ccacctcctc ccacattctc gcttgtagag gctggtgaca agtggtctg    5940 tttagtgctg gatgtgtcca gcaagatggc agaggctgac agactccttc aactacaaca    6000
agccgcagaa ttttatttga tgcagattgt tgaaattcat accttcgtgg gcattgccag    6060
tttcgacagc aaaggagaga tcagagccca gctacaccaa attaacagca atgatgatcg    6120
aaagttgctg gtttcatatc tgcccaccac tgtatcagct aaaacagaca tcagcatttg    6180
ttcagggctt aagaaaggat ttgaggtggt tgaaaaactg aatggaaaag cttatgctc    6240 tgtgatgata ttagtgacca gcggagatga taagcttctt ggcaattgct tacccactgt    6300
gctcagcagt ggttcaacaa ttcactccat tgccctgggt tcatctgcag ccccaaatct    6360
```

```
ggaggaatta tcacgtctta caggaggttt aaagttcttt gttccagata tatcaaactc    6420
caatagcatg attgatgctt tcagtagaat ttcctctgga actggagaca ttttccagca    6480
acatattcag cttgaaagta caggtgaaaa tgtcaaacct caccatcaat tgaaaaacac    6540
agtgactgtg gataatactg tgggcaacga cactatgttt ctagttacgt ggcaggccag    6600
tggtcctcct gagattatat tatttgatcc tgatggacga aaatactaca caaataattt    6660
tatcaccaat ctaacttttc ggacagctag tctttggatt ccaggaacag ctaagcctgg    6720
gcactggact tacaccctga acaataccca tcattctctg caagccctga aagtgacagt    6780
gacctctcgc gcctccaact cagctgtgcc cccagccact gtggaagcct ttgtggaaag    6840
agacagcctc cattttcctc atcctgtgat gatttatgcc aatgtgaaac agggatttta    6900
tcccattctt aatgccactg tcactgccac agttgagcca gagactggag atcctgttac    6960
gctgagactc cttgatgatg gagcaggtgc tgatgttata aaaaatgatg gaatttactc    7020
gaggtatttt ttctcctttg ctgcaaatgg tagatatagc ttgaaagtgc atgtcaatca    7080
ctctcccagc ataagcaccc cagcccactc tattccaggg agtcatgcta tgtatgtacc    7140
aggttacaca gcaaacggta atattcagat gaatgctcca aggaaatcag taggcagaaa    7200
tgaggaggag cgaaagtggg gctttagccg agtcagctca ggaggctcct tttcagtgct    7260
gggagttcca gctggccccc accctgatgt gtttccacca tgcaaaatta ttgacctgga    7320
agctgtaaaa gtagaagagg aattgaccct atcttggaca gcacctggag aagactttga    7380
tcagggccag gctacaagct atgaaataag aatgagtaaa agtctacaga atatccaaga    7440
tgactttaac aatgctattt tagtaaatac atcaaagcga aatcctcagc aagctggcat    7500
cagggagata tttacgttct caccccaaat ttccacgaat ggacctgaac atcagccaaa    7560
tggagaaaca catgaaagcc acagaattta tgttgcaata cgagcaatgg ataggaactc    7620
cttacagtct gctgtatcta acattgccca ggcgcctctg tttattcccc ccaattctga    7680
tcctgtacct gccagagatt atcttatatt gaaaggagtt ttaacagcaa tgggtttgat    7740
aggaatcatt tgccttatta tagttgtgac acatcatact ttaagcagga aaaagagagc    7800
agacaagaaa gagaatggaa caaaattatt ataatgaatt ctgcagatat ccatcacact    7860
ggcggccgct cgagcaccac caccaccacc actgagatcc ggctgctaac aaagcccgaa    7920
aggaagctga gttggctgct gccaccgctg agcaataact agcataaccc cttgggcct    7980 ctaaacgggt cttgaggggt tttttgctga aaggaggaac tatatccgga t             8031
```

COMPOUNDS AND METHODS FOR THERAPY AND DIAGNOSIS OF LUNG CANCER

This application is a continuation-in-part of U.S. patent application Ser. No. 09/466,396, filed Dec. 17, 1999, which is a continuation-in-part of U.S. patent application Ser. No. 09/285,479, filed Apr. 2, 1999, which is a continuation-in-part of PCT Application No. PCT/US99/05798, filed Mar. 17, 1999, which is a continuation-in-part of U.S. patent application Ser. No. 09/221,107, filed Dec. 22, 1998, which is a continuation-in-part of U.S. patent application Ser. No. 09/123,912, filed Jul. 27, 1998, now U.S. Pat. 6,312,695, which is a continuation-in-part of U.S. patent application Ser. No. 09/040,802, filed Mar. 18, 1998, now abandoned.

TECHNICAL FIELD

The present invention relates generally to therapy and diagnosis of cancer, such as lung cancer. The invention is more specifically related to polypeptides comprising at least a portion of a lung tumor protein, and to polynucleotides encoding such polypeptides. Such polypeptides and polynucleotides may be used in vaccines and pharmaceutical compositions for prevention and treatment of lung cancer, and for the diagnosis and monitoring of such cancers.

BACKGROUND OF THE INVENTION

Lung cancer is the primary cause of cancer death among both men and women in the U.S., with an estimated 172,000 new gases being reported in 1994. The five-year survival rate among all lung cancer patients regardless of the stage of disease at diagnosis, is only 13%. This contrasts with a five-year survival rate of 46% among cases detected while the disease is still localized. However, only 16% of lung cancers are discovered before the disease has spread.

Early detection is difficult since clinical symptoms are often not seen until the disease has reached an advanced stage. Currently, diagnosis is aided by the use of chest x-rays, analysis of the type of cells contained in sputum and fiberoptic examination of the bronchial passages. Treatment regimens are determined by the type and stage of the cancer, and include surgery, radiation therapy and/or chemotherapy. In spite of considerable research into therapies for the disease, lung cancer remains difficult to treat.

Accordingly, there remains a need in the art for improved vaccines, treatment methods and diagnostic techniques for lung cancer.

SUMMARY OF THE INVENTION

Briefly stated, the present invention provides compositions and methods for the diagnosis and therapy of cancer, such as lung cancer. In one aspect, the present invention provides polypeptides comprising at least a portion of a lung tumor protein, or a variant thereof Certain portions and other variants are immunogenic, such that the ability of the variant to react with antigen-specific antisera is not substantially diminished. Within certain embodiments, the polypeptide comprises a sequence that is encoded by a polynucleotide sequence selected from the group consisting of: (a) sequences recited in any one of SEQ ID NO: 1–3, 6–8, 10–13, 15–27, 29, 30, 32, 34–49, 51, 52, 54, 55, 57–59, 61–69, 71, 73, 74, 77, 78, 80–82, 84, 86–96, 107–109, 111, 113, 125, 127, 128, 129, 131–133, 142, 144, 148–151, 153, 154, 157, 158, 160, 167, 168, 171, 179, 132, 184–186, 188–191, 193, 194, 198–207, 209, 210, 213, 214, 217, 220–224, 253 and 254; (b) variants of a sequence recited in any one of SEQ ID NO: 1–3, 6–8, 10–13, 15–27, 29, 30, 32, 34–49, 51, 52, 54, 55, 57–59, 61–69, 71, 73. 74, 77, 78, 80–82, 84, 86–96, 107–109, 111, 113, 125, 127, 128, 129, 131–133, 142, 144, 148–151, 153, 154, 157, 158, 160, 167. 168, 171, 179, 182, 184–186, 188–191, 193, 194, 198–207, 209, 210, 213, 214, 217, 220–224, 253 and 254; and (c) complements of a sequence of (a) or (b). In specific embodiments, the polypeptides of the present invention comprise at least a portion of a tumor protein that includes an amino acid sequence selected from the group consisting of sequences recited in any one of SEQ ID NO: 152, 155, 156, 165, 166, 169, 170, 172, 174, 176 and 226–252 and variants thereof.

The present invention further provides polynucleotides that encode a polypeptide as described above, or a portion thereof (such as a portion encoding at least 15 amino acid residues of a lung tumor protein), expression vectors comprising such polynucleotides and host cells transformed or transfected with such expression vectors.

Within other aspects, the present invention provides pharmaceutical compositions comprising a polypeptide or polynucleotide as described above and a physiologically acceptable carrier.

Within a related aspect of the present invention, vaccines for prophylactic or therapeutic use are provided. Such vaccines comprise a polypeptide or polynucleotide as described above and an immunostimulant.

The present invention further provides pharmaceutical compositions that comprise: (a) an antibody or antigen-binding fragment thereof that specifically binds to a lung tumor protein; and (b) a physiologically acceptable carrier.

Within further aspects, the present invention provides pharmaceutical compositions comprising: (a) an antigen presenting cell that expresses a polypeptide as described above and (b) a pharmaceutically acceptable carrier or excipient. Antigen presenting cells include dendritic cells, macrophages, monocytes, fibroblasts and B cells.

Within related aspects, vaccines are provided that comprise: (a) an antigen presenting cell that expresses a polypeptide as described above, and (b) an immunostimulant.

The present invention further provides, in other aspects, fusion proteins that comprise at least one polypeptide as described above, as well as polynucleotides encoding such fusion proteins.

Within related aspects, pharmaceutical compositions comprising a fusion protein, or a polynucleotide encoding a fusion protein, in combination with a physiologically acceptable carrier are provided.

Vaccines are further provided, within other aspects, that comprise a fusion protein, or a polynucleotide encoding a fusion protein, in combination with an immunostimulant.

Within further aspects, the present invention provides methods for inhibiting the development of a cancer in a patient, comprising administering to a patient a pharmaceutical composition or vaccine as recited above.

The present invention further provides, within other aspects, methods for removing tumor cells from a biological sample, comprising contacting a biological sample with T cells that specifically react with a lung tumor protein, wherein the step of contacting is performed under conditions and for a time sufficient to permit the removal of cells expressing the protein from the sample.

Within related aspects, methods are provided for inhibiting the development of a cancer in a patient, comprising administering to a patient a biological sample treated as described above.

Methods are further provided, within other aspects, for stimulating and/or expanding T cells specific for a lung tumor protein, comprising contacting T cells with one or more of: (i) a polypeptide as described above; (ii) a polynucleotide encoding such a polypeptide; and/or (iii) an antigen presenting cell that expresses such a polypeptide; under conditions and for a time sufficient to permit the stimulation and/or expansion of T cells. Determined T cell populations comprising T cells prepared as described above are also provided.

Within further aspects, the present invention provides methods for inhibiting the development of a cancer in a patient, comprising administering to a patient an effective amount of a T cell population as described above.

The present invention further provides methods for inhibiting the development of a cancer in a patient, comprising the steps of: (a) incubating CD4$^+$ and/or CD8$^+$ T cells determined from a patient with one or more of: (i) a polypeptide comprising at least an immunogenic portion of a lung tumor protein, (ii) a polynucleotide encoding such a polypeptide; and (iii) an antigen-presenting cell that expressed such a polypeptide; and (b) administering to the patient an effective amount of the proliferated T cells, and thereby inhibiting the development of a cancer in the patient. Proliferated cells may, but need not, be cloned prior to administration to the patient.

Within further aspects, the present invention provides methods for determining the presence or absence of a cancer in a patient, comprising: (a) contacting a biological sample obtained from a patient with a binding agent that binds to a polypeptide as recited above; (b) detecting in the sample an amount of polypeptide that binds to the binding agent; and (c) comparing the amount of polypeptide with a predetermined cut-off value, and therefrom determining the presence or absence of a cancer in the patient. Within preferred embodiments, the binding agent is an antibody, more preferably a monoclonal antibody. The cancer may be lung cancer.

The present invention also provides, within other aspects, methods for monitoring the progression of a cancer in a patient. Such methods comprise the steps of: (a) contacting a biological sample obtained from a patient at a first point in time with a binding agent that binds to a polypeptide as recited above; (b) detecting in the sample an amount of polypeptide that binds to the binding agent; (c) repeating, steps (a) and (b) using a biological sample obtained from the patient at a subsequent point in time: and (d) comparing the amount of polypeptide detected in step (c) with the amount detected in step (b) and therefrom monitoring the progression of the cancer in the patient.

The present invention further provides, within other aspects, methods for determining the presence or absence of a cancer in a patient, comprising the steps of: (a) contacting a biological sample obtained from a patient with an oligonucleotide that hybridizes to a polynucleotide that encodes a lung tumor protein; (b) detecting in the sample a level of a polynucleotide, preferably mRNA, that hybridizes to the oligonucleotide; and (c) comparing the level of polynucleotide that hybridizes to the oligonucleotide with a predetermined cut-off value, and therefrom determining the presence or absence of a cancer in the patient. Within certain embodiments, the amount of mRNA is detected via polymerase chain reaction using, for example, at least one oligonucleotide primer that hybridizes to a polynucleotide encoding a polypeptide as recited above, or a complement of such a polynucleotide. Within other embodiments, the amount of mRNA is detected using a hybridization technique, employing an oligonucleotide probe that hybridizes to a polynucleotide that encodes a polypeptide as recited above, or a complement of such a polynucleotide.

In related aspects, methods are provided for monitoring the progression of a cancer in a patient, comprising the steps of: (a) contacting a biological sample obtained from a patient with an oligonucleotide that hybridizes to a polynucleotide that encodes a lung tumor protein; (b) detecting in the sample an amount of a polynucleotide that hybridizes to the oligonucleotide, (c) repeating steps (a) and (b) using a biological sample obtained from the patient at a subsequent point in time; and (d) comparing the amount of polynucleotide detected in step (c) with the amount detected in step (b) and therefrom monitoring the progression of the cancer in the patient.

Within further aspects, the present invention provides antibodies, such as monoclonal antibodies, that bind to a polypeptide as described above, as well as diagnostic kits comprising such antibodies. Diagnostic kits comprising one or more oligonucleotide probes or primers as described above are also provided.

These and other aspects of the present invention will become apparent upon reference to the following detailed description and attached drawings. All references disclosed herein are hereby incorporated by reference in their entirety as if each was incorporated individually.

SEQUENCE IDENTIFIERS

SEQ ID NO: 1 is the determined cDNA sequence for LST-S1-2

SEQ ID NO: 2 is the determined cDNA sequence for LST-S1-28

SEQ ID NO: 3 is the determined cDNA sequence for LST-S 1-90

SEQ ID NO: 4 is the determined cDNA sequence for LST-S1-144

SEQ ID NO: 5 is the determined cDNA sequence for LST-S1- 13

SEQ ID NO: 6 is the determined cDNA sequence for LST-S1-169

SEQ ID NO: 7 is the determined cDNA sequence for LST-S2-6

SEQ ID NO: 8 is the determined cDNA sequence for LST-S2-11

SEQ ID NO: 9 is the determined cDNA sequence for LST-S2-17

SEQ ID NO: 10 is the determined cDNA sequence for LST-S2-25

SEQ ID NO: 11 is the determined cDNA sequence for LST-S2-39

SEQ ID NO: 12 is a first determined cDNA sequence for LST-S2-43

SEQ ID NO: 13 is a second determined cDNA sequence for LST-S2 -43

SEQ ID NO: 14 is the determined cDNA sequence for LST-S2-65

SEQ ID NO: 15 is the determined cDNA sequence for LST-S2-68

SEQ ID NO: 16 is the determined cDNA sequence for LST-S2-72

SEQ ID NO: 17 is the determined cDNA sequence for LST-S2-74
SEQ ID NO: 18 is the determined cDNA sequence for LST-S2-103
SEQ ID NO: 19 is the determined cDNA sequence for LST-S2-N1-1F
SEQ ID NO: 20 is the determined cDNA sequence for LST-S2-N1-2A
SEQ ID NO: 21 is the determined cDNA sequence for LST-S2-N1-4H
SEQ ID NO: 22 is the determined cDNA sequence for LST-S2-N1-5A
SEQ ID NO: 22 is the determined cDNA sequence for LST-S2-N1-6B
SEQ ID NO: 2 4is the determined cDNA sequence for LST-S2-N1-7B
SEQ ID NO: 25 is the determined cDNA sequence for LST-S2-N1-7H
SEQ ID NO: 26 is the determined cDNA sequence for LST-S2-N1-8A
SEQ ID NO: 27 is the determined cDNA sequence for LST-S2-N1-8D
SEQ ID NO: 28 is the determined cDNA sequence for LST-S2-N1-9A
SEQ ID NO: 29 is the determined cDNA sequence for LST-S2-N1-9E
SEQ ID NO: 30 is the determined cDNA sequence for LST-S2-N1-10A
SEQ ID NO: 31 is the determined cDNA sequence for LST-S2-N1-10G
SEQ ID NO: 31 is the determined cDNA sequence for LST-S2-N1-11A
SEQ ID NO: 32 is the determined cDNA sequence for LST-S2-N1-12A
SEQ ID NO: 33 is the determined cDNA sequence for LST-S2-N1-12C
SEQ ID NO: 34 is the determined cDNA sequence for LST-S2-N1-12E
SEQ ID NO: 35 is the determined cDNA sequence for LST-S2-B1-3D
SEQ ID NO: 36 is the determined cDNA sequence for LST-S2-B1-6D
SEQ ID NO: 37 is the determined cDNA sequence for LST-S2-B1-5D
SEQ ID NO: 38 is the determined cDNA sequence for LST-S2-B1-5F
SEQ ID NO: 39 is the determined cDNA sequence for LST-S2-B1-6G
SEQ ID NO: 40 is the determined cDNA sequence for LST-S2-B1-8A
SEQ ID NO: 41 is the determined cDNA sequence for LST-S2-B1-8D
SEQ ID NO: 42 is the determined cDNA sequence for LST-S2-B1-10A
SEQ ID NO: 43 is the determined cDNA sequence for LST-S2-B1-9B
SEQ ID NO: 44 is the determined cDNA sequence for LST-S2-B1-9F
SEQ ID NO: 45 is the determined cDNA sequence for LST-S2-B1-12D
SEQ ID NO: 46 is the determined cDNA sequence for LST-S2-I2-2B
SEQ ID NO: 47 is the determined cDNA sequence for LST-S2-I2-5F
SEQ ID NO: 48 is the determined cDNA sequence for LST-S2-I2-6B
SEQ ID NO: 49 is the determined cDNA sequence for LST-S2-I2-7F
SEQ ID NO: 50 is the determined cDNA sequence for LST-S2-I2-8G
SEQ ID NO: 51 is the determined cDNA sequence for LST-S2-I2-9E
SEQ ID NO: 52 is the determined cDNA sequence for LST-S2-I2-12B
SEQ ID NO: 53 is the determined cDNA sequence for LST-S2-H2-2C
SEQ ID NO: 54 is the determined cDNA sequence for LST-S2-H2-1G
SEQ ID NO: 55 is the determined cDNA sequence for LST-S2-H2-4G
SEQ ID NO: 56 is the determined cDNA sequence for LST-S2-H2-3H
SEQ ID NO: 57 is the determined cDNA sequence for LST-S2-H2-5G
SEQ ID NO: 58 is the determined cDNA sequence for LST-S2-H2-9B
SEQ ID NO: 59 is the determined cDNA sequence for LST-S2-H2-10H
SEQ ID NO: 60 is the determined cDNA sequence for LST-S2-H2-12D
SEQ ED NO: 61 is the determined cDNA sequence for LST-S3-2
SEQ ID NO: 62 is the determined cDNA sequence for LST-S3-4
SEQ ID NO: 63 is the determined cDNA sequence for LST-S3-7
SEQ ID NO: 64 is the determined cDNA sequence for LST-S3-8
SEQ ID NO: 65 is the determined cDNA sequence for LST-S3-12
SEQ ID NO: 66 is the determined cDNA sequence for LST-S3-13
SEQ ID NO: 67 is the determined cDNA sequence for LST-S3-14
SEQ ID NO: 68 is the determined cDNA sequence for LST-S3-16
SEQ ID NO: 69 is the determined cDNA sequence for LST-S3-21
SEQ ID NO: 70 is the determined cDNA sequence for LST-S3-22
SEQ ID NO: 71 is the determined cDNA sequence for LST-S1-7
SEQ ID NO: 72 is the determined cDNA sequence for LST-S1-A-1E
SEQ ID NO: 73 is the determined cDNA sequence for LST-S1-A-1G
SEQ ID NO: 74 is the determined cDNA sequence for LST-S1-A-3E
SEQ ID NO: 75 is the determined cDNA sequence for LST-S1-A-4E
SEQ ID NO: 76 is the determined cDNA sequence for LST-S1-A-6D
SEQ ID NO: 77 is the determined cDNA sequence for LST-S1-A-8D SEQ ID NO: 78 is the determined cDNA sequence for LST-S1-A-10A SEQ ID NO: 79 is the determined cDNA sequence for LST-S1-A-10C SEQ ID NO: 80 is the determined cDNA sequence for LST-S1-A-9D SEQ ID NO: 81 is the determined cDNA sequence for LST-S1-A-10D SEQ ID NO: 82 is the determined cDNA sequence for LST-S1-A-9H SEQ ID NO: 83 is the determined cDNA sequence for LST-S1-A-11D SEQ ID NO: 84 is the determined cDNA sequence for LST-S1-A-12D SEQ ID NO: 85 is the determined cDNA sequence for LST-S1-A-11E SEQ ID NO: 86 is the determined cDNA sequence for LST-S1-A-12E SEQ ID NO: 87 is the determined cDNA sequence for L513S (T3).

SEQ ID NO: 88 is the determined cDNA sequence for L513S contig 1.

SEQ ID NO: 89 is a first determined cDNA sequence for L514S.

SEQ ID NO:.90 is a second determined cDNA sequence for L514S.

SEQ ID NO: 91 is a first determined cDNA sequence for L516S.

SEQ ID NO: 92 is a second determined cDNA sequence for L516S.

SEQ ID NO: 93 is the determined cDNA sequence for L517S.

SEQ ID NO: 94 is the extended cDNA sequence for LST-S1-169 (also known as L519S).

SEQ ID NO: 95 is a first determined cDNA sequence for L520S.

SEQ ID NO: 96 is a second determined cDNA sequence for L520s.

SEQ ID NO: 97 is a first determined cDNA sequence for L521S.

SEQ ID NO: 98 is a second determined cDNA sequence for L521 S.

SEQ ID NO: 99 is the determined cDNA sequence for L522S.

SEQ ID NO: 100 is the determined cDNA sequence for L523S.

SEQ ID NO: 101 is the determined cDNA sequence for L524S.

SEQ ID NO: 102 is the determined cDNA sequence for L525S.

SEQ ID NO: 103 is the determined cDNA sequence for L526S.

SEQ ID NO: 104 is the determined cDNA sequence for L527S.

SEQ ID NO: 105 is the determined cDNA sequence for L528S.

SEQ ID NO: 106 is the determined cDNA sequence for L529S.

SEQ ID NO: 107 is a first determined cDNA sequence for L530S.

SEQ ID NO: 108 is a second determined cDNA sequence for L530S.

SEQ ID NO: 109 is the determined full-length cDNA sequence for L531S short form

SEQ ID NO: 110 is the predicted amino acid sequence encoded by SEQ ID NO: 109.

SEQ ID NO: 111 is the determined full-length cDNA sequence for L531S long form

SEQ ID NO: 112 is the predicted amino acid sequence encoded by SEQ ID NO: 111.

SEQ ID NO: 113 is the determined full-length cDNA sequence for L520S.

SEQ ID NO: 114 is the predicted amino acid sequence encoded by SEQ ID NO: 113.

SEQ ID NO: 115 is the determined cDNA sequence for contig 1.

SEQ ID NO: 116 is the determined cDNA sequence for contig 3.

SEQ ID NO: 117 is the determined cDNA sequence for contig 4.

SEQ ID NO: 118 is the determined cDNA sequence for contig 5.

SEQ ID NO: 119 is the determined cDNA sequence for contig 7.

SEQ ID NO: 120 is the determined cDNA sequence for contig 8.

SEQ ID NO: 129 is the determined cDNA sequence for contig 9.

SEQ ED NO: 122 is the determined cDNA sequence for contig 10.

SEQ ID NO: 123 is the determined cDNA sequence for contig 12.

SEQ ID NO: 124 is the determined cDNA sequence for contig 11.

SEQ ID NO: 125 is the determined cDNA sequence for contig 13.

SEQ ID NO: 126 is the determined cDNA sequence for contig 15.

SEQ ID NO: 127 is the determined cDNA sequence for contig 16.

SEQ ID NO: 128 is the determined cDNA sequence for contig 17.

SEQ ID NO: 129 is the determined cDNA sequence for contig 19.

SEQ ID NO: 130 is the determined cDNA sequence for contig 20.

SEQ ID NO: 126 is the determined cDNA sequence for contig 21.

SEQ ID NO: 132 is the determined cDNA sequence for contig 24.

SEQ ID NO: 133 is the determined cDNA sequence for contig 29.

SEQ ID NO: 194 is the determined cDNA sequence for contig 31.

SEQ ID NO: 135 is the determined cDNA sequence for contig 33.

SEQ ID NO: 136 is the determined cDNA sequence for contig 38.

SEQ ID NO: 137 is the determined cDNA sequence for contig 39.

SEQ ID NO: 138 is the determined cDNA sequence for contig 41.

SEQ ID NO: 139 is the determined cDNA sequence for contig 43.

SEQ ID NO: 140 is the determined cDNA sequence for contig 44.

SEQ ID NO: 141 is the determined cDNA sequence for contig 45.

SEQ ID NO: 142 is the determined cDNA sequence for contig 47.

SEQ ID NO: 143 is the determined cDNA sequence for contig 48.

SEQ ID NO: 144 is the determined cDNA sequence for contig 49.

SEQ ID NO: 144 is the determined cDNA sequence for contig 49.

SEQ ID NO: 145 is the determined cDNA sequence for contig 50.

SEQ ID NO: 146 is the determined cDNA sequence for contig 53.

SEQ ID NO: 147 is the determined cDNA sequence for contig 54.

SEQ ID NO: 148 is the determined cDNA sequence for contig 56.

SEQ ID NO: 149 is the determined cDNA sequence for contig 57.

SEQ ID NO: 150 is the determined cDNA sequence for contig 58.

SEQ ID NO: 151 is the full-length cDNA sequence for L530S.

SEQ ID NO: 152 is the amino acid sequence encoded by SEQ ID NO: 151

SEQ ID NO: 153 is the full-length cDNA sequence of a first variant of L514S.

SEQ ID NO: 154 is the full-length cDNA sequence of a second variant of L514S.

SEQ ID NO: 155 is the amino acid sequence encoded by SEQ ID NO: 153.

SEQ ID NO: 156 is the amino acid sequence encoded by SEQ ID NO: 154.

SEQ ID NO: 157 is the determined cDNA sequence for contig 59.

SEQ ID NO: 158 is the full-length cDNA sequence for L763P (also referred to as contig 22).

SEQ ID NO: 159 is the amino acid sequence encoded by SEQ ID NO: 158.

SEQ ID NO: 160 is the full-length cDNA sequence for L762P (also referred to as contig 17).

SEQ ID NO: 161 is the amino acid sequence encoded by SEQ ID NO: 160.

SEQ ID NO: 162 is the determined cDNA sequence for L515S.

SEQ ID NO: 163 is the full-length cDNA sequence of a first variant of L524S.

SEQ ID NO: 164 is the full-length cDNA sequence of a second variant of L524S.

SEQ ID NO: 165 is the amino acid sequence encoded by SEQ ID NO: 163.

SEQ ID NO: 166 is the amino acid sequence encoded by SEQ ID NO: 164.

SEQ ID NO: 167 is the full-length cDNA sequence of a first variant of L762P.

SEQ ID NO: 168 is the full-length cDNA sequence of a second variant of L762P.

SEQ ID NO: 169 is the amino acid sequence encoded by SEQ ID NO: 167.

SEQ ID NO: 170 is the amino acid sequence encoded by SEQ ID NO: 168.

SEQ ID NO: 171 is the full-length cDNA sequence for L773P (also referred to as contig 56).

SEQ ID NO: 172 is the amino acid sequence encoded by SEQ ID NO: 171.

SEQ ID NO: 173 is an extended cDNA sequence for L519S.

SEQ ID NO: 174 is the predicted amino acid sequence encoded by SEQ ID NO: 174.

SEQ ID NO: 175 is the full-length cDNA sequence for L523S.

SEQ ID NO: 176 is the predicted amino acid sequence encoded by SEQ ID NO: 175.

SEQ ID NO: 177 is the determined cDNA sequence for LST-sub5-7A.

SEQ ID NO: 178 is the determined cDNA sequence for LST-sub5-8G.

SEQ ID NO: 179 is the determined cDNA sequence for LST-sub5-8H.

SEQ ID NO: 180 is the determined cDNA sequence for LST-sub5-10B.

SEQ ID NO: 181 is the determined cDNA sequence for LST-sub5-10H.

SEQ ID NO: 182 is the determined cDNA sequence for LST-sub5-12B.

SEQ ID NO: 183 is the determined cDNA sequence for LST-sub5-11C.

SEQ ID NO: 184 is the determined cDNA sequence for LST-sub6-1c.

SEQ ID NO: 185 is the determined cDNA sequence for LST-sub6-2f.

SEQ ID NO: 186 is the determined cDNA sequence for LST-sub6-2G.

SEQ ID NO: 187 is the determined cDNA sequence for LST-sub6-4d.

SEQ ID NO: 188 is the determined cDNA sequence for LST-sub6-4e.

SEQ ID NO: 189 is the determined cDNA sequence for LST-sub6-4f.

SEQ ID NO: 190 is the determined cDNA sequence for LST-sub6-3h.

SEQ ID NO: 191 is the determined cDNA sequence for LST-sub6-5d.

SEQ ID NO: 192 is the determined cDNA sequence for LST-sub6-5h.

SEQ ID NO: 193 is the determined cDNA sequence for LST-sub6-6h.

SEQ ID NO: 194 is the determined cDNA sequence for LST-sub6-7a.

SEQ ID NO: 195 is the determined cDNA sequence for LST-sub6-8a.

SEQ ID NO: 196 is the determined cDNA sequence for LST-sub6-7d.

SEQ ID NO: 197 is the determined cDNA sequence for LST-sub6-7e.

SEQ ID NO: 198 is the determined cDNA sequence for LST-sub6-8e.

SEQ ID NO: 199 is the determined cDNA sequence for LST-sub6-7g.

SEQ ID NO: 200 is the determined cDNA sequence for LST-sub6-9f

SEQ ID NO: 201 is the determined cDNA sequence for LST-sub6-9h.

SEQ ID NO: 202 is the determined cDNA sequence for LST-sub6-11b.

SEQ ID NO: 203 is the determined cDNA sequence for LST-sub6-11c.

SEQ ID NO: 204 is the determined cDNA sequence for LST-sub6-12c.

SEQ ID NO: 205 is the determined cDNA sequence for LST-sub6-12e.

SEQ ID NO: 206 is the determined cDNA sequence for LST-sub6-12f.

SEQ ID NO: 207 is the determined cDNA sequence for LST-sub6-11g.

SEQ ID NO: 208 is the determined cDNA sequence for LST-sub6-12g.

SEQ ID NO: 209 is the determined cDNA sequence for LST-sub6-12h.

SEQ ID NO: 210 is the determined cDNA sequence for LST-sub6-II-1a.

SEQ ID NO: 211 is the determined cDNA sequence for LST-sub6-II-2b.

SEQ ID NO: 212 is the determined cDNA sequence for LST-sub6-II-2g.

SEQ ID NO: 213 is the determined cDNA sequence for LST-sub6-II-1h.

SEQ ID NO: 214 is the determined cDNA sequence for LST-sub6-II-4a.

SEQ ID NO: 215 is the determined cDNA sequence for LST-sub6-II-4b.

SEQ ID NO: 216 is the determined cDNA sequence for LST-sub6-II-3e.

SEQ ID NO: 217 is the determined cDNA sequence for LST-sub6-II-4f.

SEQ ID NO: 218 is the determined cDNA sequence for LST-sub6-II-4g.

SEQ ID NO: 219 is the determined cDNA sequence for LST-sub6-II-4h.

SEQ ID NO: 220 is the determined cDNA sequence for LST-sub6-II-5c.

SEQ ID NO: 221 is the determined cDNA sequence for LST-sub6-II-5e.

SEQ ID NO: 222 is the determined cDNA sequence for LST-sub6-II-6f.

SEQ ID NO: 223 is the determined cDNA sequence for LST-sub6-II-5g.

SEQ ID NO: 224 is the determined cDNA sequence for LST-sub6-II-6g.

SEQ ID NO: 225 is the amino acid sequence for L528S.

SEQ ID NO: 226–251 are synthetic peptides derived from L762P.

SEQ ID NO: 252 is the expressed amino acid sequence of L514S.

SEQ ID NO: 253 is the DNA sequence corresponding to SEQ ID NO: 252.

SEQ ID NO: 254 is the DNA sequence of a L762P expression construct.

DETAILED DESCRIPTION OF THE INVENTION

As noted above, the present Invention is generally directed to compositions and methods for the therapy and diagnosis of cancer, such as lung cancer. The compositions described herein may include lung tumor polypeptides, polynucleotides encoding such polypeptides, binding agents such as antibodies, antigen presenting cells (APCs) and/or immune system cells (e.g., T cells). Polypeptides of ale present invention generally comprise at least a portion (such as an immunogenic portion) of a lung tumor protein or a variant thereof. A "lung tumor protein" is a protein that is expressed in lung tumor cells at a level that is at least two fold, and preferably at least five fold, greater than the level of expression in a normal tissue, as determined using a representative assay provided herein. Certain lung tumor proteins are tumor proteins that react detectably (within an immunoassay, such as an ELISA or Western blot) with antisera of a patient afflicted with lung cancer. Polynucleotides of the subject invention generally comprise a DNA or RNA sequence that encodes all or a portion of such a polypeptide, or that is complementary to such a sequence. Antibodies are generally immune system proteins, or antigen-binding fragments thereof, that are capable of binding to a polypeptide as described above. Antigen presenting cells include dendritic cells, macrophages, monocytes, fibroblasts and B-cells that express a polypeptide as described above. T cells that may be employed within such compositions are generally T cells that are specific for a polypeptide as described above.

The present invention is based on the discovery human lung tumor proteins. Sequences of polynucleotides encoding specific tumor proteins are provided in SEQ ID NO: 1–109, 111, 113, 115–151, 153, 154, 157, 158, 160, 162–164, 167, 168, 171, 173, 175 and 177–224.

Lung Tumor Protein Polynucleotides

Any polynucleotide that encodes a lung tumor protein or a portion or other variant thereof as described herein is encompassed by the present invention. Preferred polynucleotides comprise at least 15 consecutive nucleotides, preferably at least 30 consecutive nucleotides and more preferably at least 45 consecutive nucleotides, that encode a portion of a lung tumor protein. More preferably, a polynucleotide encodes an immunogenic portion of a lung tumor protein. Polynucleotides complementary to any such sequences are also encompassed by the present invention. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes a lung tumor protein or a portion thereof) or may comprise a variant of such a sequence. Polynucleotide variants may contain one or more substitutions, additions, deletions and/or insertions such that the immunogenicity of the encoded polypeptide is not diminished, relative to a native tumor protein. The effect on the immunogenicity of the encoded polypeptide may generally be assessed as described herein. Variants preferably exhibit at least about 70% identity, more preferably at least about 80% identity and most preferably at least about 90% identity to a polynucleotide sequence that encodes a native lung tumor protein or a portion thereof. The term "variants" also encompasses homologous genes of xenogenic origin.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff. Mo. (1978) A model of evolutionary change in proteins—Matrices for detecting distant relationships. In Dayhoff, Mo. (ed.) Atlas of Protein Sequence and Structure, National Biomedical Research Foundation, Washington D.C. Vol. 5, Suppl. 3, pp. 345–358; Hein J. (1990) Unified Approach to Alignment and Phylogenes pp. 626–645 *Methods in Enzymology* vol. 183, Academic Press, Inc., San Diego, Calif.; Higgins, D. G. and Sharp, P. M. (1989) *CABIOS* 5:151–153,; Myers, E. W. and Muller W. (1988) *CABIOS* 4:11–17; Robinson, E. D. (1971) *Comb. Theor* 11:105; Santou, N. Nes, M. (1987) *Mol. Biol. Evol.* 4:406–425; Sneath, P. H. A. and Sokal, R. R. (1973) *Numerical Taxonomy—the Principles and Practice of Numerical Taxonomy*, Freeman Press, San Francisco, Calif.; Wilbur, W. J. and Lipman, D. J. (1983) *Proc. Natl. Acad, Sci. USA* 80:726–730.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e. gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native lung tumor protein (or a complementary sequence). Suitable moderately stringent conditions include prewashing in a solution of 5×SSC, 0.5% SDS, 1.0 mM EDTA (pH 8.0); hybridizing at 50° C.–65° C., 5×SSC, overnight; followed by washing twice at 65° C. for 20 minutes with each of 2×, 0.5×and 0.2×SSC containing 0.1% SDS.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRiNA and protein may, but need not have an altered structure or function. Alleles may be identified using standard techniques (such as hybridization, amplification and/or database sequence comparison).

Polynucleotides may be prepared using any of a variety of techniques. For example, a polynucleotide may be identified, as described in more detail below, by screening a microarray of cDNAs for tumor-associated expression (i.e., expression that is at least two fold greater in a lung tumor than in normal tissue, as determined using a representative assay provided herein). Such screens may be performed using a Synteni microarray (Palo Alto, Calif.) according to the manufacturer's instructions (and essentially as described by Schena et al., *Proc. Natl. Acad. Sci. USA* 93:10614–10619, 1996 and Heller et al., *Proc. Natl. Acad. Sci. USA* 94:2150–2155, 1997). Alternatively, polypeptides may be amplified from cDNA prepared from cells expressing the proteins described herein, such as lung tumor cells. Such polynucleotides may be amplified via polymerase chain reaction (PCR). For this approach, sequence-specific primers may be designed based on the sequences provided herein, and may be purchased or synthesized.

An amplified portion may be used to isolate a full length gene from a suitable library (e.g., a lung tumor cDNA library) using well known techniques. Within such techniques, a library (cDNA or genomic) is screened using one or more polynucleotide probes or primers suitable for amplification. Preferably, a library is size-selected to include larger molecules. Random primed libraries may also be preferred for identifying 5' and upstream regions of genes. Genomic libraries are preferred for obtaining introns and extending 5' sequences.

For hybridization techniques, a partial sequence may be labeled (e.g., by nick-translation or end-labeling with $^{32}$P) using well known techniques. A bacterial or bacteriophage library is then screened by hybridizing filters containing denatured bacterial colonies (or lawns containing phage plaques) with the labeled probe (see Sambrook et al., *Molecular Cloning: A Laboratory Manual*, Cold Spring Harbor Laboratories, Cold Spring Harbor, N.Y., 1989). Hybridizing colonies or plaques are selected and expanded, and the DNA is isolated for further analysis. cDNA clones may be analyzed to determine the amount of additional sequence by, for example, PCR using a primer from the partial sequence and a primer from the vector. Restriction maps and partial sequences may be generated to identify one or more overlapping clones. The complete sequence may then be determined using standard techniques, which may involve generating a series of deletion clones. The resulting overlapping sequences are then assembled into a single contiguous sequence. A full length cDNA molecule can be generated by ligating suitable fragments, using well known techniques.

Alternatively, there are numerous amplification techniques for obtaining a full length coding sequence from a partial cDNA sequence. Within such techniques, amplification is generally performed via PCR. Any of a variety of commercially available kits may be used to perform the amplification step. Primers may be designed using, for example, software well known in the art. Primers are preferably 22–30 nucleotides in length, have a GC content of at least 50% and anneal to the target sequence at temperatures of about 68° C. to 72° C. The amplified region may be sequenced as described above, and overlapping sequences assembled into a contiguous sequence.

One such amplification technique is inverse PCR (see Triglia et al., *Nucl. Acids Res.* 16:8186, 1988), which uses restriction enzymes to generate a fragment in the known region of the gene. The fragment is then circularized by intramolecular ligation and used as a template for PCR with divergent primers derived from the known region. Within an alternative approach sequences adjacent to a partial sequence may be retrieved by amplification with a primer to a linker sequence and a primer specific to a known region. The amplified sequences are typically subjected to a second round of amplification with the same linker primer and a-second primer specific to the known region. A variation on this procedure, which employs two primers that initiate extension in opposite directions from the known sequence, is described in WO 96/38591. Another such technique is known as "rapid amplification of cDNA ends" or RACE. This technique involves the use of an internal primer and an external primer, which hybridizes to a polyA region or vector sequence, to identify sequences that are 5' and 3' of a known sequence. Additional techniques include capture PCR (Lagerstrom et al., *PCR Methods Applic.* 1:111–19. 1991) and walking PCR (Parker et al., *Nucl. Acids. Res.* 19:3055–60, 1991). Other methods employing amplification may also be employed to obtain a full length cDNA sequence.

In certain instances, it is possible to obtain a full length cDNA sequence by analysis of sequences provided in an expressed sequence tag (EST) database, such as that available from GenBank. Searches for overlapping ESTs may generally be performed using well known programs (e.g., NCBI BLAST searches), and such ESTs may be used to generate a contiguous full length sequence. Full length DNA sequences may also be obtained by analysis of genomic fragments.

Certain nucleic acid sequences of cDNA molecules encoding portions of lung tumor proteins are provided in SEQ ID NO: 1–109, 111, 113, 115–151, 153, 154,157, 158, 160, 162–164, 167, 168, 171, 173, 175 and 177–224.

Polynucleotide variants may generally be prepared by any method known in the art, including chemical synthesis by, for example, solid phase phosphoramidite chemical synthesis. Modifications in a polynucleotide sequence may also be introduced using standard mutagenesis techniques, such as oligonucleotide-directed site-specific mutagenesis (see Adelman et al., *DNA* 2:183, 1983). Alternatively, RNA molecules may be generated by in vitro or in vivo transcription of DNA sequences encoding a lung tumor protein, or portion thereof, provided that the DNA is incorporated into a vector with a suitable RNA polymerase promoter (such as T7 or SP6). Certain portions may be used to prepare an encoded polypeptide, as described herein. In addition, or alternatively, a portion may be administered to a patient such that the encoded polypeptide is generated in vivo (e.g., by transfecting antigen-presenting cells, such as dendritic cells, with a cDNA construct encoding a lung tumor polypeptide, and administering the transfected cells to the patient).

A portion of a sequence complementary to a coding sequence (i.e., an antisense polynucleotide) may also be used as a probe or to modulate gene expression. cDNA constructs that can be transcribed into antisense RNA may also be introduced into cells of tissues to facilitate the production of antisense RNA. An antisense polynucleotide may be used, as described herein, to inhibit expression of a tumor protein. Antisense technology can be used to control gene expression through triple-helix formation, which compromises the ability of the double helix to open sufficiently for the binding of polymerases, transcription factors or regulatory molecules (see Gee et al., In Huber and Carr, *Molecular and Immunologic Approaches*, Futura Publishing Co. (Mt. Kisco, N.Y.; 1994)). Alternatively, an antisense molecule may be designed to hybridize with a control region of a gene (e.g., promoter, enhancer or transcription initiation site), and block transcription of the gene; or to block translation by inhibiting binding of a transcript to ribosomes.

A portion of a coding sequence, or of a complementary sequence, may also be designed as a probe or primer to detect gene expression. Probes may be labeled with a variety of reporter groups, such as radionuclides and enzymes, and are preferably at least 10 nucleotides in length, more preferably at least 20 nucleotides in length and still more preferably at least 30 nucleotides in length. Primers, as noted above, are preferably 22–30 nucleotides in length.

Any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl- methyl-, thio- and other niodified forms of adenine, cytidine, guanine, thymine and uridine.

Nucleotide sequences as described herein may be joined to a variety of other nucleotide sequences using established recombinant DNA techniques. For example, a polynucleotide may be cloned into any of a variety of cloning vectors, including plasmids, phagemids, lambda phage derivatives and cosmids. Vectors of particular interest include expression vectors, replication vectors, probe generation vectors and sequencing vectors. In general, a vector will contain an origin of replication functional in at least one organism, convenient restriction endonuclease sites and one or more selectable markers. Other elements will depend upon the desired use, and will be apparent to those of ordinary skill in the art.

Within certain embodiments, polynucleotides may be formulated so as to permit entry into a cell of a mammal, and expression therein Such formulations are particularly useful for therapeutic purposes, as described below. Those of ordinary skill in the art will appreciate that there are many ways to achieve expression of a polynucleotide in a target cell, and any suitable method may be employed. For example, a polynucleotide may be incorporated into a viral vector such as, but not limited to, adenovirus, adeno-associated virus, retrovirus, or vaccinia or other pox virus (e.g., avian pox virus). ). The polynucleotides may also be administered as naked plasmid vectors. Techniques for incorporating DNA into such vectors are well known to those of ordinary skill in the art. A retroviral vector may additionally transfer or incorporate a gene for a selectable marker (to aid in the identification or selection of transduced cells) and/or a targeting moiety, such as a gene that encodes a ligand for a receptor on a specific target cell, to render the vector target specific. Targeting may also be accomplished using an antibody, by methods known to those of ordinary skill in the art.

Other formulations for therapeutic purposes include colloidal dispersion systems, such as macromolecule complexes, nanocapsules, microspheres, beads, and lipid-based systems including oil-in-water emulsions, micelles,

Lung Tumor Polypeptides

Within the context of the present invention, polypeptides may comprise at least an immunogenic portion of a lung tumor protein or a variant thereof, as described herein. As noted above, a "lung tumor protein" is a protein that is expressed by lung tumor cells. Proteins that are lung tumor proteins also react detectably within an immunoassay (such as an ELISA) with antisera from a patient with lung cancer. Polypeptides as described herein may be of any length. Additional sequences derived from the native protein and/or heterologous sequences may be present, and such sequences may (but need not) possess further immunogenic or antigenic properties.

An "immunogenic portion," as used herein is a portion of a protein that is recognized (i.e., specifically bound) by a B-cell and/or T-cell surface antigen receptor. Such immunogenic portions generally comprise at least 5 amino acid residues, more preferably at least 10, and still more preferably at least 20 amino acid residues of a lung tumor protein or a variant thereof. Certain preferred immunogenic portions include peptides in which an N-terminal leader sequence and/or transmembrane domain have been deleted. Other preferred immunogenic portions may contain a small N- and/or C-terminal deletion (e.g., 1–30 amino acids, preferably 5–15 amino acids), relative to the mature protein.

Immunogenic portions may generally be identified using well known techniques, such as those summarized in Paul, *Fundamental Immunology*, 3rd ed., 243–247 (Raven Press, 1993) and references cited therein. Such techniques include screening polypeptides for the ability to react with antigen-specific antibodies, antisera and/or T-cell lines or clones. As used herein, antisera and antibodies are "antigen-specific" if they specifically bind to an antigen (i.e., they react with the protein in an ELISA or other immunoassay, and do not react detectably with unrelated proteins). Such antisera and antibodies may be prepared as described herein, and using well known techniques. An immunogenic portion of a native lung tumor protein is a portion that reacts with such antisera and/or T-cells at a level that is not substantially less than the reactivity of the full length polypeptide (e.g., in an ELISA and/or T-cell reactivity assay). Such immunogenic portions may react within such assays at a level that is similar to or greater than the reactivity of the full length polypeptide. Such screens may generally be performed using methods well known to those of ordinary skill in the art, such as those described in Harlow and Lane, *Antibodies: A Laboratory Manual*, Cold Spring Harbor Laboratory, 1988. For example, a polypeptide may be immobilized on a solid support and contacted with patient sera to allow binding of antibodies within the sera to the immobilized polypeptide. Unbound sera may then be removed and bound antibodies detected using, for example, $^{125}$I-labeled Protein A.

As noted above, a composition may comprise a variant of a native lung tumor protein. A polypeptide "variant," as used herein, is a polypeptide that differs from a native lung tumor protein in one or more substitutions, deletions, additions and/or insertions, such that the immunogenicity of the polypeptide is not substantially diminished. In other words, the ability of a variant to react with antigen-specific antisera may be enhanced or unchanged, relative to the native protein, or may be diminished by less than 50%, and preferably less than 20%, relative to the native protein. Such variants may generally be identified by modifying one of the above polypeptide sequences and evaluating the reactivity of the modified polypeptide with antigen-specific antibodies or antisera as described herein. Preferred variants include those in which one or more portions, such as an N-terminal leader sequence or transmembrane domain, have been removed. Other preferred variants include variants in which a small portion (e.g., 1–30 amino acids, preferably 5–15 amino acids) has been removed from the N- and/or C-terminal of the mature protein.

Polypeptide variants preferably exhibit at least about 70%, more preferably at least about 90% and most preferably at least about 95% identity (determined as described above) to the identified polypeptides.

Preferably, a variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and zlutamic acid, positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gin, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

As noted above, polypeptides may comprise a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

Polypeptides may be prepared using any of a variety of well known techniques. Recombinant polypeptides encoded by DNA sequences as described above may be readily prepared from the DNA sequences using any of a variety of expression vectors known to those of ordinary skill in the art. Expression may be achieved in any appropriate host cell that has been transformed or transfected with an expression vector containing a DNA molecule that encodes a recombinant polypeptide. Suitable host cells include prokaryotes, yeast, higher eukaryotic and plant cells. Preferably, the host cells employed are *E. coli*, yeast or a mammalian cell line such as COS or CHO. Supernatants from suitable host/vector systems which secrete recombinant protein or polypeptide into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant polypeptide.

Portions and other variants having fewer than about 100 amino acids, and generally fewer than about 50 amino acids, may also be generated by synthetic means, using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is commercially available from suppliers such as Perkin Elmer/Applied BioSystems Division (Foster City, Calif.), and may be operated according to the manufacturer's instructions.

Within certain specific embodiments, a polypeptide may be a fusion protein that comprises multiple polypeptides as described herein, or that comprises at least one polypeptide as described herein and an unrelated sequence, such as a known tumor protein. A fusion partner may, for example, assist in providing T helper epitopes (an immunological fusion partner), preferably T helper epitopes recognized by humans, or may assist in expressing the protein (an expression enhancer) at higher yields than the native recombinant protein. Certain preferred fusion partners are both immunological and expression enhancing fusion partners. Other fusion partners may be selected so as to increase the solubility of the protein or to enable the protein to be targeted to desired intracellular compartments. Still further fusion partners include affinity tags, which facilitate purification of the protein.

Fusion proteins may generally be prepared using standard techniques, including chemical conjugation. Preferably, a fusion protein is expressed as a recombinant protein, allowing the production of increased levels, relative to a non-fused protein, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and the second polypeptide components by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended confirmation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:3946, 1985; Murphy et al., *Proc. Natl. Acad. Sci. USA* 83:8258–8262, 1986; U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

Fusion proteins are also provided that comprise a polypeptide of the present invention together with an unrelated immunogenic protein. Preferably the immunogenic protein is capable of eliciting a recall response. Examples of such proteins include tetanus, tuberculosis and hepatitis proteins (see, for example, Stoute et al. *New Engl. J. Med.*, 336:86–91, 1997).

Within preferred embodiments, an immunological fusion partner is derived from protein D, a surface protein of the gram-negative bacterium Haemophilus influenza B (WO 91/18926). Preferably, a protein D derivative comprises approximately the first third of the protein (e.g., the first N-terminal 100–110 amino acids), and a protein D derivative may be lipidated. Within certain preferred embodiments, the first 109 residues of a Lipoprotein D fusion partner is included on the N-terminus to provide the polypeptide with additional exogenous T-cell epitopes and to increase the expression level in *E. coli* (thus functioning as an expression enhancer). The lipid tail ensures optimal presentation of the antigen to antigen presenting cells. Other fusion partners include the non-structural protein from influenzae virus, NSI (hemaglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; *Gene* 43:265–292, 1986). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see *Biotechnology* 10:795–798, 1992). Within a preferred embodiment, a repeat portion of LYTA may be incorporated into a fusion protein. A repeat portion is found in the C-terminal region starting at residue 178. A particularly preferred repeat portion incorporates residues 188–305.

In general, polypeptides (including fusion proteins) and polynucleotides as described herein are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

Binding Agents

The present invention further provides agents, such as antibodies and antigen-binding fragments thereof, that specifically bind to a lung tumor protein. As used herein, an antibody, or antigen-binding fragment thereof, is said to "specifically bind" to a lung tumor protein if it reacts at a detectable level (within, for example, an ELISA) with a lung tumor protein, and does not react detectably with unrelated proteins under similar conditions. As used herein, "binding" refers to a noncovalent association between two separate molecules such that a complex is formed. The ability to bind may be evaluated by, for example, determining a binding constant for the formation of the complex. The binding constant is the value obtained when the concentration of the complex is divided by the product of the component concentrations. In general, two compounds are said to "bind," in the context of the present invention, when the binding constant for complex formation exceeds about $10^3$ L/mol. The binding constant may be determined using methods well known in the art.

Binding agents may be further capable of differentiating between patients with and without a cancer, such as lung cancer, using the representative assays provided herein. In other words, antibodies or other binding agents that bind to a lung tumor protein will generate a signal indicating the presence of a cancer in at least about 20% of patients with the disease, and will generate a negative signal indicating the absence of the disease in at least about 90% of individuals without the cancer. To determine whether a binding agent satisfies this requirement, biological samples (e.g., blood, sera, sputum urine and/or tumor biopsies) from patients with and without a cancer (as determined using standard clinical tests) may be assayed as described herein for the presence of polypeptides that bind to the binding agent. It will be apparent that a statistically significant number of samples with and without the disease should be assayed. Each binding agent should satisfy the above criteria; however, those of ordinary skill in the art will recognize that binding agents may be used in combination to improve sensitivity.

Any agent that satisfies the above requirements may be a binding agent. For example, a binding agent may be a ribosome, with or without a peptide component, an RNA molecule or a polypeptide. In a preferred embodiment, a binding agent is an antibody or an antigen-binding fragment thereof. Antibodies may be prepared by any of a variety of techniques known to those of ordinary skill in the art. See, e.g., Harlow and Lane, *Atitibodies: A Laboratory Manual*, Cold Spring, Harbor Laboratory, 1988. In general, antibodies can be produced by cell culture techniques, including the generation of monoclonal antibodies as described herein or via transfection of antibody genes into suitable bacterial or mammalian cell hosts, in order to allow for the production of recombinant antibodies. In one technique, an immunogen comprising the polypeptide is initially injected into any of a wide variety of mammals (e.g., mice, rats, rabbits, sheep or goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for an antigenic polypeptide of interest may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses FLST (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

Within certain embodiments, the use of antigen-binding fragments of antibodies may be preferred. Such fragments include Fab fragments, which may be prepared using standard techniques. Briefly, immunoglobulins may be purified from rabbit serum by affinity chromatography on Protein A bead columns (Harlow and Lane, *Antibodies: A Laboratory Manual*, Cold Spring Harbor Laboratory, 1988) and digested by papain to yield Fab and Fc fragments. The Fab and Fc fragments may be separated by affinity chromatography on protein A bead columns.

Monoclonal antibodies of the present invention may be coupled to one or more therapeutic agents. Suitable agents in this regard include radionuclides, differentiation inducers, drugs, toxins, and derivatives thereof Preferred radionuclides include $^{90}Y$, $^{123}I$, $^{125}I$, $^{131}I$, $^{186}Re$, $^{188}Re$, $^{211}At$, and $^{212}Bi$. Preferred drugs include methotrexate, and pyrimidin and purine analogs. Preferred differentiation inducers include phorbol esters and butyric acid. Preferred toxins include ricin, abrin, diptheria toxin, cholera toxin, gelonin, Pseudomonas exotoxin, Shigella toxin, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers which provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a lipotome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis.

A variety of routes of administration for the antibodies and immunoconjugates may be used. Typically, administration will be intravenous, intramuscular, subcutaneous or in the bed of a resected tumor. It will be evident that the precise dose of the antibody/immunoconjugate will vary depending upon the antibody used, the antigen density on the tumor, and the rate of clearance of the antibody.

T Cells

Immunotherapeutic compositions may also, or alternatively, comprise T cells specific for a lung tumor protein. Such cells may generally be prepared in vitro or ex vivo, using standard procedures. For example, T cells may be isolated from bone marrow, peripheral blood, or a fraction of bone marrow or peripheral blood of a patient, using a commercially available cell separation system, such as the Isolex™ System, available from Nexell Therapeutics, Inc. Irvine, Calif. (see also U.S. Pat. No. 5,240,856; U.S. Pat. No. 5,215,926; WO 89/06280; WO 91/16116 and WO 92/07243). Alternatively, T cells may be derived from related or unrelated humans, non-human mammals, cell lines or cultures.

T cells may be stimulated with a lung tumor polypeptide, polynucleotide encoding a lung tumor polypeptide and/or an antigen presenting cell (APC) that expresses such a polypeptide. Such stimulation is performed Linder conditions and for a time sufficient to permit the generation of T cells that are specific for the polypeptide. Preferably, a lung tumor polypeptide or polynucleotide is present within a delivery vehicle, such as a microsphere, to facilitate the generation of specific T cells.

T cells are considered to be specific for a lung tumor polypeptide if the T cells specifically proliferate, secrete cytokines or kill target cells coated with the polypeptide or expressing a gene encoding the polypeptide. T cell specificity may be evaluated using any of a variety of standard techniques. For example, within a chromium release assay or proliferation assay, a stimulation index of more than two fold increase in lysis and/or proliferation, compared to negative controls, indicates T cell specificity. Such assays may be performed, for example, as described in Chen et al., Cancer Res. 54:1065–1070, 1994. Alternatively, detection of the proliferation of T cells may be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated into DNA). Contact with a lung tumor polypeptide (100 ng/ml–100 $\mu$g/ml, preferably 200 ng/ml–25 $\mu$g/ml) for 3–7 days should result in at least a two fold increase in proliferation of the T cells. Contact as described above for 2–3 hours should result in activation of the T cells, as measured using standard cytokine assays in which a two fold increase in the level of cytokine release (e.g. TNF or IFN-$\gamma$) is indicative of T cell activation (see Coligan et al., Current Protocols in Immunology, vol. 1, Wiley Interscience (Greene 1998)). T cells that have been activated in response to a lung tumor polypeptide, polynucleotide or polypeptide-expressing APC may be $CD4^+$ and/or $CD8^+$. Lung tumor protein-specific T cells may be expanded using standard techniques. Within preferred embodiments, the T cells are derived from either a patient or a related, or unrelated, donor and are administered to the patient following stimulation and expansion.

For therapeutic purposes, $CD4^+$ or $CD8^+$ T cells that proliferate in response to a lung tumor polypeptide, polynucleotide or APC can be expanded in number either in vitro or in vivo. Proliferation of such T cells in vitro may be accomplished in a variety of ways. For example, the T cells can be re-exposed to a lung tumor polypeptide, or a short peptide corresponding to an immunogenic portion of such a polypeptide, with or without the addition of T cell growth factors, such as interleukin-2, and/or stimulator cells that synthesize a lung tumor polypeptide. Alternatively, one or more T cells that proliferate in the presence of a lung tumor protein can be expanded in number by cloning. Methods for cloning cells are well known in the art, and include limiting dilution.

Pharmaceutical Compositions and Vaccines

Within certain aspects, polypeptides, polynucleotides, T cells and/or binding agents disclosed herein may be incorporated into pharmaceutical compositions or immunogenic compositions (i.e., vaccines). Pharmaceutical compositions comprise one or more such compounds and a physiologically acceptable carrier. Vaccines may comprise one or more such compounds and an immunostimulant. An immunostimulant may be any substance that enhances or potentiates an immune response to an exogenous antigen. Examples of immunostimulants include adjuvants, biodegradable microspheres (e.g., polylactic galactide) and liposomes (into which the compound is incorporated; see e.g., Fullerton, U.S. Pat. No. 4,235,877). Vaccine preparation is generally described in, for example, M. F. Powell and M. J. Newman, eds., "Vaccine Design (the subunit and adjuvant approach)," Plenum Press (NY, 1995). Pharmaceutical compositions and vaccines within the scope of the present invention may also contain other compounds, which may be biologically active or inactive. For example, one or more immunogenic portions of other tumor antigens may be present, either incorporated into a fusion polypeptide or as a separate compound, within the composition or vaccine.

A pharmaceutical composition or vaccine may contain DNA encoding one or more of the polypeptides as described above, such that the polypeptide is generated in situ. As noted above, the DNA may be present within any of a variety of delivery systems known to those of ordinary skill in the art, including nucleic acid expression systems, bacteria and viral expression systems. Numerous gene delivery techniques are well known in the art, such as those described by Rolland, *Crit. Rev. Therap. Drug Carrier Systems* 15:143–198, 1998, and references cited therein. Appropriate nucleic acid expression systems contain the necessary DNA sequences for expression in the patient (such as a suitable promoter and terminating signal). Bacterial delivery systems involve the administration of a bacterium (such as Bacillus-Calmette-Guerrin) that expresses an immunogenic portion of the polypeptide on its cell surface or secretes such an epitope. In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., *Proc. Natl. Acad. Sci. USA* 86:317–321, 1989; Flexner et al., *Ann. N.Y. Acad. Sci.* 569:86–103, 1989; Flexner et al., *Vaccine* 8:17–21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *Biotechniques* 6:616–627, 1988; Rosenfeld et al., *Science* 252:431–434, 1991; Kolls et al., *Proc. Natl. Acad Sci. USA* 91:215–219, 1994; Kass-Eisler et al., *Proc. Natl. Acad. Sci. USA* 90:11498–11502, 1993; Guzman et al., *Circuilation* 88:2838–2848, 1993; and Guzman et al., *Cir. Res.* 73:1202–1207, 1993. Techniques for incorporating DNA into such expression systems are well known to those of ordinary skill in the art. The DNA may also be "naked," as described, for example, in Ulmer et al., *Science* 259:1745–1749, 1993 and reviewed by Cohen, *Science* 259:1691–1692, 1993. The uptake of naked DNA may be increased by coating the DNA onto biodegradable beads, which are efficiently transported into the cells.

While any suitable carrier known to those of ordinary skill in the art may be employed in the pharmaceutical compositions of this invention, the type of carrier will vary depending on the mode of administration. Compositions of the present invention may be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268 and 5,075,109.

Such compositions may also comprise buffers (e.g., neutral buffered saline or phosphate buffered saline), carbohydrates (e.g, glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Alteniatively, compositions of the present invention may be formulated as a lyophilizate. Compounds may also be encapsulated within liposomes using well known technology.

Any of a variety of immunostimulants may be employed in the vaccines of this invention. For example, an adjuvant may be included. Most adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF or interleukin-2, -7, or -12, may also be used as adjuvants.

Within the vaccines provided herein, the adjuvant composition is preferably designed to induce an immune response predominantly of the Th1 type. High levels of Th1-type cytokines (e.g., IFN-γ, TNFα, IL-2 and IL-12) tend to favor the induction of cell mediated immune responses to an administered antigen. In contrast, high levels of Th2-type cytokines (e.g., IL4, IL-5, IL-6 and IL-10) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be Feadily assessed using standard assays. For a review of the families of cytokines, see Mosmann and Coffman, *Ann. Rev. Immunol.* 7:145–173, 1989.

Preferred adjuvants for use in eliciting a predominantly Th1-type response include, for example, a combination of monophosphoryl lipid A, preferably 3-de-O-acylated monophosphoryl lipid A (3D-MPL), together with an aluminum salt. MPL adjuvants are available from Ribi ImmunoChem Research Inc. (Hamilton, Mont.) (see U.S. Pat. Nos. 4,436,727; 4,877,611; 4,866,034 and 4,912,094). CpG-containing oligonucleotides (in which the CpG dinucleotide is unmethylated) also induce a predominantly Th1 response. Such oligonucleotides are well known and are described, for example, in WO 96/02555. Another preferred adjuvant is a saponin, preferably QS21, which may be used alone or in combination with other adjuvants. For example, an enhanced system involves the combination of a monophosphoryl lipid A and saponin derivative, such as the combination of QS21 and 3D-MPL as described in WO 94/00153, or a less reactogenic composition where the QS21 is quenched with cholesterol, as described in WO 96/33739. Other preferred formulations comprises an oil-in-water emulsion and tocopherol. A particularly potent adjuvant formulation involving QS21, 3D-MPL and tocopherol in an oil-in-water emulsion is described in WO 95/17210. Any vaccine provided herein may be prepared using well known methods that result in a combination of antigen, immune response enhancer and a suitable carrier or excipient.

The compositions described herein may be administered as part of a sustained release formulation (i.e., a formulation such as a capsule, sponge or gel (composed of polysaccharides, for example) that effects a slow release of compound following administration). Such formulations may generally be prepared using well known technology and administered by, for example, oral, rectal or subcutaneous implantation, or by implantation at the desired target site. Sustained-release formulations may contain a polypeptide, polynucleotide or antibody dispersed in a carrier matrix and/or contained within a reservoir surrounded by a rate controlling membrane. Carriers for use within such formulations are biocompatible, and may also be biodegradable, preferably the formulation provides a relatively constant level of active component release. The amount of active compound contained within a sustained release formulation depends upon the site of implantation, the rate and expected duration of release and the nature of the condition to be treated or prevented.

Any of a variety of delivery vehicles may be employed within pharmaceutical compositions and vaccines to facilitate production of an antigen-specific immune response that targets tumor cells. Delivery vehicles include antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-tumor effects per se and/or to be immunologically compatible with the receiver (i.e., matched HLA haplotype). APCs may generally be isolated from any of a variety of biological fluids and organs, including tumor and peritumoral tissues, and may be autologous, allergenic, syngeneic or xenogenic cells.

Certain preferred embodiments of the present invention use dendritic cells or progenitors thereof as antigen-presenting cells. Dendritic cells are highly potent APCs (Banchereau and Steinman, *Nature* 392:245–251, 1998) and have been shown to be effective as a physiological adjuvant for eliciting prophylactic or therapeutic antitumor immunity (see Timmerman and Levy, *Ann. Rev. Med.* 50:507–529, 1999). In general, dendritic cells may be identified based on their typical shape (stellate in situ, with marked cytoplasmic processes (dendrites) visible in vitro), their ability to take up, process and present antigens with high efficiency, and their ability to activate naive T cell responses. Dendritic cells may, of course, be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within a vaccine (see Zitvogel et al., *Nature Med.* 4:,94–600, 1998).

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce differentiation, maturation and proliferation of dendritic cells.

Dendritic cells are conveniently categorized as "immature" and "mature" cells, which allows a simple way to discriminate between two well characterized phenotypes. However, this nomenclature should not be construed to exclude all possible intermediate stages of differentiation. Immature dendritic cells are characterized as APC with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e.g., CD54 and CD11) and costimulatory molecules (e.g., CD40, CD80, CD86 and 4-1BB).

APCs may generally be transfected with a polynucleotide encoding a lung tumor protein (or portion or other variant thereof) such that the lung tumor polypeptide, or an immunogenic portion thereof, is expressed on the cell surface. Such transfection may take place ex vivo, and a composition or vaccine comprising such transfected cells may then be used for therapeutic purposes, as described herein. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., *Immunology and cell Biology* 75:456460, 1997. Antigen loading of dendritic cells may be achieved by incubating dendritic cells or progenitor cells with the lung tumor polypeptide, DNA (naked or within a plasmid vector) or RNA; or with antigen-expressing recombinant bacterium or viruses (e.g., vaccinia, fowipox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide.

Cancer Therapy

In further aspects of the present invention, the compositions described herein may be used for immunotherapy of cancer, such as lung cancer. Within such methods, pharmaceutical compositions and vaccines are typically administered to a patient. As used herein, a "patient" refers to any warm-blooded animal, preferably a human. A patient may or may not be afflicted with cancer. Accordingly, the above pharmaceutical compositions and vaccines may be used to prevent the development of a cancer or to treat a patient afflicted with a cancer. A cancer may be diagnosed using criteria generally accepted in the art, including the presence of a malignant tumor. Pharmaceutical compositions and vaccines may be administered either prior to or following surgical removal of primary tumors and/or treatment such as administration of radiotherapy or, conventional chemotherapeutic drugs.

Within certain embodiments, immunotherapy may be active immunotherapy, in which treatment relies on the in vivo stimulation of-the endogenous host immune system to react against tumors with the administration of immune response-modifying agents (such as polypeptides and polynucleotides disclosed herein).

Within other embodiments, immunotherapy may be passive immunotherapy, in which treatment involves the delivery of agents with established tumor-immune reactivity (such as effector cells or antibodies) that can directly or indirectly mediate antitumor effects and does not necessarily depend on an intact host immune system. Examples of effector cells include T cells as discussed above, T lymphocytes (such as $CD8^+$ cytotoxic T lymphocytes and $CD4^+$ T-helper tumor-infiltrating lymphocytes), killer cells (such as Natural Killer cells and lymphokine-activated killer cells), B cells and antigen-presenting cells (such as dendritic cells and macrophages) expressing a polypeptide provided herein. T cell receptors and antibody receptors specific for the polypeptides recited herein may be cloned, expressed and transferred into other vectors or effector cells for adoptive immunotherapy. The polypeptides provided herein may also be used to generate antibodies or anti-idiotypic antibodies (as described above and in U.S. Pat. No. 4,918,164) for passive immunotherapy.

Effector cells may generally be obtained in sufficient quantities for adoptive immunotherapy by growth in vitro, as described herein. Culture conditions for expanding single antigen-specific effector cells to several billion in number with retention of antigen recognition in vivo are well known in the art. Such in vitro culture conditions typically use intermittent stimulation with antigen, often in the presence of cytokines (such as IL-2) and non-dividing feeder cells. As noted above, immunoreactive polypeptides as provided herein may be used to rapidly expand antigen-specific T cell cultures in order to generate a sufficient number of cells for immunotherapy. In particular, antigen-presenting cells, such as dendritic, macrophage, monocyte, fibroblast and/or B cells, may be pulsed with immunoreactive polypeptides or transfected with one or more polynucleotides using standard techniques well known in the art. For example, antigen-presenting cells can be transfected with a polynucleotide having a promoter appropriate for increasing expression in a recombinant virus or other expression system. Cultured effector cells for use in therapy must be able to grow and distribute widely, and to survive long term in vivo. Studies have shown that cultured effector cells can be induced to grow in vivo and to survive long term in substantial numbers by repeated stimulation with antigen supplemented with IL-2 (see, for example, Cheever et al., *Immunological Reviews* 157:177, 1997).

Alternatively, a vector expressing a polypeptide recited herein may be introduced into antigen presenting cells taken from a patient and clonally propagated ex vivo for transplant back into the same patient. Transfected cells may be reintroduced into the patient using any means known in the art, preferably in sterile form by intravenous, intracavitary, intraperitoneal or intratumor administration.

Routes and frequency of administration of the therapeutic compositions disclosed herein, as well as dosage, will vary from individual to individual, and may be readily established using standard techniques. In general, the pharmaceutical compositions and vaccines may be administered by injection (e.g., intracutaneous, intramuscular, intravenous or subcutaneous), intranasally (e.g., by aspiration) or orally. Preferably, between 1 and 10 doses may be administered over a 52 week period. Preferably, 6 doses are administered, at intervals of 1 month, and booster vaccinations may be given periodically thereafter. Alternate protocols may be appropriate for individual patients. A suitable dose is an amount of a compound that, when administered as described above, is capable of promoting an anti-tumor immune response, and is at least 10–50% above the basal (i.e., untreated) level. Such response can be monitored by measuring the anti-tumor antibodies in a patient or by vaccine-dependent generation of cytolytic effector cells capable of killing the patient's tumor cells in vitro. Such vaccines should also be capable of causing an immune response that leads to an improved clinical outcome (e.g., more frequent remissions, complete or partial or longer disease-free survival) in vaccinated patients as compared to non-vaccinated patients. In general, for pharmaceutical compositions and vaccines comprising one or more polypeptides, the amount of each polypeptide present in a dose ranges from about 25 $\mu$g to 5 mg per kg of host. Suitable dose sizes will vary with the size of the patient, but will typically range from about 0.1 mL to about 5 mL.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. Increases in preexisting immune responses to a lung tumor protein generally correlate with an improved clinical outcome. Such immune responses may generally be evaluated using standard proliferation, cylotoxicity or cytokine assays, which may be performed using samples obtained from a patient before and after treatment.

Methods for Detecting Cancer

In general, a cancer may be detected in a patient based on the presence of one or more lung tumor proteins and/or polynucleotides encoding such proteins in a biological sample (for example, blood, sera, sputum urine and/or tumor biopsies) obtained from the patient. In other words, such proteins may be used as markers to indicate the presence or absence of a cancer such as lung cancer. In addition, such proteins may be useful for the detection of other cancers. The binding agents provided herein generally permit detection of the level of antigen that binds to the agent in the biological sample. Polynucleotide primers and probes may be used to detect the level of mRNA encoding a tumor protein, which is also indicative of the presence or absence of a cancer. In general, a lung tumor sequence should be present at a level that is at least three fold higher in tumor tissue than in normal tissue There are a variety of assay formats known to those of ordinary skill in the art for using a binding agent to detect polypeptide markers in a sample. See, e.g., Harlow and Lane, *Antibodies: A Laboratory Manual*, Cold Spring Harbor Laboratory, 1988. In general, the presence or absence of a cancer in a patient may be determined by (a) contacting a biological sample obtained from a patient with a binding agent; (b) detecting in the sample a level of polypeptide that binds to the binding agent; and (c) comparing the level of polypeptide with a predetermined cut-off value.

In a preferred embodiment, the assay involves the use of binding agent immobilized on a solid support to bind to and remove the polypeptide from the remainder of the sample. The bound polypeptide may then be detected using a detection reagent that contains a reporter group and specifically binds to the binding agent/polypeptide complex. Such detection reagents may comprise, for example, a binding agent that specifically binds to the polypeptide or an antibody or other agent that specifically binds to the binding agent, such as an anti-immunoglobulin, protein G, protein A or a lectin. Alternatively, a competitive assay may be utilized, in which a polypeptide is labeled with a reporter group and allowed to bind to the immobilized binding agent after incubation of the binding agent with the sample. The extent to which components of the sample inhibit the binding of the labeled polypeptide to the binding agent is indicative of the reactivity of the sample with the immobilized binding agent. Suitable polypeptides for use within such assays include full length lung tumor proteins and portions thereof to which the binding agent binds, as described above.

The solid support may be any material known to those of ordinary skill in the art to which the tumor protein may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The binding agent may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the agent and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of binding agent ranging from about 10 ng to about 10 µg, and preferably about 100 ng to about 1 µg, is sufficient to immobilize an adequate amount of binding agent.

Covalent attachment of binding agent to a solid support may generally be achieved by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook, 1991, at A12–A13).

In certain embodiments, the assay is a two-antibody sandwich assay. This assay may be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a detection reagent (preferably a second antibody capable of binding to a different site on the polypeptide) containing a reporter group is added. The amount of detection reagent that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is a period of time that is sufficient to detect the presence of polypeptide within a sample obtained from an individual with lung cancer. Preferably, the contact time is sufficient to achieve a level of binding that is at least about 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. The second antibody, which contains a reporter group, may then be added to the solid support. Preferred reporter groups include those groups recited above.

The detection reagent is then incubated with the immobilized antibody-polypeptide complex for an amount of time sufficient to detect the bound polypeptide. An appropriate amount of time may generally be determined by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of a cancer, such as lung cancer, the signal detected from the reporter group that remains bound to the solid support is generally compared to a signal that corresponds to a predetermined cut-off value. In one preferred embodiment, the cut-off value for the detection of a cancer is the average mean signal obtained when the immobilized antibody is incubated with samples from patients without the cancer. In general, a sample generating a signal that is three standard deviations above the predetermined cut-off value is considered positive for the cancer. In an alternate preferred embodiment, the cut-off value is determined using a Receiver Operator Curve, according to the method of Sackett et al., *Clinical Epidemiology: A Basic Science for Clinical Medicine*, Little Brown and Co., 1985, p. 106–7. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for a cancer.

In a related embodiment, the assay is performed in a flow-through or strip test format, wherein the binding agent is immobilized on a membrane, such as nitrocellulose. In the flow-through test, polypeptides within the sample bind to the immobilized binding agent as the sample passes through the membrane. A second, labeled binding agent then binds to the binding agent-polypeptide complex as a solution containing the second binding agent flows through the membrane. The detection of bound second binding agent may then be performed as described above. In the strip test format, one end of the membrane to which binding agent is bound is immersed in a solution containing the sample. The sample migrates along the membrane through a region containing second binding agent and to the area of immobilized binding agent. Concentration of second binding agent at the area of immobilized antibody indicates the presence of a cancer. Typically, the concentration of second binding agent at that site generates a pattern, such as a line, that can be read visually. The absence of such a pattern indicates a negative result. In general, the amount of binding agent immobilized on the membrane is selected to generate a visually discernible pattern when the biological sample contains a level of polypeptide that would be sufficient to generate a positive signal in the two-antibody sandwich assay, in the format discussed above. Preferred binding agents for use in such assays are antibodies and antigen-binding fragments thereof. Preferably, the amount of antibody immobilized on the membrane ranges from about 25 ng to about 1 $\mu$g, and more preferably from about 50 ng to about 500 ng. Such tests can typically be performed with a very small amount of biological sample.

Of course, numerous other assay protocols exist that are suitable for use with the tumor proteins or binding agents of the present invention. The above descriptions are intended to be exemplary only. For example, it will be apparent to those of ordinary skill in the art that the above protocols may be readily modified to use lung tumor polypeptides to detect antibodies that bind to such polypeptides in a biological sample. The detection of such lung tunor protein specific antibodies may correlate with the presence of a cancer.

A cancer may also, or alternatively, be detected based on the presence of T cells that specifically react with a lung tumor protein in a biological sample. Within certain methods, a biological sample comprising $CD4^+$ and/or $CD8^+$ T cells isolated from a patient is incubated with a lung tumor polypeptide, a polynucleotide encoding such a polypeptide and/or an APC that expresses at least an immunogenic portion of such a polypeptide, and the presence or absence of specific activation of the T cells is detected. Suitable biological samples include, but are not limited to, isolated T cells. For example, T cells may be isolated from a patient by routine techniques (such as by Ficoll/Hypaque density gradient centrifugation of peripheral blood lymphocytes). T cells may be incubated in vitro for 2–9 days (typically 4 days) at 37° C. with polypeptide (e.g., 5–25 $\mu$g/ml). It may be desirable to incubate another aliquot of a T cell sample in the absence of lung tumor polypeptide to serve as a control. For $CD4^+$ T cells, activation is preferably detected by evaluating proliferation of the T cells. For $CD8^+$ T cells, activation is preferably detected by evaluating cytolytic activity. A level of proliferation that is at least two fold greater and/or a level of cytolytic activity that is at least 20% greater than in disease-free patients indicates the presence of a cancer in the patient.

As noted above, a cancer may also, or alternatively, be detected based on the level of mRNA encoding a lung tumor protein in a biological sample. For example, at least two oligonucleotide primers may be employed in a polymerase chain reaction (PCR) based assay to amplify a portion of a lung tumor cDNA derived from a biological sample, wherein at least one of the oligonucleotide primers is specific for (i.e., hybridizes to) a polynucleotide encoding the lung tumor protein. The amplified cDNA is then separated and detected using techniques well known in the art, such as gel electrophoresis. Similarly, oligonucleotide probes that specifically hybridize to a polynucleotide encoding a lung tumor protein may be used in a hybridization assay to detect the presence of polynucleotide encoding the tumor protein in a biological sample.

To permit hybridization under assay conditions, oligonucleotide primers and probes should comprise an oligonucleotide sequence that has at least about 60%, preferably at least about 75% and more preferably at least about 90%, identity to a portion of a polynucleotide encoding a lung tumor protein that is at least 10 nucleotides, and preferably at least 20 nucleotides, in length. Preferably, oligonucleotide primers and/or probes will hybridize to a polynucleotide encoding a polypeptide disclosed herein under moderately stringent conditions, as defined above. Oligonucleotide primers and/or probes which may be usefully employed in the diagnostic methods described herein preferably are at least 1040 nucleotides in length. In a preferred embodiment, the oligonucleotide primers comprise at least 10 contiguous nucleotides, more preferably at least 15 contiguous nucleotides, of a DNA molecule having a sequence recited in SEQ ID NO: 1–109, 111, 113, 115–151, 153, 154, 157, 158, 160, 162–164, 167, 168, 171, 173, 175 and 177–224. Techniques for both PCR based assays and hybridization assays are well known in the art (see, for example, Mullis et al., *Cold Spring Harbor Symp. Quant. Biol.*, 51:263, 1987; Erlich ed., *PCR Technolog*, Stockton Press, NY, 1989).

One preferred assay employs RT-PCR, in which PCR is applied in conjunction with reverse transcription. Typically, RNA is extracted from a biological sample, such as biopsy tissue, and is reverse transcribed to produce cDNA molecules. PCR amplification using at least one specific primer generates a cDNA molecule, which may be separated and visualized using, for example, gel electrophoresis. Amplification may be performed on biological samples taken from a test patient and from an individual who is not afflicted with a cancer. The amplification reaction may be performed on several dilutions of cDNA spanning two orders of magnitude. A two-fold or greater increase in expression in several dilutions of the test patient sample as compared to the same dilutions of the non-cancerous sample is typically considered positive.

In another embodiment, the disclosed compositions may be used as markers for the progression of cancer. In this embodiment, assays as described above for the diagnosis of a cancer may be performed over time, and the change in the level of reactive polypeptide(s) or polynucleotide evaluated. For example, the assays may be performed every 24–72 hours for a period of 6 months to 1 year, and thereafter performed as needed. In general, a cancer is progressing in those patients in whom the level of polypeptide or polynucleotide detected increases over time. In contrast, the cancer is not progressing when the level of reactive polypeptide or polynucleotide either remains constant or decreases with time.

Certain in vivo diagnostic assays may be performed directly on a tumor. One such assay involves contacting tumor cells with a binding agent. The bound binding agent may then be detected directly or indirectly via a reporter group. Such binding agents may also be used in histological applications. Alternatively, polynucleotide probes may be used within such applications.

As noted above, to improve sensitivity, multiple lung tumor protein markers may be assayed within a given sample. It will be apparent that binding agents specific for different proteins provided herein may be combined within a single assay. Further, multiple primers or probes may be used concurrently. The selection of tumor protein markers may be based on routine experiments to determine combinations that results in optimal sensitivity. In addition, or alternatively, assays for tumor proteins provided herein may be combined with assays for other known tumor antigens.

Diagnostic Kits

The present invention further provides kits for use within any of the above diagnostic methods. Such kits typically comprise two or more components necessary for performing a diagnostic assay. Components may be compounds, reagents, containers and/or equipment. For example, one container within a kit may contain a monoclonal antibody or fragment thereof that specifically binds to a lung tumor protein. Such antibodies or fragments may be provided attached to a support material, as described above. One or more additional containers may enclose elements, such as reagents or buffers, to be used in the assay. Such kits may also, or alternatively, contain a detection reagent as described above that contains a reporter group suitable for direct or indirect detection of antibody binding.

Alternatively, a kit may be designed to detect the level of mRNA encoding a lung tumor protein in a biological sample. Such kits generally comprise at least one oligonucleotide probe or primer, as described above, that hybridizes to a polynucleotide encoding a lung tumor protein. Such an oligonucleotide may be used, for example, within a PCR or hybridization assay. Additional components that may be present within such kits include a second oligonucleotide and/or a diagnostic reagent or container to facilitate the detection of a polynucleotide encoding a lung tumor protein.

The following Examples are offered by way of illustration and not by way of limitation.

EXAMPLE 1

Isolation and Charasterization of cDNA Sequences Encoding Lung Tumor Polypeptides This example illustrates the isolation of cDNA molecules encoding lung tumor-specific polypeptides from lung tumor cDNA libraries.
A. Isolation of cDNA Sequences From a Lung Squamous Cell Carcinoma Library A human lung squamous cell carcinoma cDNA expression library was constructed from poly A$^+$ RNA from a peol of two patient tissues using a Superscript Plasmid System for cDNA Synthesis and Plasmid Cloning kit (BRL Life Technologies, Gaithersburg, Md.) following the manufacturer's protocol. Specifically, lung carcinoma tissues were homogenized with polytron (Kinematica, Switzerland) and total RNA was extracted using Trizol reagent (BRL Life Technologies) as directed by the manufacturer. The poly A$^+$ RNA was then purified using an oligo dT cellulose column as described in Sambrook et al., *Molecular Cloning: A Laboratory Manual*, Cold Spring Harbor Laboratories, Cold Spring Harbor, N.Y., 1989. First-strand cDNA was synthesized using the NotI/Oligo-dT18 primer. Double-stranded cDNA was synthesized, ligated with BstXI/EcoRI adaptors (Invitrogen, San Diego, Calif.) and digested with NotI. Following size fractionation with cDNA size fractionation columns (BRL Life Technologies), the cDNA was ligated into the BstXI/NotI site of pcDNA3.1 (Invitrogen) and transformed into ElectroMax *E. coli* DH10B cells (BRL Life Technologies) by electroporation.

Using the same procedure, a normal human lung cDNA expression library was prepared from a pool of four tissue specimens. The cDNA libraries were characterized by determining the number of independent colonies, the percentage of clones that carried insert, the average insert size and by sequence analysis. The lung squamous cell carcinoma library contained $2.7 \times 10^6$ independent colonies with 100% of clones having an insert and the average insert size being 2100 base pairs. The normal lung cDNA library contained $1.4 \times 10^6$ independent colonies, with 90% of clones having inserts and the average insert size being 1800 base-pairs. For both libraries, sequence analysis showed that the majority of clones had a full length cDNA sequence and were synthesized from mRNA cDNA library subtraction was performed using the above lung squamous cell carcinoma and normal lung cDNA libraries, as described by Hara et al. (*Blood*, 84:189–199, 1994) with some modifications. Specifically, a lung squamous cell carcinoma-specific subtracted cDNA library was generated as follows. Normal tissue cDNA library (80 µg) was digested with BamffI and XhoI, followed by a filling-in reaction with DNA polymerase Klenow fragment. After phenol-chloroform extraction and ethanol precipitation, the DNA was dissolved in 133 µl of H$_2$O, heat-denatured and mixed with 133 µl (133 µg) of Photoprobe biotin (Vector Laboratories, Burlingame, Calif.). As recommended by the manufacturer, the resulting mixture was irradiated with a 270 W sunlamp on ice for 20 minutes. Additional Photoprobe biotin (67 µl) was added and the biotinylation reaction was repeated. After extraction with butanol five times, the DNA was ethanol-precipitated and dissolved in 23 µl H$_2$O to form the driver DNA.

To form the tracer DNA, 10 µg lung squamous cell carcinoma cDNA library was digested with NotI and SpeI, phenol chloroform extracted and passed through Chroma spin-400 columns (Clontech, Palo Alto, Calif.). Typically, 5 µg of cDNA was recovered after the sizing column. Following ethanol precipitation, the tracer DNA was dissolved in 5 µl H$_2$O. Tracer DNA was mixed with 15 µl driver DNA and 20 µl of 2×hybridization buffer (1.5 M NaCl/10 mM EDTA/50 mM HEPES pH 7.5/0.2% sodium dodecyl sulfate), overlaid with mineral oil, and heat-denatured completely. The sample was immediately transferred into a 68 ° C. water bath and incubated for 20 hours (long hybridization [LH]). The reaction mixture was then subjected to a streptavidin treatment followed by phenol/chloroform extraction. This process was repeated three more times. Subtracted DNA was precipitated, dissolved in 12 µl H$_2$O, mixed with 8 µl driver DNA and 20 µl of 2×hybridization buffer, and subjected to a hybridization at 68 °C. for 2 hours (short hybridization [SH]). After removal of biotinylated double-stranded DNA., subtracted cDNA was ligated into NotI/SpeI site of chloramphenicol resistant pBCSK⁻ (Stratagene, La Jolla, Calif.) and transformed into ElectroMax E. coli DH10B cells by electroporation to generate a lung squamous cell carcinoma specific subtracted cDNA library (herein after referred to as "lung subtraction I").

A second lung squamous cell carcinoma specific subtracted cDNA library (referred to as "lung subtraction II") was generated in a similar way to the lung subtraction library I, except that eight frequently recovered genes from lung subtraction I were included in the driver DNA, and 24,000 independent clones were recovered.

To analyze the subtracted cDNA libraries, ptasmid DNA was prepared from 320 independent clones, randomly picked from the subtracted lung squamous cell carcinoma specific libraries. Representative cDNA clones were further characterized by DNA sequencing with a Perkin Elmer/Applied Biosystems Division Automated Sequencer Model 373A and/or Model 377 (Foster City, Calif.). The cDNA sequences for sixty isolated clones are provided in SEQ ID NO: 1–60. These sequences were compared to known sequences in the gene bank using the EMBL and GenBank databases (release 96). No significant homologies were found to the sequences provided in SEQ ID NO: 2, 3, 19, 38 and 46. The sequences of SEQ ID NO: 1, 6–8, 10–13, 15, 17, 18, 20–27, 29, 30, 32, 34–37, 39–45, 47–49, 51, 52, 54, 55 and 57–59 were found to show some homology to previously identified expressed sequence tags (ESTs). The sequences of SEQ ID NO: 9, 28, 31 and 33 were found to show some homology to previously identified non-human gene sequences and the sequences of SEQ ID NO: 4, 5, 14, 50, 53, 56 and 60 were found to show some homology to gene sequences previously identified in humans.

The subtraction procedure described above was repeated using the above lung squamous cell carcinoma cDNA library as the tracer DNA, and the above normal lung tissue cDNA library and a cDNA library from normal liver and heart (constructed from a pool of one sample of each tissue as described above), plus twenty other cDNA clones that were frequently recovered in lung subtractions I and II, as the driver DNA (lung subtraction III). The normal liver and heart cDNA library contained 1.76×10⁶ independent colonies, with 100% of clones having inserts and the average insert size being 1600 base pairs. Ten additional clones were isolated (SEQ ID NO: 61–70). Comparison of these cDNA sequences with those in the gene bank as described above, revealed no significant homologies to the sequences provided in SEQ ID NO: 62 and 67. The sequences of SEQ ID NO: 61, 63–66, 68 and 69 were found to show some homology to previously isolated ESTs and the sequence provided in SEQ ID NO: 70 was found to show some homology to a previously identified rat gene.

In further studies, the subtraction procedure described above was repeated using the above lung squamous cell carcinoma cDNA library as the tracer DNA, and a cDNA library from a pool of normal lung, kidney, colon, pancreas, brain, resting PBMC, heart, skin and esophagus as the driver DNA, with esophagus cDNAs making up one third of the driver material. Since esophagus is enriched in normal epithelial cells, including differentiated squamous cells, this procedure is likely to enrich genes that are tumor specific rather than tissues specific. The cDNA sequences of 48 clones determined in this subtraction are provided in SEQ ID NO: 177–224. The sequences of SEQ ID NO: 177, 178, 180, 181, 183, 187, 192. 195–197, 208, 211, 212, 215, 216, 218 and 219 showed some homology to previously identified genes. The sequences of SEQ ID NO: 179, 182, 184–186, 188–191, 193, 194, 198–207, 209 210, 213, 214, 217, 220 and 224 showed some homology to previously determined ESTs. The sequence of SEQ ID NO: 221–223 showed no homology to any previously determined sequence.

B. Isolation of cDNA Sequences From a Lung Adenocarcinoma Library

A human lung adenocarcinoma cDNA expression library was constructed as described above. The library contained 3.2×106 independent colonies, with 100% of clones having an insert and the average insert size being 1500 base pairs. Library subtraction was performed as described above using the normal lung and normal liver and heart cDNA expression libraries described above as the driver DNA. Twenty-six hundred independent clones: were recovered.

Initial cDNA sequence analysis from 100 independent clones revealed many ribosomal protein genes. The cDNA sequences for fifteen clones isolated in this subtraction are provided in SEQ ID NO: 71–86. Comparison of these sequences with those in the gene bank as described above revealed no significant homologies to the sequence provided in SEQ ID NO: 84. The sequences of SEQ ID NO: 71, 73, 74, 77, 78 and 80–82 were found to show some homology to previously isolated ESTs, and the sequences of SEQ ID NO: 72, 75, 76, 79, 83 and 85 were found to show some homology to previously identified human genes.

EXAMPLE 2

Determination of Tissue Specificity of Lung Tumor Polypeptides

Using gene specific primers, mRNA expression levels for seven representative lung tumor polypeptides described in Example 1 were examined in a variety of normal and tumor tissues using RT-PCR.

Briefly, total RNA was extracted from a variety of normal and tumor tissues using Trizol reagent as described above. First strand synthesis was carried out using 2 μg of total RNA with SuperScript II reverse transcriptase (BRL Life Technologies) at 42 °C. for one hour. The cDNA was then amplified by PCR with gene-specific primers. To ensure the semi-quantitative nature of the RT-PCR, β-actin was used as an internal control for each of the tissues examined. 1 μl of 1:30 dilution of cDNA was employed to enable the linear range amplification of the β-actin template and was sensitive enough to reflect the differences in the initial copy numbers. Using these conditions, the β-actin levels were determined for each reverse transcription reaction from each tissue. DNA contamination was minimized by DNase treatment and by assuring a negative PCR result when using first strand cDNA that was prepared without adding reverse transcriptase.

mRNA Expression levels were examined in five different types of tumor tissue (lung squamous cell carcinoma from 3 patients, lung adenocarcinoma, colon tumor from 2 patients, breast tumor and prostate tumor), and thirteen different normal tissues (lung from 4 donors, prostate, brain, kidney, liver, ovary, skeletal muscle, skin, small intestine, stomach, myocardium, retina and testes). Using a 10-fold amount of cDNA, the antigen LST-S1-90 (SEQ ID NO: 3) was found to be expressed at high levels in lung squamous cell carcinoma and in breast tumor, and at low to undetectable levels in the other tissues examined.

The antigen LST-S2-68 (SEQ ID NO: 15) appears to be specific to lung and breast tumor, however, expression was also detected in normal kidney. Antigens LST-S1-169 (SEQ ID NO: 6) and LST-S1-133 (SEQ ID NO: 5) appear to be very abundant in lung tissues (both normal and tumor), with the expression of these two genes being decreased in most of the normal tissues tested. Both LST-S1-169 and LST-S1-133 were also expressed in breast and colon tumors. Antigens LST-S1-6 (SEQ ID NO: 7) and LST-S2-I2-5F (SEQ ID NO: 47) did not show tumor or tissue specific expression, with the expression of LST-S 1-28 being rare and only detectable in a few tissues. The antigen LST-S3-7 (SEQ ID NO: 63) showed lung and breast tumor specific expression, with its message only being detected in normal testes when the PCR was performed for 30 cycles. Lower level expression was detected in some normal tissues when the cycle number was increased to 35. Antigen LST-S3-13 (SEQ ED NO: 66) was found to be expressed in 3 out of 4 lung tumors, one breast tumor and both colon tumor samples. Its expression in normal tissues was lower compared to tumors, and was only detected in 1 out of 4 normal lung tissues and in normal tissues from kidney, ovary and retina. Expression of antigens LST-S3-4 (SEQ ID NO: 62) and LST-S3-14 (SEQ ID NO: 67) was rare and did not show any tissue or tumor specificity. Consistent with Northern blot analyses, the RT-PCT results on antigen LAT-S1-A-10A (SEQ ED NO: 78) suggested that its expression is high in lung, colon, stomach and small intestine tissues, including lung and colon tumors, whereas its expression was low or undetectable in other tissues.

A total of 2002 cDNA fragments isolated in lung subtractions I, II and III, described above, were colony PCR amplified and their mRNA expression levels in lung tumor, normal lung, and various other normal and tumor tissues were determined using microarray technology (Synteni, Palo Alto, Calif.). Briefly, the PCR amplification products were dotted onto slides in an array format, with each product occupying a unique location in the array. mRNA was extracted from the tissue sample to be tested, reverse transcribed, and fluorescent-labeled cDNA probes were generated. The microarrays were probed with the labeled cDNA probes, the slides scanned and fluorescence intensity was measured. This intensity correlates with the hybridization intensity. Seventeen non-redundant cDNA clones showed over-expression in luna squamous tumors, with expression in normal tissues tested (lung, skin, lymph node, colon, liver, pancreas, breast, heart, bone marrow, large intestine, kidney, stomach, brain, small intestine, bladder and salivary gland) being either undetectable, or 10-fold less compared to lung squamous tumors. The determined partial cDNA sequences for the clone L513S are provided in SEQ ID NO: 87 and 88; those for L514S are provided in SEQ ID NO: 89 and 90; those for L516S in SEQ ID NO: 91 and 92; that for L517S in SEQ ID NO: 93; that for L519S in SEQ ID NO: 94; those for L520S in SEQ ID NO: 95 and 96; those for L521S in SEQ ID NO: 97 and 98; that for L522S in SEQ ID NO: 99; that for L523 S in SEQ ID NO: 100; that for L524S in SEQ ID NO: 101; that for L525S in SEQ ID NO: 102; that for L526S in SEQ ID NO: 103; that for L527S in SEQ ID NO: 104; that for L528S in SEQ ID NO:105; that for L529S in SEQ ID NO: 106; and those for L530S in SEQ ID NO: 107 and 108. Additionally, the full-length cDNA sequence for L503S is provided in SEQ ID NO: 151, with the corresponding predicted amino acid sequence being provided in SEQ ID NO: 152. Due to polymorphisms, the clone L531 S appears to have two forms. A first determined full-length cDNA sequence for L53 1S is provided in SEQ ID NO: 109, with the corresponding predicted amino acid sequence being provided in SEQ ID NO: 110. A second determined full-length cDNA sequence for L531 S is provided in SEQ ID NO: 111, with the corresponding predicted amino acid sequence being provided in SEQ ID NO: 112. The sequence of SEQ ID NO: 111 is identical to that of SEQ ID NO: 109, except that it contains a 27 bp insertion. Similarly, L514S also has two alternatively spliced forms; the first variant cDNA is listed as SEQ ID NO: 153, with the corresponding amino acid sequence being provided in SEQ ID NO: 155. The second variant form of L514S full-length cDNA is provided in SEQ ID NO: 154, with its corresponding amino acid sequence being provided in SEQ ID NO: 156.

Full length cloning for L524S (SEQ ID NO: 101) yielded two variants (SEQ ID NO: 163 and 164) with the corresponding predicted amino acid sequences of SEQ ID NO: 165 and 166, respectively. Both variants have been shown to encode parathyroid hormone-related peptide.

Attempts to isolate the full-length cDNA for L519S, resulted in the isolation of the extended cDNA sequence provided in SEQ ID NO: 173, which contains a potential open reading frame. The predicted amino acid sequence encoded by the sequence of SEQ ID NO: 173 is provided in SEQ ID NO: 174. Additionally, the full-length cDNA sequence for L523S, a known gene, is provided in SEQ ID NO: 175, with the corresponding predicted amino acid sequence provided in SEQ ID NO: 176.

Comparison of the sequences of L514S and L531S (SEQ ID NO: 87 and 88, 89 and 90, and 109, respectively) with those in the gene bank, as described above, revealed no significant homologies to known sequences. The sequences of L513S, L516S, L517S, L519S, L520S and L530S (SEQ ID NO: 87 and 88, 91 and 92, 93, 94, 95 and 96, 107 and 108, respectively) were found to show some homology to previously identified ESTs. The sequences of L521S, L522S, L523S, L524S, L525S, L526S, L527S, L528S and L529S (SEQ ID NO: 97 and 98, 99, 99, 101, 102, 103, 104, 105, and 106, respectively) were found to represent known genes. The determined full-length cDNA sequences for L520S is provided in SEQ ID NO: 113, with the corresponding predicted amino acid sequence being provided in SEQ ID NO: 114. Subsequent microarray analysis has shown L520S to be overexpressed in breast tumors in addition to lung squamous tumors.

Further analysis has demonstrated that L529S (SEQ ID NO: 106 and 115), L525S (SEQ ID NO: 102 and 120) and L527S (SEQ ID NO: 104) are cytoskeletal components and potentially squamous cell specific proteins. L529S is connexin 26, a gap junction protein. It is highly expressed in lung squamous tumor 9688T, and moderately over-expressed in two others. However, lower level expression of connexin 26 is also detectable in normal skin, colon, liver and stomach. The over-expression of connexin 26 in some breast tumors has been reported and a mutated form of L529S may result in over-expression in lung tumors. L525S is plakophilin 1, a desmosomal protein found in plaque-bearing, adhering junctions of the skin. Expression levels for L525S mRNA is highly elevated in three out of four lung squamous tumors tested, and in normal skin. L527S has been identified as keratin 6 isoform, type II 58 Kd keratin, and cytokeratin 13 and shows over-expression in squamous tumors and low expression in normal skin, breast and colon tissues. Notably, keratin and keratin-related genes have been extensively documented as potential markers for lung cancer including CYFRA2.1 (Pastor, A., et al, *Eur. Respir. J.*, 10:603–609, 1997). L513S (SEQ ID NO: 87 and 88) shows moderate over-expression in several tumor tissues tested, and encodes a protein that was first isolated as a pemphigus vulgaris antigen.

L520S (SEQ ID NO: 95 and 96) and L521S (SEQ ID NO: 97 and 98) are highly expressed in lung squamous tumors, and L520S is up-regulated in normal salivary gland and L521S is over-expressed in normal skin. Both belong to a family of small proline rich proteins and represent markers for fully differentiated squamous cells. L521S has been described as a specific marker for lung squamous tumor (Hu, R., et al, *Lung Cancer*, 20:25–30, 1998). L515S (SEQ ID NO: 162) encodes IGF-β2 and L516S is an aldose reductase homologue and both are moderately expressed in lung squamous tumors and in normal colon. Notably, L516S (SEQ ID NO: 91 and 92) is up-regulated in metastatic tumors but not primary lung adenocarcinoma, an indication of its potential role in metatasis and a potential prognostic marker. L522S (SEQ ID NO: 99) is moderately over-expressed in lung squamous tumors with minimum expression in normal tissues. L522S has been shown to belong to a class IV alcohol dehydrogenase, ADH7, and its expression profile suggests it is a squamous cell specific antigen. L523S (SEQ ID NO: 100) is moderately overexpressed in lung squamous tumor, human pancreatic cancer cell lines and pancreatic cancer tissues, suggesting this gene may be a shared antigen between pancreatic and lung squamous cell cancer.

L524S (SEQ ID NO: 101) is over-expressed in the majority of squamous tumors tested and is homologous with parathyroid hormone-related peptide (PTHrP), which is best known to cause humoral hypercalcaemia associated with malignant tumors such as leukemia, prostate and breast cancer. It is also believed that PTHrP is most commonly associated with squamous carcinoma of lung and rarely with lung adenocarcinoma (Davidson, L. A., et al, *J. Pathol.*, 178: 398–401, 1996). L528S (SEQ ID NO: 105) is highly over-expressed in two lung squamous tumors with moderate expression in two other squamous tumors, one lung adeno-carcinoma and some normal tissues, including skin, lymph nodes, heart, stomach and lung. It encodes the NMD gene that is similar to the precursor of melanocyte specific gene Pmel17, which is reported to be preferentially expressed in low-metastatic potential melanoma cell lines. This suggests that L528S may be a shared antigen in both melanoma and lung squamous cell carcinoma. L526S (SEQ ID NO: 103) is overexpressed in all lung squamous cell tumor tissues tested and has been shown to share homology with a gene (ATM) in which a mutation causes ataxia telangiectasia, a genetic disorder in humans causing a predisposition to cancer, among other symptoms. ATM encodes a protein that activates p53 mediated cell-cycle checkpoint through direct binding and phosphorylation of the p53 molecule. Approximately 40% of lung cancer is associated with p53 mutations, and it is speculated that over-expression of ATM is a result of compensation for loss of p53 function, but it is unknown whether over-expression is the cause of result of lung squamous cell carcinoma. Additionally, expression of L526S (ATM) is also detected in a metastatic but not lung adenocarcinoma, suggesting a role in metastasis.

Expression of L523S (SEQ ID NO: 175), was also examined by real time RT-PCR as described above. In a first study using a panel of lung squamous tumors, L523S was found to be expressed in 4/7 lung squamous tumors, 2/3 head and neck squamous tumors and 2/2 lung adenocarcinomas, with low level expression being observed in skeletal muscle, soft palate and tonsil. In a second study using a lung adenocarcinoma panel, expression of L523S was observed in 4/9 primary adenocarcinomas, 2/2 lung pleural effusions, 1/1 metastatic lung adenocarcinomas and 2/2 lung squamous tumors, with little expression being observed in normal tissues.

Expression of L523S in lung tumors and various normal tissues was also examined by Northern blot analysis, using standard techniques. In a first study, L523S was found to be expressed in a number of lung adenocarcinomas and squamous cell carcinomas, as well as normal tonsil. No expression was observed in normal lung. In a second study using a normal tissue blot (HB-12) from Clontech, no expression was observed in brain, skeletal muscle, colon, thymus, spleen, kidney, liver, small intestine, lung or PBMC, although there was strong expression in placenta.

EXAMPLE 3

Isolatin and Characterization of Lung Tumor Polypeptides by Pcr-based Subtraction Eight hundred and fifty seven clones from a cDNA subtraction library, containing cDNA from a pool of two human lung squamous tumors subtracted against eight normal human tissue cDNAs including lung, PBMC, brain, heart, kidney, liver, pancreas, and skin, (Clontech, Palo Alto, Calif.) were derived and submitted to a first round of PCR amplification. This library was subjected to a second round of PCR amplification, following the manufacturer's protocol. The resulting cDNA fragments were subcloned into the vector P7- Adv vector (Clontech, Palo Alto, Calif.) and transformed into DH5αE. coli (Gibco, BRL). DNA was isolated from independent clones and sequenced using a Perkin Elmer/Applied Biosystems Division Automated Sequencer Model 373A.

One hundred and sixty two positive clones were sequenced. Comparison of the DNA sequences of these clones with those in the EMBL and GenBank databases, as described above, revealed no significant homologies to 13 of these clones, hereinafter referred to as Contigs 13, 16, 17, 19, 22, 24, 29, 47, 49, 56–59. The determined cDNA sequences for these clones are provided in SEQ ID NO: 125, 127–129, 131–133, 142, 144, 148–150, and 157, respectively. Contigs 1, 3–5, 7–10, 12, 11, 15, 20, 31, 33, 38, 39, 41, 43, 44, 45, 48, 50, 53, 54 (SEQ ID NO: 115–124, 126, 130, 134–141, 143, 145–147, respectively) were found to show some degree of homology to previously identified DNA sequences. Contig 57 (SEQ ID NO: 149) was found to represent the clone L519S (SEQ ID NO: 94) disclosed in US. Pat. Application Ser. No. 09/123,912, filed Jul. 27, 1998. To the best of the inventors knowledge, none of these sequences have been previously shown to be differentially over-expressed in lung tumors.

mRNA expression levels for representative clones in lung tumor tissues, normal lung tissues (n=4), resting PBMC, salivary gland, heart, stomach, lymph nodes, skeletal muscle, soft palate, small intestine, large intestine, bronchial, bladder, tonsil, kidney, esophagus, bone marrow, colon, adrenal gland, pancreas, and skin, (all derived from human) were determined by RT-PCR as described above. Expression levels using microarray technology, as described above, were examined in one sample of each tissue type unless otherwise indicated.

Contig 3 (SEQ ID NO: 116) was found to be highly expressed in all head and neck squamous cell tumors tested (17/17), and expressed in the majority (8/12) of lung squamous tumors, (high expression in 7/12, moderate in 2/12, and low in 2/12), while showing negative expression for 2/4 normal lung tissues and low expression in the remaining two samples. Contig 3 showed moderate expression in skin and soft palate, and lowered expression levels in resting PBMC, large intestine, salivary gland, tonsil, pancreas, esophagus, and colon. Contig 11 (SEQ ID NO: 124) was found to be expressed in all head and neck squamous cell tumors tested (17/17): highly expressed in 14/17, and moderately expressed in 3/17. Additionally, expression in lung squamous tumors showed high expression in 3/12 and moderate in 4/12. Contig 11 was negative for 3/4 normal lung samples, with the remaining sample having only low expression. Contig 11 showed low to moderate reactivity to salivary gland, soft palate, bladder, tonsil, skin, esophagus, and large intestine. Contig 13 (SEQ ID NO: 125) was found to be expressed in all head and neck squamous cell tumors tested (17/17): highly expressed in 12/17, and moderately expressed in 5/17. Contig 13 was expressed in 7/12 lung squamous tumors, with high expression in 4/12 and moderate expression in three samples. Analysis of normal lung samples showed negative expression for 2/4 and low to moderate expression in the remaining two samples. Contig 13 did show low to moderate reactivity to resting PBMC, salivary gland, bladder, pancreas, tonsil, skin, esophagus, and large intestine, as well as high expression in soft palate. Contig 16 (SEQ ID NO: 127) was found to be moderately expressed in some head and neck squamous cell tumors (6/17) and one lung squamous tumor; while showing no expression in any normal lung samples tested. Contig 16 did show low reactivity to resting PBMC, large intestine, skin, salivary gland, and soft palate. Contig 17 (SEQ ID NO: 128) was shown to be expressed in all head and neck squamous cell tumors tested (17/17): highly expressed in 5/17, and moderately expressed in 12/17. Expression levels in lung squamous tumors showed one tumor sample with high expression and 3/12 with moderate levels. Contis 17 was negative for 2/4 normal lung samples, with the remaining samples having only low expression. Additionally, low level expression was found in esophagus and soft palate. Contic 19 (SEQ ID NO: 129) was found to be expressed in most head and neck squamous cell tumors tested (11/17); with two samples having high levels, 6/17 showing moderate expression, and low expression being found in 3/17. Testing in lung squamous tumors revealed only moderate expression in 3/12 samples. Expression levels in 2/4 of normal lung samples were negative, the two other samples having only low expression. Contig 19 showed low expression levels in esophagus, resting PBMC, salivary gland, bladder, soft palate and pancreas.

Contig 22 (SEQ ID NO: 131), was shown to be expressed in most head and neck squamous cell tumors tested (13/17) with high expression in four of these samples, moderate expression in 6/17, and low expression in 3/17. Expression levels in lung squamous tumors were found to be moderate to high for 3/12 tissues tested, with negative expression in two normal lung samples and low expression in two other samples (n=4). Contig 22 showed low expression in skin, salivary gland and soft palate. Similarly, Contig 24 (SEQ ID NO: 132) was found to be expressed in most head and neck squamous cell tumors tested (13/17) with high expression in three of these samples, moderate expression in 6/17, and low expression in 4/17. Expression levels in lung squamous tumors were found to be moderate to high for 3/12 tissues tested, with negative expression for three normal lung samples and low expression in one sample (n=4). Contig 24 showed low expression in skin, salivary gland and soft palate. Contig 29 (SEQ ID NO: 133) was expressed in nearly all head and neck squamous cell tumors tested (16/17): highly expressed in 4/17, moderately expressed in 11/17, with low expression in one sample. Also, it was moderately expressed in 3/12 lung squamous tumors, while being negative for 2/4 normal lung samples. Contig 29 showed low to moderate expression in large intestine, skin, salivary gland, pancreas, tonsil, heart and soft palate. Contig 47 (SEQ ID NO: 142) was expressed in most head and neck squamous cell tumors tested (12/17): moderate expression in 10/17, and low expression in two samples. In lung squamous tumors, it was highly expressed in one sample and moderately expressed in two others (n=13). Contig 47 was negative for 2/4 normal lung samples, with the remaining two samples having moderate expression. Also, Contig 47 showed moderate expression in large intestine, and pancreas, and low expression in skin, salivary gland, soft palate, stomach, bladder, resting PBMC, and tonsil.

Contig 48 (SEQ ID NO: 143) was expressed in all head and neck squamous cell tumors tested (17/17): highly expressed in 8/17 and moderately expressed in 7/17, with low expression in two samples. Expression levels in lung squamous tumors were high to moderate in three samples (n=13). Contig 48 was negative for one out of four normal lung samples, the remaining showing low or moderate expression. Contig 48 showed moderate expression in soft palate, large intestine, pancreas, and bladder, and low expression in esophagus, salivary gland, resting PBMC, and heart. Contig 49 (SEQ ID NO: 144) was expressed at low to moderate levels in 6/17 head and neck squamous cell tumors tested. Expression levels in lung squamous tumors were moderate in three samples (n=13). Contig 49 was negative for 2/4 normal lung samples, the remaining samples showing low expression. Moderate expression levels in skin, salivary gland, large intestine, pancreas, bladder and resting PBMC were shown, as well as low expression in soft palate, lymph nodes, and tonsil. Contig 56 (SEQ ID NO: 148) was expressed in low to moderate levels in 3/17 head and neck squamous cell tumors tested, and in lung squamous tumors, showing low to moderate levels in three out of thirteen samples. Notably, low expression levels were detected in one adenocarcinoma lung tumor sample (n=2). Contig 56 was negative for 3/4 normal lung samples, and showed moderate expression levels in only large intestine, and low expression in salivary (,land., soft palate, pancreas, bladder, and resting PBMC. Contig 58, also known as L769P, (SEQ ID NO: 150) was expressed at moderate levels in 11/17 head and neck squamous cell tumors tested and low expression in one additional sample. Expression in lung, squamous tumors showed low to moderate levels in three out of thirteen samples. Contig 58 was negative for 3/4 normal lung, samples, with one sample having low expression. Moderate expression levels in skin, large intestine, and resting PBMC were demonstrated, as well as low expression in salivary gland, soft palate, pancreas, and bladder. Contig, 59 (SEQ ID NO: 157) was expressed in some head, neck, and lung squamous tumors. Low level expression of Contig 59 was also detected in salivary gland and large intestine.

The full-length cDNA sequence for Contig 22, also referred to as L763P, is provided in SEQ ID NO: 158, with the corresponding, predicted amino acid sequence-being provided in SEQ ID NO: 159. Real-time RTl-PCR analysis of L763 P revealed that it is highly expressed in 3 /4 lung squamous tumors as well as 4/4 head and neck squamous tumors, with low level expression being, observed in normal brain, skin, soft pallet and trachea.

The full-length cDNA sequence incorporating Contigs 17, 19, and 24, referred to as L762P, is provided in SEQ ID NO: 160, with the corresponding predicted amino acid sequence being provided in SEQ ID NO: 161. Further analysis of L762P has determined it to be a type I membrane protein and two additional variants have been sequenced. Variant 1 (SEQ ID NO: 167, with the corresponding amino acid sequence in SEQ ID NO 169) is an alternatively spliced form of SEQ ID NO: 160 resulting in deletion of 503 nucleotides, as well as deletion of a short segment of the expressed protein. Variant 2 (SEQ ID NO: 168, with the corresponding amino acid sequence in SEQ ID NO: 170) has a two nucleotide deletion at the 3' coding region in comparison to SEQ ID NO: 160, resulting in a secreted form of the expressed protein. Real-time RT-PCR analysis of L762P revealed that is over-expressed in 3/4 lung squamous tumors and 4/4 head & neck tumors, with low level expression being observed in normal skin, soft pallet and trachea.

The full-length cDNA sequence for contig 56 (SEQ ID NO: 148), also referred to as L773P, is provided in SEQ ID NO: 171, with the predicted amino acid sequence in SEQ ID NO: 172. L773P was found to be identical to dihydroxyl dehydrogenase at the 3' portion of the gene, with divergent 5' sequence. As a result, the 69 N-terminal amino acids are unique. Real-time PCR revealed that L773P is highly expressed in lung squamous tumor and lung adenocarcinoma, with no detectable expression in normal tissues. Subsequent Northern blot analysis of L773P demonstrated that this transcript is differentially over-expressed in squamous tumors and detected at approximately 1.6 Kb in primary lung tumor tissue and approximately 1.3 Kb in primary head and neck tumor tissue.

Subsequent microarray analysis has shown Contig 58, also referred to as L769S (SEQ ID NO: 150), to be over-expressed in breast tumors in addition to lung squamous tumors.

EXAMPLE 4

Synthesis of Polypeptides

Polypeptides may be synthesized on a Perkin Elmer/Applied Biosystems Division 430A peptide synthesizer using FMOC chemistry with HPTU (O-Benzotriazole-N,N,N',N'-tetramethyluronium hexafluorophosphate) activation. A Gly-Cys-Gly sequence may be attached to the amino terminus of the peptide to provide a method of conjugation, binding to an immobilized surface, or labeling of the peptide. Cleavage of the peptides from the solid support may be carried out using the following cleavage mixture: trifluoroacetic acid:ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0%–60% acetonitrile (containing 0.1% TFA) in water (containing 0.1% TFA) may be used to elute the peptides. Following lyophilization of the pure fractions, the peptides may be characterized using electrospray or other types of mass spectrometry and by amino acid analysis.

EXAMPLE 5

Preparation of Antibodies Against Lung Cancer Antigens

Polyclonal antibodies against the lung cancer antigens L514S, L528S and L531S (SEQ ID NO: 155, 225 and 112, respectively) were prepared as follows.

Rabbits were immunized with recombinant protein expressed in and purified from E. coli as described above. For the initial immunization, 400 μg of antigen combined with muramyl dipeptide (MDP) was injected subcutaneously (S.C.). Animals were boosted S.C. 4 weeks later with 200 μg of antigen mixed with incomplete Freund's Adjuvant (IFA). Subsequent boosts of 100 μg of antigen mixed with IFA were injected S.C. as necessary to induce high antibody titer responses. Serum bleeds from immunized rabbits were tested for antigen-specific reactivity using ELISA assays with purified protein. Polyclonal antibodies against L514S, L528S and L531S were affinity purified from high titer polyclonal sera using purified protein attached to a solid support.

Immunohistochemical analysis using polyclonal antibodies against L514S was performed on a panel of 5 lung tumor samples, 5 normal lung tissue samples and normal colon, kidney, liver, brain and bone marrow. Specifically, tissue samples were fixed in formalin solution for 24 hours and embedded in paraffin before being sliced into 10 micron sections. Tissue sections were permeabilized and incubated with antibody for 1 hr. HRP-labeled anti-mouse followed by incubation with DAB chromogen was used to visualize L514S immunoreactivity. L514S was found to be highly expressed in lung tumor tissue with little or no expression being observed in normal lung, brain or bone marrow. Light staining was observed in colon and kidney. Staining was seen in normal liver but no mRNA has been detected in this tissue making this result suspect.

EXAMPLE 6

Peptide Priming of Mice and Propagation of CTL Lines

Immunogenic peptides from the lung cancer antigen L762P (SEQ ID NO: 161) for HLA-A2/$K^b$-restricted CD8+ T cells were identified as follows.

The location of HLA-A2 binding peptides within the lung cancer antigen L762P (SEQ ID NO: 161) was predicted using a computer program which predicts peptides sequences likely to being to HLA-A*0201 by fitting to the known peptide binding motif for HLA-A*0201 (Rupert et al. (1993) Cell 74:929; Rammensee et al. (1995) Immunogenetics 41:178–228). A series of 19 synthetic peptides corresponding to a selected subset of the predicted HLA-A*0201 binding peptides was prepared as described above.

Mice expressing the transgene for human HLA A2/$K^b$ (provided by Dr L. Sherman, The Scripps Research Institute, La Jolla, Calif.) were immunized with the synthetic peptides, as described by Theobald et al., Proc. Natl. Acad. Sci. USA 92:11993–11997, 1995 with the following modifications. Mice were immunized with 50 μg of L726P peptide and 120 μg of an I-$A^b$ binding peptide derived from hepatitis B Virus protein emulsified in incomplete Freund's adjuvant. Three weeks later these mice were sacrificed and single cell suspensions prepared. Cells were then resuspended at 7×10$^6$ cells/ml in complete media (RPMI-1640; Gibco BRL, Gaithersburg, Md.) containing 10% FCS, 2 mM Glutamine (Gibco BRL), sodium pyruvate (Gibco BRL), non-essential amino acids (Gibco BRL), 2×10$^{-5}$ M 2-mercaptoethanol, 50 U/ml penicillin and streptomycin, and cultured in the presence of irradiated (3000 rads) L762P peptide- (5 μg/ml) and 10 mg/ml B$_2$-microglobulin- (3 μg/ml) LPS blasts (A2 transgenic spleens cells cultured in the presence of 7 μg/ml dextran sulfate and 25 μg/ml LPS for 3 days). After six days, cells (5×10$^5$/ml) were restimulated with 2.5×10$^6$/ml peptide pulsed irradiated (20,000 rads) EL.4A2Kb cells (Sherman et al, Science 258:815–818, 1992) and 5×10$^6$/ml irradiated (3000 rads) A2/$K^b$-transgenic spleen feeder cells. Cells were cultured in the presence of 10 U/ml IL-2. Cells were restimulated on a weekly basis as described, in preparation for cloning the line.

Peptide-specific cell lines were cloned by limiting dilution analysis with irradiated (20,000 rads) L762P peptide-pulsed EL4 A2Kb tumor cells (1×10⁴ cells/well) as stimulators and irradiated (3000 rads) A2/K$^b$-transgenic spleen cells as feeders (5×10⁵ cells/well) grown in the presence of 10 U/ml IL-2. On day 7, cells were restimulated as before. On day 14, clones that were growing were isolated and maintained in culture.

Cell lines specific for L762P-87 (SEQ ID NO: 226; corresponding to amino acids 87-95 of SEQ ID NO: 161), L726P-145 (SEQ ID NO: 227; corresponding to amino acids 145–153 of SEQ ID NO: 161), L726P-585 (SEQ ID NO: 228; corresponding to amino acids 585–593 of SEQ ID NO: 161), L762P425 (SEQ ID NO: 229; corresponding to amino acids 425–433 of SEQ ID NO: 161), L762P(10)-424 (SEQ ID NO: 230; corresponding to amino acids 424–433 of SEQ ID NO: 161) and L762P(10)-458 (SEQ ID NO: 231; corresponding to amino acids 458–467 of SEQ ID NO: 161) demonstrated significantly higher reactivity (as measured by percent specific lysis) against L762P peptide-pulsed EL4-A2/Kb tumor target cells than control peptide-pulsed EL4-A2/K$^b$ tumor target cells.

EXAMPLE 7

Identification of CD4 Immunogenic T Cell Epitopes Derived From the Lung Cancer Antigen L762P CD4 T cell lines specific for the antigen L762P (SEQ ID NO: 161) were generated as follows.

A series of 28 overlapping peptides were synthesized that spanned approximately 50% of the L762P sequence. For priming, peptides were combined into pools of 4–5 peptides, pulsed at 20 micrograms/ml into dendritic cells for 24 hours. The dendritic cells were then washed and mixed with positively selected CD4+ T cells in 96 well U-bottomed plates. Forty cultures were generated for each peptide pool. Cultures were restimulated weekly with fresh dendritic cells loaded with peptide pools. Following a total of 3 stimulation cycles, cells were rested for an additional week and tested for specificity to antigen presenting cells (APC) pulsed with peptide pools using interferon-gamma ELISA and proliferation assays. For these assays, adherent monocytes loaded with either the relevant peptide pool or an irrelevant peptide were used as APC. T cell lines that appeared to specifically recognize L762P peptide pools both by cytokine release and proliferation were identified for each pool. Emphasis was placed on identifying T cells with proliferative responses. T cell lines that demonstrated either both L762P-specific cytokine secretion and proliferation, or strong proliferation alone were further expanded to be tested for recognition of individual peptides from the pools, as well as for recognition of recombinant L762P. The source of recombinant L762P was E. coli, and the material was partially purified and endotoxin positive. For these peptides, 10 micrograms of individual peptides, 10 or 2 micrograms of an irrelevant peptide, and 2 or 0.5 micrograms of either L762P protein or an irrelevant, equally impure, E. coli generated recombinant protein. Significant interferon-gamma production and CD4 T cell proliferation was induced by a number of L762P-derived peptides in each pool. The amino acid sequences for these peptides are provided in SEQ ID NO: 232–251. These peptides correspond to amino acids 661–680, 676–696, 526–545, 874–893, 811–830, 871–891, 856–875, 826–845, 795–815, 736–755, 706–725, 706–691–710, 601–620, 571–590, 556–575, 616–635, 646–665, 631–650, 541–560 and 586 respectively, of SEQ ID NO: 161.

EXAMPLE 8

Protein Expression of Lung Tumor-specific Antigens a) Expression of L514S in E. coli The lung tumor antigen L514S (SEQ ID NO: 89) was subcloned into the expression vector pE32b at NcoI and NotI sites, and transformed into E. coli using standard techniques. The protein was expressed from residues 3–153 of SEQ ID NO: 89. The expressed amino acid sequence and the corresponding DNA sequence are provided in SEQ ID NO: 252 and 253, respectively.

b) Expression of L762P

Amino acids 32–944 of the lung tumor antigen L762P (SEQ ID NO: 161), with a 6×His Tag, were subcloned into a modified pET28 expression vector, using kanamycin resistance, and transformed into BL21 CodonPlus using standard techniques. Low to moderate levels of expression were observed. The determined DNA sequence of the L762P expression construct is provided in SEQ ID NO: 254.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An isolated polynucleotide encoding a polypeptide having an amino acid sequence provided in SEQ ID NO: 252.

2. An isolated polynucleotide comprising a sequence provided in SEQ ID NO: 253, or the complement thereof.

3. An isolated cDNA consisting of at least 45 contiguous residues of the sequence provided in SEQ ID NO: 253.

4. An expression vector comprising a polynucleotide according to any one of claims 1, 2 and 3 operably linked to an expression control sequence.

5. A host cell transformed or transfected with an expression vector according to claim 4.

6. A composition comprising a first component selected from the group consisting of physiologically acceptable carriers and immunostimulants, and a second component selected from the group consisting of a polynucleotide according to any one of claims and 1, 2 and 3.

* * * * *

UNITED STATES PATENT AND TRADEMARK OFFICE
CERTIFICATE OF CORRECTION

PATENT NO. : 6,706,262 B1  Page 1 of 1
DATED : March 16, 2004
INVENTOR(S) : Tongtong Wang It is certified that error appears in the above-identified patent and that said Letters Patent is hereby corrected as shown below:

Title page,
Item [75], Inventors, "Tongtong Wang, Medina, WA (US); Nancy A. Hosken, Seattle, WA (US); Michael D. Kalos, Seattle, WA (US); Gary R. Fanger, Mill Creek, WA (US)" should read -- Tongtong Wang, Medina, WA (US) --.

Signed and Sealed this

Thirteenth Day of December, 2005

JON W. DUDAS
*Director of the United States Patent and Trademark Office*